United States Patent
Sun

(10) Patent No.: US 10,836,807 B2
(45) Date of Patent: *Nov. 17, 2020

(54) RECOMBINANT POLYPEPTIDES AND NUCLEIC ACID MOLECULES, COMPOSITIONS, AND METHODS OF MAKING AND USES THEREOF

(71) Applicant: BioGend Therapeutics Co., Ltd., Taipei (TW)

(72) Inventor: Da-Wei Sun, Taipei (TW)

(73) Assignee: BioGend Therapeutics Co., Ltd., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/079,806

(22) PCT Filed: Dec. 29, 2017

(86) PCT No.: PCT/IB2017/058516
§ 371 (c)(1),
(2) Date: Aug. 24, 2018

(87) PCT Pub. No.: WO2018/122794
PCT Pub. Date: Jul. 5, 2018

(65) Prior Publication Data
US 2019/0071480 A1 Mar. 7, 2019

Related U.S. Application Data

(60) Provisional application No. 62/562,515, filed on Sep. 25, 2017, provisional application No. 62/440,663, filed on Dec. 30, 2016.

(51) Int. Cl.
| | | |
|---|---|---|
| C07K 14/51 | (2006.01) |
| A61K 38/18 | (2006.01) |
| A61L 27/12 | (2006.01) |
| A61L 27/22 | (2006.01) |
| A61L 27/54 | (2006.01) |
| A61L 27/56 | (2006.01) |
| C12N 15/10 | (2006.01) |
| C12N 15/64 | (2006.01) |
| A61K 38/00 | (2006.01) |

(52) U.S. Cl.
CPC .............. *C07K 14/51* (2013.01); *A61L 27/12* (2013.01); *A61L 27/227* (2013.01); *A61L 27/54* (2013.01); *A61L 27/56* (2013.01); *C12N 15/1096* (2013.01); *C12N 15/64* (2013.01); *A61K 38/00* (2013.01); *A61K 38/1875* (2013.01); *A61L 2300/252* (2013.01); *A61L 2430/02* (2013.01); *A61L 2430/38* (2013.01); *C07K 2319/00* (2013.01)

(58) Field of Classification Search
None
See application file for complete search history.

(56) References Cited

U.S. PATENT DOCUMENTS

| | | |
|---|---|---|
| 4,596,574 A | 6/1986 | Urist |
| 5,453,363 A | 9/1995 | Rudolph et al. |
| 5,650,494 A | 7/1997 | Cerletti et al. |
| 6,057,430 A | 5/2000 | Cerletti |
| 7,179,795 B2 | 2/2007 | Wiederanders et al. |
| 7,253,254 B1 | 8/2007 | Sebald |
| 7,365,051 B2 | 4/2008 | Paulista et al. |
| 8,952,130 B2 | 2/2015 | Choe et al. |
| 2004/0146948 A1 | 7/2004 | Britton et al. |
| 2014/0148387 A1 | 5/2014 | Nagaya et al. |
| 2014/0186308 A1 | 7/2014 | Belmonte et al. |

FOREIGN PATENT DOCUMENTS

| | | | |
|---|---|---|---|
| CN | 1782075 A | 6/2006 | |
| EP | 2612674 A1 * | 7/2013 | ......... A61K 38/1875 |
| JP | 2016104133 A | 6/2016 | |
| JP | 5974409 B2 | 8/2016 | |
| TW | 201215414 A | 4/2012 | |
| WO | WO-8702673 A2 | 5/1987 | |
| WO | WO-8800205 A1 | 1/1988 | |
| WO | WO-9309229 A1 | 5/1993 | |
| WO | WO-9603432 A1 | 2/1996 | |
| WO | WO-9603433 A1 | 2/1996 | |
| WO | WO-0178756 A2 | 10/2001 | |
| WO | WO-2007109668 A2 | 9/2007 | |
| WO | WO-2010098421 A1 | 9/2010 | |
| WO | WO-2010103070 A2 | 9/2010 | |
| WO | WO-2012023113 A2 | 2/2012 | |

(Continued)

OTHER PUBLICATIONS

Response to Communication Under Rules 161 and 162 EPC in European Patent Application No. 17832575.9, dated Mar. 29, 2019, European Patent Office, Munich, Germany, 14 pages.

Office Action in European Patent Application No. 17832575.9, dated Sep. 30, 2019, European Patent Office, Munich, Germany, 6 pages.

Atanassov, I.I., et al., "A Simple, Flexible and Efficient PCR-fusion/Gateway Cloning Procedure for Gene Fusion, Site-directed Mutagenesis, Short Sequence Insertion and Domain Deletions and Swaps," *Plant Methods*, 5: 14, BioMed Central, England (Oct. 2009).

(Continued)

*Primary Examiner* — Lianko G Garyu
(74) *Attorney, Agent, or Firm* — Sterne, Kessler, Goldstein & Fox P.L.L.C.

(57) ABSTRACT

The present disclosure provides recombinant polypeptides, homodimeric and heterodimeric proteins comprising the recombinant polypeptides, nucleic acid molecules encoding the recombinant polypeptides, and vectors and host cells comprising the nucleic acid molecules. The present disclosure also provides compositions comprising the recombinant polypeptides and methods of making and using the recombinant polypeptides.

19 Claims, 13 Drawing Sheets

Specification includes a Sequence Listing.

(56) References Cited

FOREIGN PATENT DOCUMENTS

| WO | WO-2012029148 A1 | 3/2012 |
|---|---|---|
| WO | WO-2018121703 A1 | 7/2018 |

OTHER PUBLICATIONS

Bessho, K., et al., "Bone Induction by *Escherichia coli*-Derived Recombinant Human Bone Morphogenetic Protein-2 Compared With Chinese Hamster Ovary Cell-derived Recombinant Human Bone Morphogenetic Protein-2," *The British Journal of Oral and Maxillofacial Surgery*, 38(6):645-649, Edinburgh, Scotland, Dec. 2000.

Chen, D., et al., "Bone Morphogenetic Proteins," *Growth Factors*, 22(4):233-341, Informa Healthcare, England (Dec. 2004).

Gamez, B., et al., "BMP Signaling in Telencephalic Neural Cell Specification and Maturation," *Frontiers in Cellular Neuroscience*, 7(87):1-13, Frontiers Research Foundation, Switzerland (Jun. 2013).

Harada, Y., et al., "Effect of *Escherichia coli*-produced recombinant human bone morphogenetic protein 2 on the regeneration of canine segmental ulnar defects," *Journal of Bone and Mineral Metabolism*, 30(4):388-399, Japanese Society of Bone and Mineral Metabolism, Japan (Jul. 2012).

Hilden, K., et al., "Expression of Type II Activin Receptor Genes During Differentiation of Human K562 Cells and cDNA Cloning of the Human Type IIB Activin Receptor," *Blood* 83(8):2163-2170, American Society of Hematology, United States (Apr. 1994).

Hu, Z., et al., "The Osteoinductive Activity of Bone Morphogenetic Protein (BMP) Purified by Repeated Extracts of Bovine Bone," *Growth Factors*, 22(1):29-33, *Informa Healthcare*, England (Mar. 2004).

International Search Report and Written Opinion for Application No. PCT/CN2017/119623, dated Mar. 16, 2018, 11 pages.

International Search Report and Written Opinion for Application No. PCT/IB2017/058516, dated Mar. 6, 2018, 12 pages.

Katagiri, T., et al., "The Non-osteogenic Mouse Pluripotent Cell Line, C3H10T1/2, Is Induced to Differentiate Into Osteoblastic Cells by Recombinant Human Bone Morphogenetic Protein-2," *Biochemical and Biophysical Research Communications*, 172(1):295-299, Elsevier, United States, Oct. 1990.

Kim, Y., et al., "Bone Morphogenetic Protein-2-induced Alkaline Phosphatase Expression Is Stimulated by Dlx5 and Repressed by MSx2," *The Journal of Biological Chemistry*, 279(49):50773-50780, American Society for Biochemistry and Molecular Biology, United States (Dec. 2004).

Kirsch, T., et al., "BMP-2 Antagonists Emerge from Alterations in the Low-Affinity Binding Epitope for Receptor BMPR-II," *The Embo Journal*, 19(13):3314-3324, Wiley Blackwell, England, Jul. 2000.

Kirsch, T., et al., "Crystal Structure of the BMP-2-BRIA Ectodomain Complex," *Nature Structural Biology*, 7(6): 492-496, Nature Publishing Corporation, United States (Jun. 2000).

Kirsch, T., et al., "Isolation of Recombinant BMP Receptor IA Ectodomain and Its 2:1 Complex With BMP-2," *Febs Letters*, 468(2-3):215-219, John Wiley & Sons Limited, England, Feb. 2000.

Kotzsch, A., et al., "Structure Analysis of Bone Morphogenetic Protein-2 Type I Receptor Complexes Reveals a Mechanism of Receptor Inactivation in Juvenile Polyposis Syndrome," *The Journal of Biological Chemistry*, 283(9):5876-5887, American Society for Biochemistry and Molecular Biology, United States, Feb. 2008.

Kubler N., et al., "Inductive Properties of Recombinant Human BMP-2 Produced in a Bacterial Expression System," *International Journal of Oral and Maxillofacial Surgery*, 27(4):305-309, Churchill Livingstone, Denmark, Aug. 1998.

Nickel, J., et al., "The Crystal Structure of the BMP-2:BMPR-IA Complex and the Generation of BMP-2 Antagonists," *The Journal of Bone and Joint Surgery*, 83-A Suppl 1(Pt 1):S7-S14, Journal of Bone and Joint Surgery, United States (Jan. 2001).

Office Action for Taiwanese Patent Application No. 1082009054001, dated Jan. 29, 2019, Taiwan Patent and Trademark Office, Taichung City, Taiwan, 10 pages.

Yano, K., et al., "Osteoinductive Capacity and Heat Stability of Recombinant Human Bone Morphogenetic Protein-2 Produced by *Escherichia coli* and Dimerized by Biochemical Processing," *Journal of Bone and Mineral Metabolism*, 27(3):355-363, Japanese Society of Bone and Mineral Metabolism, Japan (May 2009).

Giteau, A., et al., "How to Achieve Sustained and Complete Protein Release from PLGA-Based Microparticles?," Author manuscript of *International Journal of Pharmaceutics*, 350(1-2):14-26, Elsevier/North-Holland Biomedical Press, Netherlands (Feb. 2008), 51 pages.

Inoue, H., et al., "High Efficiency Transformation of *Escherichia coli* with Plasmids," *Gene*, 96(1):23-28, Elsevier/North-Holland, Netherlands (Nov. 1990).

Mardirosian, M.H., "Effects of Bone Morphogenetic Protein (rhBMP-2) and Platelet Derived Growth Factor (rhPDGF-BB) on Ectopic Bone Formation in Rats," UCLA Electronic Theses and Dissertations, University of California, Los Angeles, 2012, 39 pages.

Kokubo, S., et al., "Bone Regeneration by Recombinant Human Bone Morphogenetic Protein-2 and A Novel Biodegradable Carrier in a Rabbit Ulnar Defect Model," *Biomaterials*, 24(9):1643-1651, Elsevier Science, Netherlands (Apr. 2003).

Peel, S.A., et al., "In Search of the Ideal Bone Morphogenetic Protein Delivery System: In Vitro Studies on Demineralized Bone Matrix, Purified, and Recombinant Bone Morphogenetic Protein," *Journal of Craniofacial Surgery*, 14(3):284-291, Lippincott Williams & Wilkins, United States (May 2003).

Scheufler, C., et al., "Chain A, Bone Morphogenetic Protein-2," PDB: 1ES7_A, Source: *Homo sapiens* (human) NCBI Database, Accessed on May 14, 2018.

Ruppert, R., et al., "Chain A, Protein (Bone Morphogenetic Protein 2 (BMP-2))," PDB: 3BMP_A, Source: *Homo sapiens* (human), NCBI Database, Accessed on May 14, 2018.

Sawyer, A.A., et al., "The Stimulation of Healing within a Rat Calvarial Defect by mPCL-TCP/Collagen Scaffolds Loaded with rhBMP-2," *Biomaterials*, 30(13):2479-2488, Elsevier Science, Netherlands (May 2009).

Woodruff, M.A., et al., "Sustained Release and Osteogenic Potential of Heparan Sulfate-Doped Fibrin Glue Scaffolds within a Rat Cranial Model," Author manuscript of *Journal of Molecular Histology*, 38(5):425-433, Springer Netherlands, Netherlands (Oct. 2007), 24 pages.

Ruppert, R., et al., "Human Bone Morphogenetic Protein 2 Contains a Heparin-binding Site Which Modifies Its Biological Activity," *European Journal of Biochemistry*, 237(1):295-302, Blackwell Science, England, Apr. 1996.

Scheufler, C., et al., "Crystal Structure of Human Bone Morphogenetic Protein-2 at 2.7 A Resolution," *Journal of Molecular Biology*, 287(1):103-115, Elsevier, England (Mar. 1999).

Leung, D., et al., "A Method for random Mutatgensis of a Defined DNA Segment Using a Modified Polymerase Chain Reaction," *Technique* 1:11-15, W.B. Saunders Company, United States (1989).

Tu, Q., et al., "Calcyclin Mediates Serum Response Element (SRE) Activation by an Osteoblastic Extracellular Cation-sensing Mechanism," *Journal of Bone and Mineral Research* 18(10):1825-1833, American Society for Bone and Mineral Research, United States, Oct. 2003.

Weber, FE., et al., "Disulfide Bridge Conformers of Mature BMP are Inhibitors for Heterotopic Ossification," *Biochemical and Biophysical Research Communications*, 286(3):554-558, Elsevier, United States (Aug. 2001).

\* cited by examiner

GROUP A

GROUP B

GROUP C

GROUP D

GROUP E

GROUP F

GROUP G

SEQUENCE LISTING

```
<160> NUMBER OF SEQ ID NOS: 357

<210> SEQ ID NO 1
<211> LENGTH: 875
<212> TYPE: DNA
<213> ORGANISM: artificial sequence
<220> FEATURE:
<223> OTHER INFORMATION: Kanamycin resistance gene (+3886 to +4760)
      fragment
```

<400> SEQUENCE: 1

```
catgaacaat aaaactgtct gcttacataa acagtaatac aagggggtgtt atgagccata    60
ttcaacggga aacgtcttgc tctaggccgc gattaaattc aacatggat gctgatttat    120
atgggtataa atgggctcgc gataatgtcg ggcaatcagg tgcgacaatc tatcgattgt    180
atgggaagcc cgatgcgcca gagttgtttc tgaaacatgg caaaggtagc gttgccaatg    240
atgttacaga tgagatggtc agactaaact ggctgacgga atttatgcct cttccgacca    300
tcaagcattt tatccgtact cctgatgatg catggttact caccactgcg atccccggga    360
aaacagcatt ccaggtatta gaagaatatc ctgattcagg tgaaaatatt gttgatgcgc    420
tggcagtgtt cctgcgccgg ttgcattcga ttcctgtttg taattgtcct tttaacagcg    480
atcgcgtatt tcgtctcgct caggcgcaat cacgaatgaa taacggtttg gttgatgcga    540
gtgattttga tgacgagcgt aatggctggc ctgttgaaca gtctggaaa gaaatgcata    600
aacttttgcc attctcaccg gattcagtcg tcactcatgg tgatttctca cttgataacc    660
ttatttttga cgaggggaaa ttaataggtt gtattgatgt tggacgagtc ggaatcgcag    720
accgatacca ggatcttgcc atcctatgga actgcctcgg tgagttttct ccttcattac    780
agaaacggct ttttcaaaaa tatggtattg ataatcctga tatgaataaa ttgcagtttc    840
atttgatgct cgatgagttt ttctaagaat taatt               875
```

<210> SEQ ID NO 2
<211> LENGTH: 1113
<212> TYPE: DNA
<213> ORGANISM: artificial sequence
<220> FEATURE:
<223> OTHER INFORMATION: Ampicillin resistance gene (+3587 to +4699) fragment

<400> SEQUENCE: 2

```
catgagatta tcaaaaagga tcttcaccta gatccttttta aattaaaaat gaagttttaa    60
atcaatctaa agtatatatg agtaaacttg gtctgacagt taccaatgct taatcagtga    120
ggcacctatc tcagcgatct gtctatttcg ttcatccata gttgcctgac tccccgtcgt    180
gtagataact acgatacggg agggcttacc atctggcccc agtgctgcaa tgataccgcg    240
agacccacgc tcaccggctc cagatttatc agcaataaac cagccagccg aagggccga    300
gcgcagaagt ggtcctgcaa cttttatccgc ctccatccag tctattaatt gttgccggga    360
agctagagta agtagttcgc cagttaatag tttgcgcaac gttgttgcca ttgctacagg    420
catcgtggtg tcacgctcgt cgtttggtat ggcttcattc agctccggtt cccaacgatc    480
aaggcgagtt acatgatccc ccatgttgtg caaaaaagcg gttagctcct tcggtcctcc    540
gatcgttgtc agaagtaagt tggccgcagt gttatcactc atggttatgg cagcactgca    600
taattctctt actgtcatgc catccgtaag atgcttttct gtgactggtg agtactcaac    660
caagtcattc tgagaatagt gtatgcggcg accgagttgc tcttgcccgg cgtcaatacg    720
ggataatacc gcgccacata gcagaacttt aaaagtgctc atcattggaa aacgttcttc    780
ggggcgaaaa ctctcaagga tcttaccgct gttgagatcc agttcgatgt aacccactcg    840
tgcacccaac tgatcttcag catctttac ttcaccagc gtttctgggt gagcaaaaac    900
aggaaggcaa aatgccgcaa aaagggaat aagggcgaca cggaaatgtt gaatactcat    960
actcttcctt tttcaatatt attgaagcat ttatcagggt tattgtctca tgagcggata    1020
catatttgaa tgtatttaga aaaataaaca aataggggtt ccgcgcacat ttccccgaaa    1080
```

```
agtgccacct gacgtctaag aaaccattat tat                                1113
```

<210> SEQ ID NO 3
<211> LENGTH: 4513
<212> TYPE: DNA
<213> ORGANISM: artificial sequence
<220> FEATURE:
<223> OTHER INFORMATION: pQE-80L-Kana

<400> SEQUENCE: 3

```
ctcgagaaat cataaaaaat ttatttgctt tgtgagcgga taacaattat aatagattca     60
attgtgagcg gataacaatt tcacacagaa ttcattaaag aggagaaatt aactatgaga    120
ggatcgcatc accatcacca tcacggatcc gcatgcgagc tcggtacccc gggtcgacct    180
gcagccaagc ttaattagct gagcttggac tcctgttgat agatccagta atgacctcag    240
aactccatct ggatttgttc agaacgctcg gttgccgccg gcgttttttt attggtgaga    300
atccaagcta gcttggcgag attttcagga gctaaggaag ctaaaatgga gaaaaaaatc    360
actggatata ccaccgttga tatatcccaa tggcatcgta agaacatttt tgaggcattt    420
cagtcagttg ctcaatgtac ctataaccag accgttcagc tggatattac ggccttttta    480
aagaccgtaa agaaaaataa gcacaagttt tatccggcct ttattcacat tcttgcccgc    540
ctgatgaatg ctcatccgga atttcgtatg gcaatgaaag acggtgagct ggtgatatgg    600
gatagtgttc accttgttac accgttttc catgagcaaa ctgaaacgtt ttcatcgctc    660
tggagtgaat accacgacga tttccggcag tttctacaca tatattcgca agatgtggcg    720
tgttacggtg aaaacctggc ctatttccct aaagggttta ttgagaatat gttttcgtc     780
tcagccaatc cctgggtgag tttcaccagt tttgatttaa acgtggccaa tatggacaac    840
ttcttcgccc ccgttttcac catgggcaaa tattatacgc aaggcgacaa ggtgctgatg    900
ccgctggcga ttcaggttca tcatgccgtt tgtgatggct tccatgtcgg cagaatgctt    960
aatgaattac aacagtactg cgatgagtgg cagggcgggg cgtaattttt ttaaggcagt   1020
tattggtgcc cttaaacgcc tggggtaatg actctctagc ttgaggcatc aaataaaacg   1080
aaaggctcag tcgaaagact gggcctttcg ttttatctgt tgtttgtcgg tgaacgctct   1140
cctgagtagg acaaatccgc cctctagatt acgtgcagtc gatgataagc tgtcaaacat   1200
gagaattgtg cctaatgagt gagctaactt acattaattg cgttgcgctc actgcccgct   1260
ttccagtcgg gaaacctgtc gtgccagctg cattaatgaa tcggccaacg cgcggggaga   1320
ggcggtttgc gtattgggcg ccagggtggt ttttcttttc accagtgaga cgggcaacag   1380
ctgattgccc ttcaccgcct ggccctgaga gagttgcagc aagcggtcca cgctggtttg   1440
ccccagcagg cgaaaatcct gtttgatggt ggttaacggc gggatataac atgagctgtc   1500
ttcggtatcg tcgtatccca ctaccgagat atccgcacca acgcgcagcc cggactcggt   1560
aatggcgcgc attgcgccca cgcgcatctg atcgttggca accagcatcg cagtgggaac   1620
gatgccctca ttcagcattt gcatggtttg ttgaaaaccg gacatggcac tccagtcgcc   1680
ttcccgttcc gctatcggct gaatttgatt gcgagtgaga tatttatgcc agccagccag   1740
acgcagacgc gccgagacag aacttaatgg gcccgctaac agcgcgattt gctggtgacc   1800
caatgcgacc agatgctcca cgcccagtcg cgtaccgtct tcatgggaga aaataatact   1860
gttgatgggt gtctggtcag agacatcaag aaataacgcc ggaacattag tgcaggcagc   1920
ttccacagca atggcatcct ggtcatccag cggatagtta atgatcagcc cactgacgcg   1980
ttgcgcgaga agattgtgca ccgccgcttt acaggcttcg acgccgcttc gttctaccat   2040
```

```
cgacaccacc acgctggcac ccagttgatc ggcgcgagat ttaatcgccg cgacaatttg    2100
cgacggcgcg tgcagggcca gactggaggt ggcaacgcca atcagcaacg actgtttgcc    2160
cgccagttgt tgtgccacgc ggttgggaat gtaattcagc tccgccatcg ccgcttccac    2220
ttttccccgc gttttcgcag aaacgtggct ggcctggttc accacgcggg aaacggtctg    2280
ataagagaca ccggcatact ctgcgacatc gtataacgtt actggtttca cattcaccac    2340
cctgaattga ctctcttccg ggcgctatca tgccataccg cgaaaggttt tgcaccattc    2400
gatggtgtcg gaatttcggg cagcgttggg tcctggccac gggtgcgcat gatctagagc    2460
tgcctcgcgc gtttcggtga tgacggtgaa aacctctgac acatgcagct cccggagacg    2520
gtcacagctt gtctgtaagc ggatgccggg agcagacaag cccgtcaggg cgcgtcagcg    2580
ggtgttggcg ggtgtcgggg cgcagccatg acccagtcac gtagcgatag cggagtgtat    2640
actggcttaa ctatgcggca tcagagcaga ttgtactgag agtgcaccat atgcggtgtg    2700
aaataccgca cagatgcgta aggagaaaat accgcatcag cgctcttcc gcttcctcgc     2760 tcactgactc gctgcgctcg gtcgttcggc tgcggcgagc ggtatcagct cactcaaagg    2820
cggtaatacg gttatccaca gaatcagggg ataacgcagg aaagaacatg tgagcaaaag    2880
gccagcaaaa ggccaggaac cgtaaaaagg ccgcgttgct ggcgtttttc cataggctcc    2940
gcccccctga cgagcatcac aaaaatcgac gctcaagtca gaggtggcga acccgacag     3000 gactataaag ataccaggcg tttccccctg gaagctccct cgtgcgctct cctgttccga    3060
ccctgccgct taccggatac ctgtccgcct ttctcccttc gggaagcgtg gcgctttctc    3120
atagctcacg ctgtaggtat ctcagttcgg tgtaggtcgt tcgctccaag ctgggctgtg    3180
tgcacgaacc ccccgttcag cccgaccgct gcgccttatc cggtaactat cgtcttgagt    3240
ccaacccggt aagacacgac ttatcgccac tggcagcagc cactggtaac aggattagca    3300
gagcgaggta tgtaggcggt gctacagagt tcttgaagtg gtggcctaac tacggctaca    3360
ctagaaggac agtatttggt atctgcgctc tgctgaagcc agttaccttc ggaaaaagag    3420
ttggtagctc ttgatccggc aaacaaacca ccgctggtag cggtggtttt tttgtttgca    3480
agcagcagat tacgcgcaga aaaaaggat ctcaagaaga tcctttgatc ttttctacgg     3540
ggtctgacgc tcagtggaac gaaaactcac gttaagggat tttggtcatg aattaattct    3600
tagaaaaact catcgagcat caaatgaaac tgcaatttat tcatatcagg attatcaata    3660
ccatattttt gaaaagccg tttctgtaat gaaggagaaa actcaccgag gcagttccat     3720
aggatggcaa gatcctggta tcggtctgcg attccgactc gtccaacatc aatacaacct    3780
attaatttcc cctcgtcaaa aataaggtta tcaagtgaga aatcaccatg agtgacgact    3840
gaatccggtg agaatggcaa aagtttatgc atttctttcc agacttgttc aacaggccag    3900
ccattacgct cgtcatcaaa atcactcgca tcaaccaaac cgttattcat tcgtgattgc    3960
gcctgagcga cgaaatac gcgatcgctg ttaaaaggac aattacaaac aggaatcgaa      4020
tgcaaccggc gcaggaacac tgccagcgca tcaacaatat tttcacctga atcaggatat    4080
tcttctaata cctggaatgc tgttttcccg gggatcgcag tggtgagtaa ccatgcatca    4140
tcaggagtac ggataaaatg cttgatggtc ggaagaggca taaattccgt cagccagttt    4200
agtctgacca tctcatctgt aacatcattg gcaacgctac ctttgccatg tttcagaaac    4260
aactctggcg catcgggctt cccatacaat cgatagattg tcgcacctga ttgcccgaca    4320
ttatcgcgag cccatttata cccatataaa tcagcatcca tgttggaatt taatcgcggc    4380
```

```
ctagagcaag acgtttcccg ttgaatatgg ctcataacac cccttgtatt actgtttatg    4440
taagcagaca gttttattgt tcatgacatt aacctataaa aataggcgta tcacgaggcc    4500
ctttcgtctt cac                                                      4513

<210> SEQ ID NO 4
<211> LENGTH: 273
<212> TYPE: DNA
<213> ORGANISM: Homo sapiens

<400> SEQUENCE: 4
cgggagtgca tctactacaa cgccaactgg gagctggagc gcaccaacca gagcggcctg      60
gagcgctgcg aaggcgagca ggacaagcgg ctgcactgct acgcctcctg gcgcaacagc    120
tctggcacca tcgagctcgt gaagaagggc tgctggctag atgacttcaa ctgctacgat    180
aggcaggagt gtgtggccac tgaggagaac ccccaggtgt acttctgctg ctgtgaaggc    240
aacttctgca acgaacgctt cactcatttg cca                                273

<210> SEQ ID NO 5
<211> LENGTH: 26
<212> TYPE: DNA
<213> ORGANISM: artificial sequence
<220> FEATURE:
<223> OTHER INFORMATION: Primer

<400> SEQUENCE: 5
cccgggacgg gagtgcatct acaacg                                         26

<210> SEQ ID NO 6
<211> LENGTH: 30
<212> TYPE: DNA
<213> ORGANISM: artificial sequence
<220> FEATURE:
<223> OTHER INFORMATION: Primer

<400> SEQUENCE: 6
gtcgacttat ggcaaatgag tgaagcgttc                                     30

<210> SEQ ID NO 7
<211> LENGTH: 1539
<212> TYPE: DNA
<213> ORGANISM: Homo sapiens

<400> SEQUENCE: 7
atgacggcgc cctgggtggc cctcgccctc tctctggggat cgctgtgcgc cggctctggg     60
cgtggggagg ctgagacacg ggagtgcatc tactacaacg ccaactggga gctggagcgc    120
accaaccaga gcggcctgga gcgctgcgaa ggcgagcagg acaagcggct gcactgctac    180
gcctcctggc gcaacagctc tggcaccatc gagctcgtga agaagggctg ctggctagat    240
gacttcaact gctacgatag gcaggagtgt gtggccactg aggagaaccc ccaggtgtac    300
ttctgctgct gtgaaggcaa cttctgcaac gaacgcttca ctcatttgcc agaggctggg    360
ggcccggaag tcacgtacga gccaccccccg acagccccca cctgctcac ggtgctggcc    420 tactcactgc tgcccatcgg gggcctttcc ctcatcgtcc tgctggcctt ttggatgtac    480
cggcatcgca agccccccta cggtcatgtg gacatccatg aggaccctgg gcctccacca    540
ccatcccctc tggtgggcct gaagccactg cagctgctgg agatcaaggc tcggggcgc    600 tttggctgtg tctggaaggc ccagctcatg aatgactttg tagctgtcaa gatcttccca    660
ctccaggaca gcagtcgtg gcagagtgaa cgggagatct tcagcacacc tggcatgaag    720
```

```
cacgagaacc tgctacagtt cattgctgcc gagaagcgag gctccaacct cgaagtagag    780
ctgtggctca tcacggcctt ccatgacaag ggctccctca cggattacct caaggggaac    840
atcatcacat ggaacgaact gtgtcatgta gcagagacga tgtcacgagg cctctcatac    900
ctgcatgagg atgtgccctg gtgccgtggc gagggccaca agccgtctat tgcccacagg    960
gactttaaaa gtaagaatgt attgctgaag agcgacctca cagccgtgct ggctgacttt   1020
ggcttggctg ttcgatttga gccagggaaa cctccagggg acacccacgg acaggtaggc   1080
acgagacggt acatggctcc tgaggtgctc gagggagcca tcaacttcca gagagatgcc   1140
ttcctgcgca ttgacatgta tgccatgggg ttggtgctgt gggagcttgt gtctcgctgc   1200
aaggctgcag acggacccgt ggatgagtac atgctgccct tgaggaagag gattggccag   1260
caccttcgt tggaggagct gcaggaggtg gtggtgcaca agaagatgag gcccaccatt   1320
aaagatcact ggttgaaaca cccgggcctg gcccagcttt gtgtgaccat cgaggagtgc   1380
tgggaccatg atgcagaggc tcgcttgtcc gcgggctgtg tggaggagcg ggtgtccctg   1440
attcggaggt cggtcaacgg cactacctcg gactgtctcg tttccctggt gacctctgtc   1500
accaatgtgg acctgccccc taaagagtca agcatctaa                          1539
```

<210> SEQ ID NO 8
<211> LENGTH: 512
<212> TYPE: PRT
<213> ORGANISM: Homo sapiens

<400> SEQUENCE: 8

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220
```

```
Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 9
<211> LENGTH: 91
<212> TYPE: PRT
<213> ORGANISM: Homo sapiens

<400> SEQUENCE: 9

Arg Glu Cys Ile Tyr Tyr Asn Ala Asn Trp Glu Leu Glu Arg Thr Asn
1               5                   10                  15

Gln Ser Gly Leu Glu Arg Cys Glu Gly Glu Gln Asp Lys Arg Leu His
            20                  25                  30

Cys Tyr Ala Ser Trp Arg Asn Ser Ser Gly Thr Ile Glu Leu Val Lys
        35                  40                  45

Lys Gly Cys Trp Leu Asp Asp Phe Asn Cys Tyr Asp Arg Gln Glu Cys
    50                  55                  60

Val Ala Thr Glu Glu Asn Pro Gln Val Tyr Phe Cys Cys Cys Glu Gly
65                  70                  75                  80

Asn Phe Cys Asn Glu Arg Phe Thr His Leu Pro
                85                  90
```

<210> SEQ ID NO 10
<211> LENGTH: 18
<212> TYPE: DNA
<213> ORGANISM: artificial sequence
<220> FEATURE:
<223> OTHER INFORMATION: Primer

<400> SEQUENCE: 10
aataccacta caatggat                                                    18

<210> SEQ ID NO 11
<211> LENGTH: 63
<212> TYPE: DNA
<213> ORGANISM: artificial sequence
<220> FEATURE:
<223> OTHER INFORMATION: pACT2 library plasmid insert

<400> SEQUENCE: 11
ggccaagcca aacgcaaagg gtataaacgc cttaagtcca aatgtaacat acaccctttg      60
tac                                                                   63

<210> SEQ ID NO 12
<211> LENGTH: 24
<212> TYPE: DNA
<213> ORGANISM: artificial sequence
<220> FEATURE:
<223> OTHER INFORMATION: Primer

<400> SEQUENCE: 12
ttaaccatgg gccaagccaa acgc                                             24

<210> SEQ ID NO 13
<211> LENGTH: 29
<212> TYPE: DNA
<213> ORGANISM: artificial sequence
<220> FEATURE:
<223> OTHER INFORMATION: Primer

<400> SEQUENCE: 13
ggatccttag tacaaagggt gtatgttac                                        29

<210> SEQ ID NO 14
<211> LENGTH: 150
<212> TYPE: DNA
<213> ORGANISM: artificial sequence
<220> FEATURE:
<223> OTHER INFORMATION: pACT2 library plasmid insert

<400> SEQUENCE: 14
gtgagcttca aagacattgg gtggaatgac catgctagca gccagccggg gtatcacgcc      60
cgtccctgcc acggacaatg ccagaatatt ctggctgatc atctgaacga agattgtcat     120
gccattgttc agctgaagcc ccgctctgtt                                      150

<210> SEQ ID NO 15
<211> LENGTH: 25
<212> TYPE: DNA
<213> ORGANISM: artificial sequence
<220> FEATURE:
<223> OTHER INFORMATION: Primer

<400> SEQUENCE: 15
ttaaccatgg tgagcttcaa agaca                                            25

<210> SEQ ID NO 16
<211> LENGTH: 29
<212> TYPE: DNA
<213> ORGANISM: artificial sequence
<220> FEATURE:
<223> OTHER INFORMATION: Primer

<400> SEQUENCE: 16
ggatccttaa acagagcggg gcttcagct                                    29

<210> SEQ ID NO 17
<211> LENGTH: 132
<212> TYPE: DNA
<213> ORGANISM: artificial sequence
<220> FEATURE:
<223> OTHER INFORMATION: pACT2 library plasmid insert

<400> SEQUENCE: 17
atcgttgtgg ataataaggc atgctgtgtc ccgacagaac tcagtcttcc ccatccgctg    60
taccttgacg agaataaaaa gcctgtatat aagaactatc aggacgcgct tctgcatagt   120
tgtgggtgtc gc                                                      132

<210> SEQ ID NO 18
<211> LENGTH: 27
<212> TYPE: DNA
<213> ORGANISM: artificial sequence
<220> FEATURE:
<223> OTHER INFORMATION: Primer

<400> SEQUENCE: 18
ttaaccatga tcgttgtgga taataag                                      27

<210> SEQ ID NO 19
<211> LENGTH: 29
<212> TYPE: DNA
<213> ORGANISM: artificial sequence
<220> FEATURE:
<223> OTHER INFORMATION: Primer

<400> SEQUENCE: 19
ggatccttag cgacacccac aactatgca                                    29

<210> SEQ ID NO 20
<211> LENGTH: 90
<212> TYPE: DNA
<213> ORGANISM: artificial sequence
<220> FEATURE:
<223> OTHER INFORMATION: pACT2 library plasmid insert

<400> SEQUENCE: 20
acgtatccag cctctccgaa gccgatgagg tggtcaatgc ggagctgcgc gtgctgcgcc    60
ggaggtctcc ggaaccagac agggacagtg                                   90

<210> SEQ ID NO 21
<211> LENGTH: 27
<212> TYPE: DNA
<213> ORGANISM: artificial sequence
<220> FEATURE:
<223> OTHER INFORMATION: Primer

<400> SEQUENCE: 21
ttaaccatga cgtatccagc ctctccg                                      27

<210> SEQ ID NO 22
<211> LENGTH: 29
<212> TYPE: DNA
<213> ORGANISM: artificial sequence
<220> FEATURE:
<223> OTHER INFORMATION: Primer

<400> SEQUENCE: 22
ggatccttac actgtccctg tctggttcc                                    29

<210> SEQ ID NO 23
<211> LENGTH: 120
<212> TYPE: DNA
<213> ORGANISM: artificial sequence
<220> FEATURE:
<223> OTHER INFORMATION: pACT2 library plasmid insert

<400> SEQUENCE: 23
gagcccctgg gcggcgcgcg ctgggaagcg ttcgacgtga cggacgcggt gcagagccac    60
cgccgctggc cgcgagcctc ccgcaagtgc tgcctggtgc tgcgcgcggt gacggcctcg   120

<210> SEQ ID NO 24
<211> LENGTH: 26
<212> TYPE: DNA
<213> ORGANISM: artificial sequence
<220> FEATURE:
<223> OTHER INFORMATION: Primer

<400> SEQUENCE: 24
ttaaccatgg agcccctggg cggcgc                                       26

<210> SEQ ID NO 25
<211> LENGTH: 29
<212> TYPE: DNA
<213> ORGANISM: artificial sequence
<220> FEATURE:
<223> OTHER INFORMATION: Primer

<400> SEQUENCE: 25
ggatccttac gaggccgtca ccgcgcgca                                    29

<210> SEQ ID NO 26
<211> LENGTH: 174
<212> TYPE: DNA
<213> ORGANISM: artificial sequence
<220> FEATURE:
<223> OTHER INFORMATION: pACT2 library plasmid insert

<400> SEQUENCE: 26
actgcgctgg ctgggactcg gggagcgcag ggaagcggtg gtggcggcgg tggcggtggc    60
ggcggcggcg gcggcggcgg cggcggcggc ggcggcgcag gcaggggcca cgggcgcaga   120
ggccggagcc gctgcagtcg caagtcactg cacgtggact ttaaggagct gggc        174

<210> SEQ ID NO 27
<211> LENGTH: 26
<212> TYPE: DNA
<213> ORGANISM: artificial sequence
<220> FEATURE:
<223> OTHER INFORMATION: Primer

<400> SEQUENCE: 27
ttaaccatga ctgcgctggc tgggac                                       26

<210> SEQ ID NO 28

```
<211> LENGTH: 29
<212> TYPE: DNA
<213> ORGANISM: artificial sequence
<220> FEATURE:
<223> OTHER INFORMATION: Primer

<400> SEQUENCE: 28
ggatccttag cccagctcct taaagtcca                                       29

<210> SEQ ID NO 29
<211> LENGTH: 25
<212> TYPE: DNA
<213> ORGANISM: artificial sequence
<220> FEATURE:
<223> OTHER INFORMATION: Primer

<400> SEQUENCE: 29
gaattcatta aagaggagaa attaa                                           25

<210> SEQ ID NO 30
<211> LENGTH: 31
<212> TYPE: DNA
<213> ORGANISM: artificial sequence
<220> FEATURE:
<223> OTHER INFORMATION: Primer

<400> SEQUENCE: 30
ccggggtacc gagctcgcat gcggatcctt a                                    31

<210> SEQ ID NO 31
<211> LENGTH: 27
<212> TYPE: DNA
<213> ORGANISM: artificial sequence
<220> FEATURE:
<223> OTHER INFORMATION: Primer

<400> SEQUENCE: 31
ctcgagaaat cataaaaaat ttatttg                                         27

<210> SEQ ID NO 32
<211> LENGTH: 63
<212> TYPE: DNA
<213> ORGANISM: artificial sequence
<220> FEATURE:
<223> OTHER INFORMATION: pQE-80L-Kana derivative

<400> SEQUENCE: 32
gctcaagcca aacacaaagg gtataaacgc cttaagtcca attgtaaaag gcacccttcg     60
tac                                                                   63

<210> SEQ ID NO 33
<211> LENGTH: 21
<212> TYPE: PRT
<213> ORGANISM: artificial sequence
<220> FEATURE:
<223> OTHER INFORMATION: pQE-80L-Kana derivative

<400> SEQUENCE: 33

Ala Gln Ala Lys His Lys Gly Tyr Lys Arg Leu Lys Ser Asn Cys Lys
1               5                   10                  15

Arg His Pro Leu Tyr
            20

<210> SEQ ID NO 34
<211> LENGTH: 63
```

<212> TYPE: DNA
<213> ORGANISM: artificial sequence
<220> FEATURE:
<223> OTHER INFORMATION: pQE-80L-Kana derivative

<400> SEQUENCE: 34
ggccaagcca aacgcaaagg gtataaacgc cttaagtcca gctgtaagag acacccttg    60 tac                                                                 63

<210> SEQ ID NO 35
<211> LENGTH: 21
<212> TYPE: PRT
<213> ORGANISM: artificial sequence
<220> FEATURE:
<223> OTHER INFORMATION: pQE-80L-Kana derivative

<400> SEQUENCE: 35

Gly Gln Ala Lys Arg Lys Gly Tyr Lys Arg Leu Lys Ser Ser Cys Lys
1               5                   10                  15

Arg His Pro Leu Tyr
            20

<210> SEQ ID NO 36
<211> LENGTH: 63
<212> TYPE: DNA
<213> ORGANISM: artificial sequence
<220> FEATURE:
<223> OTHER INFORMATION: pQE-80L-Kana derivative

<400> SEQUENCE: 36
gcccaagcca aacataaagg gtataaacgc cttaagtcca gctgtaagag acacccttg    60 tac                                                                 63

<210> SEQ ID NO 37
<211> LENGTH: 21
<212> TYPE: PRT
<213> ORGANISM: artificial sequence
<220> FEATURE:
<223> OTHER INFORMATION: pQE-80L-Kana derivative

<400> SEQUENCE: 37

Ala Gln Ala Lys His Lys Gly Tyr Lys Arg Leu Lys Ser Ser Cys Lys
1               5                   10                  15

Arg His Pro Leu Tyr
            20

<210> SEQ ID NO 38
<211> LENGTH: 63
<212> TYPE: DNA
<213> ORGANISM: artificial sequence
<220> FEATURE:
<223> OTHER INFORMATION: pQE-80L-Kana derivative

<400> SEQUENCE: 38
gctcaagcca aacacaaaca gcggaaacgc cttaagtcca gctgtaagag acacccttg    60 tac                                                                 63

<210> SEQ ID NO 39
<211> LENGTH: 21
<212> TYPE: PRT
<213> ORGANISM: artificial sequence
<220> FEATURE:
<223> OTHER INFORMATION: pQE-80L-Kana derivative

<400> SEQUENCE: 39

Ala Gln Ala Lys His Lys Gln Arg Lys Arg Leu Lys Ser Ser Cys Lys
1               5                   10                  15

Arg His Pro Leu Tyr
            20

<210> SEQ ID NO 40
<211> LENGTH: 63
<212> TYPE: DNA
<213> ORGANISM: artificial sequence
<220> FEATURE:
<223> OTHER INFORMATION: pQE-80L-Kana derivative

<400> SEQUENCE: 40
gctcaagcca aacacaaagg tcggaaacgc cttaagtcca gctgtaagag acacccttg     60 tac                                                                 63

<210> SEQ ID NO 41
<211> LENGTH: 21
<212> TYPE: PRT
<213> ORGANISM: artificial sequence
<220> FEATURE:
<223> OTHER INFORMATION: pQE-80L-Kana derivative

<400> SEQUENCE: 41

Ala Gln Ala Lys His Lys Gly Arg Lys Arg Leu Lys Ser Ser Cys Lys
1               5                   10                  15

Arg His Pro Leu Tyr
            20

<210> SEQ ID NO 42
<211> LENGTH: 63
<212> TYPE: DNA
<213> ORGANISM: artificial sequence
<220> FEATURE:
<223> OTHER INFORMATION: pQE-80L-Kana derivative

<400> SEQUENCE: 42
gctcaagcca aacacaaaca gtacaaacgc cttaagtcca gctgtaagag acacccttg     60 tac                                                                 63

<210> SEQ ID NO 43
<211> LENGTH: 21
<212> TYPE: PRT
<213> ORGANISM: artificial sequence
<220> FEATURE:
<223> OTHER INFORMATION: pQE-80L-Kana derivative

<400> SEQUENCE: 43

Ala Gln Ala Lys His Lys Gln Tyr Lys Arg Leu Lys Ser Ser Cys Lys
1               5                   10                  15

Arg His Pro Leu Tyr
            20

<210> SEQ ID NO 44
<211> LENGTH: 150
<212> TYPE: DNA
<213> ORGANISM: artificial sequence
<220> FEATURE:
<223> OTHER INFORMATION: pQE-80L-Kana derivative

<400> SEQUENCE: 44
gtggatttca aggacgttgg gtggaatgac catgctgtgg caccgccggg gtatcacgcc   60

```
ttctattgcc acggagaatg cccgcatcca ctggctgatc atctgaactc agataaccat    120
gccattgttc agaccaaggt taattctgtt                                    150
```

<210> SEQ ID NO 45
<211> LENGTH: 50
<212> TYPE: PRT
<213> ORGANISM: artificial sequence
<220> FEATURE:
<223> OTHER INFORMATION: pQE-80L-Kana derivative

<400> SEQUENCE: 45

```
Val Asp Phe Lys Asp Val Gly Trp Asn Asp His Ala Val Ala Pro Pro
1               5                   10                  15

Gly Tyr His Ala Phe Tyr Cys His Gly Glu Cys Pro His Pro Leu Ala
            20                  25                  30

Asp His Leu Asn Ser Asp Asn His Ala Ile Val Gln Thr Lys Val Asn
        35                  40                  45

Ser Val
    50
```

<210> SEQ ID NO 46
<211> LENGTH: 150
<212> TYPE: DNA
<213> ORGANISM: artificial sequence
<220> FEATURE:
<223> OTHER INFORMATION: pQE-80L-Kana derivative

<400> SEQUENCE: 46

```
gtggatttca aggacgttgg gtggaatgac catgctgtgg caccgccggg gtatcacgcc     60
ttctattgcc acggagaatg cccgttccca ctggctgatc atctgaactc agataaccat    120
gccattgttc agaccaaggt taattctgtt                                    150
```

<210> SEQ ID NO 47
<211> LENGTH: 50
<212> TYPE: PRT
<213> ORGANISM: artificial sequence
<220> FEATURE:
<223> OTHER INFORMATION: pQE-80L-Kana derivative

<400> SEQUENCE: 47

```
Val Asp Phe Lys Asp Val Gly Trp Asn Asp His Ala Val Ala Pro Pro
1               5                   10                  15

Gly Tyr His Ala Phe Tyr Cys His Gly Glu Cys Pro Phe Pro Leu Ala
            20                  25                  30

Asp His Leu Asn Ser Asp Asn His Ala Ile Val Gln Thr Lys Val Asn
        35                  40                  45

Ser Val
    50
```

<210> SEQ ID NO 48
<211> LENGTH: 150
<212> TYPE: DNA
<213> ORGANISM: artificial sequence
<220> FEATURE:
<223> OTHER INFORMATION: pQE-80L-Kana derivative

<400> SEQUENCE: 48

```
gtggacttca gtgacgtggg gtggaatgac tggattgtgg ctcccccggg gtatcacgcc     60
ttttactgcc acggagaatg ccctttttcct ctggctgatc atctgaactc cactaatcat    120
```

```
gccattgttc agacgttggt caactctgtt                                    150
```

<210> SEQ ID NO 49
<211> LENGTH: 50
<212> TYPE: PRT
<213> ORGANISM: artificial sequence
<220> FEATURE:
<223> OTHER INFORMATION: pQE-80L-Kana derivative

<400> SEQUENCE: 49

```
Val Asp Phe Ser Asp Val Gly Trp Asn Asp Trp Ile Val Ala Pro Pro
1               5                   10                  15

Gly Tyr His Ala Phe Tyr Cys His Gly Glu Cys Pro Phe Pro Leu Ala
            20                  25                  30

Asp His Leu Asn Ser Thr Asn His Ala Ile Val Gln Thr Leu Val Asn
        35                  40                  45

Ser Val
    50
```

<210> SEQ ID NO 50
<211> LENGTH: 150
<212> TYPE: DNA
<213> ORGANISM: artificial sequence
<220> FEATURE:
<223> OTHER INFORMATION: pQE-80L-Kana derivative

<400> SEQUENCE: 50

```
gtggatttca gcgacgttgg gtggaatgac tgggctgtgg caccgccggg gtatcacgcc    60
ttctattgcc acggagaatg cccgttccca ctggctgatc atctgaactc agataaccat   120
gccattgttc agaccctcgt taattctgtt                                    150
```

<210> SEQ ID NO 51
<211> LENGTH: 50
<212> TYPE: PRT
<213> ORGANISM: artificial sequence
<220> FEATURE:
<223> OTHER INFORMATION: pQE-80L-Kana derivative

<400> SEQUENCE: 51

```
Val Asp Phe Ser Asp Val Gly Trp Asn Asp Trp Ala Val Ala Pro Pro
1               5                   10                  15

Gly Tyr His Ala Phe Tyr Cys His Gly Glu Cys Pro Phe Pro Leu Ala
            20                  25                  30

Asp His Leu Asn Ser Asp Asn His Ala Ile Val Gln Thr Leu Val Asn
        35                  40                  45

Ser Val
    50
```

<210> SEQ ID NO 52
<211> LENGTH: 150
<212> TYPE: DNA
<213> ORGANISM: artificial sequence
<220> FEATURE:
<223> OTHER INFORMATION: pQE-80L-Kana derivative

<400> SEQUENCE: 52

```
gtggatttca gcgacgttgg gtggaatgac tggatcgtgg caccgccggg gtatcacgcc    60
ttctattgcc acggagaatg cccgttccca ctggctgatc atctgaactc agataaccat   120
gccattgttc agaccctcgt taattctgtt                                    150
```

```
<210> SEQ ID NO 53
<211> LENGTH: 50
<212> TYPE: PRT
<213> ORGANISM: artificial sequence
<220> FEATURE:
<223> OTHER INFORMATION: pQE-80L-Kana derivative

<400> SEQUENCE: 53

Val Asp Phe Ser Asp Val Gly Trp Asn Asp Trp Ile Val Ala Pro Pro
1               5                   10                  15

Gly Tyr His Ala Phe Tyr Cys His Gly Glu Cys Pro Phe Pro Leu Ala
            20                  25                  30

Asp His Leu Asn Ser Asp Asn His Ala Ile Val Gln Thr Leu Val Asn
        35                  40                  45

Ser Val
    50

<210> SEQ ID NO 54
<211> LENGTH: 150
<212> TYPE: DNA
<213> ORGANISM: artificial sequence
<220> FEATURE:
<223> OTHER INFORMATION: pQE-80L-Kana derivative

<400> SEQUENCE: 54
gtggatttct ctgacgttgg gtggaatgac catgctgtgg caccgccggg gtatcacgcc     60
ttctattgcc acggagaatg cccgttccca ctggctgatc atctgaactc aacgaaccat    120
gccattgttc agacccttgt taattctgtt                                     150

<210> SEQ ID NO 55
<211> LENGTH: 50
<212> TYPE: PRT
<213> ORGANISM: artificial sequence
<220> FEATURE:
<223> OTHER INFORMATION: pQE-80L-Kana derivative

<400> SEQUENCE: 55

Val Asp Phe Ser Asp Val Gly Trp Asn Asp His Ala Val Ala Pro Pro
1               5                   10                  15

Gly Tyr His Ala Phe Tyr Cys His Gly Glu Cys Pro Phe Pro Leu Ala
            20                  25                  30

Asp His Leu Asn Ser Thr Asn His Ala Ile Val Gln Thr Leu Val Asn
        35                  40                  45

Ser Val
    50

<210> SEQ ID NO 56
<211> LENGTH: 132
<212> TYPE: DNA
<213> ORGANISM: artificial sequence
<220> FEATURE:
<223> OTHER INFORMATION: pQE-80L-Kana derivative

<400> SEQUENCE: 56
aatagcaaag atcccaaggc atgctgtgtc ccgacagaac tcagtgcccc cagcccgctg     60
taccttgacg agaatgagaa gcctgtactc aagaactatc aggacatggt agtccatggg    120
tgtgggtgtc gc                                                        132

<210> SEQ ID NO 57
<211> LENGTH: 44
<212> TYPE: PRT
```

```
<213> ORGANISM: artificial sequence
<220> FEATURE:
<223> OTHER INFORMATION: pQE-80L-Kana derivative

<400> SEQUENCE: 57

Asn Ser Lys Asp Pro Lys Ala Cys Cys Val Pro Thr Glu Leu Ser Ala
1               5                   10                  15

Pro Ser Pro Leu Tyr Leu Asp Glu Asn Glu Lys Pro Val Leu Lys Asn
            20                  25                  30

Tyr Gln Asp Met Val Val His Gly Cys Gly Cys Arg
        35                  40

<210> SEQ ID NO 58
<211> LENGTH: 132
<212> TYPE: DNA
<213> ORGANISM: artificial sequence
<220> FEATURE:
<223> OTHER INFORMATION: pQE-80L-Kana derivative

<400> SEQUENCE: 58
aatagcaaaa tccccaaggc atgctgtcag ccgacagaac tcagtgcccc cagcccgctg    60
taccttgacg agaatgagaa gcctgtactc aagaactatc aggacatggt agtcgaaggg   120
tgtgggtgtc gc                                                      132

<210> SEQ ID NO 59
<211> LENGTH: 44
<212> TYPE: PRT
<213> ORGANISM: artificial sequence
<220> FEATURE:
<223> OTHER INFORMATION: pQE-80L-Kana derivative

<400> SEQUENCE: 59

Asn Ser Lys Ile Pro Lys Ala Cys Cys Gln Pro Thr Glu Leu Ser Ala
1               5                   10                  15

Pro Ser Pro Leu Tyr Leu Asp Glu Asn Glu Lys Pro Val Leu Lys Asn
            20                  25                  30

Tyr Gln Asp Met Val Val Glu Gly Cys Gly Cys Arg
        35                  40

<210> SEQ ID NO 60
<211> LENGTH: 132
<212> TYPE: DNA
<213> ORGANISM: artificial sequence
<220> FEATURE:
<223> OTHER INFORMATION: pQE-80L-Kana derivative

<400> SEQUENCE: 60
aactctaaga ttcctaaggc atgctgtgtc ccgacagaac tcagtgctat ctcgatgctg    60
taccttgacg agaatgaaaa ggttgtatta aagaactatc aggacatggt tgtggagggt   120
tgtgggtgtc gc                                                      132

<210> SEQ ID NO 61
<211> LENGTH: 44
<212> TYPE: PRT
<213> ORGANISM: artificial sequence
<220> FEATURE:
<223> OTHER INFORMATION: pQE-80L-Kana derivative

<400> SEQUENCE: 61

Asn Ser Lys Ile Pro Lys Ala Cys Cys Val Pro Thr Glu Leu Ser Ala
1               5                   10                  15
```

Ile Ser Met Leu Tyr Leu Asp Glu Asn Glu Lys Val Val Leu Lys Asn
            20                  25                  30

Tyr Gln Asp Met Val Val Glu Gly Cys Gly Cys Arg
        35                  40

<210> SEQ ID NO 62
<211> LENGTH: 132
<212> TYPE: DNA
<213> ORGANISM: artificial sequence
<220> FEATURE:
<223> OTHER INFORMATION: pQE-80L-Kana derivative

<400> SEQUENCE: 62
aatagcaaaa tccccaaggc atgctgtgtc ccgacagaac tcagtgccat aagcccgctg      60
taccttgacg agaatgagaa ggtcgtactc aagaactatc aggacatggt agtccatggg     120
tgtgggtgtc gc                                                        132

<210> SEQ ID NO 63
<211> LENGTH: 44
<212> TYPE: PRT
<213> ORGANISM: artificial sequence
<220> FEATURE:
<223> OTHER INFORMATION: pQE-80L-Kana derivative

<400> SEQUENCE: 63

Asn Ser Lys Ile Pro Lys Ala Cys Cys Val Pro Thr Glu Leu Ser Ala
1               5                   10                  15

Ile Ser Pro Leu Tyr Leu Asp Glu Asn Glu Lys Val Val Leu Lys Asn
            20                  25                  30

Tyr Gln Asp Met Val Val His Gly Cys Gly Cys Arg
        35                  40

<210> SEQ ID NO 64
<211> LENGTH: 132
<212> TYPE: DNA
<213> ORGANISM: artificial sequence
<220> FEATURE:
<223> OTHER INFORMATION: pQE-80L-Kana derivative

<400> SEQUENCE: 64
aatagcaaaa tacccaaggc atgctgtgtc ccgacagaac tcagtgccat tagcatgctg      60
taccttgacg agaatgagaa gcctgtactc aagaactatc aggacatggt agtcgaaggg     120
tgtgggtgtc gc                                                        132

<210> SEQ ID NO 65
<211> LENGTH: 44
<212> TYPE: PRT
<213> ORGANISM: artificial sequence
<220> FEATURE:
<223> OTHER INFORMATION: pQE-80L-Kana derivative

<400> SEQUENCE: 65

Asn Ser Lys Ile Pro Lys Ala Cys Cys Val Pro Thr Glu Leu Ser Ala
1               5                   10                  15

Ile Ser Met Leu Tyr Leu Asp Glu Asn Glu Lys Pro Val Leu Lys Asn
            20                  25                  30

Tyr Gln Asp Met Val Val Glu Gly Cys Gly Cys Arg
        35                  40

<210> SEQ ID NO 66
<211> LENGTH: 132

```
<212> TYPE: DNA
<213> ORGANISM: artificial sequence
<220> FEATURE:
<223> OTHER INFORMATION: pQE-80L-Kana derivative

<400> SEQUENCE: 66
aatagcaaag atcccaaggc atgctgtgtc ccgacagaac tcagtgccat aagcatgctg      60
taccttgacg agaatgagaa ggtggtactc aagaactatc aggacatggt agtccatggg     120
tgtgggtgtc gc                                                         132

<210> SEQ ID NO 67
<211> LENGTH: 44
<212> TYPE: PRT
<213> ORGANISM: artificial sequence
<220> FEATURE:
<223> OTHER INFORMATION: pQE-80L-Kana derivative

<400> SEQUENCE: 67

Asn Ser Lys Asp Pro Lys Ala Cys Cys Val Pro Thr Glu Leu Ser Ala
1               5                   10                  15

Ile Ser Met Leu Tyr Leu Asp Glu Asn Glu Lys Val Val Leu Lys Asn
            20                  25                  30

Tyr Gln Asp Met Val Val His Gly Cys Gly Cys Arg
        35                  40

<210> SEQ ID NO 68
<211> LENGTH: 90
<212> TYPE: DNA
<213> ORGANISM: artificial sequence
<220> FEATURE:
<223> OTHER INFORMATION: pQE-80L-Kana derivative

<400> SEQUENCE: 68
acgtatccag cctctccgaa gccgatgagg cataaaatgc ggagctgcgc gtgctgcgcc      60
ggaggtctcc ggaaccgaac agggacagtg                                       90

<210> SEQ ID NO 69
<211> LENGTH: 30
<212> TYPE: PRT
<213> ORGANISM: artificial sequence
<220> FEATURE:
<223> OTHER INFORMATION: pQE-80L-Kana derivative

<400> SEQUENCE: 69

Thr Tyr Pro Ala Ser Pro Lys Pro Met Arg His Lys Met Arg Ser Cys
1               5                   10                  15

Ala Cys Cys Ala Gly Gly Leu Arg Asn Arg Thr Gly Thr Val
            20                  25                  30

<210> SEQ ID NO 70
<211> LENGTH: 90
<212> TYPE: DNA
<213> ORGANISM: artificial sequence
<220> FEATURE:
<223> OTHER INFORMATION: pQE-80L-Kana derivative

<400> SEQUENCE: 70
acgtatcccg cctctccgaa gccgatgagg cattcaatgc ggagctgcgc gtgctgcgcc      60
ggaggtctcc ggaaccagac agggacagtg                                       90

<210> SEQ ID NO 71
<211> LENGTH: 30
```

```
<212> TYPE: PRT
<213> ORGANISM: artificial sequence
<220> FEATURE:
<223> OTHER INFORMATION: pQE-80L-Kana derivative

<400> SEQUENCE: 71

Thr Tyr Pro Ala Ser Pro Lys Pro Met Arg His Ser Met Arg Ser Cys
1               5                   10                  15

Ala Cys Cys Ala Gly Gly Leu Arg Asn Gln Thr Gly Thr Val
            20                  25                  30

<210> SEQ ID NO 72
<211> LENGTH: 90
<212> TYPE: DNA
<213> ORGANISM: artificial sequence
<220> FEATURE:
<223> OTHER INFORMATION: pQE-80L-Kana derivative

<400> SEQUENCE: 72
acgtatccag cctctccgaa gccgatgagg tggaagatgc ggagctgcgc gtgctgcgcc      60
ggaggtctcc ggaaccggac agggacagtg                                      90

<210> SEQ ID NO 73
<211> LENGTH: 30
<212> TYPE: PRT
<213> ORGANISM: artificial sequence
<220> FEATURE:
<223> OTHER INFORMATION: pQE-80L-Kana derivative

<400> SEQUENCE: 73

Thr Tyr Pro Ala Ser Pro Lys Pro Met Arg Trp Lys Met Arg Ser Cys
1               5                   10                  15

Ala Cys Cys Ala Gly Gly Leu Arg Asn Arg Thr Gly Thr Val
            20                  25                  30

<210> SEQ ID NO 74
<211> LENGTH: 120
<212> TYPE: DNA
<213> ORGANISM: artificial sequence
<220> FEATURE:
<223> OTHER INFORMATION: pQE-80L-Kana derivative

<400> SEQUENCE: 74
gagcccctgg gcggcgcgcg ctgggaagcg ttcgacgtga cggacgcggt gcagagccac      60
cgccgctcgc cacgagcctc ccgcaagtgc tgcctggggc tgcgcgcggt gacggcctcg     120

<210> SEQ ID NO 75
<211> LENGTH: 40
<212> TYPE: PRT
<213> ORGANISM: artificial sequence
<220> FEATURE:
<223> OTHER INFORMATION: pQE-80L-Kana derivative

<400> SEQUENCE: 75

Glu Pro Leu Gly Gly Ala Arg Trp Glu Ala Phe Asp Val Thr Asp Ala
1               5                   10                  15

Val Gln Ser His Arg Arg Ser Pro Arg Ala Ser Arg Lys Cys Cys Leu
            20                  25                  30

Gly Leu Arg Ala Val Thr Ala Ser
        35                  40

<210> SEQ ID NO 76
<211> LENGTH: 120
```

```
<212> TYPE: DNA
<213> ORGANISM: artificial sequence
<220> FEATURE:
<223> OTHER INFORMATION: pQE-80L-Kana derivative

<400> SEQUENCE: 76
gagcccctgg cggcgcgcg ctgggaagcg ttcgacgtga cggacgcggt gcagagccac      60
cgccgctcgc agcgagcctc ccgcaagtgc tgcctggttc tgcgcgcggt gacggcctcg     120

<210> SEQ ID NO 77
<211> LENGTH: 40
<212> TYPE: PRT
<213> ORGANISM: artificial sequence
<220> FEATURE:
<223> OTHER INFORMATION: pQE-80L-Kana derivative

<400> SEQUENCE: 77

Glu Pro Leu Gly Gly Ala Arg Trp Glu Ala Phe Asp Val Thr Asp Ala
 1               5                  10                  15

Val Gln Ser His Arg Arg Ser Gln Arg Ala Ser Arg Lys Cys Cys Leu
            20                  25                  30

Val Leu Arg Ala Val Thr Ala Ser
        35                  40

<210> SEQ ID NO 78
<211> LENGTH: 174
<212> TYPE: DNA
<213> ORGANISM: artificial sequence
<220> FEATURE:
<223> OTHER INFORMATION: pQE-80L-Kana derivative

<400> SEQUENCE: 78
accgccctag atgggactcg gggagcgcag ggaagcggtg gtggcggcgg tggcggtggc      60
ggcggcggcg gcggcggcgg cggcggcggc ggcggcgcag gcaggggcca cgggcgcaga     120
ggccggagcc gctgcagtcg caagtcactg cacgtggact taaggagct gggc            174

<210> SEQ ID NO 79
<211> LENGTH: 126
<212> TYPE: DNA
<213> ORGANISM: artificial sequence
<220> FEATURE:
<223> OTHER INFORMATION: pQE-80L-Kana derivative PCR fusion product

<400> SEQUENCE: 79
gcccaagcca acataaagg gtataaacgc cttaagtcca gctgtaagag acaccctttg      60
tacgctcaag ccaaacacaa aggtcggaaa cgccttaagt ccagctgtaa agacaccct     120 ttgtac                                                               126

<210> SEQ ID NO 80
<211> LENGTH: 42
<212> TYPE: PRT
<213> ORGANISM: artificial sequence
<220> FEATURE:
<223> OTHER INFORMATION: pQE-80L-Kana derivative PCR fusion product

<400> SEQUENCE: 80

Ala Gln Ala Lys His Lys Gly Tyr Lys Arg Leu Lys Ser Ser Cys Lys
 1               5                  10                  15

Arg His Pro Leu Tyr Ala Gln Ala Lys His Lys Gly Arg Lys Arg Leu
            20                  25                  30

Lys Ser Ser Cys Lys Arg His Pro Leu Tyr
        35                  40
```

<210> SEQ ID NO 81
<211> LENGTH: 24
<212> TYPE: DNA
<213> ORGANISM: artificial sequence
<220> FEATURE:
<223> OTHER INFORMATION: Primer

<400> SEQUENCE: 81
ttaaccatgg cccaagccaa acat                                              24

<210> SEQ ID NO 82
<211> LENGTH: 25
<212> TYPE: DNA
<213> ORGANISM: artificial sequence
<220> FEATURE:
<223> OTHER INFORMATION: Primer

<400> SEQUENCE: 82
gtttggcttg agcgtacaaa gggtg                                             25

<210> SEQ ID NO 83
<211> LENGTH: 25
<212> TYPE: DNA
<213> ORGANISM: artificial sequence
<220> FEATURE:
<223> OTHER INFORMATION: Primer

<400> SEQUENCE: 83
caccctttgt acgctcaagc caaac                                             25

<210> SEQ ID NO 84
<211> LENGTH: 25
<212> TYPE: DNA
<213> ORGANISM: artificial sequence
<220> FEATURE:
<223> OTHER INFORMATION: Primer

<400> SEQUENCE: 84
ggatccttag tacaaagggt gtctc                                             25

<210> SEQ ID NO 85
<211> LENGTH: 126
<212> TYPE: DNA
<213> ORGANISM: artificial sequence
<220> FEATURE:
<223> OTHER INFORMATION: pQE-80L-Kana derivative PCR fusion product

<400> SEQUENCE: 85
gctcaagcca aacacaaagg tcggaaacgc cttaagtcca gctgtaagag acaccctttg       60
tacgcccaag ccaaacataa agggtataaa cgccttaagt ccagctgtaa gagacaccct      120
ttgtac                                                                 126

<210> SEQ ID NO 86
<211> LENGTH: 42
<212> TYPE: PRT
<213> ORGANISM: artificial sequence
<220> FEATURE:
<223> OTHER INFORMATION: pQE-80L-Kana derivative PCR fusion product

<400> SEQUENCE: 86

Ala Gln Ala Lys His Lys Gly Arg Lys Arg Leu Lys Ser Ser Cys Lys
1               5                   10                  15

Arg His Pro Leu Tyr Ala Gln Ala Lys His Lys Gly Tyr Lys Arg Leu
            20                  25                  30

Lys Ser Ser Cys Lys Arg His Pro Leu Tyr
        35                  40

<210> SEQ ID NO 87
<211> LENGTH: 25
<212> TYPE: DNA
<213> ORGANISM: artificial sequence
<220> FEATURE:
<223> OTHER INFORMATION: Primer

<400> SEQUENCE: 87
ttaaccatgg ctcaagccaa acaca                                    25

<210> SEQ ID NO 88
<211> LENGTH: 25
<212> TYPE: DNA
<213> ORGANISM: artificial sequence
<220> FEATURE:
<223> OTHER INFORMATION: Primer

<400> SEQUENCE: 88
gtttggcttg ggcgtacaaa gggtg                                    25

<210> SEQ ID NO 89
<211> LENGTH: 25
<212> TYPE: DNA
<213> ORGANISM: artificial sequence
<220> FEATURE:
<223> OTHER INFORMATION: Primer

<400> SEQUENCE: 89 cacccttgt acgcccaagc caaac                                     25

<210> SEQ ID NO 90
<211> LENGTH: 25
<212> TYPE: DNA
<213> ORGANISM: artificial sequence
<220> FEATURE:
<223> OTHER INFORMATION: Primer

<400> SEQUENCE: 90
ggatccttag tacaaagggt gtctc                                    25

<210> SEQ ID NO 91
<211> LENGTH: 300
<212> TYPE: DNA
<213> ORGANISM: artificial sequence
<220> FEATURE:
<223> OTHER INFORMATION: pQE-80L-Kana derivative PCR fusion product

<400> SEQUENCE: 91
gtggatttca gcgacgttgg gtggaatgac tggatcgtgg caccgccggg gtatcacgcc      60
ttctattgcc acggagaatg cccgttccca ctggctgatc atctgaactc agataaccat    120
gccattgttc agaccctcgt taattctgtt gtggatttct ctgacgttgg gtggaatgac    180
catgctgtgg caccgccggg gtatcacgcc ttctattgcc acggagaatg cccgttccca    240
ctggctgatc atctgaactc aacgaaccat gccattgttc agacccttgt taattctgtt    300

<210> SEQ ID NO 92
<211> LENGTH: 100
<212> TYPE: PRT
<213> ORGANISM: artificial sequence

```
<220> FEATURE:
<223> OTHER INFORMATION: pQE-80L-Kana derivative PCR fusion product

<400> SEQUENCE: 92

Val Asp Phe Ser Asp Val Gly Trp Asn Asp Trp Ile Val Ala Pro Pro
1               5                   10                  15

Gly Tyr His Ala Phe Tyr Cys His Gly Glu Cys Pro Phe Pro Leu Ala
            20                  25                  30

Asp His Leu Asn Ser Asp Asn His Ala Ile Val Gln Thr Leu Val Asn
        35                  40                  45

Ser Val Val Asp Phe Ser Asp Val Gly Trp Asn Asp His Ala Val Ala
    50                  55                  60

Pro Pro Gly Tyr His Ala Phe Tyr Cys His Gly Glu Cys Pro Phe Pro
65              70                  75                  80

Leu Ala Asp His Leu Asn Ser Thr Asn His Ala Ile Val Gln Thr Leu
                85                  90                  95

Val Asn Ser Val
            100

<210> SEQ ID NO 93
<211> LENGTH: 25
<212> TYPE: DNA
<213> ORGANISM: artificial sequence
<220> FEATURE:
<223> OTHER INFORMATION: Primer

<400> SEQUENCE: 93
ttaaccatgg tggatttcag cgacg                                        25

<210> SEQ ID NO 94
<211> LENGTH: 25
<212> TYPE: DNA
<213> ORGANISM: artificial sequence
<220> FEATURE:
<223> OTHER INFORMATION: Primer

<400> SEQUENCE: 94
cagagaaatc cacaacagaa ttaac                                        25

<210> SEQ ID NO 95
<211> LENGTH: 25
<212> TYPE: DNA
<213> ORGANISM: artificial sequence
<220> FEATURE:
<223> OTHER INFORMATION: Primer

<400> SEQUENCE: 95
gttaattctg ttgtggattt ctctg                                        25

<210> SEQ ID NO 96
<211> LENGTH: 25
<212> TYPE: DNA
<213> ORGANISM: artificial sequence
<220> FEATURE:
<223> OTHER INFORMATION: Primer

<400> SEQUENCE: 96
ggatccttaa acagaattaa caagg                                        25

<210> SEQ ID NO 97
<211> LENGTH: 300
<212> TYPE: DNA
<213> ORGANISM: artificial sequence
```

<220> FEATURE:
<223> OTHER INFORMATION: pQE-80L-Kana derivative PCR fusion product

<400> SEQUENCE: 97

```
gtggatttct ctgacgttgg gtggaatgac catgctgtgg caccgccggg gtatcacgcc      60
ttctattgcc acggagaatg cccgttccca ctggctgatc atctgaactc aacgaaccat     120
gccattgttc agacccttgt taattctgtt gtggatttca gcgacgttgg gtggaatgac     180
tggatcgtgg caccgccggg gtatcacgcc ttctattgcc acggagaatg cccgttccca     240
ctggctgatc atctgaactc agataaccat gccattgttc agaccctcgt taattctgtt     300
```

<210> SEQ ID NO 98
<211> LENGTH: 100
<212> TYPE: PRT
<213> ORGANISM: artificial sequence
<220> FEATURE:
<223> OTHER INFORMATION: pQE-80L-Kana derivative PCR fusion product

<400> SEQUENCE: 98

```
Val Asp Phe Ser Asp Val Gly Trp Asn Asp His Ala Val Ala Pro Pro
1               5                   10                  15
Gly Tyr His Ala Phe Tyr Cys His Gly Glu Cys Pro Phe Pro Leu Ala
            20                  25                  30
Asp His Leu Asn Ser Thr Asn His Ala Ile Val Gln Thr Leu Val Asn
        35                  40                  45
Ser Val Val Asp Phe Ser Asp Val Gly Trp Asn Asp Trp Ile Val Ala
    50                  55                  60
Pro Pro Gly Tyr His Ala Phe Tyr Cys His Gly Glu Cys Pro Phe Pro
65                  70                  75                  80
Leu Ala Asp His Leu Asn Ser Asp Asn His Ala Ile Val Gln Thr Leu
                85                  90                  95
Val Asn Ser Val
            100
```

<210> SEQ ID NO 99
<211> LENGTH: 25
<212> TYPE: DNA
<213> ORGANISM: artificial sequence
<220> FEATURE:
<223> OTHER INFORMATION: Primer

<400> SEQUENCE: 99

```
ttaaccatgg tggatttctc tgacg                                            25
```

<210> SEQ ID NO 100
<211> LENGTH: 25
<212> TYPE: DNA
<213> ORGANISM: artificial sequence
<220> FEATURE:
<223> OTHER INFORMATION: Primer

<400> SEQUENCE: 100

```
cgctgaaatc cacaacagaa ttaac                                            25
```

<210> SEQ ID NO 101
<211> LENGTH: 25
<212> TYPE: DNA
<213> ORGANISM: artificial sequence
<220> FEATURE:
<223> OTHER INFORMATION: Primer

<400> SEQUENCE: 101

```
gttaattctg ttgtggattt cagcg                                              25

<210> SEQ ID NO 102
<211> LENGTH: 25
<212> TYPE: DNA
<213> ORGANISM: artificial sequence
<220> FEATURE:
<223> OTHER INFORMATION: Primer

<400> SEQUENCE: 102
ggatccttaa acagaattaa cgagg                                              25

<210> SEQ ID NO 103
<211> LENGTH: 264
<212> TYPE: DNA
<213> ORGANISM: artificial sequence
<220> FEATURE:
<223> OTHER INFORMATION: pQE-80L-Kana derivative PCR fusion product

<400> SEQUENCE: 103
aatagcaaaa tacccaaggc atgctgtgtc ccgacagaac tcagtgccat tagcatgctg        60
taccttgacg agaatgagaa gcctgtactc aagaactatc aggacatggt agtcgaaggg       120
tgtgggtgtc gcaatagcaa agatcccaag gcatgctgtg tcccgacaga actcagtgcc       180
ataagcatgc tgtaccttga cgagaatgag aaggtggtac tcaagaacta tcaggacatg       240
gtagtccatg ggtgtgggtg tcgc                                              264

<210> SEQ ID NO 104
<211> LENGTH: 88
<212> TYPE: PRT
<213> ORGANISM: artificial sequence
<220> FEATURE:
<223> OTHER INFORMATION: pQE-80L-Kana derivative PCR fusion product

<400> SEQUENCE: 104

Asn Ser Lys Ile Pro Lys Ala Cys Cys Val Pro Thr Glu Leu Ser Ala
1               5                   10                  15

Ile Ser Met Leu Tyr Leu Asp Glu Asn Glu Lys Pro Val Leu Lys Asn
            20                  25                  30

Tyr Gln Asp Met Val Val Glu Gly Cys Gly Cys Arg Asn Ser Lys Asp
        35                  40                  45

Pro Lys Ala Cys Cys Val Pro Thr Glu Leu Ser Ala Ile Ser Met Leu
    50                  55                  60

Tyr Leu Asp Glu Asn Glu Lys Val Val Leu Lys Asn Tyr Gln Asp Met
65                  70                  75                  80

Val Val His Gly Cys Gly Cys Arg
                85

<210> SEQ ID NO 105
<211> LENGTH: 25
<212> TYPE: DNA
<213> ORGANISM: artificial sequence
<220> FEATURE:
<223> OTHER INFORMATION: Primer

<400> SEQUENCE: 105
ttaaccatga atagcaaaat accca                                              25

<210> SEQ ID NO 106
<211> LENGTH: 26
<212> TYPE: DNA
```

```
<213> ORGANISM: artificial sequence
<220> FEATURE:
<223> OTHER INFORMATION: Primer

<400> SEQUENCE: 106
gatctttgct attgcgacac ccacac                                          26

<210> SEQ ID NO 107
<211> LENGTH: 26
<212> TYPE: DNA
<213> ORGANISM: artificial sequence
<220> FEATURE:
<223> OTHER INFORMATION: Primer

<400> SEQUENCE: 107
gtgtgggtgt cgcaatagca aagatc                                          26

<210> SEQ ID NO 108
<211> LENGTH: 25
<212> TYPE: DNA
<213> ORGANISM: artificial sequence
<220> FEATURE:
<223> OTHER INFORMATION: Primer

<400> SEQUENCE: 108
ggatccttac gacacccaca cccat                                           25

<210> SEQ ID NO 109
<211> LENGTH: 264
<212> TYPE: DNA
<213> ORGANISM: artificial sequence
<220> FEATURE:
<223> OTHER INFORMATION: pQE-80L-Kana derivative PCR fusion product

<400> SEQUENCE: 109
aatagcaaag atcccaaggc atgctgtgtc ccgacagaac tcagtgccat aagcatgctg     60
taccttgacg agaatgagaa ggtggtactc aagaactatc aggacatggt agtccatggg   120
tgtgggtgtc gcaatagcaa atacccaagg catgctgtg tcccgacaga actcagtgcc    180
attagcatgc tgtaccttga cgagaatgag aagcctgtac tcaagaacta tcaggacatg   240
gtagtcgaag ggtgtgggtg tcgc                                          264

<210> SEQ ID NO 110
<211> LENGTH: 88
<212> TYPE: PRT
<213> ORGANISM: artificial sequence
<220> FEATURE:
<223> OTHER INFORMATION: pQE-80L-Kana derivative PCR fusion product

<400> SEQUENCE: 110

Asn Ser Lys Asp Pro Lys Ala Cys Cys Val Pro Thr Glu Leu Ser Ala
1               5                   10                  15

Ile Ser Met Leu Tyr Leu Asp Glu Asn Glu Lys Val Val Leu Lys Asn
            20                  25                  30

Tyr Gln Asp Met Val Val His Gly Cys Gly Cys Arg Asn Ser Lys Ile
        35                  40                  45

Pro Lys Ala Cys Cys Val Pro Thr Glu Leu Ser Ala Ile Ser Met Leu
    50                  55                  60

Tyr Leu Asp Glu Asn Glu Lys Pro Val Leu Lys Asn Tyr Gln Asp Met
65                  70                  75                  80

Val Val Glu Gly Cys Gly Cys Arg
                85
```

-continued

<210> SEQ ID NO 111
<211> LENGTH: 25
<212> TYPE: DNA
<213> ORGANISM: artificial sequence
<220> FEATURE:
<223> OTHER INFORMATION: Primer

<400> SEQUENCE: 111
ttaaccatga atagcaaaga tccca                                           25

<210> SEQ ID NO 112
<211> LENGTH: 26
<212> TYPE: DNA
<213> ORGANISM: artificial sequence
<220> FEATURE:
<223> OTHER INFORMATION: Primer

<400> SEQUENCE: 112 gtatttgct attgcgacac ccacac                                           26

<210> SEQ ID NO 113
<211> LENGTH: 26
<212> TYPE: DNA
<213> ORGANISM: artificial sequence
<220> FEATURE:
<223> OTHER INFORMATION: Primer

<400> SEQUENCE: 113
gtgtgggtgt cgcaatagca aaatac                                          26

<210> SEQ ID NO 114
<211> LENGTH: 25
<212> TYPE: DNA
<213> ORGANISM: artificial sequence
<220> FEATURE:
<223> OTHER INFORMATION: Primer

<400> SEQUENCE: 114
ggatccttag cgacacccac accct                                           25

<210> SEQ ID NO 115
<211> LENGTH: 153
<212> TYPE: DNA
<213> ORGANISM: artificial sequence
<220> FEATURE:
<223> OTHER INFORMATION: pQE-80L-Kana derivative PCR fusion product

<400> SEQUENCE: 115
gctcaagcca aacacaaaca gtacaaacgc cttaagtcca gctgtaagag acacccttg      60 tacacgtatc cagcctctcc gaagccgatg aggcataaaa tgcggagctg cgcgtgctgc   120
gccggaggtc tccggaaccg aacagggaca gtg                                 153

<210> SEQ ID NO 116
<211> LENGTH: 51
<212> TYPE: PRT
<213> ORGANISM: artificial sequence
<220> FEATURE:
<223> OTHER INFORMATION: pQE-80L-Kana derivative PCR fusion product

<400> SEQUENCE: 116

Ala Gln Ala Lys His Lys Gln Tyr Lys Arg Leu Lys Ser Ser Cys Lys
1               5                   10                  15

Arg His Pro Leu Tyr Thr Tyr Pro Ala Ser Pro Lys Pro Met Arg His

```
                        20                  25                  30
Lys Met Arg Ser Cys Ala Cys Cys Ala Gly Gly Leu Arg Asn Arg Thr
        35                  40                  45
Gly Thr Val
    50
```

<210> SEQ ID NO 117
<211> LENGTH: 26
<212> TYPE: DNA
<213> ORGANISM: artificial sequence
<220> FEATURE:
<223> OTHER INFORMATION: Primer

<400> SEQUENCE: 117
ttaaccatgg ctcaagccaa acacaa                                        26

<210> SEQ ID NO 118
<211> LENGTH: 26
<212> TYPE: DNA
<213> ORGANISM: artificial sequence
<220> FEATURE:
<223> OTHER INFORMATION: Primer

<400> SEQUENCE: 118
gaggctggat acgtgtacaa agggtg                                        26

<210> SEQ ID NO 119
<211> LENGTH: 26
<212> TYPE: DNA
<213> ORGANISM: artificial sequence
<220> FEATURE:
<223> OTHER INFORMATION: Primer

<400> SEQUENCE: 119
caccctttgt acacgtatcc agcctc                                        26

<210> SEQ ID NO 120
<211> LENGTH: 25
<212> TYPE: DNA
<213> ORGANISM: artificial sequence
<220> FEATURE:
<223> OTHER INFORMATION: Primer

<400> SEQUENCE: 120
ggatccttac actgtccctg ttcgg                                         25

<210> SEQ ID NO 121
<211> LENGTH: 153
<212> TYPE: DNA
<213> ORGANISM: artificial sequence
<220> FEATURE:
<223> OTHER INFORMATION: pQE-80L-Kana derivative PCR fusion product

<400> SEQUENCE: 121
acgtatccag cctctccgaa gccgatgagg cataaaatgc ggagctgcgc gtgctgcgcc     60
ggaggtctcc ggaaccgaac agggacagtg gctcaagcca acacaaaca gtacaaacgc    120 cttaagtcca gctgtaagag acccctttg tac                                 153

<210> SEQ ID NO 122
<211> LENGTH: 51
<212> TYPE: PRT
<213> ORGANISM: artificial sequence
<220> FEATURE:
<223> OTHER INFORMATION: pQE-80L-Kana derivative PCR fusion product -continued

<400> SEQUENCE: 122

Thr Tyr Pro Ala Ser Pro Lys Pro Met Arg His Lys Met Arg Ser Cys
1               5                   10                  15

Ala Cys Cys Ala Gly Gly Leu Arg Asn Arg Thr Gly Thr Val Ala Gln
            20                  25                  30

Ala Lys His Lys Gln Tyr Lys Arg Leu Lys Ser Ser Cys Lys Arg His
        35                  40                  45

Pro Leu Tyr
    50

<210> SEQ ID NO 123
<211> LENGTH: 26
<212> TYPE: DNA
<213> ORGANISM: artificial sequence
<220> FEATURE:
<223> OTHER INFORMATION: Primer

<400> SEQUENCE: 123
ttaaccatga cgtatccagc ctctcc                                    26

<210> SEQ ID NO 124
<211> LENGTH: 27
<212> TYPE: DNA
<213> ORGANISM: artificial sequence
<220> FEATURE:
<223> OTHER INFORMATION: Primer

<400> SEQUENCE: 124
gtttggcttg agccactgtc cctgttc                                   27

<210> SEQ ID NO 125
<211> LENGTH: 27
<212> TYPE: DNA
<213> ORGANISM: artificial sequence
<220> FEATURE:
<223> OTHER INFORMATION: Primer

<400> SEQUENCE: 125
gaacagggac agtggctcaa gccaaac                                   27

<210> SEQ ID NO 126
<211> LENGTH: 25
<212> TYPE: DNA
<213> ORGANISM: artificial sequence
<220> FEATURE:
<223> OTHER INFORMATION: Primer

<400> SEQUENCE: 126
ggatccttag tacaaagggt gtctc                                     25

<210> SEQ ID NO 127
<211> LENGTH: 240
<212> TYPE: DNA
<213> ORGANISM: artificial sequence
<220> FEATURE:
<223> OTHER INFORMATION: pQE-80L-Kana derivative PCR fusion product

<400> SEQUENCE: 127
gtggatttca gcgacgttgg gtggaatgac tgggctgtgg caccgccggg gtatcacgcc   60
ttctattgcc acgagaatg cccgttccca ctggctgatc atctgaactc agataaccat   120
gccattgttc agaccctcgt taattctgtt acgtatcccg cctctccgaa gccgatgagg   180
cattcaatgc ggagctgcgc gtgctgcgcc ggaggtctcc ggaaccagac agggacagtg    240

<210> SEQ ID NO 128
<211> LENGTH: 80
<212> TYPE: PRT
<213> ORGANISM: artificial sequence
<220> FEATURE:
<223> OTHER INFORMATION: pQE-80L-Kana derivative PCR fusion product

<400> SEQUENCE: 128

Val Asp Phe Ser Asp Val Gly Trp Asn Asp Trp Ala Val Ala Pro Pro
1               5                   10                  15

Gly Tyr His Ala Phe Tyr Cys His Gly Glu Cys Pro Phe Pro Leu Ala
            20                  25                  30

Asp His Leu Asn Ser Asp Asn His Ala Ile Val Gln Thr Leu Val Asn
        35                  40                  45

Ser Val Thr Tyr Pro Ala Ser Pro Lys Pro Met Arg His Ser Met Arg
    50                  55                  60

Ser Cys Ala Cys Cys Ala Gly Gly Leu Arg Asn Gln Thr Gly Thr Val
65                  70                  75                  80

<210> SEQ ID NO 129
<211> LENGTH: 25
<212> TYPE: DNA
<213> ORGANISM: artificial sequence
<220> FEATURE:
<223> OTHER INFORMATION: Primer

<400> SEQUENCE: 129
ttaaccatgg tggatttcag cgacg                                          25

<210> SEQ ID NO 130
<211> LENGTH: 25
<212> TYPE: DNA
<213> ORGANISM: artificial sequence
<220> FEATURE:
<223> OTHER INFORMATION: Primer

<400> SEQUENCE: 130
ggcgggatac gtaacagaat taacg                                          25

<210> SEQ ID NO 131
<211> LENGTH: 25
<212> TYPE: DNA
<213> ORGANISM: artificial sequence
<220> FEATURE:
<223> OTHER INFORMATION: Primer

<400> SEQUENCE: 131
cgttaattct gttacgtatc ccgcc                                          25

<210> SEQ ID NO 132
<211> LENGTH: 25
<212> TYPE: DNA
<213> ORGANISM: artificial sequence
<220> FEATURE:
<223> OTHER INFORMATION: Primer

<400> SEQUENCE: 132
ggatccttac actgtccctg tctgg                                          25

<210> SEQ ID NO 133
<211> LENGTH: 240
<212> TYPE: DNA

<213> ORGANISM: artificial sequence
<220> FEATURE:
<223> OTHER INFORMATION: pQE-80L-Kana derivative PCR fusion product

<400> SEQUENCE: 133

```
acgtatcccg cctctccgaa gccgatgagg cattcaatgc ggagctgcgc gtgctgcgcc      60
ggaggtctcc ggaaccagac agggacagtg gtggatttca gcgacgttgg gtggaatgac    120
tgggctgtgg caccgccggg gtatcacgcc ttctattgcc acggagaatg cccgttccca    180
ctggctgatc atctgaactc agataaccat gccattgttc agaccctcgt taattctgtt    240
```

<210> SEQ ID NO 134
<211> LENGTH: 80
<212> TYPE: PRT
<213> ORGANISM: artificial sequence
<220> FEATURE:
<223> OTHER INFORMATION: pQE-80L-Kana derivative PCR fusion product

<400> SEQUENCE: 134

```
Thr Tyr Pro Ala Ser Pro Lys Pro Met Arg His Ser Met Arg Ser Cys
1               5                  10                  15

Ala Cys Cys Ala Gly Gly Leu Arg Asn Gln Thr Gly Thr Val Val Asp
            20                  25                  30

Phe Ser Asp Val Gly Trp Asn Asp Trp Ala Val Ala Pro Pro Gly Tyr
        35                  40                  45

His Ala Phe Tyr Cys His Gly Glu Cys Pro Phe Pro Leu Ala Asp His
    50                  55                  60

Leu Asn Ser Asp Asn His Ala Ile Val Gln Thr Leu Val Asn Ser Val
65                  70                  75                  80
```

<210> SEQ ID NO 135
<211> LENGTH: 26
<212> TYPE: DNA
<213> ORGANISM: artificial sequence
<220> FEATURE:
<223> OTHER INFORMATION: Primer

<400> SEQUENCE: 135

```
ttaaccatga cgtatcccgc ctctcc                                          26
```

<210> SEQ ID NO 136
<211> LENGTH: 26
<212> TYPE: DNA
<213> ORGANISM: artificial sequence
<220> FEATURE:
<223> OTHER INFORMATION: Primer

<400> SEQUENCE: 136

```
cgctgaaatc caccactgtc cctgtc                                          26
```

<210> SEQ ID NO 137
<211> LENGTH: 26
<212> TYPE: DNA
<213> ORGANISM: artificial sequence
<220> FEATURE:
<223> OTHER INFORMATION: Primer

<400> SEQUENCE: 137

```
gacagggaca gtggtggatt tcagcg                                          26
```

<210> SEQ ID NO 138
<211> LENGTH: 26
<212> TYPE: DNA

<213> ORGANISM: artificial sequence
<220> FEATURE:
<223> OTHER INFORMATION: Primer

<400> SEQUENCE: 138
ggatccttaa acagaattaa cgaggg 26

<210> SEQ ID NO 139
<211> LENGTH: 183
<212> TYPE: DNA
<213> ORGANISM: artificial sequence
<220> FEATURE:
<223> OTHER INFORMATION: pQE-80L-Kana derivative PCR fusion product

<400> SEQUENCE: 139
gctcaagcca aacacaaaca gtacaaacgc cttaagtcca gctgtaagag acaccctttg 60
tacgagcccc tgggcggcgc gcgctgggaa gcgttcgacg tgacggacgc ggtgcagagc 120
caccgccgct cgccacgagc ctcccgcaag tgctgcctgg ggctgcgcgc ggtgacggcc 180
tcg 183

<210> SEQ ID NO 140
<211> LENGTH: 61
<212> TYPE: PRT
<213> ORGANISM: artificial sequence
<220> FEATURE:
<223> OTHER INFORMATION: pQE-80L-Kana derivative PCR fusion product

<400> SEQUENCE: 140

Ala Gln Ala Lys His Lys Gln Tyr Lys Arg Leu Lys Ser Ser Cys Lys
1               5                   10                  15

Arg His Pro Leu Tyr Glu Pro Leu Gly Gly Ala Arg Trp Glu Ala Phe
            20                  25                  30

Asp Val Thr Asp Ala Val Gln Ser His Arg Arg Ser Pro Arg Ala Ser
        35                  40                  45

Arg Lys Cys Cys Leu Gly Leu Arg Ala Val Thr Ala Ser
    50                  55                  60

<210> SEQ ID NO 141
<211> LENGTH: 28
<212> TYPE: DNA
<213> ORGANISM: artificial sequence
<220> FEATURE:
<223> OTHER INFORMATION: Primer

<400> SEQUENCE: 141
ttaaccatgg ctcaagccaa acacaaac 28

<210> SEQ ID NO 142
<211> LENGTH: 28
<212> TYPE: DNA
<213> ORGANISM: artificial sequence
<220> FEATURE:
<223> OTHER INFORMATION: Primer

<400> SEQUENCE: 142
ccgcccaggg gctcgtacaa agggtgtc 28

<210> SEQ ID NO 143
<211> LENGTH: 28
<212> TYPE: DNA
<213> ORGANISM: artificial sequence
<220> FEATURE:
<223> OTHER INFORMATION: Primer

```
<400> SEQUENCE: 143
gacacccttt gtacgagccc ctgggcgg                                            28

<210> SEQ ID NO 144
<211> LENGTH: 28
<212> TYPE: DNA
<213> ORGANISM: artificial sequence
<220> FEATURE:
<223> OTHER INFORMATION: Primer

<400> SEQUENCE: 144
ggatccttac gaggccgtca ccgcgcgc                                            28

<210> SEQ ID NO 145
<211> LENGTH: 183
<212> TYPE: DNA
<213> ORGANISM: artificial sequence
<220> FEATURE:
<223> OTHER INFORMATION: pQE-80L-Kana derivative PCR fusion product

<400> SEQUENCE: 145
gagcccctgg gcggcgcgcg ctgggaagcg ttcgacgtga cggacgcggt gcagagccac         60
cgccgctcgc cacgagcctc ccgcaagtgc tgcctggggc tgcgcgcggt gacggcctcg        120
gctcaagcca acacaaaca gtacaaacgc cttaagtcca gctgtaagag acacccttg         180 tac                                                                      183

<210> SEQ ID NO 146
<211> LENGTH: 61
<212> TYPE: PRT
<213> ORGANISM: artificial sequence
<220> FEATURE:
<223> OTHER INFORMATION: pQE-80L-Kana derivative PCR fusion product

<400> SEQUENCE: 146

Glu Pro Leu Gly Gly Ala Arg Trp Glu Ala Phe Asp Val Thr Asp Ala
1               5                   10                  15

Val Gln Ser His Arg Arg Ser Pro Arg Ala Ser Arg Lys Cys Cys Leu
            20                  25                  30

Gly Leu Arg Ala Val Thr Ala Ser Ala Gln Ala Lys His Lys Gln Tyr
        35                  40                  45

Lys Arg Leu Lys Ser Ser Cys Lys Arg His Pro Leu Tyr
    50                  55                  60

<210> SEQ ID NO 147
<211> LENGTH: 25
<212> TYPE: DNA
<213> ORGANISM: artificial sequence
<220> FEATURE:
<223> OTHER INFORMATION: Primer

<400> SEQUENCE: 147
ttaaccatgg agcccctggg cggcg                                               25

<210> SEQ ID NO 148
<211> LENGTH: 25
<212> TYPE: DNA
<213> ORGANISM: artificial sequence
<220> FEATURE:
<223> OTHER INFORMATION: Primer

<400> SEQUENCE: 148
```
gtttggcttg agccgaggcc gtcac                                    25

<210> SEQ ID NO 149
<211> LENGTH: 25
<212> TYPE: DNA
<213> ORGANISM: artificial sequence
<220> FEATURE:
<223> OTHER INFORMATION: Primer

<400> SEQUENCE: 149
gtgacggcct cggctcaagc caaac                                    25

<210> SEQ ID NO 150
<211> LENGTH: 25
<212> TYPE: DNA
<213> ORGANISM: artificial sequence
<220> FEATURE:
<223> OTHER INFORMATION: Primer

<400> SEQUENCE: 150
ggatccttag tacaaagggt gtctc                                    25

<210> SEQ ID NO 151
<211> LENGTH: 270
<212> TYPE: DNA
<213> ORGANISM: artificial sequence
<220> FEATURE:
<223> OTHER INFORMATION: pQE-80L-Kana derivative PCR fusion product

<400> SEQUENCE: 151
gtggatttca gcgacgttgg gtggaatgac tgggctgtgg caccgccggg gtatcacgcc      60
ttctattgcc acggagaatg cccgttccca ctggctgatc atctgaactc agataaccat     120
gccattgttc agaccctcgt taattctgtt gagcccctgg gcggcgcgcg ctgggaagcg     180
ttcgacgtga cggacgcggt gcagagccac cgccgctcgc agcgagcctc ccgcaagtgc     240
tgcctggttc tgcgcgcggt gacggcctcg                                     270

<210> SEQ ID NO 152
<211> LENGTH: 90
<212> TYPE: PRT
<213> ORGANISM: artificial sequence
<220> FEATURE:
<223> OTHER INFORMATION: pQE-80L-Kana derivative PCR fusion product

<400> SEQUENCE: 152

Val Asp Phe Ser Asp Val Gly Trp Asn Asp Trp Ala Val Ala Pro Pro
1               5                   10                  15

Gly Tyr His Ala Phe Tyr Cys His Gly Glu Cys Pro Phe Pro Leu Ala
            20                  25                  30

Asp His Leu Asn Ser Asp Asn His Ala Ile Val Gln Thr Leu Val Asn
        35                  40                  45

Ser Val Glu Pro Leu Gly Gly Ala Arg Trp Glu Ala Phe Asp Val Thr
    50                  55                  60

Asp Ala Val Gln Ser His Arg Arg Ser Gln Arg Ala Ser Arg Lys Cys
65                  70                  75                  80

Cys Leu Val Leu Arg Ala Val Thr Ala Ser
                85                  90

<210> SEQ ID NO 153
<211> LENGTH: 25
<212> TYPE: DNA
<213> ORGANISM: artificial sequence

```
<220> FEATURE:
<223> OTHER INFORMATION: Primer

<400> SEQUENCE: 153
ttaaccatgg tggatttcag cgacg                                              25

<210> SEQ ID NO 154
<211> LENGTH: 25
<212> TYPE: DNA
<213> ORGANISM: artificial sequence
<220> FEATURE:
<223> OTHER INFORMATION: Primer

<400> SEQUENCE: 154
gcccaggggc tcaacagaat aacg                                               25

<210> SEQ ID NO 155
<211> LENGTH: 25
<212> TYPE: DNA
<213> ORGANISM: artificial sequence
<220> FEATURE:
<223> OTHER INFORMATION: Primer

<400> SEQUENCE: 155
cgttaattct gttgagcccc tgggc                                              25

<210> SEQ ID NO 156
<211> LENGTH: 25
<212> TYPE: DNA
<213> ORGANISM: artificial sequence
<220> FEATURE:
<223> OTHER INFORMATION: Primer

<400> SEQUENCE: 156
ggatccttac gaggccgtca ccgcg                                              25

<210> SEQ ID NO 157
<211> LENGTH: 270
<212> TYPE: DNA
<213> ORGANISM: artificial sequence
<220> FEATURE:
<223> OTHER INFORMATION: pQE-80L-Kana derivative PCR fusion product

<400> SEQUENCE: 157
gagcccctgg gcggcgcgcg ctgggaagcg ttcgacgtga cggacgcggt gcagagccac        60
cgccgctcgc agcgagcctc ccgcaagtgc tgcctggttc tgcgcgcggt gacggcctcg       120
gtggatttca gcgacgttgg gtggaatgac tgggctgtgg caccgccggg gtatcacgcc       180
ttctattgcc acggagaatg cccgttccca ctggctgatc atctgaactc agataaccat       240
gccattgttc agaccctcgt taattctgtt                                        270

<210> SEQ ID NO 158
<211> LENGTH: 90
<212> TYPE: PRT
<213> ORGANISM: artificial sequence
<220> FEATURE:
<223> OTHER INFORMATION: pQE-80L-Kana derivative PCR fusion product

<400> SEQUENCE: 158

Glu Pro Leu Gly Gly Ala Arg Trp Glu Ala Phe Asp Val Thr Asp Ala
1               5                   10                  15

Val Gln Ser His Arg Arg Ser Gln Arg Ala Ser Arg Lys Cys Cys Leu
            20                  25                  30
```

```
Val Leu Arg Ala Val Thr Ala Ser Val Asp Phe Ser Asp Val Gly Trp
         35                  40                  45

Asn Asp Trp Ala Val Ala Pro Pro Gly Tyr His Ala Phe Tyr Cys His
 50                  55                  60

Gly Glu Cys Pro Phe Pro Leu Ala Asp His Leu Asn Ser Asp Asn His
 65                  70                  75                  80

Ala Ile Val Gln Thr Leu Val Asn Ser Val
                 85                  90
```

```
<210> SEQ ID NO 159
<211> LENGTH: 25
<212> TYPE: DNA
<213> ORGANISM: artificial sequence
<220> FEATURE:
<223> OTHER INFORMATION: Primer

<400> SEQUENCE: 159
ttaaccatgg agcccctggg cggcg                                   25

<210> SEQ ID NO 160
<211> LENGTH: 25
<212> TYPE: DNA
<213> ORGANISM: artificial sequence
<220> FEATURE:
<223> OTHER INFORMATION: Primer

<400> SEQUENCE: 160
gctgaaatcc accgaggccg tcacc                                   25

<210> SEQ ID NO 161
<211> LENGTH: 25
<212> TYPE: DNA
<213> ORGANISM: artificial sequence
<220> FEATURE:
<223> OTHER INFORMATION: Primer

<400> SEQUENCE: 161
ggtgacggcc tcggtggatt tcagc                                   25

<210> SEQ ID NO 162
<211> LENGTH: 25
<212> TYPE: DNA
<213> ORGANISM: artificial sequence
<220> FEATURE:
<223> OTHER INFORMATION: Primer

<400> SEQUENCE: 162
ggatccttaa acagaattaa cgagg                                   25

<210> SEQ ID NO 163
<211> LENGTH: 237
<212> TYPE: DNA
<213> ORGANISM: artificial sequence
<220> FEATURE:
<223> OTHER INFORMATION: pQE-80L-Kana derivative PCR fusion product

<400> SEQUENCE: 163
accgccctag atgggactcg ggagcgcag ggaagcggtg gtggcggcgg tggcggtggc    60
ggcggcggcg gcggcggcgg cggcggcggc ggcggcgcag gcaggggcca cgggcgcaga   120
ggccggagcc gctgcagtcg caagtcactg cacgtggact ttaaggagct gggcgctcaa   180
gccaaacaca acagtacaa acgccttaag tccagctgta agagacaccc tttgtac       237
```

<210> SEQ ID NO 164
<211> LENGTH: 79
<212> TYPE: PRT
<213> ORGANISM: artificial sequence
<220> FEATURE:
<223> OTHER INFORMATION: pQE-80L-Kana derivative PCR fusion product

<400> SEQUENCE: 164

Thr Ala Leu Asp Gly Thr Arg Gly Ala Gln Gly Ser Gly Gly Gly
1               5                   10                  15

Gly Gly Gly Gly Gly Gly Gly Gly Gly Gly Gly Gly Gly Gly Gly
            20                  25                  30

Ala Gly Arg Gly His Gly Arg Arg Gly Arg Ser Arg Cys Ser Arg Lys
        35                  40                  45

Ser Leu His Val Asp Phe Lys Glu Leu Gly Ala Gln Ala Lys His Lys
    50                  55                  60

Gln Tyr Lys Arg Leu Lys Ser Ser Cys Lys Arg His Pro Leu Tyr
65                  70                  75

<210> SEQ ID NO 165
<211> LENGTH: 26
<212> TYPE: DNA
<213> ORGANISM: artificial sequence
<220> FEATURE:
<223> OTHER INFORMATION: Primer

<400> SEQUENCE: 165
ttaaccatga ccgccctaga tgggac                                      26

<210> SEQ ID NO 166
<211> LENGTH: 26
<212> TYPE: DNA
<213> ORGANISM: artificial sequence
<220> FEATURE:
<223> OTHER INFORMATION: Primer

<400> SEQUENCE: 166
gtttggcttg agcgcccagc tcctta                                      26

<210> SEQ ID NO 167
<211> LENGTH: 26
<212> TYPE: DNA
<213> ORGANISM: artificial sequence
<220> FEATURE:
<223> OTHER INFORMATION: Primer

<400> SEQUENCE: 167
taaggagctg ggcgctcaag ccaaac                                      26

<210> SEQ ID NO 168
<211> LENGTH: 26
<212> TYPE: DNA
<213> ORGANISM: artificial sequence
<220> FEATURE:
<223> OTHER INFORMATION: Primer

<400> SEQUENCE: 168
ggatccttag tacaaagggt gtctct                                      26

<210> SEQ ID NO 169
<211> LENGTH: 237
<212> TYPE: DNA
<213> ORGANISM: artificial sequence
<220> FEATURE:
<223> OTHER INFORMATION: pQE-80L-Kana derivative PCR fusion product

<400> SEQUENCE: 169

```
gctcaagcca aacacaaaca gtacaaacgc cttaagtcca gctgtaagag acaccctttg    60
tacaccgccc tagatgggac tcggggagcg cagggaagcg gtggtggcgg cggtggcggt   120
ggcggcggcg gcggcggcgg cggcggcggc ggcggcggcg caggcagggg ccacgggcgc   180
agaggccgga gccgctgcag tcgcaagtca ctgcacgtgg actttaagga gctgggc      237
```

<210> SEQ ID NO 170
<211> LENGTH: 79
<212> TYPE: PRT
<213> ORGANISM: artificial sequence
<220> FEATURE:
<223> OTHER INFORMATION: pQE-80L-Kana derivative PCR fusion product

<400> SEQUENCE: 170

```
Ala Gln Ala Lys His Lys Gln Tyr Lys Arg Leu Lys Ser Ser Cys Lys
 1               5                  10                  15
Arg His Pro Leu Tyr Thr Ala Leu Asp Gly Thr Arg Gly Ala Gln Gly
             20                  25                  30
Ser Gly Gly Gly Gly Gly Gly Gly Gly Gly Gly Gly Gly Gly Gly Gly
         35                  40                  45
Gly Gly Gly Gly Gly Ala Gly Arg Gly His Arg Arg Gly Arg Ser
     50                  55                  60
Arg Cys Ser Arg Lys Ser Leu His Val Asp Phe Lys Glu Leu Gly
 65                  70                  75
```

<210> SEQ ID NO 171
<211> LENGTH: 25
<212> TYPE: DNA
<213> ORGANISM: artificial sequence
<220> FEATURE:
<223> OTHER INFORMATION: Primer

<400> SEQUENCE: 171

```
ttaaccatgg ctcaagccaa acaca                                          25
```

<210> SEQ ID NO 172
<211> LENGTH: 25
<212> TYPE: DNA
<213> ORGANISM: artificial sequence
<220> FEATURE:
<223> OTHER INFORMATION: Primer

<400> SEQUENCE: 172

```
catctagggc ggtgtacaaa gggtg                                          25
```

<210> SEQ ID NO 173
<211> LENGTH: 25
<212> TYPE: DNA
<213> ORGANISM: artificial sequence
<220> FEATURE:
<223> OTHER INFORMATION: Primer

<400> SEQUENCE: 173

```
cacccctttgt acaccgccct agatg                                         25
```

<210> SEQ ID NO 174
<211> LENGTH: 25
<212> TYPE: DNA
<213> ORGANISM: artificial sequence
<220> FEATURE:
<223> OTHER INFORMATION: Primer

<400> SEQUENCE: 174
ggatccttag cccagctcct taaag                                    25

<210> SEQ ID NO 175
<211> LENGTH: 324
<212> TYPE: DNA
<213> ORGANISM: artificial sequence
<220> FEATURE:
<223> OTHER INFORMATION: pQE-80L-Kana derivative PCR fusion product

<400> SEQUENCE: 175
gtggatttca gcgacgttgg gtggaatgac tgggctgtgg caccgccggg gtatcacgcc     60
ttctattgcc acggagaatg cccgttccca ctggctgatc atctgaactc agataaccat    120
gccattgttc agaccctcgt taattctgtt accgccctag atgggactcg gggagcgcag    180
ggaagcggtg gtggcggcgg tggcggtggc ggcggcggcg gcggcggcgg cggcggcggc    240
ggcggcgcag gcaggggcca cgggcgcaga ggccggagcc gctgcagtcg caagtcactg    300
cacgtggact ttaaggagct gggc                                         324

<210> SEQ ID NO 176
<211> LENGTH: 108
<212> TYPE: PRT
<213> ORGANISM: artificial sequence
<220> FEATURE:
<223> OTHER INFORMATION: pQE-80L-Kana derivative PCR fusion product

<400> SEQUENCE: 176

Val Asp Phe Ser Asp Val Gly Trp Asn Asp Trp Ala Val Ala Pro Pro
1               5                   10                  15

Gly Tyr His Ala Phe Tyr Cys His Gly Glu Cys Pro Phe Pro Leu Ala
            20                  25                  30

Asp His Leu Asn Ser Asp Asn His Ala Ile Val Gln Thr Leu Val Asn
        35                  40                  45

Ser Val Thr Ala Leu Asp Gly Thr Arg Gly Ala Gln Gly Ser Gly Gly
    50                  55                  60

Gly Gly Gly Gly Gly Gly Gly Gly Gly Gly Gly Gly Gly Gly Gly Gly
65                  70                  75                  80

Gly Gly Ala Gly Arg Gly His Gly Arg Arg Gly Arg Ser Arg Cys Ser
                85                  90                  95

Arg Lys Ser Leu His Val Asp Phe Lys Glu Leu Gly
            100                 105

<210> SEQ ID NO 177
<211> LENGTH: 25
<212> TYPE: DNA
<213> ORGANISM: artificial sequence
<220> FEATURE:
<223> OTHER INFORMATION: Primer

<400> SEQUENCE: 177
ttaaccatgg tggatttcag cgacg                                    25

<210> SEQ ID NO 178
<211> LENGTH: 25
<212> TYPE: DNA
<213> ORGANISM: artificial sequence
<220> FEATURE:
<223> OTHER INFORMATION: Primer

<400> SEQUENCE: 178

```
catctagggc ggtaacagaa ttaac                                          25
```

<210> SEQ ID NO 179
<211> LENGTH: 25
<212> TYPE: DNA
<213> ORGANISM: artificial sequence
<220> FEATURE:
<223> OTHER INFORMATION: Primer

<400> SEQUENCE: 179

```
gttaattctg ttaccgccct agatg                                          25
```

<210> SEQ ID NO 180
<211> LENGTH: 25
<212> TYPE: DNA
<213> ORGANISM: artificial sequence
<220> FEATURE:
<223> OTHER INFORMATION: Primer

<400> SEQUENCE: 180

```
ggatccttag cccagctcct taaag                                          25
```

<210> SEQ ID NO 181
<211> LENGTH: 213
<212> TYPE: DNA
<213> ORGANISM: artificial sequence
<220> FEATURE:
<223> OTHER INFORMATION: pQE-80L-Kana derivative PCR fusion product

<400> SEQUENCE: 181

```
gctcaagcca aacacaaaca gtacaaacgc cttaagtcca gctgtaagag acacccttt g   60 tacgtggatt tcagcgacgt tgggtggaat gactgggctg tggcaccgcc ggggtatcac   120
gccttctatt gccacggaga atgcccgttc ccactggctg atcatctgaa ctcagataac   180
catgccattg ttcagaccct cgttaattct gtt                                213
```

<210> SEQ ID NO 182
<211> LENGTH: 71
<212> TYPE: PRT
<213> ORGANISM: artificial sequence
<220> FEATURE:
<223> OTHER INFORMATION: pQE-80L-Kana derivative PCR fusion product

<400> SEQUENCE: 182

```
Ala Gln Ala Lys His Lys Gln Tyr Lys Arg Leu Lys Ser Ser Cys Lys
1               5                   10                  15

Arg His Pro Leu Tyr Val Asp Phe Ser Asp Val Gly Trp Asn Asp Trp
            20                  25                  30

Ala Val Ala Pro Pro Gly Tyr His Ala Phe Tyr Cys His Gly Glu Cys
        35                  40                  45

Pro Phe Pro Leu Ala Asp His Leu Asn Ser Asp Asn His Ala Ile Val
    50                  55                  60

Gln Thr Leu Val Asn Ser Val
65                  70
```

<210> SEQ ID NO 183
<211> LENGTH: 25
<212> TYPE: DNA
<213> ORGANISM: artificial sequence
<220> FEATURE:
<223> OTHER INFORMATION: Primer

<400> SEQUENCE: 183
ttaaccatgg ctcaagccaa acaca 25

<210> SEQ ID NO 184
<211> LENGTH: 25
<212> TYPE: DNA
<213> ORGANISM: artificial sequence
<220> FEATURE:
<223> OTHER INFORMATION: Primer

<400> SEQUENCE: 184
cgctgaaatc cacgtacaaa gggtg 25

<210> SEQ ID NO 185
<211> LENGTH: 25
<212> TYPE: DNA
<213> ORGANISM: artificial sequence
<220> FEATURE:
<223> OTHER INFORMATION: Primer

<400> SEQUENCE: 185
caccctttgt acgtggattt cagcg 25

<210> SEQ ID NO 186
<211> LENGTH: 25
<212> TYPE: DNA
<213> ORGANISM: artificial sequence
<220> FEATURE:
<223> OTHER INFORMATION: Primer

<400> SEQUENCE: 186
ggatccttaa acagaattaa cgagg 25

<210> SEQ ID NO 187
<211> LENGTH: 213
<212> TYPE: DNA
<213> ORGANISM: artificial sequence
<220> FEATURE:
<223> OTHER INFORMATION: pQE-80L-Kana derivative PCR fusion product

<400> SEQUENCE: 187
gctcaagcca aacacaaaca gcggaaacgc cttaagtcca gctgtaagag acaccctttg      60
tacgtggact tcagtgacgt ggggtggaat gactggattg tggctccccc ggggtatcac     120
gccttttact gccacggaga atgcccttt cctctggctg atcatctgaa ctccactaat     180
catgccattg ttcagacgtt ggtcaactct gtt                                  213

<210> SEQ ID NO 188
<211> LENGTH: 71
<212> TYPE: PRT
<213> ORGANISM: artificial sequence
<220> FEATURE:
<223> OTHER INFORMATION: pQE-80L-Kana derivative PCR fusion product

<400> SEQUENCE: 188

Ala Gln Ala Lys His Lys Gln Arg Lys Arg Leu Lys Ser Ser Cys Lys
1               5                   10                  15

Arg His Pro Leu Tyr Val Asp Phe Ser Asp Val Gly Trp Asn Asp Trp
            20                  25                  30

Ile Val Ala Pro Pro Gly Tyr His Ala Phe Tyr Cys His Gly Glu Cys
        35                  40                  45

Pro Phe Pro Leu Ala Asp His Leu Asn Ser Thr Asn His Ala Ile Val
    50                  55                  60

Gln Thr Leu Val Asn Ser Val
65                  70

<210> SEQ ID NO 189
<211> LENGTH: 25
<212> TYPE: DNA
<213> ORGANISM: artificial sequence
<220> FEATURE:
<223> OTHER INFORMATION: Primer

<400> SEQUENCE: 189
ttaaccatgg ctcaagccaa acaca                                    25

<210> SEQ ID NO 190
<211> LENGTH: 25
<212> TYPE: DNA
<213> ORGANISM: artificial sequence
<220> FEATURE:
<223> OTHER INFORMATION: Primer

<400> SEQUENCE: 190
cactgaagtc cacgtacaaa gggtg                                    25

<210> SEQ ID NO 191
<211> LENGTH: 25
<212> TYPE: DNA
<213> ORGANISM: artificial sequence
<220> FEATURE:
<223> OTHER INFORMATION: Primer

<400> SEQUENCE: 191
cacccttkgt acgtggactt cagtg                                    25

<210> SEQ ID NO 192
<211> LENGTH: 25
<212> TYPE: DNA
<213> ORGANISM: artificial sequence
<220> FEATURE:
<223> OTHER INFORMATION: Primer

<400> SEQUENCE: 192
ggatccttaa acagagttga ccaac                                    25

<210> SEQ ID NO 193
<211> LENGTH: 213
<212> TYPE: DNA
<213> ORGANISM: artificial sequence
<220> FEATURE:
<223> OTHER INFORMATION: pQE-80L-Kana derivative PCR fusion product

<400> SEQUENCE: 193
gtggacttca gtgacgtggg gtggaatgac tggattgtgg ctcccccggg gtatcacgcc      60
ttttactgcc acggagaatg ccctttttcct ctggctgatc atctgaactc cactaatcat   120
gccattgttc agacgttggt caactctgtt gctcaagcca aacacaaaca gcggaaacgc   180
cttaagtcca gctgtaagag acacccttg tac                                  213

<210> SEQ ID NO 194
<211> LENGTH: 71
<212> TYPE: PRT
<213> ORGANISM: artificial sequence
<220> FEATURE:
<223> OTHER INFORMATION: pQE-80L-Kana derivative PCR fusion product

<400> SEQUENCE: 194

```
Val Asp Phe Ser Asp Val Gly Trp Asn Asp Trp Ile Val Ala Pro Pro
1               5                   10                  15

Gly Tyr His Ala Phe Tyr Cys His Gly Glu Cys Pro Phe Pro Leu Ala
            20                  25                  30

Asp His Leu Asn Ser Thr Asn His Ala Ile Val Gln Thr Leu Val Asn
                35                  40                  45

Ser Val Ala Gln Ala Lys His Lys Gln Arg Lys Arg Leu Lys Ser Ser
        50                  55                  60

Cys Lys Arg His Pro Leu Tyr
65                  70

<210> SEQ ID NO 195
<211> LENGTH: 25
<212> TYPE: DNA
<213> ORGANISM: artificial sequence
<220> FEATURE:
<223> OTHER INFORMATION: Primer

<400> SEQUENCE: 195
ttaaccatgg tggacttcag tgacg                                              25

<210> SEQ ID NO 196
<211> LENGTH: 25
<212> TYPE: DNA
<213> ORGANISM: artificial sequence
<220> FEATURE:
<223> OTHER INFORMATION: Primer

<400> SEQUENCE: 196
gtttggcttg agcaacagag ttgac                                              25

<210> SEQ ID NO 197
<211> LENGTH: 25
<212> TYPE: DNA
<213> ORGANISM: artificial sequence
<220> FEATURE:
<223> OTHER INFORMATION: Primer

<400> SEQUENCE: 197
gtcaactctg ttgctcaagc caaac                                              25

<210> SEQ ID NO 198
<211> LENGTH: 25
<212> TYPE: DNA
<213> ORGANISM: artificial sequence
<220> FEATURE:
<223> OTHER INFORMATION: Primer

<400> SEQUENCE: 198
ggatccttag tacaaagggt gtctc                                              25

<210> SEQ ID NO 199
<211> LENGTH: 282
<212> TYPE: DNA
<213> ORGANISM: artificial sequence
<220> FEATURE:
<223> OTHER INFORMATION: pQE-80L-Kana derivative PCR fusion product

<400> SEQUENCE: 199
gtggacttca gtgacgtggg gtggaatgac tggattgtgg ctcccccggg gtatcacgcc        60
ttttactgcc acggagaatg ccctttttcct ctggctgatc atctgaactc cactaatcat      120
gccattgttc agacgttggt caactctgtt aactctaaga ttcctaaggc atgctgtgtc       180
```

```
ccgacagaac tcagtgctat ctcgatgctg taccttgacg agaatgaaaa ggttgtatta    240
aagaactatc aggacatggt tgtggagggt tgtgggtgtc gc                        282
```

<210> SEQ ID NO 200
<211> LENGTH: 94
<212> TYPE: PRT
<213> ORGANISM: artificial sequence
<220> FEATURE:
<223> OTHER INFORMATION: pQE-80L-Kana derivative PCR fusion product

<400> SEQUENCE: 200

```
Val Asp Phe Ser Asp Val Gly Trp Asn Asp Trp Ile Val Ala Pro Pro
1               5                   10                  15

Gly Tyr His Ala Phe Tyr Cys His Gly Glu Cys Pro Phe Pro Leu Ala
                20                  25                  30

Asp His Leu Asn Ser Thr Asn His Ala Ile Val Gln Thr Leu Val Asn
            35                  40                  45

Ser Val Asn Ser Lys Ile Pro Lys Ala Cys Cys Val Pro Thr Glu Leu
    50                  55                  60

Ser Ala Ile Ser Met Leu Tyr Leu Asp Glu Asn Glu Lys Val Val Leu
65                  70                  75                  80

Lys Asn Tyr Gln Asp Met Val Val Glu Gly Cys Gly Cys Arg
                85                  90
```

<210> SEQ ID NO 201
<211> LENGTH: 25
<212> TYPE: DNA
<213> ORGANISM: artificial sequence
<220> FEATURE:
<223> OTHER INFORMATION: Primer

<400> SEQUENCE: 201

```
ttaaccatgg tggacttcag tgacg                                           25
```

<210> SEQ ID NO 202
<211> LENGTH: 25
<212> TYPE: DNA
<213> ORGANISM: artificial sequence
<220> FEATURE:
<223> OTHER INFORMATION: Primer

<400> SEQUENCE: 202

```
gaatcttaga gttaacagag ttgac                                           25
```

<210> SEQ ID NO 203
<211> LENGTH: 25
<212> TYPE: DNA
<213> ORGANISM: artificial sequence
<220> FEATURE:
<223> OTHER INFORMATION: Primer

<400> SEQUENCE: 203

```
gtcaactctg ttaactctaa gattc                                           25
```

<210> SEQ ID NO 204
<211> LENGTH: 25
<212> TYPE: DNA
<213> ORGANISM: artificial sequence
<220> FEATURE:
<223> OTHER INFORMATION: Primer

<400> SEQUENCE: 204

```
ggatccttag cgacacccac aaccc                                           25
```

<210> SEQ ID NO 205
<211> LENGTH: 282
<212> TYPE: DNA
<213> ORGANISM: artificial sequence
<220> FEATURE:
<223> OTHER INFORMATION: pQE-80L-Kana derivative PCR fusion product

<400> SEQUENCE: 205

```
aactctaaga ttcctaaggc atgctgtgtc ccgacagaac tcagtgctat ctcgatgctg    60
taccttgacg agaatgaaaa ggttgtatta aagaactatc aggacatggt tgtggagggt   120
tgtgggtgtc gcgtggactt cagtgacgtg gggtggaatg actggattgt ggctcccccg   180
gggtatcacg ccttttactg ccacggagaa tgcccttttc ctctggctga tcatctgaac   240
tccactaatc atgccattgt tcagacgttg gtcaactctg tt                      282
```

<210> SEQ ID NO 206
<211> LENGTH: 94
<212> TYPE: PRT
<213> ORGANISM: artificial sequence
<220> FEATURE:
<223> OTHER INFORMATION: pQE-80L-Kana derivative PCR fusion product

<400> SEQUENCE: 206

```
Asn Ser Lys Ile Pro Lys Ala Cys Cys Val Pro Thr Glu Leu Ser Ala
1               5                  10                  15

Ile Ser Met Leu Tyr Leu Asp Glu Asn Glu Lys Val Val Leu Lys Asn
            20                  25                  30

Tyr Gln Asp Met Val Val Glu Gly Cys Gly Cys Arg Val Asp Phe Ser
        35                  40                  45

Asp Val Gly Trp Asn Asp Trp Ile Val Ala Pro Pro Gly Tyr His Ala
    50                  55                  60

Phe Tyr Cys His Gly Glu Cys Pro Phe Pro Leu Ala Asp His Leu Asn
65                  70                  75                  80

Ser Thr Asn His Ala Ile Val Gln Thr Leu Val Asn Ser Val
                85                  90
```

<210> SEQ ID NO 207
<211> LENGTH: 25
<212> TYPE: DNA
<213> ORGANISM: artificial sequence
<220> FEATURE:
<223> OTHER INFORMATION: Primer

<400> SEQUENCE: 207

```
ttaaccatga actctaagat tccta                                          25
```

<210> SEQ ID NO 208
<211> LENGTH: 25
<212> TYPE: DNA
<213> ORGANISM: artificial sequence
<220> FEATURE:
<223> OTHER INFORMATION: Primer

<400> SEQUENCE: 208

```
actgaagtcc acgcgacacc cacaa                                          25
```

<210> SEQ ID NO 209
<211> LENGTH: 25
<212> TYPE: DNA
<213> ORGANISM: artificial sequence
<220> FEATURE:

<223> OTHER INFORMATION: Primer

<400> SEQUENCE: 209
ttgtgggtgt cgcgtggact tcagt                                    25

<210> SEQ ID NO 210
<211> LENGTH: 25
<212> TYPE: DNA
<213> ORGANISM: artificial sequence
<220> FEATURE:
<223> OTHER INFORMATION: Primer

<400> SEQUENCE: 210
ggatccttaa acagagttga ccaac                                    25

<210> SEQ ID NO 211
<211> LENGTH: 195
<212> TYPE: DNA
<213> ORGANISM: artificial sequence
<220> FEATURE:
<223> OTHER INFORMATION: pQE-80L-Kana derivative PCR fusion product

<400> SEQUENCE: 211
aactctaaga ttcctaaggc atgctgtgtc ccgacagaac tcagtgctat ctcgatgctg    60
taccttgacg agaatgaaaa ggttgtatta aagaactatc aggacatggt tgtggagggt   120
tgtgggtgtc gcgctcaagc caaacacaaa cagcggaaac gccttaagtc cagctgtaag   180 agacacccctt tgtac                                                   195

<210> SEQ ID NO 212
<211> LENGTH: 65
<212> TYPE: PRT
<213> ORGANISM: artificial sequence
<220> FEATURE:
<223> OTHER INFORMATION: pQE-80L-Kana derivative PCR fusion product

<400> SEQUENCE: 212

Asn Ser Lys Ile Pro Lys Ala Cys Cys Val Pro Thr Glu Leu Ser Ala
1               5                   10                  15

Ile Ser Met Leu Tyr Leu Asp Glu Asn Glu Lys Val Val Leu Lys Asn
            20                  25                  30

Tyr Gln Asp Met Val Val Glu Gly Cys Gly Cys Arg Ala Gln Ala Lys
        35                  40                  45

His Lys Gln Arg Lys Arg Leu Lys Ser Ser Cys Lys Arg His Pro Leu
    50                  55                  60

Tyr
65

<210> SEQ ID NO 213
<211> LENGTH: 25
<212> TYPE: DNA
<213> ORGANISM: artificial sequence
<220> FEATURE:
<223> OTHER INFORMATION: Primer

<400> SEQUENCE: 213
ttaaccatga actctaagat tccta                                    25

<210> SEQ ID NO 214
<211> LENGTH: 25
<212> TYPE: DNA
<213> ORGANISM: artificial sequence
<220> FEATURE:

```
<223> OTHER INFORMATION: Primer

<400> SEQUENCE: 214
ttggcttgag cgcgacaccc acaac                                            25

<210> SEQ ID NO 215
<211> LENGTH: 25
<212> TYPE: DNA
<213> ORGANISM: artificial sequence
<220> FEATURE:
<223> OTHER INFORMATION: Primer

<400> SEQUENCE: 215
gttgtgggtg tcgcgctcaa gccaa                                            25

<210> SEQ ID NO 216
<211> LENGTH: 25
<212> TYPE: DNA
<213> ORGANISM: artificial sequence
<220> FEATURE:
<223> OTHER INFORMATION: Primer

<400> SEQUENCE: 216
ggatccttag tacaaagggt gtctc                                            25

<210> SEQ ID NO 217
<211> LENGTH: 195
<212> TYPE: DNA
<213> ORGANISM: artificial sequence
<220> FEATURE:
<223> OTHER INFORMATION: pQE-80L-Kana derivative PCR fusion product

<400> SEQUENCE: 217
gctcaagcca aacacaaaca gcggaaacgc cttaagtcca gctgtaagag acacccttgt      60
tacaactcta agattcctaa ggcatgctgt gtcccgacag aactcagtgc tatctcgatg     120
ctgtaccttg acgagaatga aaaggttgta ttaaagaact atcaggacat ggttgtggag     180
ggttgtgggt gtcgc                                                     195

<210> SEQ ID NO 218
<211> LENGTH: 65
<212> TYPE: PRT
<213> ORGANISM: artificial sequence
<220> FEATURE:
<223> OTHER INFORMATION: pQE-80L-Kana derivative PCR fusion product

<400> SEQUENCE: 218

Ala Gln Ala Lys His Lys Gln Arg Lys Arg Leu Lys Ser Ser Cys Lys
1               5                   10                  15

Arg His Pro Leu Tyr Asn Ser Lys Ile Pro Lys Ala Cys Cys Val Pro
            20                  25                  30

Thr Glu Leu Ser Ala Ile Ser Met Leu Tyr Leu Asp Glu Asn Glu Lys
        35                  40                  45

Val Val Leu Lys Asn Tyr Gln Asp Met Val Val Glu Gly Cys Gly Cys
    50                  55                  60

Arg
65

<210> SEQ ID NO 219
<211> LENGTH: 25
<212> TYPE: DNA
<213> ORGANISM: artificial sequence
<220> FEATURE:
```

<223> OTHER INFORMATION: Primer

<400> SEQUENCE: 219
ttaaccatgg ctcaagccaa acaca                                              25

<210> SEQ ID NO 220
<211> LENGTH: 25
<212> TYPE: DNA
<213> ORGANISM: artificial sequence
<220> FEATURE:
<223> OTHER INFORMATION: Primer

<400> SEQUENCE: 220
gaatcttaga gttgtacaaa gggtg                                              25

<210> SEQ ID NO 221
<211> LENGTH: 25
<212> TYPE: DNA
<213> ORGANISM: artificial sequence
<220> FEATURE:
<223> OTHER INFORMATION: Primer

<400> SEQUENCE: 221
caccctttgt acaactctaa gattc                                              25

<210> SEQ ID NO 222
<211> LENGTH: 25
<212> TYPE: DNA
<213> ORGANISM: artificial sequence
<220> FEATURE:
<223> OTHER INFORMATION: Primer

<400> SEQUENCE: 222
ggatccttag cgacacccac aaccc                                              25

<210> SEQ ID NO 223
<211> LENGTH: 213
<212> TYPE: DNA
<213> ORGANISM: artificial sequence
<220> FEATURE:
<223> OTHER INFORMATION: pQE-80L-Kana derivative PCR fusion product

<400> SEQUENCE: 223
ggccaagcca aacgcaaagg gtataaacgc cttaagtcca gctgtaagag acaccctttg        60
tacgtggatt tcaaggacgt tgggtggaat gaccatgctg tggcaccgcc ggggtatcac       120
gccttctatt gccacggaga atgcccgttc ccactggctg atcatctgaa ctcagataac       180
catgccattg ttcagaccaa ggttaattct gtt                                   213

<210> SEQ ID NO 224
<211> LENGTH: 71
<212> TYPE: PRT
<213> ORGANISM: artificial sequence
<220> FEATURE:
<223> OTHER INFORMATION: pQE-80L-Kana derivative PCR fusion product

<400> SEQUENCE: 224

Gly Gln Ala Lys Arg Lys Gly Tyr Lys Arg Leu Lys Ser Ser Cys Lys
1               5                   10                  15

Arg His Pro Leu Tyr Val Asp Phe Lys Asp Val Gly Trp Asn Asp His
            20                  25                  30

Ala Val Ala Pro Pro Gly Tyr His Ala Phe Tyr Cys His Gly Glu Cys
        35                  40                  45

```
Pro Phe Pro Leu Ala Asp His Leu Asn Ser Asp Asn His Ala Ile Val
        50                  55                  60
Gln Thr Lys Val Asn Ser Val
 65                 70
```

<210> SEQ ID NO 225
<211> LENGTH: 25
<212> TYPE: DNA
<213> ORGANISM: artificial sequence
<220> FEATURE:
<223> OTHER INFORMATION: Primer

<400> SEQUENCE: 225
ttaaccatgg gccaagccaa acgca                                    25

<210> SEQ ID NO 226
<211> LENGTH: 25
<212> TYPE: DNA
<213> ORGANISM: artificial sequence
<220> FEATURE:
<223> OTHER INFORMATION: Primer

<400> SEQUENCE: 226
ccttgaaatc cacgtacaaa gggtg                                    25

<210> SEQ ID NO 227
<211> LENGTH: 25
<212> TYPE: DNA
<213> ORGANISM: artificial sequence
<220> FEATURE:
<223> OTHER INFORMATION: Primer

<400> SEQUENCE: 227 cacccttttgt acgtggattt caagg                                   25

<210> SEQ ID NO 228
<211> LENGTH: 25
<212> TYPE: DNA
<213> ORGANISM: artificial sequence
<220> FEATURE:
<223> OTHER INFORMATION: Primer

<400> SEQUENCE: 228
ggatccttaa acagaattaa ccttg                                    25

<210> SEQ ID NO 229
<211> LENGTH: 213
<212> TYPE: DNA
<213> ORGANISM: artificial sequence
<220> FEATURE:
<223> OTHER INFORMATION: pQE-80L-Kana derivative PCR fusion product

<400> SEQUENCE: 229
gtggatttca aggacgttgg gtggaatgac catgctgtgg caccgccggg gtatcacgcc      60
ttctattgcc acggagaatg cccgttccca ctggctgatc atctgaactc agataaccat     120
gccattgttc agaccaaggt taattctgtt ggccaagcca aacgcaaagg gtataaacgc     180
cttaagtcca gctgtaagag acacccttttg tac                                 213

<210> SEQ ID NO 230
<211> LENGTH: 71
<212> TYPE: PRT
<213> ORGANISM: artificial sequence
<220> FEATURE:
<223> OTHER INFORMATION: pQE-80L-Kana derivative PCR fusion product

<400> SEQUENCE: 230

Val Asp Phe Lys Asp Val Gly Trp Asn Asp His Ala Val Ala Pro Pro
1               5                   10                  15

Gly Tyr His Ala Phe Tyr Cys His Gly Glu Cys Pro Phe Pro Leu Ala
            20                  25                  30

Asp His Leu Asn Ser Asp Asn His Ala Ile Val Gln Thr Lys Val Asn
        35                  40                  45

Ser Val Gly Gln Ala Lys Arg Lys Gly Tyr Lys Arg Leu Lys Ser Ser
    50                  55                  60

Cys Lys Arg His Pro Leu Tyr
65                  70

<210> SEQ ID NO 231
<211> LENGTH: 25
<212> TYPE: DNA
<213> ORGANISM: artificial sequence
<220> FEATURE:
<223> OTHER INFORMATION: Primer

<400> SEQUENCE: 231
ttaaccatgg tggatttcaa ggacg                                   25

<210> SEQ ID NO 232
<211> LENGTH: 25
<212> TYPE: DNA
<213> ORGANISM: artificial sequence
<220> FEATURE:
<223> OTHER INFORMATION: Primer

<400> SEQUENCE: 232
gtttggcttg gccaacagaa ttaac                                   25

<210> SEQ ID NO 233
<211> LENGTH: 25
<212> TYPE: DNA
<213> ORGANISM: artificial sequence
<220> FEATURE:
<223> OTHER INFORMATION: Primer

<400> SEQUENCE: 233
gttaattctg ttggccaagc caaac                                   25

<210> SEQ ID NO 234
<211> LENGTH: 25
<212> TYPE: DNA
<213> ORGANISM: artificial sequence
<220> FEATURE:
<223> OTHER INFORMATION: Primer

<400> SEQUENCE: 234
ggatccttag tacaaagggt gtctc                                   25

<210> SEQ ID NO 235
<211> LENGTH: 195
<212> TYPE: DNA
<213> ORGANISM: artificial sequence
<220> FEATURE:
<223> OTHER INFORMATION: pQE-80L-Kana derivative PCR fusion product

<400> SEQUENCE: 235
aatagcaaag atcccaaggc atgctgtgtc ccgacagaac tcagtgcccc cagcccgctg    60
taccttgacg agaatgagaa gcctgtactc aagaactatc aggacatggt agtccatggg   120

```
tgtgggtgtc gcggccaagc caaacgcaaa gggtataaac gccttaagtc cagctgtaag    180
agacacccct tgtac                                                     195
```

```
<210> SEQ ID NO 236
<211> LENGTH: 65
<212> TYPE: PRT
<213> ORGANISM: artificial sequence
<220> FEATURE:
<223> OTHER INFORMATION: pQE-80L-Kana derivative PCR fusion product

<400> SEQUENCE: 236
```

Asn Ser Lys Asp Pro Lys Ala Cys Cys Val Pro Thr Glu Leu Ser Ala
1               5                   10                  15

Pro Ser Pro Leu Tyr Leu Asp Glu Asn Glu Lys Pro Val Leu Lys Asn
            20                  25                  30

Tyr Gln Asp Met Val Val His Gly Cys Gly Cys Arg Gly Gln Ala Lys
        35                  40                  45

Arg Lys Gly Tyr Lys Arg Leu Lys Ser Ser Cys Lys Arg His Pro Leu
    50                  55                  60

Tyr
65

```
<210> SEQ ID NO 237
<211> LENGTH: 25
<212> TYPE: DNA
<213> ORGANISM: artificial sequence
<220> FEATURE:
<223> OTHER INFORMATION: Primer

<400> SEQUENCE: 237
ttaaccatga atagcaaaga tccca                                          25

<210> SEQ ID NO 238
<211> LENGTH: 25
<212> TYPE: DNA
<213> ORGANISM: artificial sequence
<220> FEATURE:
<223> OTHER INFORMATION: Primer

<400> SEQUENCE: 238
ttggcttggc cgcgacaccc acacc                                          25

<210> SEQ ID NO 239
<211> LENGTH: 25
<212> TYPE: DNA
<213> ORGANISM: artificial sequence
<220> FEATURE:
<223> OTHER INFORMATION: Primer

<400> SEQUENCE: 239
ggtgtgggtg tcgcggccaa gccaa                                          25

<210> SEQ ID NO 240
<211> LENGTH: 25
<212> TYPE: DNA
<213> ORGANISM: artificial sequence
<220> FEATURE:
<223> OTHER INFORMATION: Primer

<400> SEQUENCE: 240
ggatccttag tacaaagggt gtctc                                          25
```

```
<210> SEQ ID NO 241
<211> LENGTH: 195
<212> TYPE: DNA
<213> ORGANISM: artificial sequence
<220> FEATURE:
<223> OTHER INFORMATION: pQE-80L-Kana derivative PCR fusion product

<400> SEQUENCE: 241
ggccaagcca aacgcaaagg gtataaacgc cttaagtcca gctgtaagag acacccttttg      60 tacaatagca aagatcccaa ggcatgctgt gtcccgacag aactcagtgc ccccagcccg     120
ctgtaccttg acgagaatga gaagcctgta ctcaagaact atcaggacat ggtagtccat     180
gggtgtgggt gtcgc                                                      195

<210> SEQ ID NO 242
<211> LENGTH: 65
<212> TYPE: PRT
<213> ORGANISM: artificial sequence
<220> FEATURE:
<223> OTHER INFORMATION: pQE-80L-Kana derivative PCR fusion product

<400> SEQUENCE: 242

Gly Gln Ala Lys Arg Lys Gly Tyr Lys Arg Leu Lys Ser Ser Cys Lys
1               5                   10                  15

Arg His Pro Leu Tyr Asn Ser Lys Asp Pro Lys Ala Cys Cys Val Pro
            20                  25                  30

Thr Glu Leu Ser Ala Pro Ser Pro Leu Tyr Leu Asp Glu Asn Glu Lys
        35                  40                  45

Pro Val Leu Lys Asn Tyr Gln Asp Met Val Val His Gly Cys Gly Cys
    50                  55                  60

Arg
65

<210> SEQ ID NO 243
<211> LENGTH: 25
<212> TYPE: DNA
<213> ORGANISM: artificial sequence
<220> FEATURE:
<223> OTHER INFORMATION: Primer

<400> SEQUENCE: 243
ttaaccatgg gccaagccaa acgca                                            25

<210> SEQ ID NO 244
<211> LENGTH: 25
<212> TYPE: DNA
<213> ORGANISM: artificial sequence
<220> FEATURE:
<223> OTHER INFORMATION: Primer

<400> SEQUENCE: 244
gatctttgct attgtacaaa gggtg                                            25

<210> SEQ ID NO 245
<211> LENGTH: 25
<212> TYPE: DNA
<213> ORGANISM: artificial sequence
<220> FEATURE:
<223> OTHER INFORMATION: Primer

<400> SEQUENCE: 245
caccctttgt acaatagcaa agatc                                            25
```

<210> SEQ ID NO 246
<211> LENGTH: 25
<212> TYPE: DNA
<213> ORGANISM: artificial sequence
<220> FEATURE:
<223> OTHER INFORMATION: Primer

<400> SEQUENCE: 246
ggatccttag cgacacccac accca                                          25

<210> SEQ ID NO 247
<211> LENGTH: 282
<212> TYPE: DNA
<213> ORGANISM: artificial sequence
<220> FEATURE:
<223> OTHER INFORMATION: pQE-80L-Kana derivative PCR fusion product

<400> SEQUENCE: 247
aatagcaaag atcccaaggc atgctgtgtc ccgacagaac tcagtgcccc cagcccgctg    60
taccttgacg agaatgagaa gcctgtactc aagaactatc aggacatggt agtccatggg   120
tgtgggtgtc gcgtggattt caaggacgtt gggtggaatg accatgctgt ggcaccgccg   180
gggtatcacg ccttctattg ccacggagaa tgcccgttcc cactggctga tcatctgaac   240
tcagataacc atgccattgt tcagaccaag gttaattctg tt                      282

<210> SEQ ID NO 248
<211> LENGTH: 94
<212> TYPE: PRT
<213> ORGANISM: artificial sequence
<220> FEATURE:
<223> OTHER INFORMATION: pQE-80L-Kana derivative PCR fusion product

<400> SEQUENCE: 248

Asn Ser Lys Asp Pro Lys Ala Cys Cys Val Pro Thr Glu Leu Ser Ala
1               5                   10                  15

Pro Ser Pro Leu Tyr Leu Asp Glu Asn Glu Lys Pro Val Leu Lys Asn
            20                  25                  30

Tyr Gln Asp Met Val Val His Gly Cys Gly Cys Arg Val Asp Phe Lys
        35                  40                  45

Asp Val Gly Trp Asn Asp His Ala Val Ala Pro Pro Gly Tyr His Ala
    50                  55                  60

Phe Tyr Cys His Gly Glu Cys Pro Phe Pro Leu Ala Asp His Leu Asn
65                  70                  75                  80

Ser Asp Asn His Ala Ile Val Gln Thr Lys Val Asn Ser Val
                85                  90

<210> SEQ ID NO 249
<211> LENGTH: 25
<212> TYPE: DNA
<213> ORGANISM: artificial sequence
<220> FEATURE:
<223> OTHER INFORMATION: Primer

<400> SEQUENCE: 249
ttaaccatga atagcaaaga tccca                                          25

<210> SEQ ID NO 250
<211> LENGTH: 25
<212> TYPE: DNA
<213> ORGANISM: artificial sequence
<220> FEATURE:
<223> OTHER INFORMATION: Primer

```
<400> SEQUENCE: 250
cttgaaatcc acgcgacacc cacac                                          25

<210> SEQ ID NO 251
<211> LENGTH: 25
<212> TYPE: DNA
<213> ORGANISM: artificial sequence
<220> FEATURE:
<223> OTHER INFORMATION: Primer

<400> SEQUENCE: 251
gtgtgggtgt cgcgtggatt tcaag                                          25

<210> SEQ ID NO 252
<211> LENGTH: 25
<212> TYPE: DNA
<213> ORGANISM: artificial sequence
<220> FEATURE:
<223> OTHER INFORMATION: Primer

<400> SEQUENCE: 252
ggatccttaa acagaattaa ccttg                                          25

<210> SEQ ID NO 253
<211> LENGTH: 282
<212> TYPE: DNA
<213> ORGANISM: artificial sequence
<220> FEATURE:
<223> OTHER INFORMATION: pQE-80L-Kana derivative PCR fusion product

<400> SEQUENCE: 253
gtggatttca aggacgttgg gtggaatgac catgctgtgg caccgccggg gtatcacgcc    60
ttctattgcc acgagaatg cccgttccca ctggctgatc atctgaactc agataaccat   120
gccattgttc agaccaaggt taattctgtt aatagcaaag atcccaaggc atgctgtgtc   180
ccgacagaac tcagtgcccc cagcccgctg taccttgacg agaatgagaa gcctgtactc   240
aagaactatc aggacatggt agtccatggg tgtgggtgtc gc                      282

<210> SEQ ID NO 254
<211> LENGTH: 94
<212> TYPE: PRT
<213> ORGANISM: artificial sequence
<220> FEATURE:
<223> OTHER INFORMATION: pQE-80L-Kana derivative PCR fusion product

<400> SEQUENCE: 254

Val Asp Phe Lys Asp Val Gly Trp Asn Asp His Ala Val Ala Pro Pro
1               5                   10                  15

Gly Tyr His Ala Phe Tyr Cys His Gly Glu Cys Pro Phe Pro Leu Ala
            20                  25                  30

Asp His Leu Asn Ser Asp Asn His Ala Ile Val Gln Thr Lys Val Asn
        35                  40                  45

Ser Val Asn Ser Lys Asp Pro Lys Ala Cys Cys Val Pro Thr Glu Leu
    50                  55                  60

Ser Ala Pro Ser Pro Leu Tyr Leu Asp Glu Asn Glu Lys Pro Val Leu
65                  70                  75                  80

Lys Asn Tyr Gln Asp Met Val Val His Gly Cys Gly Cys Arg
                85                  90

<210> SEQ ID NO 255
<211> LENGTH: 25
```

```
<212> TYPE: DNA
<213> ORGANISM: artificial sequence
<220> FEATURE:
<223> OTHER INFORMATION: Primer

<400> SEQUENCE: 255
ttaaccatgg tggatttcaa ggacg                                   25

<210> SEQ ID NO 256
<211> LENGTH: 25
<212> TYPE: DNA
<213> ORGANISM: artificial sequence
<220> FEATURE:
<223> OTHER INFORMATION: Primer

<400> SEQUENCE: 256
gatctttgct attaacagaa ttaac                                   25

<210> SEQ ID NO 257
<211> LENGTH: 25
<212> TYPE: DNA
<213> ORGANISM: artificial sequence
<220> FEATURE:
<223> OTHER INFORMATION: Primer

<400> SEQUENCE: 257
gttaattctg ttaatagcaa agatc                                   25

<210> SEQ ID NO 258
<211> LENGTH: 25
<212> TYPE: DNA
<213> ORGANISM: artificial sequence
<220> FEATURE:
<223> OTHER INFORMATION: Primer

<400> SEQUENCE: 258
ggatccttag cgacacccac accca                                   25

<210> SEQ ID NO 259
<211> LENGTH: 345
<212> TYPE: DNA
<213> ORGANISM: artificial sequence
<220> FEATURE:
<223> OTHER INFORMATION: pQE-80L-Kana derivative PCR fusion product

<400> SEQUENCE: 259
gctcaagcca aacacaaaca gcggaaacgc cttaagtcca gctgtaagag acacccttig    60 tacgtggact tcagtgacgt ggggtggaat gactggattg tggctccccc ggggtatcac   120
gccttttact gccacggaga atgccctttt cctctggctg atcatctgaa ctccactaat   180
catgccattg ttcagacgtt ggtcaactct gttaactcta agattcctaa gcatgctgt    240 gtcccgacag aactcagtgc tatctcgatg ctgtaccttg acgagaatga aaaggttgta   300
ttaaagaact atcaggacat ggttgtggag ggttgtgggt gtcgc                  345

<210> SEQ ID NO 260
<211> LENGTH: 115
<212> TYPE: PRT
<213> ORGANISM: artificial sequence
<220> FEATURE:
<223> OTHER INFORMATION: pQE-80L-Kana derivative PCR fusion product

<400> SEQUENCE: 260

Ala Gln Ala Lys His Lys Gln Arg Lys Arg Leu Lys Ser Ser Cys Lys
1               5                   10                  15
```

```
Arg His Pro Leu Tyr Val Asp Phe Ser Asp Val Gly Trp Asn Asp Trp
             20                  25                  30

Ile Val Ala Pro Pro Gly Tyr His Ala Phe Tyr Cys His Gly Glu Cys
         35                  40                  45

Pro Phe Pro Leu Ala Asp His Leu Asn Ser Thr Asn His Ala Ile Val
 50                  55                  60

Gln Thr Leu Val Asn Ser Val Asn Ser Lys Ile Pro Lys Ala Cys Cys
 65                  70                  75                  80

Val Pro Thr Glu Leu Ser Ala Ile Ser Met Leu Tyr Leu Asp Glu Asn
             85                  90                  95

Glu Lys Val Val Leu Lys Asn Tyr Gln Asp Met Val Val Glu Gly Cys
            100                 105                 110

Gly Cys Arg
        115

<210> SEQ ID NO 261
<211> LENGTH: 25
<212> TYPE: DNA
<213> ORGANISM: artificial sequence
<220> FEATURE:
<223> OTHER INFORMATION: Primer

<400> SEQUENCE: 261
ttaaccatgg ctcaagccaa acaca                                     25

<210> SEQ ID NO 262
<211> LENGTH: 25
<212> TYPE: DNA
<213> ORGANISM: artificial sequence
<220> FEATURE:
<223> OTHER INFORMATION: Primer

<400> SEQUENCE: 262
cactgaagtc cacgtacaaa gggtg                                     25

<210> SEQ ID NO 263
<211> LENGTH: 25
<212> TYPE: DNA
<213> ORGANISM: artificial sequence
<220> FEATURE:
<223> OTHER INFORMATION: Primer

<400> SEQUENCE: 263
caccctttgt acgtggactt cagtg                                     25

<210> SEQ ID NO 264
<211> LENGTH: 25
<212> TYPE: DNA
<213> ORGANISM: artificial sequence
<220> FEATURE:
<223> OTHER INFORMATION: Primer

<400> SEQUENCE: 264
gaatcttaga gttaacagag ttgac                                     25

<210> SEQ ID NO 265
<211> LENGTH: 25
<212> TYPE: DNA
<213> ORGANISM: artificial sequence
<220> FEATURE:
<223> OTHER INFORMATION: Primer

<400> SEQUENCE: 265
```

```
gtcaactctg ttaactctaa gattc                                         25
```

<210> SEQ ID NO 266
<211> LENGTH: 25
<212> TYPE: DNA
<213> ORGANISM: artificial sequence
<220> FEATURE:
<223> OTHER INFORMATION: Primer

<400> SEQUENCE: 266

```
ggatccttag cgacacccac aaccc                                         25
```

<210> SEQ ID NO 267
<211> LENGTH: 345
<212> TYPE: DNA
<213> ORGANISM: artificial sequence
<220> FEATURE:
<223> OTHER INFORMATION: pQE-80L-Kana derivative PCR fusion product

<400> SEQUENCE: 267

```
gtggacttca gtgacgtggg gtggaatgac tggattgtgg ctcccccggg gtatcacgcc    60
ttttactgcc acggagaatg ccctttttcct ctggctgatc atctgaactc cactaatcat  120
gccattgttc agacgttggt caactctgtt gctcaagcca acacaaaaca gcggaaacgc  180
cttaagtcca gctgtaagag acacccttttg tacaactcta agattcctaa ggcatgctgt  240
gtcccgacag aactcagtgc tatctcgatg ctgtaccttg acgagaatga aaaggttgta  300
ttaaagaact atcaggacat ggttgtggag ggttgtgggt gtcgc                   345
```

<210> SEQ ID NO 268
<211> LENGTH: 115
<212> TYPE: PRT
<213> ORGANISM: artificial sequence
<220> FEATURE:
<223> OTHER INFORMATION: pQE-80L-Kana derivative PCR fusion product

<400> SEQUENCE: 268

```
Val Asp Phe Ser Asp Val Gly Trp Asn Asp Trp Ile Val Ala Pro Pro
1               5                   10                  15

Gly Tyr His Ala Phe Tyr Cys His Gly Glu Cys Pro Phe Pro Leu Ala
                20                  25                  30

Asp His Leu Asn Ser Thr Asn His Ala Ile Val Gln Thr Leu Val Asn
            35                  40                  45

Ser Val Ala Gln Ala Lys His Lys Gln Arg Lys Arg Leu Lys Ser Ser
        50                  55                  60

Cys Lys Arg His Pro Leu Tyr Asn Ser Lys Ile Pro Lys Ala Cys Cys
65                  70                  75                  80

Val Pro Thr Glu Leu Ser Ala Ile Ser Met Leu Tyr Leu Asp Glu Asn
                85                  90                  95

Glu Lys Val Val Leu Lys Asn Tyr Gln Asp Met Val Val Glu Gly Cys
                100                 105                 110

Gly Cys Arg
        115
```

<210> SEQ ID NO 269
<211> LENGTH: 25
<212> TYPE: DNA
<213> ORGANISM: artificial sequence
<220> FEATURE:
<223> OTHER INFORMATION: Primer

<400> SEQUENCE: 269
ttaaccatgg tggacttcag tgacg                                    25

<210> SEQ ID NO 270
<211> LENGTH: 25
<212> TYPE: DNA
<213> ORGANISM: artificial sequence
<220> FEATURE:
<223> OTHER INFORMATION: Primer

<400> SEQUENCE: 270
gtttggcttg agcaacagag ttgac                                    25

<210> SEQ ID NO 271
<211> LENGTH: 25
<212> TYPE: DNA
<213> ORGANISM: artificial sequence
<220> FEATURE:
<223> OTHER INFORMATION: Primer

<400> SEQUENCE: 271
gtcaactctg ttgctcaagc caaac                                    25

<210> SEQ ID NO 272
<211> LENGTH: 25
<212> TYPE: DNA
<213> ORGANISM: artificial sequence
<220> FEATURE:
<223> OTHER INFORMATION: Primer

<400> SEQUENCE: 272
gaatcttaga gttgtacaaa gggtg                                    25

<210> SEQ ID NO 273
<211> LENGTH: 25
<212> TYPE: DNA
<213> ORGANISM: artificial sequence
<220> FEATURE:
<223> OTHER INFORMATION: Primer

<400> SEQUENCE: 273
caccctttgt acaactctaa gattc                                    25

<210> SEQ ID NO 274
<211> LENGTH: 25
<212> TYPE: DNA
<213> ORGANISM: artificial sequence
<220> FEATURE:
<223> OTHER INFORMATION: Primer

<400> SEQUENCE: 274
ggatccttag cgacacccac aaccc                                    25

<210> SEQ ID NO 275
<211> LENGTH: 345
<212> TYPE: DNA
<213> ORGANISM: artificial sequence
<220> FEATURE:
<223> OTHER INFORMATION: pQE-80L-Kana derivative PCR fusion product

<400> SEQUENCE: 275
aactctaaga ttcctaaggc atgctgtgtc ccgacagaac tcagtgctat ctcgatgctg    60
taccttgacg agaatgaaaa ggttgtatta aagaactatc aggacatggt tgtggagggt   120
tgtgggtgtc gcgtggactt cagtgacgtg gggtggaatg actggattgt ggctcccccg   180

```
gggtatcacg cctttactg ccacggagaa tgcccttttc ctctggctga tcatctgaac      240
tccactaatc atgccattgt tcagacgttg gtcaactctg ttgctcaagc caaacacaaa      300
cagcggaaac gccttaagtc cagctgtaag agacacccct tgtac                      345
```

```
<210> SEQ ID NO 276
<211> LENGTH: 115
<212> TYPE: PRT
<213> ORGANISM: artificial sequence
<220> FEATURE:
<223> OTHER INFORMATION: pQE-80L-Kana derivative PCR fusion product

<400> SEQUENCE: 276
```

| Asn | Ser | Lys | Ile | Pro | Lys | Ala | Cys | Cys | Val | Pro | Thr | Glu | Leu | Ser | Ala |
|---|---|---|---|---|---|---|---|---|---|---|---|---|---|---|---|
| 1 | | | | 5 | | | | | 10 | | | | | 15 | |
| Ile | Ser | Met | Leu | Tyr | Leu | Asp | Glu | Asn | Glu | Lys | Val | Val | Leu | Lys | Asn |
| | | | 20 | | | | | 25 | | | | | 30 | | |
| Tyr | Gln | Asp | Met | Val | Val | Glu | Gly | Cys | Gly | Cys | Arg | Val | Asp | Phe | Ser |
| | | | | 35 | | | | | 40 | | | | 45 | | |
| Asp | Val | Gly | Trp | Asn | Asp | Trp | Ile | Val | Ala | Pro | Pro | Gly | Tyr | His | Ala |
| | | | 50 | | | | | 55 | | | | | 60 | | |
| Phe | Tyr | Cys | His | Gly | Glu | Cys | Pro | Phe | Pro | Leu | Ala | Asp | His | Leu | Asn |
| 65 | | | | | 70 | | | | | 75 | | | | | 80 |
| Ser | Thr | Asn | His | Ala | Ile | Val | Gln | Thr | Leu | Val | Asn | Ser | Val | Ala | Gln |
| | | | | 85 | | | | | 90 | | | | | 95 | |
| Ala | Lys | His | Lys | Gln | Arg | Lys | Arg | Leu | Lys | Ser | Ser | Cys | Lys | Arg | His |
| | | | 100 | | | | | 105 | | | | | 110 | | |
| Pro | Leu | Tyr |
| | | 115 |

```
<210> SEQ ID NO 277
<211> LENGTH: 25
<212> TYPE: DNA
<213> ORGANISM: artificial sequence
<220> FEATURE:
<223> OTHER INFORMATION: Primer

<400> SEQUENCE: 277
ttaaccatga actctaagat tccta                                            25

<210> SEQ ID NO 278
<211> LENGTH: 25
<212> TYPE: DNA
<213> ORGANISM: artificial sequence
<220> FEATURE:
<223> OTHER INFORMATION: Primer

<400> SEQUENCE: 278
cactgaagtc cacgcgacac ccaca                                            25

<210> SEQ ID NO 279
<211> LENGTH: 25
<212> TYPE: DNA
<213> ORGANISM: artificial sequence
<220> FEATURE:
<223> OTHER INFORMATION: Primer

<400> SEQUENCE: 279
tgtgggtgtc gcgtggactt cagtg                                            25

<210> SEQ ID NO 280
```

```
<211> LENGTH: 25
<212> TYPE: DNA
<213> ORGANISM: artificial sequence
<220> FEATURE:
<223> OTHER INFORMATION: Primer

<400> SEQUENCE: 280
gtttggcttg agcaacagag ttgac                                        25

<210> SEQ ID NO 281
<211> LENGTH: 25
<212> TYPE: DNA
<213> ORGANISM: artificial sequence
<220> FEATURE:
<223> OTHER INFORMATION: Primer

<400> SEQUENCE: 281
gtcaactctg ttgctcaagc caaac                                        25

<210> SEQ ID NO 282
<211> LENGTH: 25
<212> TYPE: DNA
<213> ORGANISM: artificial sequence
<220> FEATURE:
<223> OTHER INFORMATION: Primer

<400> SEQUENCE: 282
ggatccttag tacaaagggt gtctc                                        25

<210> SEQ ID NO 283
<211> LENGTH: 345
<212> TYPE: DNA
<213> ORGANISM: artificial sequence
<220> FEATURE:
<223> OTHER INFORMATION: pQE-80L-Kana derivative PCR fusion product

<400> SEQUENCE: 283
aactctaaga ttcctaaggc atgctgtgtc ccgacagaac tcagtgctat ctcgatgctg    60
taccttgacg agaatgaaaa ggttgtatta agaactatc aggacatggt tgtggagggt   120
tgtgggtgtc gcgctcaagc caaacacaaa cagcggaaac gccttaagtc cagctgtaag   180
agacaccctt tgtacgtgga cttcagtgac gtggggtgga atgactggat tgtggctccc   240
ccggggtatc acgccttta ctgccacgga gaatgccctt ttcctctggc tgatcatctg    300
aactccacta atcatgccat tgttcagacg ttggtcaact ctgtt                  345

<210> SEQ ID NO 284
<211> LENGTH: 115
<212> TYPE: PRT
<213> ORGANISM: artificial sequence
<220> FEATURE:
<223> OTHER INFORMATION: pQE-80L-Kana derivative PCR fusion product

<400> SEQUENCE: 284

Asn Ser Lys Ile Pro Lys Ala Cys Cys Val Pro Thr Glu Leu Ser Ala
1               5                  10                  15

Ile Ser Met Leu Tyr Leu Asp Glu Asn Glu Lys Val Val Leu Lys Asn
            20                  25                  30

Tyr Gln Asp Met Val Val Glu Gly Cys Gly Cys Arg Ala Gln Ala Lys
        35                  40                  45

His Lys Gln Arg Lys Arg Leu Lys Ser Ser Cys Lys Arg His Pro Leu
    50                  55                  60

Tyr Val Asp Phe Ser Asp Val Gly Trp Asn Asp Trp Ile Val Ala Pro
```

```
            65                  70                  75                  80
Pro Gly Tyr His Ala Phe Tyr Cys His Gly Glu Cys Pro Phe Pro Leu
                        85                  90                  95

Ala Asp His Leu Asn Ser Thr Asn His Ala Ile Val Gln Thr Leu Val
                100                 105                 110

Asn Ser Val
        115
```

<210> SEQ ID NO 285
<211> LENGTH: 25
<212> TYPE: DNA
<213> ORGANISM: artificial sequence
<220> FEATURE:
<223> OTHER INFORMATION: Primer

<400> SEQUENCE: 285
ttaaccatga actctaagat tccta                                          25

<210> SEQ ID NO 286
<211> LENGTH: 25
<212> TYPE: DNA
<213> ORGANISM: artificial sequence
<220> FEATURE:
<223> OTHER INFORMATION: Primer

<400> SEQUENCE: 286
gtttggcttg agcgcgacac ccaca                                          25

<210> SEQ ID NO 287
<211> LENGTH: 25
<212> TYPE: DNA
<213> ORGANISM: artificial sequence
<220> FEATURE:
<223> OTHER INFORMATION: Primer

<400> SEQUENCE: 287
tgtgggtgtc gcgctcaagc caaac                                          25

<210> SEQ ID NO 288
<211> LENGTH: 25
<212> TYPE: DNA
<213> ORGANISM: artificial sequence
<220> FEATURE:
<223> OTHER INFORMATION: Primer

<400> SEQUENCE: 288
cactgaagtc cacgtacaaa gggtg                                          25

<210> SEQ ID NO 289
<211> LENGTH: 25
<212> TYPE: DNA
<213> ORGANISM: artificial sequence
<220> FEATURE:
<223> OTHER INFORMATION: Primer

<400> SEQUENCE: 289
caccctttgt acgtggactt cagtg                                          25

<210> SEQ ID NO 290
<211> LENGTH: 25
<212> TYPE: DNA
<213> ORGANISM: artificial sequence
<220> FEATURE:
<223> OTHER INFORMATION: Primer

<400> SEQUENCE: 290
ggatccttaa acagagttga ccaac                                          25

<210> SEQ ID NO 291
<211> LENGTH: 345
<212> TYPE: DNA
<213> ORGANISM: artificial sequence
<220> FEATURE:
<223> OTHER INFORMATION: pQE-80L-Kana derivative PCR fusion product

<400> SEQUENCE: 291
ggccaagcca aacgcaaagg gtataaacgc cttaagtcca gctgtaagag acaccctttg    60
tacgtggatt tcaaggacgt tgggtggaat gaccatgctg tggcaccgcc ggggtatcac   120
gccttctatt gccacggaga atgcccgttc ccactggctg atcatctgaa ctcagataac   180
catgccattg ttcagaccaa ggttaattct gttaatagca aagatcccaa ggcatgctgt   240
gtcccgacag aactcagtgc ccccagcccg ctgtaccttg acgagaatga agcctgta     300 ctcaagaact atcaggacat ggtagtccat gggtgtgggt gtcgc                   345

<210> SEQ ID NO 292
<211> LENGTH: 115
<212> TYPE: PRT
<213> ORGANISM: artificial sequence
<220> FEATURE:
<223> OTHER INFORMATION: pQE-80L-Kana derivative PCR fusion product

<400> SEQUENCE: 292

Gly Gln Ala Lys Arg Lys Gly Tyr Lys Arg Leu Lys Ser Ser Cys Lys
1               5                   10                  15

Arg His Pro Leu Tyr Val Asp Phe Lys Asp Val Gly Trp Asn Asp His
                20                  25                  30

Ala Val Ala Pro Pro Gly Tyr His Ala Phe Tyr Cys His Gly Glu Cys
            35                  40                  45

Pro Phe Pro Leu Ala Asp His Leu Asn Ser Asp Asn His Ala Ile Val
        50                  55                  60

Gln Thr Lys Val Asn Ser Val Asn Ser Lys Asp Pro Lys Ala Cys Cys
65                  70                  75                  80

Val Pro Thr Glu Leu Ser Ala Pro Ser Pro Leu Tyr Leu Asp Glu Asn
                85                  90                  95

Glu Lys Pro Val Leu Lys Asn Tyr Gln Asp Met Val Val His Gly Cys
            100                 105                 110

Gly Cys Arg
        115

<210> SEQ ID NO 293
<211> LENGTH: 25
<212> TYPE: DNA
<213> ORGANISM: artificial sequence
<220> FEATURE:
<223> OTHER INFORMATION: Primer

<400> SEQUENCE: 293
ttaaccatgg gccaagccaa acgca                                         25

<210> SEQ ID NO 294
<211> LENGTH: 25
<212> TYPE: DNA
<213> ORGANISM: artificial sequence
<220> FEATURE:
<223> OTHER INFORMATION: Primer

<400> SEQUENCE: 294
ccttgaaatc cacgtacaaa gggtg     25

<210> SEQ ID NO 295
<211> LENGTH: 25
<212> TYPE: DNA
<213> ORGANISM: artificial sequence
<220> FEATURE:
<223> OTHER INFORMATION: Primer

<400> SEQUENCE: 295
caccctttgt acgtggattt caagg     25

<210> SEQ ID NO 296
<211> LENGTH: 25
<212> TYPE: DNA
<213> ORGANISM: artificial sequence
<220> FEATURE:
<223> OTHER INFORMATION: Primer

<400> SEQUENCE: 296
gatctttgct attaacagaa ttaac     25

<210> SEQ ID NO 297
<211> LENGTH: 25
<212> TYPE: DNA
<213> ORGANISM: artificial sequence
<220> FEATURE:
<223> OTHER INFORMATION: Primer

<400> SEQUENCE: 297
gttaattctg ttaatagcaa agatc     25

<210> SEQ ID NO 298
<211> LENGTH: 25
<212> TYPE: DNA
<213> ORGANISM: artificial sequence
<220> FEATURE:
<223> OTHER INFORMATION: Primer

<400> SEQUENCE: 298
ggatccttag cgacacccac accca     25

<210> SEQ ID NO 299
<211> LENGTH: 345
<212> TYPE: DNA
<213> ORGANISM: artificial sequence
<220> FEATURE:
<223> OTHER INFORMATION: pQE-80L-Kana derivative PCR fusion product

<400> SEQUENCE: 299
gtggatttca aggacgttgg gtggaatgac catgctgtgg caccgccggg gtatcacgcc     60
ttctattgcc acggagaatg cccgttccca ctggctgatc atctgaactc agataaccat    120
gccattgttc agaccaaggt taattctgtt ggccaagcca acgcaaagg gtataaacgc    180 cttaagtcca gctgtaagag cacccctttg tacaatagca agatcccaa ggcatgctgt    240 gtcccgacag aactcagtgc ccccagcccg ctgtaccttg acgagaatga gaagcctgta    300
ctcaagaact atcaggacat ggtagtccat gggtgtgggt gtcgc                    345

<210> SEQ ID NO 300
<211> LENGTH: 115
<212> TYPE: PRT

<213> ORGANISM: artificial sequence
<220> FEATURE:
<223> OTHER INFORMATION: pQE-80L-Kana derivative PCR fusion product

<400> SEQUENCE: 300

```
Val Asp Phe Lys Asp Val Gly Trp Asn Asp His Ala Val Ala Pro Pro
1               5                   10                  15
Gly Tyr His Ala Phe Tyr Cys His Gly Glu Cys Pro Phe Pro Leu Ala
            20                  25                  30
Asp His Leu Asn Ser Asp Asn His Ala Ile Val Gln Thr Lys Val Asn
        35                  40                  45
Ser Val Gly Gln Ala Lys Arg Lys Gly Tyr Lys Arg Leu Lys Ser Ser
    50                  55                  60
Cys Lys Arg His Pro Leu Tyr Asn Ser Lys Pro Lys Ala Cys Cys
65                  70                  75                  80
Val Pro Thr Glu Leu Ser Ala Pro Ser Pro Leu Tyr Leu Asp Glu Asn
                85                  90                  95
Glu Lys Pro Val Leu Lys Asn Tyr Gln Asp Met Val Val His Gly Cys
            100                 105                 110
Gly Cys Arg
        115
```

<210> SEQ ID NO 301
<211> LENGTH: 25
<212> TYPE: DNA
<213> ORGANISM: artificial sequence
<220> FEATURE:
<223> OTHER INFORMATION: Primer

<400> SEQUENCE: 301
ttaaccatgg tggatttcaa ggacg                                        25

<210> SEQ ID NO 302
<211> LENGTH: 25
<212> TYPE: DNA
<213> ORGANISM: artificial sequence
<220> FEATURE:
<223> OTHER INFORMATION: Primer

<400> SEQUENCE: 302
gtttggcttg gccaacagaa ttaac                                        25

<210> SEQ ID NO 303
<211> LENGTH: 25
<212> TYPE: DNA
<213> ORGANISM: artificial sequence
<220> FEATURE:
<223> OTHER INFORMATION: Primer

<400> SEQUENCE: 303
gttaattctg ttggccaagc caaac                                        25

<210> SEQ ID NO 304
<211> LENGTH: 25
<212> TYPE: DNA
<213> ORGANISM: artificial sequence
<220> FEATURE:
<223> OTHER INFORMATION: Primer

<400> SEQUENCE: 304
gatctttgct attgtacaaa gggtg                                        25

<210> SEQ ID NO 305
<211> LENGTH: 25
<212> TYPE: DNA
<213> ORGANISM: artificial sequence
<220> FEATURE:
<223> OTHER INFORMATION: Primer

<400> SEQUENCE: 305
caccctttgt acaatagcaa agatc                                              25

<210> SEQ ID NO 306
<211> LENGTH: 25
<212> TYPE: DNA
<213> ORGANISM: artificial sequence
<220> FEATURE:
<223> OTHER INFORMATION: Primer

<400> SEQUENCE: 306
ggatccttag cgacacccac accca                                              25

<210> SEQ ID NO 307
<211> LENGTH: 345
<212> TYPE: DNA
<213> ORGANISM: artificial sequence
<220> FEATURE:
<223> OTHER INFORMATION: pQE-80L-Kana derivative PCR fusion product

<400> SEQUENCE: 307
aatagcaaag atcccaaggc atgctgtgtc ccgacagaac tcagtgcccc cagcccgctg         60
taccttgacg agaatgagaa gcctgtactc aagaactatc aggacatggt agtccatggg        120
tgtgggtgtc gcggccaagc caaacgcaaa gggtataaac gccttaagtc cagctgtaag        180 agacacccctt tgtacgtgga tttcaaggac gttgggtgga atgaccatgc tgtggcaccg       240
ccggggtatc acgccttcta ttgccacgga gaatgcccgt tcccactggc tgatcatctg       300
aactcagata accatgccat tgttcagacc aaggttaatt ctgtt                       345

<210> SEQ ID NO 308
<211> LENGTH: 115
<212> TYPE: PRT
<213> ORGANISM: artificial sequence
<220> FEATURE:
<223> OTHER INFORMATION: pQE-80L-Kana derivative PCR fusion product

<400> SEQUENCE: 308

Asn Ser Lys Asp Pro Lys Ala Cys Cys Val Pro Thr Glu Leu Ser Ala
1               5                  10                  15

Pro Ser Pro Leu Tyr Leu Asp Glu Asn Glu Lys Pro Val Leu Lys Asn
            20                  25                  30

Tyr Gln Asp Met Val Val His Gly Cys Gly Cys Arg Gly Gln Ala Lys
        35                  40                  45

Arg Lys Gly Tyr Lys Arg Leu Lys Ser Ser Cys Lys Arg His Pro Leu
    50                  55                  60

Tyr Val Asp Phe Lys Asp Val Gly Trp Asn Asp His Ala Val Ala Pro
65                  70                  75                  80

Pro Gly Tyr His Ala Phe Tyr Cys His Gly Glu Cys Pro Phe Pro Leu
                85                  90                  95

Ala Asp His Leu Asn Ser Asp Asn His Ala Ile Val Gln Thr Lys Val
            100                 105                 110

Asn Ser Val
        115

```
<210> SEQ ID NO 309
<211> LENGTH: 25
<212> TYPE: DNA
<213> ORGANISM: artificial sequence
<220> FEATURE:
<223> OTHER INFORMATION: Primer

<400> SEQUENCE: 309
ttaaccatga atagcaaaga tccca                                           25

<210> SEQ ID NO 310
<211> LENGTH: 25
<212> TYPE: DNA
<213> ORGANISM: artificial sequence
<220> FEATURE:
<223> OTHER INFORMATION: Primer

<400> SEQUENCE: 310
gtttggcttg gccgcgacac ccaca                                           25

<210> SEQ ID NO 311
<211> LENGTH: 25
<212> TYPE: DNA
<213> ORGANISM: artificial sequence
<220> FEATURE:
<223> OTHER INFORMATION: Primer

<400> SEQUENCE: 311
tgtgggtgtc gcggccaagc caaac                                           25

<210> SEQ ID NO 312
<211> LENGTH: 25
<212> TYPE: DNA
<213> ORGANISM: artificial sequence
<220> FEATURE:
<223> OTHER INFORMATION: Primer

<400> SEQUENCE: 312
ccttgaaatc cacgtacaaa gggtg                                           25

<210> SEQ ID NO 313
<211> LENGTH: 25
<212> TYPE: DNA
<213> ORGANISM: artificial sequence
<220> FEATURE:
<223> OTHER INFORMATION: Primer

<400> SEQUENCE: 313
caccctttgt acgtggattt caagg                                           25

<210> SEQ ID NO 314
<211> LENGTH: 25
<212> TYPE: DNA
<213> ORGANISM: artificial sequence
<220> FEATURE:
<223> OTHER INFORMATION: Primer

<400> SEQUENCE: 314
ggatccttaa acagaattaa ccttg                                           25

<210> SEQ ID NO 315
<211> LENGTH: 345
<212> TYPE: DNA
<213> ORGANISM: artificial sequence
<220> FEATURE:
<223> OTHER INFORMATION: pQE-80L-Kana derivative PCR fusion product
```

-continued

<400> SEQUENCE: 315

```
aatagcaaag atcccaaggc atgctgtgtc ccgacagaac tcagtgcccc cagcccgctg      60
taccttgacg agaatgagaa gcctgtactc aagaactatc aggacatggt agtccatggg     120
tgtgggtgtc gcgtggattt caaggacgtt gggtggaatg accatgctgt ggcaccgccg     180
gggtatcacg ccttctattg ccacggagaa tgcccgttcc cactggctga tcatctgaac     240
tcagataacc atgccattgt tcagaccaag gttaattctg ttggccaagc caaacgcaaa     300
gggtataaac gccttaagtc cagctgtaag agacacccct tgtac                     345
```

<210> SEQ ID NO 316
<211> LENGTH: 115
<212> TYPE: PRT
<213> ORGANISM: artificial sequence
<220> FEATURE:
<223> OTHER INFORMATION: pQE-80L-Kana derivative PCR fusion product

<400> SEQUENCE: 316

```
Asn Ser Lys Asp Pro Lys Ala Cys Cys Val Pro Thr Glu Leu Ser Ala
 1               5                  10                  15

Pro Ser Pro Leu Tyr Leu Asp Glu Asn Glu Lys Pro Val Leu Lys Asn
            20                  25                  30

Tyr Gln Asp Met Val Val His Gly Cys Gly Cys Arg Val Asp Phe Lys
        35                  40                  45

Asp Val Gly Trp Asn Asp His Ala Val Ala Pro Pro Gly Tyr His Ala
    50                  55                  60

Phe Tyr Cys His Gly Glu Cys Pro Phe Pro Leu Ala Asp His Leu Asn
65                  70                  75                  80

Ser Asp Asn His Ala Ile Val Gln Thr Lys Val Asn Ser Val Gly Gln
                85                  90                  95

Ala Lys Arg Lys Gly Tyr Lys Arg Leu Lys Ser Ser Cys Lys Arg His
            100                 105                 110

Pro Leu Tyr
        115
```

<210> SEQ ID NO 317
<211> LENGTH: 25
<212> TYPE: DNA
<213> ORGANISM: artificial sequence
<220> FEATURE:
<223> OTHER INFORMATION: Primer

<400> SEQUENCE: 317

```
ttaaccatga atagcaaaga tccca                                            25
```

<210> SEQ ID NO 318
<211> LENGTH: 25
<212> TYPE: DNA
<213> ORGANISM: artificial sequence
<220> FEATURE:
<223> OTHER INFORMATION: Primer

<400> SEQUENCE: 318

```
cttgaaatcc acgcgacacc cacac                                            25
```

<210> SEQ ID NO 319
<211> LENGTH: 25
<212> TYPE: DNA
<213> ORGANISM: artificial sequence
<220> FEATURE:

<223> OTHER INFORMATION: Primer

<400> SEQUENCE: 319
gtgtgggtgt cgcgtggatt tcaag								25

<210> SEQ ID NO 320
<211> LENGTH: 25
<212> TYPE: DNA
<213> ORGANISM: artificial sequence
<220> FEATURE:
<223> OTHER INFORMATION: Primer

<400> SEQUENCE: 320
gtttggcttg gccaacagaa ttaac								25

<210> SEQ ID NO 321
<211> LENGTH: 25
<212> TYPE: DNA
<213> ORGANISM: artificial sequence
<220> FEATURE:
<223> OTHER INFORMATION: Primer

<400> SEQUENCE: 321
gttaattctg ttggccaagc caaac								25

<210> SEQ ID NO 322
<211> LENGTH: 25
<212> TYPE: DNA
<213> ORGANISM: artificial sequence
<220> FEATURE:
<223> OTHER INFORMATION: Primer

<400> SEQUENCE: 322
ggatccttag tacaaagggt gtctc								25

<210> SEQ ID NO 323
<211> LENGTH: 345
<212> TYPE: DNA
<213> ORGANISM: artificial sequence
<220> FEATURE:
<223> OTHER INFORMATION: pQE-80L-Kana derivative PCR fusion product

<400> SEQUENCE: 323
gctcaagcca aacacaaaca gcggaaacgc cttaagtcca gctgtaagag acaccctttg      60
tacgtggatt tcaaggacgt tgggtggaat gaccatgctg tggcaccgcc ggggtatcac     120
gccttctatt gccacggaga atgcccgttc ccactggctg atcatctgaa ctcagataac     180
catgccattg ttcagaccaa ggttaattct gttaactcta agattcctaa ggcatgctgt     240
gtcccgacag aactcagtgc tatctcgatg ctgtaccttg acgagaatga aaaggttgta     300
ttaaagaact atcaggacat ggttgtggag ggttgtgggt gtcgc                    345

<210> SEQ ID NO 324
<211> LENGTH: 115
<212> TYPE: PRT
<213> ORGANISM: artificial sequence
<220> FEATURE:
<223> OTHER INFORMATION: pQE-80L-Kana derivative PCR fusion product

<400> SEQUENCE: 324

Ala Gln Ala Lys His Lys Gln Arg Lys Arg Leu Lys Ser Ser Cys Lys
1               5                   10                  15

Arg His Pro Leu Tyr Val Asp Phe Lys Asp Val Gly Trp Asn Asp His
            20                  25                  30

```
Ala Val Ala Pro Gly Tyr His Ala Phe Tyr Cys His Gly Glu Cys
        35                  40                  45

Pro Phe Pro Leu Ala Asp His Leu Asn Ser Asp Asn His Ala Ile Val
    50                  55                  60

Gln Thr Lys Val Asn Ser Val Asn Ser Lys Ile Pro Lys Ala Cys Cys
65                  70                  75                  80

Val Pro Thr Glu Leu Ser Ala Ile Ser Met Leu Tyr Leu Asp Glu Asn
                85                  90                  95

Glu Lys Val Val Leu Lys Asn Tyr Gln Asp Met Val Val Glu Gly Cys
            100                 105                 110

Gly Cys Arg
        115

<210> SEQ ID NO 325
<211> LENGTH: 24
<212> TYPE: DNA
<213> ORGANISM: artificial sequence
<220> FEATURE:
<223> OTHER INFORMATION: Primer

<400> SEQUENCE: 325
ttaaccatgg ctcaagccaa acac                                      24

<210> SEQ ID NO 326
<211> LENGTH: 24
<212> TYPE: DNA
<213> ORGANISM: artificial sequence
<220> FEATURE:
<223> OTHER INFORMATION: Primer

<400> SEQUENCE: 326
cttgaaatcc acgtacaaag ggtg                                      24

<210> SEQ ID NO 327
<211> LENGTH: 24
<212> TYPE: DNA
<213> ORGANISM: artificial sequence
<220> FEATURE:
<223> OTHER INFORMATION: Primer

<400> SEQUENCE: 327
caccctttgt acgtggattt caag                                      24

<210> SEQ ID NO 328
<211> LENGTH: 25
<212> TYPE: DNA
<213> ORGANISM: artificial sequence
<220> FEATURE:
<223> OTHER INFORMATION: Primer

<400> SEQUENCE: 328
gaatcttaga gttaacagaa ttaag                                     25

<210> SEQ ID NO 329
<211> LENGTH: 25
<212> TYPE: DNA
<213> ORGANISM: artificial sequence
<220> FEATURE:
<223> OTHER INFORMATION: Primer

<400> SEQUENCE: 329
gttaattctg ttaactctaa gattc                                     25
```

```
<210> SEQ ID NO 330
<211> LENGTH: 25
<212> TYPE: DNA
<213> ORGANISM: artificial sequence
<220> FEATURE:
<223> OTHER INFORMATION: Primer

<400> SEQUENCE: 330
ggatccttag cgacacccac aaccc                                          25

<210> SEQ ID NO 331
<211> LENGTH: 345
<212> TYPE: DNA
<213> ORGANISM: artificial sequence
<220> FEATURE:
<223> OTHER INFORMATION: pQE-80L-Kana derivative PCR fusion product

<400> SEQUENCE: 331
ggccaagcca acgcaaagg gtataaacgc cttaagtcca gctgtaagag acacccttg       60 tacgtggact tcagtgacgt ggggtggaat gactggattg tggctccccc ggggtatcac    120 gcctttact gccacggaga atgccctttt cctctggctg atcatctgaa ctccactaat     180
catgccattg ttcagacgtt ggtcaactct gttaatagca aagatcccaa ggcatgctgt    240
gtcccgacag aactcagtgc ccccagcccg ctgtaccttg acgagaatga aagcctgta     300 ctcaagaact atcaggacat ggtagtccat gggtgtgggt gtcgc                   345

<210> SEQ ID NO 332
<211> LENGTH: 115
<212> TYPE: PRT
<213> ORGANISM: artificial sequence
<220> FEATURE:
<223> OTHER INFORMATION: pQE-80L-Kana derivative PCR fusion product

<400> SEQUENCE: 332

Gly Gln Ala Lys Arg Lys Gly Tyr Lys Arg Leu Lys Ser Ser Cys Lys
1               5                   10                  15

Arg His Pro Leu Tyr Val Asp Phe Ser Asp Val Gly Trp Asn Asp Trp
            20                  25                  30

Ile Val Ala Pro Pro Gly Tyr His Ala Phe Tyr Cys His Gly Glu Cys
        35                  40                  45

Pro Phe Pro Leu Ala Asp His Leu Asn Ser Thr Asn His Ala Ile Val
    50                  55                  60

Gln Thr Leu Val Asn Ser Val Asn Ser Lys Asp Pro Lys Ala Cys Cys
65                  70                  75                  80

Val Pro Thr Glu Leu Ser Ala Pro Ser Pro Leu Tyr Leu Asp Glu Asn
                85                  90                  95

Glu Lys Pro Val Leu Lys Asn Tyr Gln Asp Met Val Val His Gly Cys
            100                 105                 110

Gly Cys Arg
        115

<210> SEQ ID NO 333
<211> LENGTH: 24
<212> TYPE: DNA
<213> ORGANISM: artificial sequence
<220> FEATURE:
<223> OTHER INFORMATION: Primer

<400> SEQUENCE: 333
ttaaccatgg gccaagccaa acgc                                           24
```

<210> SEQ ID NO 334
<211> LENGTH: 24
<212> TYPE: DNA
<213> ORGANISM: artificial sequence
<220> FEATURE:
<223> OTHER INFORMATION: Primer

<400> SEQUENCE: 334
actgaagtcc acgtacaaag ggtc                                         24

<210> SEQ ID NO 335
<211> LENGTH: 24
<212> TYPE: DNA
<213> ORGANISM: artificial sequence
<220> FEATURE:
<223> OTHER INFORMATION: Primer

<400> SEQUENCE: 335
caccctttgt acgtggactt cagt                                         24

<210> SEQ ID NO 336
<211> LENGTH: 25
<212> TYPE: DNA
<213> ORGANISM: artificial sequence
<220> FEATURE:
<223> OTHER INFORMATION: Primer

<400> SEQUENCE: 336
gatctttgct attaacagag ttgac                                        25

<210> SEQ ID NO 337
<211> LENGTH: 25
<212> TYPE: DNA
<213> ORGANISM: artificial sequence
<220> FEATURE:
<223> OTHER INFORMATION: Primer

<400> SEQUENCE: 337
gtcaactctg ttaatagcaa agatc                                        25

<210> SEQ ID NO 338
<211> LENGTH: 25
<212> TYPE: DNA
<213> ORGANISM: artificial sequence
<220> FEATURE:
<223> OTHER INFORMATION: Primer

<400> SEQUENCE: 338
ggatccttag cgacacccac accca                                        25

<210> SEQ ID NO 339
<211> LENGTH: 345
<212> TYPE: DNA
<213> ORGANISM: artificial sequence
<220> FEATURE:
<223> OTHER INFORMATION: pQE-80L-Kana derivative PCR fusion product

<400> SEQUENCE: 339
gctcaagcca aacacaaaca gcggaaacgc ttaagtcca gctgtaagag acaccctttg    60
tacaatagca agatcccaa ggcatgctgt gtcccgacag aactcagtgc ccccagcccg   120
ctgtaccttg acgagaatga gaagcctgta ctcaagaact atcaggacat ggtagtccat   180
gggtgtgggt gtcgcgtgga tttcaaggac gttgggtgga atgaccatgc tgtggcaccg   240

```
ccggggtatc acgccttcta ttgccacgga gaatgcccgt tcccactggc tgatcatctg    300
aactcagata accatgccat tgttcagacc aaggttaatt ctgtt                    345
```

<210> SEQ ID NO 340
<211> LENGTH: 115
<212> TYPE: PRT
<213> ORGANISM: artificial sequence
<220> FEATURE:
<223> OTHER INFORMATION: pQE-80L-Kana derivative PCR fusion product

<400> SEQUENCE: 340

```
Ala Gln Ala Lys His Lys Gln Arg Lys Arg Leu Lys Ser Ser Cys Lys
1               5                   10                  15

Arg His Pro Leu Tyr Asn Ser Lys Asp Pro Lys Ala Cys Cys Val Pro
            20                  25                  30

Thr Glu Leu Ser Ala Pro Ser Pro Leu Tyr Leu Asp Glu Asn Glu Lys
        35                  40                  45

Pro Val Leu Lys Asn Tyr Gln Asp Met Val Val His Gly Cys Gly Cys
    50                  55                  60

Arg Val Asp Phe Lys Asp Val Gly Trp Asn Asp His Ala Val Ala Pro
65                  70                  75                  80

Pro Gly Tyr His Ala Phe Tyr Cys His Gly Glu Cys Pro Phe Pro Leu
                85                  90                  95

Ala Asp His Leu Asn Ser Asp Asn His Ala Ile Val Gln Thr Lys Val
            100                 105                 110

Asn Ser Val
        115
```

<210> SEQ ID NO 341
<211> LENGTH: 25
<212> TYPE: DNA
<213> ORGANISM: artificial sequence
<220> FEATURE:
<223> OTHER INFORMATION: Primer

<400> SEQUENCE: 341

```
ttaaccatgg ctcaagccaa acaca                                          25
```

<210> SEQ ID NO 342
<211> LENGTH: 25
<212> TYPE: DNA
<213> ORGANISM: artificial sequence
<220> FEATURE:
<223> OTHER INFORMATION: Primer

<400> SEQUENCE: 342

```
gatctttgct attgtacaaa gggtg                                          25
```

<210> SEQ ID NO 343
<211> LENGTH: 25
<212> TYPE: DNA
<213> ORGANISM: artificial sequence
<220> FEATURE:
<223> OTHER INFORMATION: Primer

<400> SEQUENCE: 343

```
cacccttttgt acaatagcaa agatc                                         25
```

<210> SEQ ID NO 344
<211> LENGTH: 25
<212> TYPE: DNA
<213> ORGANISM: artificial sequence

```
<220> FEATURE:
<223> OTHER INFORMATION: Primer

<400> SEQUENCE: 344
cttgaaatcc acgcgacacc cacac                                      25

<210> SEQ ID NO 345
<211> LENGTH: 25
<212> TYPE: DNA
<213> ORGANISM: artificial sequence
<220> FEATURE:
<223> OTHER INFORMATION: Primer

<400> SEQUENCE: 345
gtgtgggtgt cgcgtggatt tcaag                                      25

<210> SEQ ID NO 346
<211> LENGTH: 25
<212> TYPE: DNA
<213> ORGANISM: artificial sequence
<220> FEATURE:
<223> OTHER INFORMATION: Primer

<400> SEQUENCE: 346
ggatccttaa acagaattaa ccttg                                      25

<210> SEQ ID NO 347
<211> LENGTH: 345
<212> TYPE: DNA
<213> ORGANISM: artificial sequence
<220> FEATURE:
<223> OTHER INFORMATION: pQE-80L-Kana derivative PCR fusion product

<400> SEQUENCE: 347
ggccaagcca aacgcaaagg gtataaacgc cttaagtcca gctgtaagag acaccctttg    60
tacaactcta agattcctaa ggcatgctgt gtcccgacag aactcagtgc tatctcgatg   120
ctgtaccttg acgagaatga aaaggttgta ttaaagaact atcaggacat ggttgtggag   180
ggttgtgggt gtcgcgtgga cttcagtgac gtggggtgga atgactggat tgtggctccc   240
ccggggtatc acgcctttta ctgccacgga gaatgccctt ttcctctggc tgatcatctg   300
aactccacta atcatgccat tgttcagacg ttggtcaact ctgtt                  345

<210> SEQ ID NO 348
<211> LENGTH: 115
<212> TYPE: PRT
<213> ORGANISM: artificial sequence
<220> FEATURE:
<223> OTHER INFORMATION: pQE-80L-Kana derivative PCR fusion product

<400> SEQUENCE: 348

Gly Gln Ala Lys Arg Lys Gly Tyr Lys Arg Leu Lys Ser Ser Cys Lys
1               5                   10                  15

Arg His Pro Leu Tyr Asn Ser Lys Ile Pro Lys Ala Cys Cys Val Pro
            20                  25                  30

Thr Glu Leu Ser Ala Ile Ser Met Leu Tyr Leu Asp Glu Asn Glu Lys
        35                  40                  45

Val Val Leu Lys Asn Tyr Gln Asp Met Val Val Glu Gly Cys Gly Cys
    50                  55                  60

Arg Val Asp Phe Ser Asp Val Gly Trp Asn Asp Trp Ile Val Ala Pro
65                  70                  75                  80

Pro Gly Tyr His Ala Phe Tyr Cys His Gly Glu Cys Pro Phe Pro Leu
```

```
                85                  90                  95
Ala Asp His Leu Asn Ser Thr Asn His Ala Ile Val Gln Thr Leu Val
            100                 105                 110

Asn Ser Val
        115
```

<210> SEQ ID NO 349
<211> LENGTH: 24
<212> TYPE: DNA
<213> ORGANISM: artificial sequence
<220> FEATURE:
<223> OTHER INFORMATION: Primer

<400> SEQUENCE: 349
ttaaccatgg gccaagccaa acgc                                      24

<210> SEQ ID NO 350
<211> LENGTH: 25
<212> TYPE: DNA
<213> ORGANISM: artificial sequence
<220> FEATURE:
<223> OTHER INFORMATION: Primer

<400> SEQUENCE: 350
gaatcttaga gttgtacaaa gggtg                                     25

<210> SEQ ID NO 351
<211> LENGTH: 25
<212> TYPE: DNA
<213> ORGANISM: artificial sequence
<220> FEATURE:
<223> OTHER INFORMATION: Primer

<400> SEQUENCE: 351
caccctttgt acaactctaa gattc                                     25

<210> SEQ ID NO 352
<211> LENGTH: 25
<212> TYPE: DNA
<213> ORGANISM: artificial sequence
<220> FEATURE:
<223> OTHER INFORMATION: Primer

<400> SEQUENCE: 352
tcactgaagt ccacgcgaca cccac                                     25

<210> SEQ ID NO 353
<211> LENGTH: 25
<212> TYPE: DNA
<213> ORGANISM: artificial sequence
<220> FEATURE:
<223> OTHER INFORMATION: Primer

<400> SEQUENCE: 353
gtgggtgtcg cgtggacttc agtga                                     25

<210> SEQ ID NO 354
<211> LENGTH: 25
<212> TYPE: DNA
<213> ORGANISM: artificial sequence
<220> FEATURE:
<223> OTHER INFORMATION: Primer

<400> SEQUENCE: 354
ggatccttaa acagagttga ccaac                                     25

```
<210> SEQ ID NO 355
<211> LENGTH: 58
<212> TYPE: PRT
<213> ORGANISM: artificial sequence
<220> FEATURE:
<223> OTHER INFORMATION: pQE-80L-Kana derivative

<400> SEQUENCE: 355

Thr Ala Leu Asp Gly Thr Arg Gly Ala Gln Gly Ser Gly Gly Gly
1               5                   10                  15

Gly Gly Gly Gly Gly Gly Gly Gly Gly Gly Gly Gly Gly Gly Gly
            20                  25                  30

Ala Gly Arg Gly His Gly Arg Arg Gly Arg Ser Arg Cys Ser Arg Lys
            35                  40                  45

Ser Leu His Val Asp Phe Lys Glu Leu Gly
        50                  55

<210> SEQ ID NO 356
<211> LENGTH: 9
<212> TYPE: PRT
<213> ORGANISM: artificial sequence
<220> FEATURE:
<223> OTHER INFORMATION: third domain fragment of recombinant
      polypeptide

<400> SEQUENCE: 356

Pro Lys Ala Cys Cys Val Pro Thr Glu
1               5

<210> SEQ ID NO 357
<211> LENGTH: 5
<212> TYPE: PRT
<213> ORGANISM: artificial sequence
<220> FEATURE:
<223> OTHER INFORMATION: third domain fragment of recombinant
      polypeptide

<400> SEQUENCE: 357

Gly Cys Gly Cys Arg
1               5
```

RECOMBINANT POLYPEPTIDES AND NUCLEIC ACID MOLECULES, COMPOSITIONS, AND METHODS OF MAKING AND USES THEREOF

REFERENCE TO SEQUENCE LISTING SUBMITTED ELECTRONICALLY

The content of the electronically submitted sequence listing (Name: 3902.001PC01_SeqListing_ST25.txt, Size: 134,451 bytes; and Date of Creation: Dec. 21, 2017) submitted in this application is incorporated herein by reference in its entirety.

BACKGROUND

Bone is a highly rigid tissue that constitutes part of the vertebral skeleton with unique mechanical properties derived from its extensive matrix structure. Throughout the life of animals, bone tissue is continuously renewed.

Processes of bone formation and renewal are carried out by specialized cells. Osteogenesis (bone formation or growth of bone) is carried out by "osteoblasts" (bone-forming cells). Bone remodeling occurs through an interplay between the activities of bone-resorbing cells called "osteoclasts" and the bone-forming osteoblasts. Since these processes are carried out by specialized living cells, chemical (for example, pharmaceutical and/or hormonal), physical, and physicochemical alterations can affect the quality, quantity, and shaping of bone tissue.

A variety of growth factors (for example, PDGF) as well as cytokines are involved in bone formation processes. It is thus valuable to identify physiologically acceptable chemical agents (for example, hormones, pharmaceuticals, growth factors, and cytokines) that can induce the formation of bone at a predetermined site. However, for the chemical agents to be successfully used as therapeutic tools, several hurdles need to be overcome. One hurdle includes developing recombinant polypeptides that have osteoinductive activity. For example, osteoinductive activity in recombinant human platelet-derived growth factor-BB has not been demonstrated. Another hurdle is osteoinductive variability in chemical agents. For example, demineralized bone matrix (DBM) is a chemical agent that is an osteoinductive allograft derived from processed bone. An increasing number of DBM-based products are commercially available, but osteoinductive variability has been found across different products and among production lots for the same product. Thus, there is a need for chemical agents, such as recombinant polypeptides and associated compositions, that demonstrate consistent osteoinductive activity.

BRIEF SUMMARY

The present disclosure is directed to a recombinant polypeptide comprising: a first domain selected from the group consisting of SEQ ID NO: 35 and SEQ ID NO: 39; a second domain selected from the group consisting of SEQ ID NO: 47 and SEQ ID NO: 49; and a third domain selected from the group consisting of SEQ ID NO: 57 and SEQ ID NO: 61; wherein the second domain comprises an intramolecular disulfide bond.

In certain embodiments, the second domain of the recombinant polypeptide comprises an intramolecular disulfide bond between the twenty-third amino acid of the second domain and the twenty-seventh amino acid of the second domain.

In certain embodiments, the recombinant polypeptide is capable of inducing alkaline phosphatase activity.

In certain embodiments, the third domain of the recombinant polypeptide comprises a first amino acid sequence of PKACCVPTE (SEQ ID NO: 356) and a second amino acid sequence of GCGCR (SEQ ID NO: 357), wherein the third domain comprises two intramolecular disulfide bonds between the first and second amino acid sequences.

In certain embodiments, the recombinant polypeptide comprises a first intramolecular disulfide bond between the fourth amino acid of the first amino acid sequence and the second amino acid of the second amino acid sequence, and a second intramolecular disulfide bond between the fifth amino acid of the first amino acid sequence and the fourth amino acid of the second amino acid sequence.

In certain embodiments, the recombinant polypeptide comprises a first intramolecular disulfide bond between the fifth amino acid of the first amino acid sequence and the second amino acid of the second amino acid sequence, and a second intramolecular disulfide bond between the fourth amino acid of the first amino acid sequence and the fourth amino acid of the second amino acid sequence.

In certain embodiments, the recombinant polypeptide is selected from the group consisting of: SEQ ID NO: 260, SEQ ID NO: 268, SEQ ID NO: 276, SEQ ID NO: 284, SEQ ID NO: 292, SEQ ID NO: 300, SEQ ID NO: 308, SEQ ID NO: 316, SEQ ID NO: 324, SEQ ID NO: 332, SEQ ID NO: 340, and SEQ ID NO: 348.

The present disclosure is directed to a homodimeric protein comprising two identical recombinant polypeptides of any of the above recombinant polypeptides, wherein the homodimeric protein comprises an intermolecular disulfide bond between the first domains of the two recombinant polypeptides.

In certain embodiments, the homodimeric protein comprises an intermolecular disulfide bond between the fifteenth amino acid in the first domain of one recombinant polypeptide and the fifteenth amino acid in the first domain of the other recombinant polypeptide.

In certain embodiments, the third domain of each recombinant polypeptide of the homodimeric protein comprises a first amino acid sequence of PKACCVPTE (SEQ ID NO: 356) and a second amino acid sequence of GCGCR (SEQ ID NO: 357), and the homodimeric protein comprises two intermolecular disulfide bonds between the first amino acid sequence in the third domain of one recombinant polypeptide and the second amino acid sequence in the third domain of the other recombinant polypeptide. In certain embodiments, the homodimeric protein comprises a first intermolecular disulfide bond between the fourth amino acid of the first amino acid sequence of the one recombinant polypeptide and the second amino acid of the second amino acid sequence of the other recombinant polypeptide, and a second intermolecular disulfide bond between the fifth amino acid of the first amino acid sequence of the one recombinant polypeptide and the fourth amino acid of the second amino acid sequence of the other recombinant polypeptide. In certain embodiments, the homodimeric protein comprises a first intermolecular disulfide bond between the fifth amino acid of the first amino acid sequence of the one recombinant polypeptide and the second amino acid of the second amino acid sequence of the other recombinant polypeptide, and a second intermolecular disulfide bond between the fourth amino acid of the first amino acid sequence of the one recombinant polypeptide and the fourth amino acid of the second amino acid sequence of the other recombinant polypeptide.

The present disclosure is directed to a heterodimeric protein comprising two different recombinant polypeptides of any of the above recombinant polypeptides, wherein the heterodimeric protein comprises an intermolecular disulfide bond between the first domains of the two different recombinant polypeptides.

In certain embodiments, the heterodimeric protein comprises an intermolecular disulfide bond between the fifteenth amino acid in the first domain of one recombinant polypeptide and the fifteenth amino acid in the first domain of the other recombinant polypeptide.

The present disclosure is directed to an isolated nucleic acid molecule comprising a polynucleotide sequence encoding any of the above recombinant polypeptides.

The present disclosure is directed to a recombinant nucleic acid molecule comprising an expression control region operably linked to the above isolated nucleic acid molecule.

The present disclosure is directed to an isolated host cell comprising the above isolated nucleic acid molecule or the above recombinant nucleic acid molecule.

The present disclosure is directed to a method of making a recombinant vector comprising inserting the above isolated nucleic acid molecule into a vector.

The present disclosure is directed to a method of making a recombinant host cell comprising introducing the above isolated nucleic acid molecule or the above recombinant nucleic acid molecule into a host cell.

The present disclosure is directed to a method of producing a recombinant polypeptide, comprising: culturing the above isolated host cell, and isolating the recombinant polypeptide.

The present disclosure is directed to a composition comprising any of the above recombinant polypeptides, any of the above homodimeric proteins, or any of the above heterodimeric proteins.

The present disclosure is directed to a biodegradable composition, comprising: any of the above homodimeric proteins, being able to induce bone growth to form a bone mass in a location; and a biodegradable calcium phosphate carrier with pores that extend throughout the biodegradable calcium phosphate carrier, wherein the homodimeric protein is in an effective amount of from about 0.03 mg/g to about 3.2 mg/g of the biodegradable calcium phosphate carrier and porosity of the biodegradable calcium phosphate carrier is more than 70% with pore size from about 300 μm to about 600 μm. In certain embodiments, the biodegradable composition is suitable for augmentation of a tissue selected from the group consisting of: nasal furrows, frown lines, midfacial tissue, jaw-line, chin, cheeks, and combinations thereof. In certain embodiments, the location is selected from the group consisting of: a long-bone fracture defect, a space between two adjacent vertebra bodies, a non-union bone defect, maxilla osteotomy incision, mandible osteotomy incision, sagittal split osteotomy incision, genioplasty osteotomy incision, rapid palatal expansion osteotomy incision, a space extending lengthwise between two adjacent transverse processes of two adjacent vertebrae, and combinations thereof. In certain embodiments, a single dose of the homodimeric protein is from about 0.006 mg to about 15 mg. In certain embodiments, the biodegradable calcium phosphate carrier hardens so as to be impermeable to efflux of the homodimeric protein in vivo sufficiently that the formed bone mass is confined to the volume of the biodegradable calcium phosphate carrier.

The present disclosure is directed to a sustained release composition, comprising a calcium phosphate carrier, a biodegradable matrix, and any of the above homodimeric proteins. In certain embodiments, the calcium phosphate carrier is selected from the group consisting of: tricalcium phosphate (TCP), alpha-tricalcium phosphate (α-TCP), beta-tricalcium phosphate (β-TCP), biphasic calcium phosphate (BCP), and combinations thereof. In certain embodiments, the biodegradable matrix is selected from the group consisting of: polylactic acid (PLA), polyglycolic acid (PGA), polylactic-co-glycolic acid (PLGA), Polyvinyl alcohol (PVA), and combinations thereof. In certain embodiments, the sustained release composition comprises: (a) about 2-11% (w/w) of the calcium phosphate carrier; (b) about 88-97% (w/w) of the biodegradable matrix; and (c) about 0.017-0.039% (w/w) of the homodimeric protein.

The present disclosure is directed to a moldable composition for filling an osseous void, comprising: a moldable matrix comprising about 90% to about 99.5% by weight of the moldable composition; and any of the above homodimeric proteins, wherein less than about 25% by percentage of the homodimeric protein is released from the moldable composition after about 1, 24, 48, 72, 168, 240 or about 336 hours post implantation.

The present disclosure is directed to a spinal fusion device comprising any of the above biodegradable compositions; and a spinal fusion cage, configured to retain the biodegradable calcium phosphate carrier.

The present disclosure is directed to a method of promoting healing of a long-bone fracture in a subject in need of such treatment, comprising: preparing a composition including any of the above homodimeric proteins homogeneously entrained within a slow release biodegradable calcium phosphate carrier that hardens so as to be impermeable to efflux of the homodimeric protein in vivo sufficiently that the long-bone fracture healing is confined to the volume of the calcium phosphate carrier; and implanting the composition at a location where the long-bone fracture occurs, wherein the homodimeric protein is in an amount of from about 0.03 mg/g to about 3.2 mg/g of the calcium phosphate carrier. In certain embodiments, the method of promoting healing of a long-bone fracture further comprises gradually exposing the entrained homodimeric protein at the location as the calcium phosphate carrier degrades, wherein the calcium phosphate carrier has a calcium to phosphate ratio of about 0.4 to about 1.8.

The present disclosure is directed to a method for promoting spinal fusion, comprising: exposing an upper vertebra and a lower vertebra; identifying a site for fusion between the upper and the lower vertebra; exposing a bone surface on each of the upper and the lower vertebra at the site for fusion; and administering any of the above homodimeric proteins and a biodegradable calcium phosphate carrier to the site. In certain embodiments, the biodegradable calcium phosphate carrier is a non-compressible delivery vehicle, and wherein the non-compressible delivery vehicle is for application to the site between the two bone surfaces where bone growth is desired but does not naturally occur. In certain embodiments, the biodegradable calcium phosphate carrier comprises at least one implantation stick for application to the site such that the implantation stick extends lengthwise between the upper and the lower vertebrae. In certain embodiments, the site is selected from a space between two adjacent vertebra bodies, and a space extending lengthwise between two adjacent transverse processes of two adjacent vertebrae.

The present disclosure is directed to a method for promoting arthrodesis, comprising administering any of the above homodimeric proteins and a biodegradable calcium phosphate carrier to a malformed or degenerated joint. In certain embodiments, administering the homodimeric protein includes administering from about 0.006 mg to about 10.5 mg of the homodimeric protein to the malformed or degenerated joint.

The present disclosure is directed to a method of generating a bone mass to fuse two adjacent vertebrae bodies in a spine of a subject in need, comprising: preparing a composition for generating the bone mass, the composition including any of the above homodimeric proteins homogeneously entrained within a slow release biodegradable carrier that hardens so as to be impermeable to efflux of the homodimeric protein in vivo sufficiently that the formed bone mass is confined to the volume of the slow release biodegradable carrier; and introducing the composition in a location between the two adjacent vertebrae bodies, and wherein the slow release biodegradable carrier gradually exposes the entrained homodimeric protein at the location as the slow release biodegradable carrier degrades, and further wherein the homodimeric protein is in an amount of from about 0.2 mg/site to about 10.5 mg/site of the location. In certain embodiments, the slow release biodegradable carrier has a porous structure, wherein cells from the two adjacent vertebrae migrate into the porous structure so as to generate the bone mass. In certain embodiments, the slow release biodegradable carrier has an initial volume, and the bone mass replaces the initial volume of the slow release biodegradable carrier as the slow release biodegradable carrier is resorbed.

The present disclosure is directed to a method for fusing adjacent vertebrae bodies in a subject in need by a posterior or transforaminal fusion approach, comprising: preparing a disc space for receipt of an intervertebral disc implant in an intervertebral space between the adjacent vertebrae; introducing a slow-release carrier into the intervertebral disc implant, wherein any of the above homodimeric proteins is in an amount of from about 0.2 mg/site to about 10.5 mg/site of the slow-release carrier; and introducing the intervertebral disc implant in the disc space between the adjacent vertebrae for generating a bone mass in the disc space.

BRIEF DESCRIPTION OF THE DRAWINGS

FIGS. 4-9 show, from left to right in each figure, radiographs taken post-operatively, at 4 weeks, and at 12 weeks (harvest) from Groups 1-6, respectively. Groups 1-6 are designated in FIGS. 4-9 as "2179," "2192," "2187," "2160," "2162," and "2166," respectively.

DETAILED DESCRIPTION

Figure 1A:
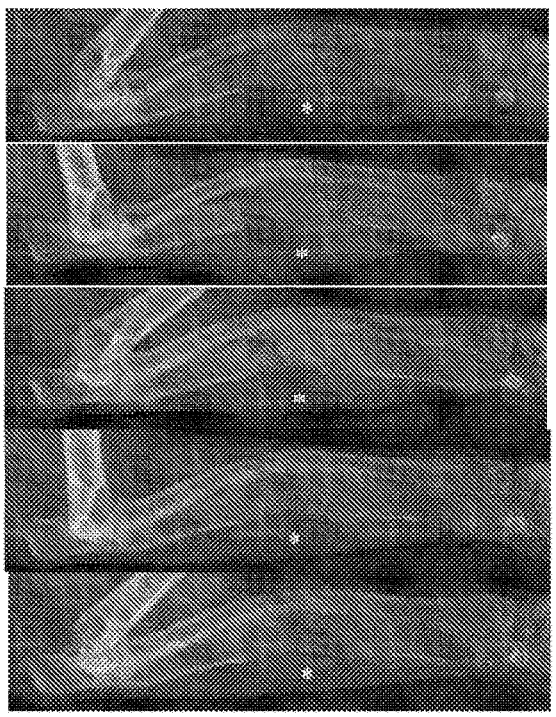
FIGS. 1A to 1B show representative X-ray images of female rabbit (strain NZW) ulnae for experimental Groups A-G. The ulna in each experimental group contained a surgically created 20 mm-sized circumferential defect (i.e., a defect site). For Groups A-F, implants were made into the defect sites. The ulna in each of Groups A-E received an implant of 200 mg β-TCP. The β-TCP in Groups A, B, C, and D served as a carrier for 2, 6, 20, and 60 g, respectively, of a homodimeric protein including two recombinant polypeptides (i.e., SEQ ID NO:260, including intramolecular disulfide bond C44-C48). The β-TCP in Group E did not carry any recombinant polypeptide. Group F received an autograft implant of iliac bone fragments. Group G did not receive any implant into the defect site. X-ray images were taken for each of Groups A-G at: 0 weeks (i.e., immediately after surgery, "0 W") and at 2, 4, 6, and 8 weeks after surgery (i.e., "2 W," "4 W," "6 W," and "8 W," respectively). The site of the implant (Groups A-F) or the defect site (Group G) in the ulna is located immediately above the white asterisk in each image.
Figure 1A:
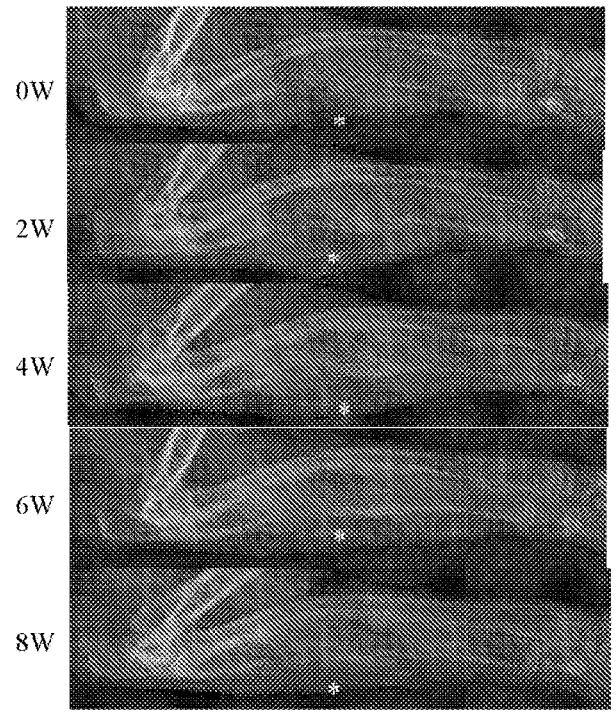
Figure 1A:
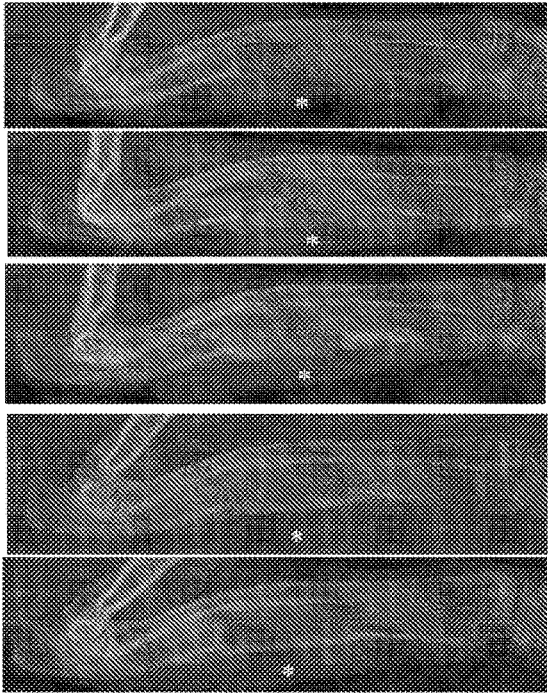
Figure 1A:
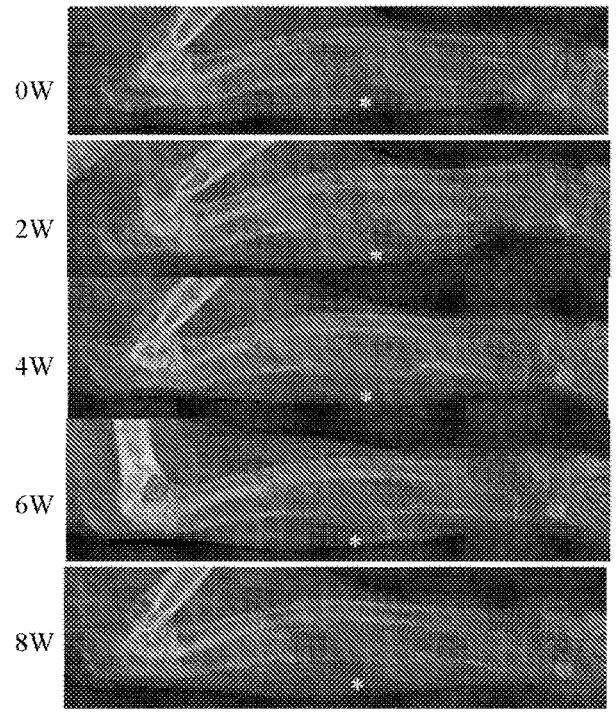

Provided herein are recombinant polypeptides, homodimeric and heterodimeric proteins comprising the recombinant polypeptides, nucleic acid molecules and vectors encoding the recombinant polypeptides, and host cells for expressing the recombinant polypeptides. The present disclosure also provides compositions of the recombinant polypeptides and methods of making and using the recombinant polypeptides.

All publications cited herein are hereby incorporated by reference in their entireties, including without limitation all journal articles, books, manuals, patent applications, and patents cited herein, to the same extent as if each individual publication was specifically and individually indicated to be incorporated by reference.

Terminology

Unless defined otherwise, all technical and scientific terms used herein have the same meaning as commonly understood to one of ordinary skill in the art to which this disclosure belongs. As used throughout the instant application, the following terms shall have the following meanings.

As used herein and in the appended claims, the singular forms "a," "an," and "the" include plural referents unless the context dictates otherwise. Thus, for example, reference to "a domain" includes a domain or a plurality of such domains and reference to "the recombinant polypeptide" includes reference to one or more recombinant polypeptides, and so forth. The terms "a", "an," "the," "one or more," and "at least one," for example, can be used interchangeably herein.

The use of "or" means "and/or" unless stated otherwise. Similarly, "comprise," "comprises," "comprising" "include," "includes," and "including" are interchangeable and not intended to be limiting.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

"Amino acid" is a molecule having the structure wherein a central carbon atom (the alpha-carbon atom) is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R. When incorporated into a peptide, polypeptide, or protein, an amino acid loses one or more atoms of its amino acid carboxylic groups in the dehydration reaction that links one amino acid to another. As a result, when incorporated into a protein, an amino acid is referred to as an "amino acid residue."

"Protein" or "polypeptide" refers to any polymer of two or more individual amino acids (whether or not naturally occurring) linked via a peptide bond, and occurs when the carboxyl carbon atom of the carboxylic acid group bonded to the alpha-carbon of one amino acid (or amino acid residue) becomes covalently bound to the amino nitrogen atom of amino group bonded to the non alpha-carbon of an adjacent amino acid. The term "protein" is understood to include the terms "polypeptide" and "peptide" (which, at times may be used interchangeably herein) within its meaning. In addition, proteins comprising multiple polypeptide subunits (e.g., DNA polymerase III, RNA polymerase II) or other components (for example, an RNA molecule, as occurs in telomerase) will also be understood to be included within the meaning of "protein" as used herein. Similarly, fragments of proteins and polypeptides are also within the scope of the disclosure and may be referred to herein as "proteins." In one aspect of the disclosure, a polypeptide comprises a chimera of two or more parental peptide segments. The term "polypeptide" is also intended to refer to and encompass the products of post-translation modification ("PTM") of the polypeptide, including without limitation disulfide bond formation, glycosylation, carbamylation, lipidation, acetylation, phosphorylation, amidation, derivatization by known protecting/blocking groups, proteolytic cleavage, modification by non-naturally occurring amino acids, or any other manipulation or modification, such as conjugation with a labeling component. A polypeptide can be derived from a natural biological source or produced by recombinant technology, but is not necessarily translated from a designated nucleic acid sequence. It can be generated in any manner, including by chemical synthesis. An "isolated" polypeptide or a fragment, variant, or derivative thereof refers to a polypeptide that is not in its natural milieu. No particular level of purification is required. For example, an isolated polypeptide can simply be removed from its native or natural environment. Recombinantly produced polypeptides and proteins expressed in host cells are considered isolated for the purpose of the disclosure, as are native or recombinant polypeptides which have been separated, fractionated, or partially or substantially purified by any suitable technique.

"Domain" as used herein can be used interchangeably with the term "peptide segment" and refers to a portion or fragment of a larger polypeptide or protein. A domain need not on its own have functional activity, although in some instances, a domain can have its own biological activity.

A particular amino acid sequence of a given protein (i.e., the polypeptide's "primary structure" when written from the amino-terminus to the carboxyl-terminus) is determined by the nucleotide sequence of the coding portion of a mRNA, which is in turn specified by genetic information, typically genomic DNA (including organelle DNA, e.g., mitochondrial or chloroplast DNA). Thus, determining the sequence of a gene assists in predicting the primary sequence of a corresponding polypeptide and more particular the role or activity of the polypeptide or proteins encoded by that gene or polynucleotide sequence.

"N-terminal" as used herein refers to position or location of an amino acid, domain, or peptide segment within a polypeptide in relation to the amino-terminus of the polypeptide. For example, "domain A is N-terminal to domains B and C" means that domain A is located closer to the amino-terminus than domains B and C, such that the order of domains in the polypeptide from the amino-terminus is understood to be either A-B-C or A-C-B when the locations of domains B and C are not otherwise specified. Additionally, any number of amino acids, including none, can be present between a domain that is N-terminal to another domain. Similarly, any number of amino acids, including none, can be present between the N-terminus of the polypeptide and a domain that is N-terminal the other domains in the polypeptide.

"C-terminal" as used herein refers to position or location of an amino acid, domain, or peptide segment within a polypeptide in relation to the carboxyl-terminus of the polypeptide. For example, "domain A is C-terminal to domains B and C" means that domain A is located closer to the carboxyl-terminus than domains B and C, such that the order of domains in the polypeptide from the amino-terminus is understood to be either B-C-A or C-B-A when the locations of domains B and C are not otherwise specified. Additionally, any number of amino acids, including none, can be present between a domain that is C-terminal to another domain. Similarly, any number of amino acids, including none, can be present between the C-terminus of the polypeptide and a domain that is C-terminal the other domains in the polypeptide.

"Fused," "operably linked," and "operably associated" are used interchangeably herein when referring to two or more domains to broadly refer to any chemical or physical coupling of the two or more domains in the formation of a recombinant polypeptide as disclosed herein. In one embodiment, a recombinant polypeptide as disclosed herein is a chimeric polypeptide comprising a plurality of domains from two or more different polypeptides.

Recombinant polypeptides comprising two or more domains as disclosed herein can be encoded by a single coding sequence that comprises polynucleotide sequences encoding each domain. Unless stated otherwise, the polynucleotide sequences encoding each domain are "in frame" such that translation of a single mRNA comprising the polynucleotide sequences results in a single polypeptide comprising each domain. Typically, the domains in a recombinant polypeptide as described herein will be fused directly to one another or will be separated by a peptide linker. Various polynucleotide sequences encoding peptide linkers are known in the art.

"Polynucleotide" or "nucleic acid" as used herein refers to a polymeric form of nucleotides. In some instances, a polynucleotide comprises a sequence that is either not immediately contiguous with the coding sequences or is immediately contiguous (on the 5' end or on the 3' end) with the coding sequences in the naturally occurring genome of the organism from which it is derived. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA) independent of other sequences. The nucleotides of the disclosure can be ribonucleotides, deoxyribonucleotides, or modified forms of either nucleotide. A polynucleotide as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The term polynucleotide encompasses genomic DNA or RNA (depending upon the organism, i.e., RNA genome of viruses), as well as mRNA encoded by the genomic DNA, and cDNA. In certain embodiments, a polynucleotide comprises a conventional phosphodiester bond or a non-conventional bond (e.g., an amide bond, such as found in peptide nucleic acids (PNA)). By "isolated" nucleic acid or polynucleotide is intended a nucleic acid molecule, e.g., DNA or RNA, which has been removed from its native environment. For example, a nucleic acid molecule comprising a polynucleotide encoding a recombinant polypeptide contained in a vector is considered "isolated" for the purposes of the present disclosure. Further examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present disclosure. Isolated polynucleotides or nucleic acids according to the present disclosure further include polynucleotides and nucleic acids (e.g., nucleic acid molecules) produced synthetically.

As used herein, a "coding region" or "coding sequence" is a portion of a polynucleotide, which consists of codons translatable into amino acids. Although a "stop codon" (TAG, TGA, or TAA) is typically not translated into an amino acid, it may be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino-terminus of the resultant polypeptide, and a translation stop codon at the 3' terminus, encoding the carboxyl-terminus of the resulting polypeptide.

As used herein, the term "expression control region" refers to a transcription control element that is operably associated with a coding region to direct or control expression of the product encoded by the coding region, including, for example, promoters, enhancers, operators, repressors, ribosome binding sites, translation leader sequences, introns, polyadenylation recognition sequences, RNA processing sites, effector binding sites, stem-loop structures, and transcription termination signals. For example, a coding region and a promoter are "operably associated" if induction of promoter function results in the transcription of mRNA comprising a coding region that encodes the product, and if the nature of the linkage between the promoter and the coding region does not interfere with the ability of the promoter to direct the expression of the product encoded by the coding region or interfere with the ability of the DNA template to be transcribed. Expression control regions include nucleotide sequences located upstream (5' non-coding sequences), within, or downstream (3' non-coding sequences) of a coding region, and which influence the transcription, RNA processing, stability, or translation of the associated coding region. If a coding region is intended for expression in a eukaryotic cell, a polyadenylation signal and transcription termination sequence will usually be located 3' to the coding sequence.

"Nucleic acid segment," "oligonucleotide segment" or "polynucleotide segment" refers to a portion of a larger polynucleotide molecule. The polynucleotide segment need not correspond to an encoded functional domain of a protein; however, in some instances the segment will encode a functional domain of a protein. A polynucleotide segment can be about 6 nucleotides or more in length (e.g., 6-20, 20-50, 50-100, 100-200, 200-300, 300-400 or more nucleotides in length).

A "vector" refers to any vehicle for the cloning of and/or transfer of a nucleic acid molecule into a host cell. The term "vector" includes both viral and nonviral vehicles (e.g., plasmid, phage, cosmid, virus) for introducing the nucleic acid into a cell in vitro, ex vivo or in vivo.

As used herein, the terms "host cell" and "cell" can be used interchangeably and can refer to any type of cell or a population of cells, e.g., a primary cell, a cell in culture, or a cell from a cell line, that harbors or is capable of harboring a nucleic acid molecule (e.g., a recombinant nucleic acid molecule). Host cells can be a prokaryotic cell, or alternatively, the host cells can be eukaryotic, for example, fungal cells, such as yeast cells, and various animal cells, such as insect cells or mammalian cells.

"Culture," "to culture" and "culturing," as used herein, means to incubate cells under in vitro conditions that allow for cell growth or division or to maintain cells in a living state. "Cultured cells," as used herein, means cells that are propagated in vitro.

"Osteoinductive" as used herein refers to the induction of bone and/or cartilage formation or growth, including, for example, the induction of a marker associated with bone and/or cartilage formation or growth (e.g., the induction of alkaline phosphatase activity).

"Yeast two-hybrid assay" or "yeast two-hybrid system" is used interchangeably herein and refers to an assay or system for the detection of interactions between protein pairs. In a typical two-hybrid screening assay/system, a transcription factor is split into two separate fragments, the binding domain (BD) and the activation domain (AD), each of which is provided on a separate plasmid, and each of which is fused to a protein of interest. The yeast two-hybrid assay system comprises (i) a "bait" vector, comprising a bait protein and the BD of the transcription factor utilized in the system; (ii) a "prey" vector, comprising a prey protein (or a library of prey proteins to be screened for interaction with the bait protein) and the AD of the transcription factor; and (iii) a suitable reporter yeast strain containing the binding sequence for the BD of the transcription factor used in the system. When the bait-prey interaction occurs, the AD of the transcription factor drives the expression of one or more reporter proteins. The bait and prey vectors are introduced into the reporter yeast strain, wherein the expressed bait and prey proteins may interact. Alternatively, separate haploid yeast strains each containing either a bait vector or a prey vector can be mated and the resulting diploid yeast strain expresses both proteins. Interacting bait and prey protein pairs result in the reconstitution and activation of the transcription factor, which then binds to its compatible activation domain provided in the reporter yeast strain, which in turn triggers the expression of the reporter gene, which may then be detected.

Recombinant Polypeptides and Compositions

The present disclosure is directed to a recombinant polypeptide comprising any two or more domains selected from the group consisting of SEQ ID NOs: 33, 35, 37, 39, 41, 43, 45, 47, 49, 51, 53, 55, 57, 59, 61, 63, 65, 67, 69, 71, 73, 75, 77, and 355, including, without limitation, any of the combinations of two domains disclosed in Table 3 herein. In certain embodiments, the recombinant polypeptide comprises any three of the domains, including, without limitation to, any of the combinations of three domains disclosed in Table 3, herein.

Any domain of a recombinant polypeptide as described herein can be located at any position with respect to the amino-terminus or carboxyl-terminus of the recombinant polypeptide. For example, any domain of a recombinant polypeptide as disclosed herein can be located N-terminal to any one or more other domains in the recombinant polypeptide. Similarly, any domain of a recombinant polypeptide as disclosed here can be located C-terminal to any one or more other domains in the recombinant polypeptide.

The present disclosure is directed to a recombinant polypeptide comprising any two or more domains selected from the group consisting SEQ ID NOs: 33, 35, 37, 39, 41, 43, 45, 47, 49, 51, 53, 55, 57, 59, 61, 63, 65, 67, 69, 71, 73, 75, 77, and 355 that has a higher affinity for the extracellular domain of activin receptor IIB protein (i.e., ActRIIBecd) than any of the individual domains in the recombinant polypeptide. Nucleic acid sequences and polypeptide sequences of ActRIIB and naturally occurring variants are known. For example, ActRIIBecd can be SEQ ID NO: 9 as disclosed herein, which corresponds to residues 27-117 of SEQ ID NO: 8 as disclosed herein. Affinity can be as measured, e.g., by a radioimmunoassay (RIA), surface plasmon resonance, such as BIAcore™, or any other binding assay known in the art. In some embodiments, such recombinant polypeptides include the combination of two domains, wherein either of the two domains is located N-terminal or C-terminal to the other domain, selected from the following combinations of domains: SEQ ID NO: 39 and SEQ ID NO: 49, SEQ ID NO: 49 and SEQ ID NO: 61, SEQ ID NO: 61 and SEQ ID NO:39, SEQ ID NO: 35 and SEQ ID NO: 47, SEQ ID NO: 57 and SEQ ID NO: 35, and SEQ ID NO: 57 and SEQ ID NO: 47. In some embodiments, such combination of two domains yields a recombinant polypeptide comprising a sequence selected from the group consisting of: SEQ ID NOs: 188, 194, 200, 206, 212, 218, 224, 230, 236, 242, 248, and 254. In some embodiments, such recombinant polypeptides include the combination of three domains, wherein any domain is located N-terminal or C-terminal to one or both of the other domains, selected from the following combinations of domains: SEQ ID NOs: 39, 49, and 61; SEQ ID NOs: 35, 47, and 57; SEQ ID NOs: 39, 47, and 61; SEQ ID NOs: 35, 49, and 57; SEQ ID NOs: 39, 57, and 47; and SEQ ID NOs: 35, 61, and 49. In some embodiments, such combination of three domains yields a recombinant polypeptide comprising a sequence selected from the group consisting of: SEQ ID NOs: 260, 268, 276, 284, 292, 300, 308, 316, 324, 332, 340, and 348.

The present disclosure is directed to a recombinant polypeptide comprising a first domain of SEQ ID NO: 39, a second domain of SEQ ID NO: 49, and a third domain of SEQ ID NO: 61, wherein the first domain is located C-terminal to the second domain, the third domain is located N-terminal to the second domain, or a combination thereof. In certain embodiments, the recombinant polypeptide comprises a first domain selected from the group consisting of SEQ ID NO: 35 and SEQ ID NO: 39, a second domain selected from the group consisting of SEQ ID NO: 47 and SEQ ID NO: 49, and a third domain selected from the group consisting of SEQ ID NO: 57 and SEQ ID NO: 61, wherein the first domain is located C-terminal to the second domain, the third domain is located N-terminal to the second domain, or a combination thereof when the first, second, and third domains are SEQ ID NOs: 39, 49, and 61, respectively.

In certain embodiments, a recombinant polypeptide as described herein comprises a post-translation modification ("PTM"), including without limitation disulfide bond formation, glycosylation, carbamylation, lipidation, acetylation, phosphorylation, amidation, derivatization by known protecting/blocking groups, proteolytic cleavage, modification by non-naturally occurring amino acids, or any other manipulation or modification, such as conjugation with a labeling component.

In certain embodiments, a recombinant polypeptide can include one or more cysteines capable of participating in formation of one or more disulfide bonds under physiological conditions or any other standard condition (e.g., purification conditions or storage conditions). In certain embodiments, a disulfide bond is an intramolecular disulfide bond formed between two cysteine residues in the recombinant polypeptide. In certain embodiments, a disulfide bond is an intermolecular disulfide bond formed between two recombinant polypeptides in a dimer. In certain embodiments, an intermolecular disulfide bond is formed between two identical recombinant polypeptides as described herein, wherein the two identical recombinant polypeptides form a homodimer. In certain embodiments, a homodimer includes at least one or more than three intermolecular disulfide bonds. In certain embodiments, an intermolecular disulfide bond is formed between two different recombinant polypeptides as described herein, wherein the two different recombinant polypeptides form a heterodimer. In certain embodiments, a heterodimer includes at least one or more than three intermolecular disulfide bonds.

The present disclosure is directed to a recombinant polypeptide comprising a first domain selected from the group consisting of SEQ ID NO: 35 and SEQ ID NO: 39, a second domain selected from the group consisting of SEQ ID NO: 47 and SEQ ID NO: 49, and a third domain selected from the group consisting of SEQ ID NO: 57 and SEQ ID NO: 61, wherein the recombinant polypeptide comprises an intramolecular disulfide bond.

In certain embodiments, the first domain, second domain, third domain, or combinations thereof comprise an intramolecular disulfide bond. In certain embodiments, one or more intramolecular disulfide bonds are within a single domain, are between one domain and another domain, are between one domain with more than two cysteines and one or more other domains, or a combination thereof. In certain embodiments, the first domain comprises a disulfide bond. In certain embodiments, the second domain comprises a disulfide bond. In certain embodiments, the third domain comprises a disulfide bond. In certain embodiments, each domain comprises a disulfide bond. "Domain comprises a disulfide bond" as used herein when referring to an intramolecular disulfide bond refers to a disulfide bond between two cysteines in a single domain when more than one cysteine is present in a domain or between a cysteine in one domain and a cysteine in another domain.

In certain embodiments, the second domain of a recombinant polypeptide as described herein comprises an intramolecular disulfide bond between the twenty-third amino acid of the second domain and the twenty-seventh amino acid of the second domain. In certain embodiments, the recombinant polypeptide further comprises one or more additional intramolecular disulfide bonds between the first domain and the third domain, within the third domain, or both. In certain embodiments, the recombinant polypeptide further comprises an intramolecular disulfide bond between the ninth amino acid of the third domain and the forty-third amino acid of the third domain, between the eighth amino acid of the third domain and the forty-first amino acid of the third domain, between the eighth amino acid of the third domain and the forty-third amino acid of the third domain, or between the ninth amino acid of the third domain and the forty-first amino acid of the third domain. In certain embodiments, the recombinant polypeptide further comprises a disulfide bond between the ninth amino acid of the third domain and the forty-third amino acid of the third domain, and a disulfide bond between the eighth amino acid of the third domain and the forty-first amino acid of the third domain. In certain embodiments, the recombinant polypeptide further comprises a disulfide bond between the eighth amino acid of the third domain and the forty-third amino acid of the third domain, and a disulfide bond between the ninth amino acid of the third domain and the forty-first amino acid of the third domain.

In certain embodiments, the third domain of a recombinant polypeptide as described herein comprises a first amino acid sequence of PKACCVPTE (SEQ ID NO: 356) and a second amino acid sequence of GCGCR (SEQ ID NO: 357), wherein the third domain comprises either two intramolecular disulfide bonds or two intermolecular disulfide bonds between the first and second amino acid sequences. In certain embodiments, the recombinant polypeptide comprises a first intramolecular or intermolecular disulfide bond between the fourth amino acid of the first amino acid sequence and the second amino acid of the second amino acid sequence, and a second intramolecular or intermolecular disulfide bond between the fifth amino acid of the first amino acid sequence and the fourth amino acid of the second amino acid sequence. In certain embodiments, the recombinant polypeptide comprises a first intramolecular or intermolecular disulfide bond between the fifth amino acid of the first amino acid sequence and the second amino acid of the second amino acid sequence, and a second intramolecular or intermolecular disulfide bond between the fourth amino acid of the first amino acid sequence and the fourth amino acid of the second amino acid sequence. In certain embodiments, the recombinant polypeptide further comprises an intramolecular disulfide bond between the twenty-third amino acid of the second domain and the twenty-seventh amino acid of the second domain.

The present disclosure is directed to a recombinant polypeptide comprising an amino acid sequence selected from the group consisting of: SEQ ID NO: 260, SEQ ID NO: 268, SEQ ID NO: 276, SEQ ID NO: 284, SEQ ID NO: 292, SEQ ID NO: 300, SEQ ID NO: 308, SEQ ID NO: 316, SEQ ID NO: 324, SEQ ID NO: 332, SEQ ID NO: 340, and SEQ ID NO: 348, wherein the recombinant polypeptide comprises an intramolecular disulfide bond.

In certain embodiments, the intramolecular disulfide bond comprises one or more disulfide bonds comprising cysteine 15, cysteine 44, cysteine 48, cysteine 79, cysteine 80, cysteine 112, cysteine 114, and combinations thereof, as numbered from the amino-terminus of a recombinant polypeptide selected from the group consisting of: SEQ ID NO: 260, SEQ ID NO:292, SEQ ID NO: 324, and SEQ ID NO: 332. In certain embodiments, the intramolecular disulfide bond comprises cysteine 44, cysteine 48, or both as numbered from the amino-terminus of a recombinant polypeptide selected from the group consisting of: SEQ ID NO: 260, SEQ ID NO:292, SEQ ID NO: 324, and SEQ ID NO: 332.

In certain embodiments, the intramolecular disulfide bond comprises one or more disulfide bonds comprising cysteine 15, cysteine 29, cysteine 30, cysteine 62, cysteine 64, cysteine 88, cysteine 92, and combinations thereof, as numbered from the amino-terminus of a recombinant polypeptide selected from the group consisting of: SEQ ID NO: 340 and SEQ ID NO: 348. In certain embodiments, the intramolecular disulfide bond comprises cysteine 88, cysteine 92, or both as numbered from the amino-terminus of a recombinant polypeptide selected from the group consisting of: SEQ ID NO: 340 and SEQ ID NO: 348.

In certain embodiments, the intramolecular disulfide bond comprises one or more disulfide bonds comprising cysteine 23, cysteine 27, cysteine 65, cysteine 79, cysteine 80, cysteine 112, cysteine 114, and combinations thereof, as numbered from the amino-terminus of a recombinant polypeptide selected from the group consisting of: SEQ ID NO: 268 and SEQ ID NO: 300. In certain embodiments, the intramolecular disulfide bond comprises cysteine 23, cysteine 27, or both as numbered from the amino-terminus of a recombinant polypeptide selected from the group consisting of: SEQ ID NO: 268 and SEQ ID NO: 300.

In certain embodiments, the intramolecular disulfide bond comprises one or more disulfide bonds comprising cysteine 8, cysteine 9, cysteine 41, cysteine 43, cysteine 59, cysteine 88, cysteine 92, and combinations thereof, as numbered from the amino-terminus of a recombinant polypeptide selected from the group consisting of: SEQ ID NO: 284 and SEQ ID NO: 308. In certain embodiments, the intramolecular disulfide bond comprises cysteine 88, cysteine 92, or both as numbered from the amino-terminus of a recombinant polypeptide selected from the group consisting of: SEQ ID NO: 284 and SEQ ID NO: 308.

In certain embodiments, the intramolecular disulfide bond comprises one or more disulfide bonds comprising cysteine 8, cysteine 9, cysteine 41, cysteine 43, cysteine 67, cysteine 71, cysteine 109, and combinations thereof, as numbered from the amino-terminus of a recombinant polypeptide selected from the group consisting of: SEQ ID NO: 276 and SEQ ID NO: 316. In certain embodiments, the intramolecular disulfide bond comprises cysteine 67, cysteine 71, or both as numbered from the amino-terminus of a recombinant polypeptide selected from the group consisting of: SEQ ID NO: 276 and SEQ ID NO: 316.

In certain embodiments, a recombinant polypeptide selected from the group consisting of: SEQ ID NO: 260, SEQ ID NO:292, SEQ ID NO: 324, and SEQ ID NO: 332 comprises an intramolecular disulfide bond between cysteine 44 and cysteine 48, as numbered from the amino-terminus of the recombinant polypeptide. In certain embodiments, the recombinant polypeptide further comprises either an intramolecular or intermolecular (i.e., in a dimer) disulfide bond between cysteine 79 and cysteine 112, between cysteine 80 and cysteine 114, between cysteine 80 and cysteine 112, or between cysteine 79 and cysteine 114. In certain embodiments, the recombinant polypeptide further comprises either an intramolecular or intermolecular disulfide bond between cysteine 79 and cysteine 112, and either an intramolecular or intermolecular disulfide bond between cysteine 80 and cysteine 114. In certain embodiments, the recombinant polypeptide further comprises either an intramolecular or intermolecular disulfide bond between cysteine 80 and cysteine 112, and either an intramolecular or intermolecular disulfide bond between cysteine 79 and cysteine 114.

In certain embodiments, a recombinant polypeptide selected from the group consisting of: SEQ ID NO: 340 and SEQ ID NO: 348 comprises an intramolecular disulfide bond between cysteine 88 and cysteine 92, as numbered from the amino-terminus of the recombinant polypeptide. In certain embodiments, the recombinant polypeptide further comprises either an intramolecular or intermolecular disulfide bond between cysteine 29 and cysteine 62, between cysteine 30 and cysteine 64, between cysteine 30 and cysteine 62, or between cysteine 29 and cysteine 64. In certain embodiments, the recombinant polypeptide further comprises either an intramolecular or intermolecular disulfide bond between cysteine 29 and cysteine 62, and either an intramolecular or intermolecular disulfide bond between cysteine 30 and cysteine 64. In certain embodiments, the recombinant polypeptide further comprises either an intramolecular or intermolecular disulfide bond between cysteine 30 and cysteine 62, and either an intramolecular or intermolecular disulfide bond between cysteine 29 and cysteine 64.

In certain embodiments, a recombinant polypeptide selected from the group consisting of: SEQ ID NO: 268 and SEQ ID NO: 300 comprises an intramolecular disulfide bond between cysteine 23 and cysteine 27, as numbered from the amino-terminus of the recombinant polypeptide. In certain embodiments, the recombinant polypeptide further comprises either an intramolecular or intermolecular disulfide bond between cysteine 79 and cysteine 112, between cysteine 80 and cysteine 114, between cysteine 80 and cysteine 112, or between cysteine 79 and cysteine 114. In certain embodiments, the recombinant polypeptide further comprises either an intramolecular or intermolecular disulfide bond between cysteine 79 and cysteine 112, and either an intramolecular or intermolecular disulfide bond between cysteine 80 and cysteine 114. In certain embodiments, the recombinant polypeptide further comprises either an intramolecular or intermolecular disulfide bond between cysteine 80 and cysteine 112, and either an intramolecular or intermolecular disulfide bond between cysteine 79 and cysteine 114.

In certain embodiments, a recombinant polypeptide selected from the group consisting of: SEQ ID NO: 284 and SEQ ID NO: 308 comprises an intramolecular disulfide bond between cysteine 88 and cysteine 92, as numbered from the amino-terminus of the recombinant polypeptide. In certain embodiments, the recombinant polypeptide further comprises either an intramolecular or intermolecular disulfide bond between cysteine 8 and cysteine 41, between cysteine 9 and cysteine 43, between cysteine 9 and cysteine 41, or between cysteine 8 and cysteine 43. In certain embodiments, the recombinant polypeptide further comprises either an intramolecular or intermolecular disulfide bond between cysteine 8 and cysteine 41, and either an intramolecular or intermolecular disulfide bond between cysteine 9 and cysteine 43. In certain embodiments, the recombinant polypeptide further comprises either an intramolecular or intermolecular disulfide bond between cysteine 9 and cysteine 41, and either an intramolecular or intermolecular disulfide bond between cysteine 8 and cysteine 43.

In certain embodiments, a recombinant polypeptide selected from the group consisting of: SEQ ID NO: 276 and SEQ ID NO: 316 comprises an intramolecular disulfide bond between cysteine 67 and cysteine 71, as numbered from the amino-terminus of the recombinant polypeptide. In certain embodiments, the recombinant polypeptide further comprises either an intramolecular or intermolecular disulfide bond between cysteine 8 and cysteine 41, between cysteine 9 and cysteine 43, between cysteine 9 and cysteine 41, or between cysteine 8 and cysteine 43. In certain embodiments, the recombinant polypeptide further comprises either an intramolecular or intermolecular disulfide bond between cysteine 8 and cysteine 41, and either an intramolecular or intermolecular disulfide bond between cysteine 9 and cysteine 43. In certain embodiments, the recombinant polypeptide further comprises either an intramolecular or intermolecular disulfide bond between cysteine 9 and cysteine 41, and either an intramolecular or intermolecular disulfide bond between cysteine 8 and cysteine 43.

The present disclosure is directed to a homodimeric protein comprising two identical recombinant polypeptides as described herein.

The present disclosure is directed to a heterodimeric protein comprising two different recombinant polypeptides as described herein.

In certain embodiments, a homodimeric protein or heterodimeric protein as described herein comprises one or more intermolecular disulfide bonds between the first domains of the two recombinant polypeptides, between the second domains of the two recombinant polypeptides, between the third domains of the two recombinant polypeptides, between the first and second domains of the two recombinant polypeptides, between the first and third domains of the two recombinant polypeptides, between the second and third domains of the two recombinant polypeptides, or combinations thereof.

In certain embodiments, a homodimeric or heterodimeric protein as described herein comprises an intermolecular disulfide bond between the fifteenth amino acid of the first domain of one recombinant polypeptide and the fifteenth amino acid of the first domain of the other recombinant polypeptide. In certain embodiments, the homodimeric or heterodimeric protein further comprises an intermolecular disulfide bond between the ninth amino acid of the third domain of one recombinant polypeptide and the forty-third amino acid of the third domain of the other recombinant polypeptide, between the eighth amino acid of the third domain of one recombinant polypeptide and the forty-first amino acid of the third domain of the other recombinant polypeptide, between the eighth amino acid of the third domain of one recombinant polypeptide and the forty-third amino acid of the third domain of the other recombinant polypeptide, or between the ninth amino acid of the third domain of one recombinant polypeptide and the forty-first amino acid of the third domain of the other recombinant polypeptide. In certain embodiments, the homodimeric or heterodimeric protein further comprises a disulfide bond between the ninth amino acid of the third domain of one recombinant polypeptide and the forty-third amino acid of the third domain of the other recombinant polypeptide, and a disulfide bond between the eighth amino acid of the third domain of one recombinant polypeptide and the forty-first amino acid of the third domain of the other recombinant polypeptide. In certain embodiments, the homodimeric or heterodimeric protein further comprises a disulfide bond between the eighth amino acid of the third domain of one recombinant polypeptide and the forty-third amino acid of the third domain of the other recombinant polypeptide, and a disulfide bond between the ninth amino acid of the third domain of one recombinant polypeptide and the forty-first amino acid of the third domain of the other recombinant polypeptide.

In certain embodiments, the homodimeric or heterodimeric protein comprises an intermolecular disulfide bond between one recombinant polypeptide and the other recombinant polypeptide, wherein the one recombinant polypeptide and the other recombinant polypeptide comprise the same sequence for a homodimeric protein and comprise different sequences for a heterodimeric protein, and wherein the location of the disulfide bond is: cysteine 15 when the one recombinant polypeptide and/or the other recombinant polypeptide is any of SEQ ID NOs: 260, 292, 324, 332, 340, or 348; cysteine 65 when the one recombinant polypeptide and/or the other recombinant polypeptide is SEQ ID NO: 268 or 300; cysteine 59 when the one recombinant polypeptide and/or the other recombinant polypeptide is SEQ ID NO: 284 or 308; and cysteine 109 when the one recombinant polypeptide and/or the other recombinant polypeptide is SEQ ID NO: 276 or 316, as numbered from the amino-terminus of the one and/or the other recombinant polypeptide. In certain embodiments, the homodimeric or heterodimeric protein further comprises an intermolecular disulfide bond: (a) between (1) the one recombinant polypeptide at cysteine 79 for any of SEQ ID NOs: 260, 292, 324, 332, 268, or 300, cysteine 29 for SEQ ID NOs: 340 or 348, or cysteine 8 for any of SEQ ID NOs: 284, 308, 276, or 316, and (2) the other recombinant polypeptide at cysteine 112 for any of SEQ ID NOs: 260, 292, 324, 332, 268, or 300, cysteine 62 for SEQ ID NOs: 340 or 348, or cysteine 41 for any of SEQ ID NOs: 284, 308, 276, or 316, (b) between (1) the one recombinant polypeptide at cysteine 80 for any of SEQ ID NOs: 260, 292, 324, 332, 268, or 300, cysteine 30 for SEQ ID NOs: 340 or 348, or cysteine 9 for any of SEQ ID NOs: 284, 308, 276, or 316, and (2) the other recombinant polypeptide at cysteine 114 for any of SEQ ID NOs: 260, 292, 324, 332, 268, or 300, cysteine 64 for SEQ ID NOs: 340 or 348, or cysteine 43 for any of SEQ ID NOs: 284, 308, 276, or 316, (c) between (1) the one recombinant polypeptide at cysteine 80 for any of SEQ ID NOs: 260, 292, 324, 332, 268, or 300, cysteine 30 for SEQ ID NOs: 340 or 348, or cysteine 9 for any of SEQ ID NOs: 284, 308, 276, or 316, and (2) the other recombinant polypeptide at cysteine 112 for any of SEQ ID NOs: 260, 292, 324, 332, 268, or 300, cysteine 62 for SEQ ID NOs: 340 or 348, or cysteine 41 for any of SEQ ID NOs: 284, 308, 276, or 316, or (d) between (1) the one recombinant polypeptide at cysteine 79 for any of SEQ ID NOs: 260, 292, 324, 332, 268, or 300, cysteine 29 for SEQ ID NOs: 340 or 348, or cysteine 8 for any of SEQ ID NOs: 284, 308, 276, or 316, and (2) the other recombinant polypeptide at cysteine 114 for any of SEQ ID NOs: 260, 292, 324, 332, 268, or 300, cysteine 64 for SEQ ID NOs: 340 or 348, or cysteine 43 for any of SEQ ID NOs: 284, 308, 276, or 316. In certain embodiments, the homodimeric or heterodimeric protein further comprises an intermolecular disulfide bond: (a) between (1) the one recombinant polypeptide at cysteine 79 for any of SEQ ID NOs: 260, 292, 324, 332, 268, or 300, cysteine 29 for SEQ ID NOs: 340 or 348, or cysteine 8 for any of SEQ ID NOs: 284, 308, 276, or 316, and (2) the other recombinant polypeptide at cysteine 112 for any of SEQ ID NOs: 260, 292, 324, 332, 268, or 300, cysteine 62 for SEQ ID NOs: 340 or 348, or cysteine 41 for any of SEQ ID NOs: 284, 308, 276, or 316, and (b) between (1) the one recombinant polypeptide at cysteine 80 for any of SEQ ID NOs: 260, 292, 324, 332, 268, or 300, cysteine 30 for SEQ ID NOs: 340 or 348, or cysteine 9 for any of SEQ ID NOs: 284, 308, 276, or 316, and (2) the other recombinant polypeptide at cysteine 114 for any of SEQ ID NOs: 260, 292, 324, 332, 268, or 300, cysteine 64 for SEQ ID NOs: 340 or 348, or cysteine 43 for any of SEQ ID NOs: 284, 308, 276, or 316. In certain embodiments, the homodimeric or heterodimeric protein further comprises an intermolecular disulfide bond: (a) between (1) the one recombinant polypeptide at cysteine 80 for any of SEQ ID NOs: 260, 292, 324, 332, 268, or 300, cysteine 30 for SEQ ID NOs: 340 or 348, or cysteine 9 for any of SEQ ID NOs: 284, 308, 276, or 316, and (2) the other recombinant polypeptide at cysteine 112 for any of SEQ ID NOs: 260, 292, 324, 332, 268, or 300, cysteine 62 for SEQ ID NOs: 340 or 348, or cysteine 41 for any of SEQ ID NOs: 284, 308, 276, or 316, and (b) between (1) the one recombinant polypeptide at cysteine 79 for any of SEQ ID NOs: 260, 292, 324, 332, 268, or 300, cysteine 29 for SEQ ID NOs: 340 or 348, or cysteine 8 for any of SEQ ID NOs: 284, 308, 276, or 316, and (2) the other recombinant polypeptide at cysteine 114 for any of SEQ ID NOs: 260, 292, 324, 332, 268, or 300, cysteine 64 for SEQ ID NOs: 340 or 348, or cysteine 43 for any of SEQ ID NOs: 284, 308, 276, or 316.

In certain embodiments, the homodimeric or heterodimeric protein comprises an intermolecular disulfide bond between the ninth amino acid of the third domain of one recombinant polypeptide and the forty-third amino acid of the third domain of the other recombinant polypeptide, between the eighth amino acid of the third domain of one recombinant polypeptide and the forty-first amino acid of the third domain of the other recombinant polypeptide, between the eighth amino acid of the third domain of one recombinant polypeptide and the forty-third amino acid of the third domain of the other recombinant polypeptide, or between the ninth amino acid of the third domain of one recombinant polypeptide and the forty-first amino acid of the third domain of the other recombinant polypeptide. In certain embodiments, the homodimeric or heterodimeric protein comprises a disulfide bond between the ninth amino acid of the third domain of one recombinant polypeptide and the forty-third amino acid of the third domain of the other recombinant polypeptide, and a disulfide bond between the eighth amino acid of the third domain of one recombinant polypeptide and the forty-first amino acid of the third domain of the other recombinant polypeptide. In certain embodiments, the homodimeric or heterodimeric protein comprises a disulfide bond between the eighth amino acid of the third domain of one recombinant polypeptide and the forty-third amino acid of the third domain of the other recombinant polypeptide, and a disulfide bond between the ninth amino acid of the third domain of one recombinant polypeptide and the forty-first amino acid of the third domain of the other recombinant polypeptide.

In certain embodiments, the homodimeric or heterodimeric protein comprises an intermolecular disulfide bond: (a) between (1) the one recombinant polypeptide at cysteine 79 for any of SEQ ID NOs: 260, 292, 324, 332, 268, or 300, cysteine 29 for SEQ ID NOs: 340 or 348, or cysteine 8 for any of SEQ ID NOs: 284, 308, 276, or 316, and (2) the other recombinant polypeptide at cysteine 112 for any of SEQ ID NOs: 260, 292, 324, 332, 268, or 300, cysteine 62 for SEQ ID NOs: 340 or 348, or cysteine 41 for any of SEQ ID NOs: 284, 308, 276, or 316, (b) between (1) the one recombinant polypeptide at cysteine 80 for any of SEQ ID NOs: 260, 292, 324, 332, 268, or 300, cysteine 30 for SEQ ID NOs: 340 or 348, or cysteine 9 for any of SEQ ID NOs: 284, 308, 276, or 316, and (2) the other recombinant polypeptide at cysteine 114 for any of SEQ ID NOs: 260, 292, 324, 332, 268, or 300, cysteine 64 for SEQ ID NOs: 340 or 348, or cysteine 43 for any of SEQ ID NOs: 284, 308, 276, or 316, (c) between (1) the one recombinant polypeptide at cysteine 80 for any of SEQ ID NOs: 260, 292, 324, 332, 268, or 300, cysteine 30 for SEQ ID NOs: 340 or 348, or cysteine 9 for any of SEQ ID NOs: 284, 308, 276, or 316, and (2) the other recombinant polypeptide at cysteine 112 for any of SEQ ID NOs: 260, 292, 324, 332, 268, or 300, cysteine 62 for SEQ ID NOs: 340 or 348, or cysteine 41 for any of SEQ ID NOs: 284, 308, 276, or 316, or (d) between (1) the one recombinant polypeptide at cysteine 79 for any of SEQ ID NOs: 260, 292, 324, 332, 268, or 300, cysteine 29 for SEQ ID NOs: 340 or 348, or cysteine 8 for any of SEQ ID NOs: 284, 308, 276, or 316, and (2) the other recombinant polypeptide at cysteine 114 for any of SEQ ID NOs: 260, 292, 324, 332, 268, or 300, cysteine 64 for SEQ ID NOs: 340 or 348, or cysteine 43 for any of SEQ ID NOs: 284, 308, 276, or 316. In certain embodiments, the homodimeric or heterodimeric protein further comprises an intermolecular disulfide bond: (a) between (1) the one recombinant polypeptide at cysteine 79 for any of SEQ ID NOs: 260, 292, 324, 332, 268, or 300, cysteine 29 for SEQ ID NOs: 340 or 348, or cysteine 8 for any of SEQ ID NOs: 284, 308, 276, or 316, and (2) the other recombinant polypeptide at cysteine 112 for any of SEQ ID NOs: 260, 292, 324, 332, 268, or 300, cysteine 62 for SEQ ID NOs: 340 or 348, or cysteine 41 for any of SEQ ID NOs: 284, 308, 276, or 316, and (b) between (1) the one recombinant polypeptide at cysteine 80 for any of SEQ ID NOs: 260, 292, 324, 332, 268, or 300, cysteine 30 for SEQ ID NOs: 340 or 348, or cysteine 9 for any of SEQ ID NOs: 284, 308, 276, or 316, and (2) the other recombinant polypeptide at cysteine 114 for any of SEQ ID NOs: 260, 292, 324, 332, 268, or 300, cysteine 64 for SEQ ID NOs: 340 or 348, or cysteine 43 for any of SEQ ID NOs: 284, 308, 276, or 316. In certain embodiments, the homodimeric or heterodimeric protein further comprises an intermolecular disulfide bond: (a) between (1) the one recombinant polypeptide at cysteine 80 for any of SEQ ID NOs: 260, 292, 324, 332, 268, or 300, cysteine 30 for SEQ ID NOs: 340 or 348, or cysteine 9 for any of SEQ ID NOs: 284, 308, 276, or 316, and (2) the other recombinant polypeptide at cysteine 112 for any of SEQ ID NOs: 260, 292, 324, 332, 268, or 300, cysteine 62 for SEQ ID NOs: 340 or 348, or cysteine 41 for any of SEQ ID NOs: 284, 308, 276, or 316, and (b) between (1) the one recombinant polypeptide at cysteine 79 for any of SEQ ID NOs: 260, 292, 324, 332, 268, or 300, cysteine 29 for SEQ ID NOs: 340 or 348, or cysteine 8 for any of SEQ ID NOs: 284, 308, 276, or 316, and (2) the other recombinant polypeptide at cysteine 114 for any of SEQ ID NOs: 260, 292, 324, 332, 268, or 300, cysteine 64 for SEQ ID NOs: 340 or 348, or cysteine 43 for any of SEQ ID NOs: 284, 308, 276, or 316.

In certain embodiments, the third domain of each recombinant polypeptide of a homodimeric or heterodimeric protein as described herein comprises a first amino acid sequence of PKACCVPTE (SEQ ID NO: 356) and a second amino acid sequence of GCGCR (SEQ ID NO: 357), wherein the homodimeric or heterodimeric protein comprises two intermolecular disulfide bonds between the first amino acid sequence in the third domain of one recombinant polypeptide and the second amino acid sequence in the third domain of the other recombinant polypeptide. In certain embodiments, the homodimeric or heterodimeric protein comprises a first intermolecular disulfide bond between the fourth amino acid of the first amino acid sequence of the one recombinant polypeptide and the second amino acid of the second amino acid sequence of the other recombinant polypeptide, and a second intermolecular disulfide bond between the fifth amino acid of the first amino acid sequence of the one recombinant polypeptide and the fourth amino acid of the second amino acid sequence of the other recombinant polypeptide. In certain embodiments, the homodimeric or heterodimeric protein comprises a first intermolecular disulfide bond between the fifth amino acid of the first amino acid sequence of the one recombinant polypeptide and the second amino acid of the second amino acid sequence of the other recombinant polypeptide, and a second intermolecular disulfide bond between the fourth amino acid of the first amino acid sequence of the one recombinant polypeptide and the fourth amino acid of the second amino acid sequence of the other recombinant polypeptide.

In certain embodiments, one or both of the recombinant polypeptides of a homodimeric or heterodimeric protein as described herein comprises any one or more of the intramolecular disulfide bonds as described herein.

In certain embodiments, the second domain of one or both of the recombinant polypeptides of a homodimeric or heterodimeric protein as described herein comprises an intramolecular disulfide bond. In certain embodiments, one or both of the recombinant polypeptides of a homodimeric or heterodimeric protein as described herein comprises an intramolecular disulfide bond between the twenty-third amino acid of the second domain and the twenty-seventh amino acid of the second domain.

In certain embodiments, one or both of the recombinant polypeptides of a homodimeric or heterodimeric protein as described herein comprises an intramolecular disulfide bond between cysteine 44 and cysteine 48 for any of SEQ ID NOs: 260, 292, 324, or 332, between cysteine 88 and cysteine 92 for any of SEQ ID NOs: 284, 308, 340, 348, between cysteine 23 and cysteine 27 for SEQ ID NOs: 268 or 300, or between cysteine 67 and cysteine 71 for SEQ ID NOs: 276 or 316, as numbered from the amino-terminus of the recombinant polypeptide.

In certain embodiments, a homodimeric protein as described herein comprises two recombinant polypeptides, wherein each polypeptide comprises the same sequence, and wherein the sequence is selected from the group consisting of: SEQ ID NO: 260, SEQ ID NO: 268, SEQ ID NO: 276, SEQ ID NO: 284, SEQ ID NO: 292, SEQ ID NO: 300, SEQ ID NO: 308, SEQ ID NO: 316, SEQ ID NO: 324, SEQ ID NO: 332, SEQ ID NO: 340, and SEQ ID NO: 348. In some embodiments, the recombinant polypeptides comprise identical intramolecular disulfide bonds as described herein. In some embodiments, the recombinant polypeptides comprise different intramolecular disulfide bonds as described herein.

In certain embodiments, a heterodimeric protein as described herein comprises two different recombinant polypeptides, wherein each polypeptide comprises a different sequence selected from the group consisting of: SEQ ID NO: 260, SEQ ID NO: 268, SEQ ID NO: 276, SEQ ID NO: 284, SEQ ID NO: 292, SEQ ID NO: 300, SEQ ID NO: 308, SEQ ID NO: 316, SEQ ID NO: 324, SEQ ID NO: 332, SEQ ID NO: 340, and SEQ ID NO: 348. In certain embodiments, one recombinant polypeptide in the heterodimeric protein comprises the sequence of SEQ ID NO: 260 and the other recombinant polypeptide comprises a sequence selected from the group consisting of: SEQ ID NO: 268, SEQ ID NO: 276, SEQ ID NO: 284, SEQ ID NO: 292, SEQ ID NO: 300, SEQ ID NO: 308, SEQ ID NO: 316, SEQ ID NO: 324, SEQ ID NO: 332, SEQ ID NO: 340, and SEQ ID NO: 348. In some embodiments, the recombinant polypeptides comprise identical intramolecular disulfide bonds as described herein. In some embodiments, the recombinant polypeptides comprise different intramolecular disulfide bonds as described herein.

In certain embodiments, a recombinant polypeptide, homodimeric protein, or heterodimeric protein as described herein comprises one or more of the disulfide bonds between cysteine pairs as listed in Table 4 or Table 5 herein.

In certain embodiments, a recombinant polypeptide, homodimeric protein, or heterodimeric protein as described herein comprises an osteoinductive activity. Osteoinductive activity can be measured under any conditions routinely practiced for measuring such activity (i.e., "osteoinductive conditions").

For example, C2C12 cells are a murine myoblast cell line from dystrophic mouse muscle. Exposure of C2C12 cells to a polypeptide with osteoinductive activity can shift C2C12 cell differentiation from muscle to bone, for example, by inducing osteoblast formation characterized by expression of a bone-associated protein such as alkaline phosphatase. Alkaline phosphatase is a widely accepted bone marker, and assays for detection of alkaline phosphatase activity are accepted as demonstrating osteoinductive activity. See, e.g., Peel et al., *J. Craniofacial Surg.* 14: 284-291 (2003); Hu et al., *Growth Factors* 22: 29033 (2004); and Kim et al., *J. Biol. Chem.* 279: 50773-50780 (2004).

In certain embodiments, a recombinant polypeptide, homodimeric protein, or heterodimeric protein as described herein is capable of inducing alkaline phosphatase activity.

In certain embodiments, osteoinductive activity is detected by a medical imaging technology or histological examination of bone samples, or any other method routinely practiced for detection of bone formation or growth. In certain embodiments, the detection comprises radiographic imaging, such as X-ray imaging. In certain embodiments, the detection comprises computed tomography (CT) scanning. In some embodiments, the detection comprises molecular imaging or nuclear imaging (i.e., positron emission tomography (PET)). In certain embodiments, the detection comprises histological examination. In certain embodiments, the detection comprises hematoxylin and eosin (HE)-staining.

In certain embodiments, a recombinant polypeptide, homodimeric protein, or heterodimeric protein as described herein can include fragment, variant, or derivative molecules thereof without limitation. The terms "fragment," "variant," "derivative" and "analog" when referring to a polypeptide include any polypeptide which retains at least some property or biological activity of the reference polypeptide. Polypeptide fragments can include proteolytic fragments, deletion fragments, and fragments which more easily reach the site of action when implanted in an animal. Polypeptide fragments can comprise variant regions, including fragments as described above, and also polypeptides with altered amino acid sequences due to amino acid substitutions, deletions, or insertions. Non-naturally occurring variants can be produced using art-known mutagenesis techniques. Polypeptide fragments of the disclosure can comprise conservative or non-conservative amino acid substitutions, deletions, or additions. Variant polypeptides can also be referred to herein as "polypeptide analogs." Polypeptide fragments of the present disclosure can also include derivative molecules. As used herein a "derivative" of a polypeptide or a polypeptide fragment refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

In certain embodiments, a recombinant polypeptide, homodimeric protein, or heterodimeric protein as described herein comprises a label. In certain embodiments, the label is an enzymatic label that can catalyze the chemical alteration of a substrate compound or composition, a radiolabel, a fluorophore, a chromophore, an imaging agent, or a metal, including a metal ion.

In certain embodiments, a recombinant polypeptide as described herein comprises one or more conservative amino acid substitutions. A "conservative amino acid substitution" is a substitution of an amino acid with different amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

In certain embodiments, a recombinant polypeptide of the disclosure is encoded by a nucleic acid molecule or vector of the disclosure as described herein, or is expressed by a host cell as described herein.

Nucleic Acid Molecules, Vectors, and Host Cells

The present disclosure is directed to an isolated nucleic acid molecule comprising a polynucleotide sequence encoding any of the recombinant polypeptides described herein.

In certain embodiments, the isolated nucleic acid molecule comprises any two or more polynucleotide sequences encoding a domain as described herein. In certain embodiments, the isolated nucleic acid molecule comprises any two or more polynucleotide sequences selected from the group consisting of SEQ ID NOs: 32, 34, 36, 38, 40, 42, 44, 46, 48, 50, 52, 54, 56, 58, 60, 62, 64, 66, 68, 70, 72, 74, 76, and 78, which encode domains described herein corresponding to SEQ ID NOs: 33, 35, 37, 39, 41, 43, 45, 47, 49, 51, 53, 55, 57, 59, 61, 63, 65, 67, 69, 71, 73, 75, 77, and 355, respectively. In certain embodiments, the isolated nucleic acid molecule comprises any combination of two or three polynucleotide sequences encoding the corresponding combinations of two or three domains shown in Table 3, herein.

In certain embodiments, the isolated nucleic acid molecule comprises a polynucleotide sequence selected from the group consisting of SEQ ID NOs: 115, 157, 187, 193, 199, 205, 211, 217, 223, 229, 235, 241, 247, 253, 259, 267, 275, 283, 291, 299, 307, 315, 323, 331, 339, and 347, which encodes a recombinant polypeptide described herein corresponding to SEQ ID NOs: 116, 158, 188, 194, 200, 206, 212, 218, 224, 230, 236, 242, 248, 254, 260, 268, 276, 284, 292, 300, 308, 316, 324, 332, 340, and 348, respectively.

In certain embodiments, the polynucleotide sequence is codon-optimized.

The present disclosure is directed to a recombinant nucleic acid molecule comprising an expression control region operably linked to an isolated nucleic acid molecule as described herein. In certain embodiments, the expression control region is a promoter, enhancer, operator, repressor, ribosome binding site, translation leader sequence, intron, polyadenylation recognition sequence, RNA processing site, effector binding site, stem-loop structure, transcription termination signal, or combination thereof. In certain embodiments, the expression control region is a promoter. An expression control region can be a transcription control region and/or a translation control region.

A variety of transcription control regions are known to those skilled in the art. These include, without limitation, transcription control regions, which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit 8-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In certain embodiments, the recombinant nucleic acid molecule is a recombinant vector.

A vector can be any vehicle for the cloning of and/or transfer of a nucleic acid into a host cell. A large number of vectors are known and used in the art including, for example, plasmids, phages, cosmids, chromosomes, viruses, modified eukaryotic viruses, modified bacterial viruses. Insertion of a polynucleotide into a suitable vector can be accomplished by ligating the appropriate polynucleotide fragments into a chosen vector that has complementary cohesive termini.

Vectors can be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, neomycin, puromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), beta-galactosidase (LacZ), beta-glucuronidase (Gus), and the like. Selectable markers may also be considered to be reporters.

The term "plasmid" refers to an extra-chromosomal element often carrying a gene that is not part of the central metabolism of the cell, and usually in the form of circular double-stranded DNA molecules. Such elements can be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Eukaryotic viral vectors that can be used include, but are not limited to, adenovirus vectors, retrovirus vectors, adeno-associated virus vectors, and poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

The recombinant vector can be a "recombinant expression vector," which refers to any nucleic acid construct which contains the necessary elements for the transcription and translation of an inserted coding sequence, or in the case of an RNA viral vector, the necessary elements for replication and translation, when introduced into an appropriate host cell.

The present disclosure is directed to a method of making a recombinant vector comprising inserting an isolated nucleic acid molecule as described herein into a vector.

The present disclosure is directed to an isolated host cell comprising an isolated nucleic acid molecule or recombinant nucleic acid molecule as described herein. In certain embodiments, the isolated host cell comprises a recombinant vector as described herein.

Nucleic acid molecules can be introduced into host cells by methods well known in the art, e.g., transfection, electroporation, microinjection, transduction, cell fusion, DEAE dextran, calcium phosphate precipitation, lipofection (lysosome fusion), use of a gene gun, or a DNA vector transporter.

The present disclosure is directed to a method of making a recombinant host cell comprising introducing an isolated nucleic acid molecule or recombinant nucleic acid molecule as described herein into a host cell. In certain embodiments, the method comprises introducing a recombinant vector as described herein into a host cell.

A host cell as described herein can express any of the isolated nucleic acid molecules or recombinant nucleic acid molecules described herein. The term "express" as used with respect to expression of a nucleic acid molecule in a host cell refers to a process by which a gene produces a biochemical, for example, a RNA or polypeptide. The process includes any manifestation of the functional presence of the gene within the cell including, without limitation, transient expression or stable expression. It includes, without limitation, transcription of the gene into messenger RNA (mRNA), and the translation of such mRNA into polypeptide(s).

Host cells include, without limitation, prokaryotes or eukaryotes. Representative examples of appropriate host cells include bacterial cells; fungal cells, such as yeast; insect cells; and isolated animal cells. Bacterial cells can include, without limitation, gram negative and gram positive bacteria, for example *Escherichia coli*. Alternatively, a *Lactobacillus* species or *Bacillus* species can be used as a host cell. Eukaryotic cells can include, but are not limited to, established cell lines of mammalian origin. Examples of suitable mammalian cell lines include COS-7, L, C127, 3T3, Chinese hamster ovary (CHO), HeLa, and BHK cell lines.

The host cells can be cultured in conventional nutrient media modified as appropriate for activating promoters, selecting transformants, or amplifying nucleic acid molecules of the present disclosure. The culture conditions, such as temperature, pH, and the like, can be any conditions known to be used or routinely modified when using the host cell selected for expression, and will be apparent to the ordinarily skilled artisan.

The present disclosure is directed to a method of producing a recombinant polypeptide, comprising: culturing an isolated host cell as described herein and isolating the recombinant polypeptide from the host cell. Techniques for isolating polypeptides from cultured host cells can be any technique known to be used or routinely modified when isolating polypeptides from the host cell selected for expression, and will be apparent to the ordinarily skilled artisan.

Compositions and Devices

The present disclosure is directed to a composition comprising a recombinant polypeptide, homodimeric protein, or heterodimeric protein as described herein.

In certain embodiments, the composition further comprises a physiologically acceptable carrier, excipient, or stabilizer. See, e.g., Remington's Pharmaceutical Sciences (1990) Mack Publishing Co., Easton, Pa. Acceptable carriers, excipients, or stabilizers can include those that are nontoxic to a subject. In certain embodiments, the composition or one or more components of the composition are sterile. A sterile component can be prepared, for example, by filtration (e.g., by a sterile filtration membrane) or by irradiation (e.g., by gamma irradiation).

In certain embodiments, a composition as described herein further comprises an allograft or autograft of bone or bone fragments.

In certain embodiments, a composition as described herein further comprises a bone graft substitute.

In certain embodiments, the bone graft substitute is a bioceramic material. The terms "bioceramic material" and "bioceramic" can be used interchangeably herein. In certain embodiments, the bioceramic is biocompatible and is resorbable in vivo. In certain embodiments, the bioceramic is any calcium phosphate salt-based bioceramic. In certain embodiments, the bioceramic is selected from the group consisting of tricalcium phosphate (TCP), alpha-tricalcium phosphate (α-TCP), beta-tricalcium phosphate (β-TCP), biphasic calcium phosphate (BCP), hydroxylapatite, calcium sulfate, and calcium carbonate. In certain embodiments, the bioceramic is beta-tricalcium phosphate (β-TCP).

In certain embodiments, the bone graft substitute is a bioactive glass. In certain embodiments, the bioactive glass comprises silicon dioxide ($SiO_2$), sodium oxide ($Na_2O$), calcium oxide (CaO), or platinum oxide ($Pt_2O_5$).

The present disclosure is directed to a biodegradable composition, comprising: a homodimeric protein as disclosed herein, being able to induce bone growth to form a bone mass in a location; and a biodegradable calcium phosphate carrier (e.g., β-TCP) with pores that extend throughout the biodegradable calcium phosphate carrier, wherein the homodimeric protein is in an effective amount of from about 0.03 mg/g to about 3.2 mg/g of the biodegradable calcium phosphate carrier and porosity of the biodegradable calcium phosphate carrier is more than 70% with pore size from about 300 μm to about 600 μm.

In certain embodiments, the biodegradable composition is suitable for augmentation of a tissue selected from the group consisting of: nasal furrows, frown lines, midfacial tissue, jaw-line, chin, cheeks, and combinations thereof.

In certain embodiments, the location is selected from the group consisting of: a long-bone fracture defect, a space between two adjacent vertebra bodies, a non-union bone defect, maxilla osteotomy incision, mandible osteotomy incision, sagittal split osteotomy incision, genioplasty osteotomy incision, rapid palatal expansion osteotomy incision, a space extending lengthwise between two adjacent transverse processes of two adjacent vertebrae, and combinations thereof.

In certain embodiments, a single dose of the homodimeric protein is from about 0.006 mg to about 15 mg.

In certain embodiments, the biodegradable calcium phosphate carrier hardens so as to be impermeable to efflux of the homodimeric protein in vivo sufficiently that the formed bone mass is confined to the volume of the biodegradable calcium phosphate carrier.

The present disclosure is directed to a sustained release composition, comprising a calcium phosphate carrier, a biodegradable matrix, and a homodimeric protein as disclosed herein.

In certain embodiments, the calcium phosphate carrier is selected from the group consisting of: tricalcium phosphate (TCP), alpha-tricalcium phosphate (α-TCP), beta-tricalcium phosphate (β-TCP), biphasic calcium phosphate (BCP), and combinations thereof.

In certain embodiments, the biodegradable matrix is selected from the group consisting of: polylactic acid (PLA), polyglycolic acid (PGA), polylactic-co-glycolic acid (PLGA), Polyvinyl alcohol (PVA), and combinations thereof.

In certain embodiments, the sustained release composition comprises: (a) about 2-11% (w/w) of the calcium phosphate carrier; (b) about 88-97% (w/w) of the biodegradable matrix; and (c) about 0.017-0.039% (w/w) of the homodimeric protein.

The present disclosure is directed to a moldable composition for filling an osseous void, comprising: a moldable matrix comprising about 90% to about 99.5% by weight of the moldable composition; and a homodimeric protein as disclosed herein, wherein less than about 25% by percentage of the homodimeric protein is released from the moldable composition after about 1, 24, 48, 72, 168, 240 or about 336 hours post implantation.

The present disclosure is directed to a spinal fusion device comprising a biodegradable composition as disclosed herein; and a spinal fusion cage (e.g., peek cage), configured to retain the biodegradable calcium phosphate carrier.

Methods

The present disclosure is directed to a method of promoting healing of a long-bone fracture in a subject in need of such treatment, comprising: preparing a composition including a homodimeric protein as disclosed herein homogeneously entrained within a slow release biodegradable calcium phosphate carrier (e.g., β-TCP) that hardens so as to be impermeable to efflux of the homodimeric protein in vivo sufficiently that the long-bone fracture healing is confined to the volume of the calcium phosphate carrier; and implanting the composition at a location where the long-bone fracture occurs, wherein the homodimeric protein is in an amount of from about 0.03 mg/g to about 3.2 mg/g of the calcium phosphate carrier.

In certain embodiments, the method of promoting healing of a long-bone fracture further comprises gradually exposing the entrained homodimeric protein at the location as the calcium phosphate carrier degrades, wherein the calcium phosphate carrier has a calcium to phosphate ratio of about 0.4 to about 1.8.

The present disclosure is directed to a method for promoting spinal fusion, comprising: exposing an upper vertebra and a lower vertebra; identifying a site for fusion between the upper and the lower vertebra; exposing a bone surface on each of the upper and the lower vertebra at the site for fusion; and administering a homodimeric protein as disclosed herein and a biodegradable calcium phosphate carrier (e.g., β-TCP) to the site.

In certain embodiments, the biodegradable calcium phosphate carrier is a non-compressible delivery vehicle, and wherein the non-compressible delivery vehicle is for application to the site between the two bone surfaces where bone growth is desired but does not naturally occur.

In certain embodiments, the biodegradable calcium phosphate carrier comprises at least one implantation stick for application to the site such that the implantation stick extends lengthwise between the upper and the lower vertebrae.

In certain embodiments, the site is selected from a space between two adjacent vertebra bodies, and a space extending lengthwise between two adjacent transverse processes of two adjacent vertebrae.

The present disclosure is directed to a method for promoting arthrodesis, comprising administering a homodimeric protein as disclosed herein and a biodegradable calcium phosphate carrier to a malformed or degenerated joint.

In certain embodiments, administering the homodimeric protein includes administering from about 0.006 mg to about 10.5 mg of the homodimeric protein to the malformed or degenerated joint.

The present disclosure is directed to a method of generating a bone mass to fuse two adjacent vertebrae bodies in a spine of a subject in need, comprising: preparing a composition for generating the bone mass, the composition including a homodimeric protein as disclosed herein homogeneously entrained within a slow release biodegradable carrier that hardens so as to be impermeable to efflux of the homodimeric protein in vivo sufficiently that the formed bone mass is confined to the volume of the slow release biodegradable carrier; and introducing the composition in a location between the two adjacent vertebrae bodies, and wherein the slow release biodegradable carrier gradually exposes the entrained homodimeric protein at the location as the slow release biodegradable carrier degrades, and further wherein the homodimeric protein is in an amount of from about 0.2 mg/site to about 10.5 mg/site of the location.

In certain embodiments, the slow release biodegradable carrier has a porous structure, wherein cells from the two adjacent vertebrae migrate into the porous structure so as to generate the bone mass.

In certain embodiments, the slow release biodegradable carrier has an initial volume, and the bone mass replaces the initial volume of the slow release biodegradable carrier as the slow release biodegradable carrier is resorbed.

The present disclosure is directed to a method for fusing adjacent vertebrae bodies in a subject in need by a posterior or transforaminal fusion approach, comprising: preparing a disc space for receipt of an intervertebral disc implant in an intervertebral space between the adjacent vertebrae; introducing a slow-release carrier into the intervertebral disc implant, wherein a homodimeric protein as disclosed herein is in an amount of from about 0.2 mg/site to about 10.5 mg/site of the slow-release carrier; and introducing the intervertebral disc implant in the disc space between the adjacent vertebrae for generating a bone mass in the disc space.

The following examples are offered by way of illustration and not by way of limitation.

EXAMPLES

Example 1: Plasmid Construction

For construction of plasmid pQE-80L-Kana, Kanamycin resistance gene was cleaved from pET-24a(+) (Novagen) by BspHI (BioLab) to generate a 875-bp Kanamycin resistance gene (+3886 to +4760) fragment (SEQ ID NO: 1). The pQE-80L (Qiagen) vector was digested with BspHI to remove Ampicillin resistance gene (+3587 to +4699) fragment (SEQ ID NO:2) and then the Kanamycin resistance gene fragment was ligated into the pQE-80L vector to generate a 4513-bp plasmid (pQE-80L-Kana). (SEQ ID NO:3)

Example 2: Yeast Two-Hybrid Screening

A. Construction of Bait Plasmid

Yeast two-hybrid screening was performed using a commercially available system (Matchmaker Two-Hybrid System 2; CLONTECH, Palo Alto, Calif.). To construct the bait plasmids, the coding region of the extracellular domain (+103 to +375 bp) (SEQ ID NO: 4) of activin receptor type IIB (ActRIIB) protein was produced by PCR with pCRII/ActRIIB (Hilden., et al. (1994) *Blood* 83(8):2163-70) as the template. The primers (Xma: 5'-CCCGGGACGGGAGTG-CATCTACAACG-3'(SEQ ID NO: 5); SalI: 5'-GTCGACT-TATGGCAAATGAGTGAAGCGTTC-3'(SEQ ID NO: 6)) used to amplify the extracellular domain of ActRIIB (ActRIIBecd) were designed to include an XmaI and SalI restriction site in the 5'-end, respectively. PCR was carried out using 10 ng template DNA, 0.2 μM each primer, 0.2 mM each dNTP, 1×PCR buffer (10 mM Tris-HCl, pH 8.3, 50 mM KCl and 1.5 mM MgCl$_2$), and 1.25 U pfu DNA polymerase (Promega) in a total volume of 50 μl. PCR was performed with 30 cycles of: 30 seconds of denaturing at 95° C., followed by annealing at 45° C. for 1 min, and extension at 68° C. for 5 min. The PCR products were digested with XmaI-SalI and then subcloned in frame into the same restriction sites in the DNA-binding domain of GAL4 in the pAS2-1 vector (CLONTECH, GenBank Accession No.: U30497) to generate plasmid pAS-ActRIIBecd.

The nucleic acid sequences and polypeptide sequences of ActRIIB and naturally occurring variants are known. For example, a wild-type ActRIIB nucleic acid sequence is SEQ ID NO: 7. The corresponding polypeptide sequence is SEQ ID NO: 8. The extracellular domain of ActRIIB (ActRIIBecd) is SEQ ID NO: 9, which corresponds to residues 27-117 of SEQ ID NO: 8 and is encoded by the nucleic acid sequence of SEQ ID NO: 4.

B. Construction of pACT2/MC3T3 cDNA Library

To construct pACT2/MC3T3 cDNA library, approximately 7×10$^6$ clones of a mouse MC3T3-E1 osteoblast cDNA library described by Tu Q., et al. (2003, *J Bone Miner Res*. 18(10):1825-33), with some modifications to allow cDNA library inserts smaller than 1.5 kb, were constructed into pACT2 vector (CLONTECH, GenBank Accession No.: U29899), wherein after S1 nuclease treatment (Invitrogen life technologies cDNA Synthesis System CAT. No. 18267-013), the double-stranded cDNA was cloned in the pACT2 vector, which had been digested with SmaI to express fusion proteins with the GAL4 activation domain. The pACT2/MC3T3 cDNA library was then screened by the "HIS3 Jump-Start" procedure according to the protocol from the manufacturer (CLONTECH, Palo Alto, Calif.). In another embodiment, the pACT2 cDNA library is obtained as a commercial product.

C. Selection of Yeast Strain

*Saccharomyces cerevisiae* Y190 cells (MATa, ura3-52, his3-D200, lys2-801, ade2-101, trp1-901, leu2-3, 112, gal4D, gal80D, URA3::GAL1$_{UAS}$-GAL1$_{TATA}$-lacZ, cyh$^r$2, LYS2::GAL$_{UAS}$-HIS3$_{TATA}$-HIS3; CLONTECH, Palo Alto, Calif.) were first transformed with bait plasmids and selected on synthetic dextrose medium lacking tryptophan (SD-Trp). The transformants grown on the SD-Trp medium were subsequently transformed with the pACT2/MC3T3 cDNA library and selected on medium lacking tryptophan and leucine (SD-Trp-Leu). The clones co-transformed with the bait and library were collected and replated onto medium lacking tryptophan, leucine and histidine (SD-Trp-Leu-His) with 30 mM 3-amino-1,2,4-triazole (Sigma-Aldrich, St. Louis, Mo.) to inhibit the leaking growth of Y190 cells. The clones selected in this step were further assayed for their β-galactosidase activity. Plates were photo-graphed after incubation at 30° C. for 3 days. At least three independent experiments were performed, with similar results. The pACT2 library plasmids were purified from individual positive clones and amplified in *Escherichia coli*. Sequencing (primer 5'-AATACCACTACAATGGAT-3' (SEQ ID NO: 10)) of the cDNA insert in the positive clones shown in Table 1 was performed with a Perkin-Elmer ABI Automated DNA Sequencer.

TABLE 1

| Clone No./ SEQ ID No. | DNA sequence | Primers |
|---|---|---|
| 1/SEQ ID NO: 11 | 5'-GGCCAAGCCAAACGCAAAGGGTAT AAACGCCTTAAGTCCAAATGTAAC ATACACCCTTTGTAC-3' | 5'-TTAACCATGGGCCAAGCCAAAC GC-3' (SEQ ID NO: 12) (The bold font bases is the recognition site of restriction endonuclease MseI) 5'-GGATCCTTAGTACAAAGGGTGT ATGTTAC-3' (SEQ ID NO: 13) (The bold font bases is the recognition site of restriction endonuclease BamHI) |

TABLE 1-continued

| Clone No./ SEQ ID No. | DNA sequence | Primers |
|---|---|---|
| 2/SEQ ID NO: 14 | 5'-GTGAGCTTCAAAGACATTGGGTGGAATGACCATGCTAGCAGCCAGCCGGGGTATCACGCCCGTCCCTGCCACGGACAATGCCAGAATATTCTGGCTGATCATCTGAACGAAGATTGTCATGCCATTGTTCAGCTGAAGCCCCGCTCTGTT-3' | 5'-TTAACCATGGTGAGCTTCAAAGACA-3' (SEQ ID NO: 15) (The bold font bases is the recognition site of restriction endonuclease MseI)<br>5'-GGATCCTTAAACAGAGCGGGGCTTCAGCT-3' (SEQ ID NO: 16) (The bold font bases is the recognition site of restriction endonuclease BamHI) |
| 3/SEQ ID NO: 17 | 5'-ATCGTTGTGGATAATAAGGCATGCTGTGTCCCGACAGAACTCAGTCTTCCCCATCCGCTGTACCTTGACGAGAATAAAAAGCCTGTATATAAGAACTATCAGGACGCGCTTCTGCATAGTTGTGGGTGTCGC-3' | 5'-TTAACCATGATCGTTGTGGATAATAAG-3' (SEQ ID NO: 18) (The bold font bases is the recognition site of restriction endonuclease MseI)<br>5'-GGATCCTTAGCGACACCCACAACTATGCA-3' (SEQ ID NO: 19) (The bold font bases is the recognition site of restriction endonuclease BamHI) |
| 4/SEQ ID NO: 20 | 5'-ACGTATCCAGCCTCTCCGAAGCCGATGAGGTGGTCAATGCGGAGCTGCGCGTGCTGCGCCGGAGGTCTCCGGAACCAGACAGGGACAGTG-3' | 5'-TTAACCATGACGTATCCAGCCTCTCCG-3' (SEQ ID NO: 21) (The bold font bases is the recognition site of restriction endonuclease MseI)<br>5'-GGATCCTTACACTGTCCCTGTCTGGTTCC-3' (SEQ ID NO: 22) (The bold font bases is the recognition site of restriction endonuclease BamHI) |
| 5/SEQ ID NO: 23 | 5'-GAGCCCCTGGGCGGCGCGCGCTGGGAAGCGTTCGACGTGACGGACGCGGTGCAGAGCCACCGCCGCTGGCCGCGAGCCTCCCGCAAGTGCTGCCTGGTGCTGCGCGCGGTGACGGCCTCG-3' | 5'-TTAACCATGGAGCCCCTGGGCGGCGC-3' (SEQ ID NO: 24) (The bold font bases is the recognition site of restriction endonuclease MseI)<br>5'-GGATCCTTACGAGGCCGTCACCGCGCGCA-3' (SEQ ID NO: 25) (The bold font bases is the recognition site of restriction endonuclease BamHI) |
| 6/SEQ ID NO: 26 | 5'-ACTGCGCTGGCTGGGACTCGGGAGCGCAGGGAAGCGGTGGTGGCGGCGGTGGCGGTGGCGGCGGCGGCGGCGGCGGCGCAGGCAGGGGCCACGGGCGCAGAGGCCGGAGCCGCTGCAGTCGCAAGTCACTGCACGTGGACTTTAAGGAGCTGGGC-3' | 5'-TTAACCATGACTGCGCTGGCTGGGAC-3' (SEQ ID NO: 27) (The bold font bases is the recognition site of restriction endonuclease MseI)<br>5'-GGATCCTTAGCCCAGCTCCTTAAAGTCCA-3' (SEQ ID NO: 28) (The bold font bases is the recognition site of restriction endonuclease BamHI) |

Example 3: Error-Prone Random Mutagenic PCR

A. Mutagenization with Primers Designed from Plasmid

The DNA sequences of positive clones from Example 2 were mutagenized.

In one embodiment, sequenced positive clones were subcloned into pQE-80L-Kana and then random mutageneic PCR was performed. The primers in Table 1 used to amplify DNA sequence of positive clones were designed to include a MseI or BamHI restriction site in the 5'-end. The PCR conditions were as described in Example 2. The PCR products were digested with MseI-BamHI and then subcloned in frame into the same restriction sites in the pQE-80L-Kana vector. Random mutagenesis was introduced into the subcloned pQE-80L-Kana plasmids on the basis of the error-prone PCR described by Leung et al. (1989, *Technique*, 1, 11-15), with some modifications. The linearized pQE-80L-Kana (XhoI-digested) was used as template DNA. The primers (Mse: 5'-GAATTCATTAAAGAGGAGAAAT-TAA (SEQ ID NO: 29); BamHI: 5'-CCGGGGTAC-CGAGCTCGCATGCGGATCCTTA (SEQ ID NO: 30)) used for mutagenic PCR amplification were designed to include a MseI or BamHI restriction site in the 5'-end, respectively. Mutagenic PCR was carried out using 10 ng template DNA, 40 pM each primer, 0.2 mM each dNTP, 1×PCR buffer (10 mM Tris-HCl, pH 8.3, 50 mM KCl and 1.5 mM $MgCl_2$), 0.2-0.3 mM $MnCl_2$, 1% dimethyl sulfoxide, and 1.25 U Taq DNA polymerase (Invitrogen, Carlsbad, Calif.) in a total volume of 50 μl. Mutagenic PCR was performed with 30 cycles of: 30 seconds of denaturing at 94°

C., followed by annealing at 55° C. for 2 min, and extension at 72° C. for 3 min. The PCR product was digested by MseI and BamHI. This fragment was ligated with the 4.5-kb fragment of pQE-80L-Kana digested with MseI and BamHI. The resulting pQE-80L-Kana derivatives were used to transform E. coli BL21 (Novagen). Colonies were grown on a plate of LTB-agar medium (LB supplemented with 1% v/v tributyrin, 0.1% v/v Tween 80, 100 mg/L of kanamycin, 0.01 µM isopropyl β-D-thiogalactopyranoside, and 1.5% agar) at 37° C.

B. Mutagenization with Primers in TABLE I

In another embodiment, random mutagenesis was introduced into the pACT2 library plasmids from the positive clone on the basis of the error-prone PCR previously described by Leung with some modifications. The linearized pACT2 (XbaI-digested) was used as template DNA. Synthetic oligonucleotides with MseI and BamHI restriction sites shown in Table 1 were used primers for mutagenic PCR amplification. Mutagenic PCR was carried out using 10 ng template DNA, 40 pM each primer, 0.2 mM each dNTP, 1×PCR buffer (10 mM Tris-HCl, pH 8.3, 50 mM KCl and 1.5 mM $MgCl_2$), 0.2-0.3 mM $MnCl_2$, 1% dimethyl sulfoxide, and 1.25 U Taq DNA polymerase (Invitrogen, Carlsbad, Calif.) in a total volume of 50 µl. Mutagenic PCR was performed with 30 cycles of: 30 seconds of denaturing at 94° C., followed by annealing at 55° C. for 1.5 min, and extension at 72° C. for 4 min. The PCR product was digested by MseI and BamHI. This fragment was ligated with the 4.5-kb fragment of pQE-80L-Kana digested with MseI and BamHI. The resulting pQE-80L-Kana derivatives were used to transform E. coli BL21 (Novagen). Colonies were grown on a plate of LTB-agar medium (LB supplemented with 1% v/v tributyrin, 0.1% v/v Tween 80, 100 mg/L of kanamycin, 0.01 µM isopropyl β-D-thiogalactopyranoside, and 1.5% agar) at 37° C.

Example 4: Expression of ActRIIBecd-Associated Polypeptides

Stably transformed E. coli cells as described in Example 3 were used to express ActRIIBecd-associated polypeptides (i.e., "domains") from the mutagenized DNA of Example 2.

A. Fermentation of Transformants

In one embodiment, overnight cultures (about 10 hrs) of E. coli BL21 transformants with pQE-80L-Kana derivatives in 500 mL Erlenmeyer flasks containing 65 mL of medium (10 g/L BBL PhytonePeptone、5 g/L BactoYeast Extract、10 g/L NaCl) with 25-32 µg/mL of kanamycin were grown at 30° C. to 370 and agitated with 180±20 rpm. 37-420 mL of the overnight cultures were added to 3.7-42 L of TB medium (BBL Phytone Peptone 18 g, Bacto yeast extract 36 g, $KH_2PO_4$ 18.81 g, Glycerol 6 mL in 1 L water) containing 23.8-38.5 g/mL of kanamycin and 1-3 mmol/L isopropyl β-D-thiogalactopyranoside (IPTG) in 5-50 L fermentation tank and temperature control ranging from 37° C. to 42° C., and the culture media was agitated with 260-450 rpm for 10-24 hours. The cells were collected, in an ice water bath, after centrifugation for 10 minutes at 8,000 rpm in a GSA rotor (Sorvall).

In another embodiment, 1 L of LB liquid medium (with 100 mg/L of kanamycin) is inoculated with a freshly grown colony (E. coli BL21 transformants with pQE-80L-Kana derivatives) or 10 mL of freshly grown culture and incubated at 37° C. until $OD_{600}$ reaches 0.4-0.8. The expression of the polypeptides is induced by adding 40 or 400 µM IPTG for 3 to 5 hours at 37° C. After centrifugation (about 8,000 rpm), cells are collected at 4° C.

B. Recovery and Purification of polypeptides from E. coli

E. coli BL21/pQE-80L-Kana derivatives cells were fermented as previously described in Example 4A. In one embodiment, cell disruption and recovery of polypeptides from those derivatives was performed at 4° C. About 18 g of wet cells were suspended in 60 mL of 0.1M TRIS/HCl, 10 mM EDTA (Ethylenediaminetetraacetic acid), 1 mM PMSF (Phenyl Methan Sulphonyl Fluoride), pH 8.3 (disruption buffer). The cells were passed two times through a French-press (SLM Instruments, Inc.) according to the manufacturer's instructions and the volume was brought to 200 mL with the disruption buffer. The suspension was centrifuged for 20 min at 15,000 g. The pellet obtained was suspended in 100 mL disruption buffer containing 1M NaCl and centrifuged for 10 min as above. The pellet was suspended in 100 mL disruption buffer containing 1% Triton X-100 (Pierce) and again centrifuged for 10 min as above. The washed pellet was then suspended in 50 mL of 20 mM Tris/HCl, 1 mM EDTA, 1 mM PMSF, 1% DTT (Dithiothreitol) and homogenised in a Teflon tissue grinder. The resulting suspension contained crude polypeptides in a non-soluble form.

10 mL of the polypeptide suspension obtained according to previous embodiment were acidified with 10% acetic acid to pH 2.5 and centrifuged in an Eppendorf centrifuge for 10 min at room temperature. The supernatant was chromatographed on a Sephacryl 5-100 column (Pharmacia, 2.6×78 cm) in 10% acetic acid at a flow rate of 1.4 mL/min. Fractions containing polypeptide eluting between appropriate time periods were pooled. This material was used for refolding to get biologically active polypeptides or for further purification.

5 mg of polypeptide from previous embodiment was dissolved in 140 mL 50 mM Tris/HCl pH 8.0, 1M NaCl, 5 mM EDTA, 2 mM reduced glutathione, 1 mM oxidised glutathione and 33 mM Chaps (Calbiochem). After 72 hours at 4° C., the pH of the solution was adjusted to pH 2.5 with HCl and the mixture was concentrated 10 times by ultrafiltration on a YM 10 membrane (Amicon, Danvers, Mass., USA) in an Amicon stirred cell. The concentrated solution was diluted to the original volume with 10 mM HCl and concentrated to a final volume of 10 mL by the same method. The precipitate formed was removed by centrifugation at 5000 g for 30 minutes. The supernatant contained disulfide linked polypeptide as judged by SDS-PAGE under non-reducing conditions. The biological activity of the preparation was measured by BIAcore™ assay (Example 5).

The concentrated solution from the previous embodiment was applied at a flow rate of 1 mL/min onto a Mono S HR 5/5 column (Pharmacia) equilibrated in a mixture of 85% buffer A (20 mM sodium acetate, 30% isopropanol, pH 4.0) and 15% buffer B (buffer A containing 1M sodium chloride). The column was then washed at the same flow rate keeping the buffer mixture composition constant until the absorbance reading at 280 nm has reached baseline level, followed by a linear gradient over 20 minutes starting upon injection at the equilibration conditions and ending with a mixture of 50% buffer A/50% buffer B. The biologically active polypeptide was eluted about 9 minutes after the start of the gradient and collected. As judged by biological activity determination, and SDS-PAGE under non-reducing conditions.

In another embodiment, the polypeptides are prepared from inclusion bodies of collected cells in Example 4A. After extraction (50 mM sodium acetate, pH 5, 8 M urea, 14 mM 2-mercaptoethanol) at room temperature overnight and exhaustive dialysis against water, the polypeptides are refolded, concentrated and enriched by Sephacryl S-100 HR column (Pharmacia) in 1% acetic acid or 5 mM HCl at a flow rate of 1.8 mL/min. It is finally purified by FPLC (Fractogel EMD $SO_3^-$ 650, 50 mM sodium acetate, pH 5, 30% 2-propanol) eluting with a NaCl gradient from 0 to 1.5 M. Fractions containing polypeptide eluting between appropriate time periods are pooled. After dialysis against water, the polypeptides are freeze/dried and stored at −20° C. The purity of the polypeptides is analyzed by SDS-PAGE, followed by staining with Coomassie Brilliant Blue R.

In other embodiment, each 1 gram of cell pellet, derived for example from the above Example 4A, was resuspended in 10-20 mL of 10 mM TRIS/HCl, 150 mM NaCl, 1 mM EDTA, 5 mM DTT, pH 8.0 (disruption buffer), and the cells burst by sonication, using a Misonix S4000 instrument, with a Enhance Booster #1 probe, at 30 A (instrument scale) for 5 minutes. Optionally, the cell lysate mixture was clarified by centrifugation (either 18,000×g for 20 min or 15,000×g for 30 min) and the pellet was washed several times with 10-20 mL disruption buffer containing 1 v/v % Triton X-100 and centrifuged for 10 min as above. The cell lysate was dissolved with 100-200 mL disruption buffer containing 6 M urea and centrifuged for 10 min as above and the supernatant containing the polypeptides was retained for further purification.

The previous mentioned supernatant was dissolved in refolding buffer (100 mL Tris/HCl pH 8.0, 500 mM Arginine-HCl, 5 mM EDTA, 25 mM Chaps, 2 mM oxidised glutathione and 1 mM reduced glutathione). After 4-7 days at room temperature, the polypeptides were purified by FPLC (Fractogel EMD $SO_3^-$ 650, 20 mM sodium acetate, pH 4-5, 30% 2-propanol and 25 mM Chaps) eluting with a NaCl gradient from 0 to 3 M. Fractions containing polypeptide eluting between appropriate time periods were pooled. The purity of the polypeptides was analyzed by SDS-PAGE, followed by staining with Coomassie Brilliant Blue R.

In certain embodiments, the heterodimers of the present disclosure can be prepared by co-expression in a transient expression system as previously mentioned in Example 3 and the heterodimers can be isolated from the culture medium for screening in the assays of Example 5.

Example 5: In Vitro BIAcore™ Assay

Biosensor experiments. In one embodiment, experiments were performed on a BIAcore™ T100/T200 instrument (Pharmacia Biosensor AB) in the multichannel mode (serial flow path involving flow cells 1+2+3+4). Flow rate was 10 l/min; temperature was 25° C.; and data were recorded at 2.5 points/s. All four segments of a sensor chip CM5 were coated with streptavidin (Sigma) to a density of 2000 $pg/mm^2$ (2000 resonance units) by the aminocoupling procedure. ActRIIBecd (10 mg) and amine-PEG3-Biotin (10 mg, Pierce, Rockford, Ill.) were dissolved in 200 μl $H_2O$ and 10 mg $NaCNBH_3$ was added to prepare biotinylated ActRIIBecd. The reaction mixture was heated at 70° C. for 24 h, after that a further 10 mg $NaCNBH_3$ was added and the reaction was heated at 70° C. for another 24 h. After cooling to room temperature, the mixture was desalted with the spin column (3,000 molecular weight cut off (MWCO)). Biotinylated ActRIIBecd was collected, freeze-dried and used for streptavidin (SA) chip preparation. Amino-biotinylated ActRIIBecd was then immobilized independently on flow cells 2-4 for 10 minutes at a flow rate of 5 μL/min and a concentration of 2 μM in 10 mM sodium acetate, pH 4.0, at a density of 50-250 resonance units (RU). The stored polypeptides were dissolved in glycine buffer (2.5 g of glycine, 0.5 g of sucrose, 370 mg of L-glutamate, 10 mg of sodium chloride, and 10 mg of Tween 80 in 100 mL water, pH 4.5) to prepare 10 mg/mL solution and then diluted with previous glycine buffer to prepare analytes with various concentration. Sensograms were recorded during flow of the analyte (the ActRIIBecd-associated polypeptides (i.e., domains) as previously described) first through flow cell 1 (control) then through flow cell 2 (biotinylated ActRIIBecd). The sensogram obtained for flow cell 1 was subtracted from the sensogram obtained for flow cell 2. The sensograms obtained at 1.11, 3.33, 10, 30, and 90 nM analyte were evaluated for equilibrium binding, association rate, and dissociation rate by using the programs supplied with the instrument (BIA evaluation 2.1; Software Handbook. 1995; Pharmacia Biosensor AB). Analytes and bovine serum albumin (negative control) were listed in Table 2. Sequencing (primer 5'-CTCGAGAAAT CATAAAAAAT TTATTTG-3' (SEQ ID NO: 31)) of the pQE-80L-Kana derivatives in the clone related to analyte, which has a higher affinity constant than that of albumin, was performed with a Perkin-Elmer ABI Automated DNA Sequencer as previously described.

TABLE 2

| Clone | | | Affinity constant | |
|---|---|---|---|---|
| No. | DNA sequence | Domain sequence | Mean$_{[nM]}$ | SD$_{[nM]}$ |
| 7 | 5'-GCTCAAGCCAAACACAA AGGGTATAAACGCCTTAA GTCCAATTGTAAAAGGCA CCCTTTGTAC-3' (SEQ ID NO: 32) | AQAKHKGYKRLKSNCK RHPLY (SEQ ID NO: 33) | NB | |
| 8 | 5'-GGCCAAGCCAAACGCAA AGGGTATAAACGCCTTAA GTCCAGCTGTAAGAGAC ACCCTTTGTAC-3' (SEQ ID NO: 34) | GQAKRKGYKRLKSSCKR HPLY (SEQ ID NO: 35) | 45.12 | ±15.39 |
| 9 | 5'-GCCCAAGCCAAACATAA AGGGTATAAACGCCTTAA GTCCAGCTGTAAGAGAC ACCCTTTGTAC-3' (SEQ ID NO: 36) | AQAKHKGYKRLKSSCKR HPLY (SEQ ID NO: 37) | 52.41 | ±16.71 |

TABLE 2-continued

| Clone No. | DNA sequence | Domain sequence | Affinity constant Mean[nM] | SD[nM] |
|---|---|---|---|---|
| 10 | 5'-GCTCAAGCCAAACACAAACAGCGGAAACGCCTTAAGTCCAGCTGTAAGAGACACCCTTTGTAC-3' (SEQ ID NO: 38) | AQAKHKQRKRLKSSCKRHPLY (SEQ ID NO: 39) | 36.39 | ±12.12 |
| 11 | 5'-GCTCAAGCCAAACACAAAGGTCGGAAACGCCTTAAGTCCAGCTGTAAGAGACACCCTTTGTAC-3' (SEQ ID NO: 40) | AQAKHKGRKRLKSSCKRHPLY (SEQ ID NO: 41) | 63.72 | ±23.17 |
| 12 | 5'-GCTCAAGCCAAACACAAACAGTACAAACGCCTTAAGTCCAGCTGTAAGAGACACCCTTTGTAC-3' (SEQ ID NO: 42) | AQAKHKQYKRLKSSCKRHPLY (SEQ ID NO: 43) | 58.42 | ±24.42 |
| 13 | 5'-GTGGATTTCAAGGACGTTGGGTGGAATGACCATGCTGTGGCACCGCCGGGGTATCACGCCTTCTATTGCCACGGAGAATGCCCGCATCCACTGGCTGATCATCTGAACTCAGATAACCATGCCATTGTTCAGACCAAGGTTAATTCTGTT-3' (SEQ ID NO: 44) | VDFKDVGWNDHAVAPPGYHAFYCHGECPHPLADHLNSDNHAIVQTKVNSV (SEQ ID NO: 45) | NB | |
| 14 | 5'-GTGGATTTCAAGGACGTTGGGTGGAATGACCATGCTGTGGCACCGCCGGGGTATCACGCCTTCTATTGCCACGGAGAATGCCCGTTCCCACTGGCTGATCATCTGAACTCAGATAACCATGCCATTGTTCAGACCAAGGTTAATTCTGTT-3' (SEQ ID NO: 46) | VDFKDVGWNDHAVAPPGYHAFYCHGECPFPLADHLNSDNHAIVQTKVNSV (SEQ ID NO: 47) | 38.32 | ±12.79 |
| 15 | 5'-GTGGACTTCAGTGACGTGGGGTGGAATGACTGGATTGTGGCTCCCCCGGGGTATCACGCCTTTTACTGCCACGGAGAATGCCCTTTTCCTCTGGCTGATCATCTGAACTCCACTAATCATGCCATTGTTCAGACGTTGGTCAACTCTGTT-3' (SEQ ID NO: 48) | VDFSDVGWNDWIVAPPGYHAFYCHGECPFPLADHLNSTNHAIVQTLVNSV (SEQ ID NO: 49) | 39.45 | ±14.11 |
| 16 | 5'-GTGGATTTCAGCGACGTTGGGTGGAATGACTGGGCTGTGGCACCGCCGGGGTATCACGCCTTCTATTGCCACGGAGAATGCCCGTTCCCACTGGCTGATCATCTGAACTCAGATAACCATGCCATTGTTCAGACCCTCGTTAATTCTGTT-3' (SEQ ID NO: 50) | VDFSDVGWNDWAVAPPGYHAFYCHGECPFPLADHLNSDNHAIVQTLVNSV (SEQ ID NO: 51) | 55.98 | ±18.12 |
| 17 | 5'-GTGGATTTCAGCGACGTTGGGTGGAATGACTGGATCGTGGCACCGCCGGGGTATCACGCCTTCTATTGCCACGGAGAATGCCCGTTCCCACTGGCTGATCATCTGAACTCAGATAACCATGCCATTGTTCAGACCCTCGTTA | VDFSDVGWNDWIVAPPGYHAFYCHGECPFPLADHLNSDNHAIVQTLVNSV (SEQ ID NO: 53) | 67.42 | ±17.89 |

TABLE 2-continued

| Clone No. | DNA sequence | Domain sequence | Affinity constant Mean[nM] | SD[nM] |
|---|---|---|---|---|
| | ATTCTGTT-3' (SEQ ID NO: 52) | | | |
| 18 | 5'-GTGGATTTCTCTGACGTTGGGTGGAATGACCATGCTGTGGCACCGCCGGGGTATCACGCCTTCTATTGCCACGGAGAATGCCCGTTCCCACTGGCTGATCATCTGAACTCAACGAACCATGCCATTGTTCAGACCCTTGTTAATTCTGTT-3' (SEQ ID NO: 54) | VDFSDVGWNDHAVAPPGYHAFYCHGECPFPLADHLNSTNHAIVQTLVNSV (SEQ ID NO: 55) | 64.12 | ±16.78 |
| 19 | 5'-AATAGCAAAGATCCCAAGGCATGCTGTGTCCCGACAGAACTCAGTGCCCCCAGCCCGCTGTACCTTGACGAGAATGAGAAGCCTGTACTCAAGAACTATCAGGACATGGTAGTCCATGGGTGTGGGTGTCGC-3' (SEQ ID NO: 56) | NSKDPKACCVPTELSAPSPLYLDENEKPVLKNYQDMVVHGCGCR (SEQ ID NO: 57) | 40.12 | ±13.69 |
| 20 | 5'-AATAGCAAAATCCCCAAGGCATGCTGTCAGCCGACAGAACTCAGTGCCCCCAGCCCGCTGTACCTTGACGAGAATGAGAAGCCTGTACTCAAGAACTATCAGGACATGGTAGTCGAAGGGTGTGGGTGTCGC-3' (SEQ ID NO: 58) | NSKIPKACCQPTELSAPSPLYLDENEKPVLKNYQDMVVEGCGCR (SEQ ID NO: 59) | NB | |
| 21 | 5'-AACTCTAAGATTCCTAAGGCATGCTGTGTCCCGACAGAACTCAGTGCTATCTCGATGCTGTACCTTGACGAGAATGAAAAGGTTGTATTAAAGAACTATCAGGACATGGTTGTGGAGGGTTGTGGGTGTCGC-3' (SEQ ID NO: 60) | NSKIPKACCVPTELSAISMLYLDENEKVVLKNYQDMVVEGCGCR (SEQ ID NO: 61) | 37.12 | ±11.88 |
| 22 | 5'-AATAGCAAAATCCCCAAGGCATGCTGTGTCCCGACAGAACTCAGTGCCATAAGCCCGCTGTACCTTGACGAGAATGAAGGTCGTACTCAAGAACTATCAGGACATGGTAGTCCATGGGTGTGGGTGTCGC-3' (SEQ ID NO: 62) | NSKIPKACCVPTELSAISPLYLDENEKVVLKNYQDMVVHGCGCR (SEQ ID NO: 63) | 51.72 | ±18.52 |
| 23 | 5'-AATAGCAAAATACCCAAGGCATGCTGTGTCCCGACAGAACTCAGTGCCATTAGCATGCTGTACCTTGACGAGAATGAGAAGCCTGTACTCAAGAACTATCAGGACATGGTAGTCGAAGGGTGTGGGTGTCGC-3' (SEQ ID NO: 64) | NSKIPKACCVPTELSAISMLYLDENEKPVLKNYQDMVVEGCGCR (SEQ ID NO: 65) | 64.41 | ±17.42 |
| 24 | 5'-AATAGCAAAGATCCCAAGGCATGCTGTGTCCCGACAGAACTCAGTGCCATAAGCATGCTGTACCTTGACGAGAATGAGAAGGTGGTACTCAAGAACTATCAGGAC | NSKDPKACCVPTELSAISMLYLDENEKVVLKNYQDMVVHGCGCR (SEQ ID NO: 67) | 56.74 | ±13.59 |

TABLE 2-continued

| Clone No. | DNA sequence | Domain sequence | Affinity constant Mean[nM] | SD[nM] |
|---|---|---|---|---|
| | ATGGTAGTCCATGGGTGT GGGTGTCGC-3' (SEQ ID NO: 66) | | | |
| 25 | 5'-ACGTATCCAGCCTCTCCG AAGCCGATGAGGCATAA AATGCGGAGCTGCGCGT GCTGCGCCGGAGGTCTCC GGAACCGAACAGGGACA GTG-3' (SEQ ID NO: 68) | TYPASPKPMRHKMRSCA CCAGGLRNRTGTV (SEQ ID NO: 69) | 41.09 | ±14.15 |
| 26 | 5'-ACGTATCCCGCCTCTCCG AAGCCGATGAGGCATTC AATGCGGAGCTGCGCGT GCTGCGCCGGAGGTCTCC GGAACCAGACAGGGACA GTG-3' (SEQ ID NO: 70) | TYPASPKPMRHSMRSCA CCAGGLRNQTGTV (SEQ ID NO: 71) | 39.58 | ±16.14 |
| 27 | 5'-ACGTATCCAGCCTCTCCG AAGCCGATGAGGTGGAA GATGCGGAGCTGCGCGT GCTGCGCCGGAGGTCTCC GGAACCGGACAGGGACA GTG-3' (SEQ ID NO: 72) | TYPASPKPMRWKMRSCA CCAGGLRNRTGTV (SEQ ID NO: 73) | 49.33 | ±14.11 |
| 28 | 5'-GAGCCCCTGGGCGGCGC GCGCTGGGAAGCGTTCG ACGTGACGGACGCGGTG CAGAGCCACCGCCGCTCG CCACGAGCCTCCCGCAAG TGCTGCCTGGGGCTGCGC GCGGTGACGGCCTCG-3' (SEQ ID NO: 74) | EPLGGARWEAFDVTDAV QSHRRSPRASRKCCLGLR AVTAS (SEQ ID NO: 75) | 53.78 | ±14.42 |
| 29 | 5'-GAGCCCCTGGGCGGCGC GCGCTGGGAAGCGTTCG ACGTGACGGACGCGGTG CAGAGCCACCGCCGCTCG CAGCGAGCCTCCCGCAA GTGCTGCCTGGTTCTGCG CGCGGTGACGGCCTCG-3' (SEQ ID NO: 76) | EPLGGARWEAFDVTDAV QSHRRSQRASRKCCLVL RAVTAS (SEQ ID NO: 77) | 57.89 | ±13.44 |
| 30 | 5'-ACCGCCCTAGATGGGACT CGGGGAGCGCAGGGAAG CGGTGGTGGCGGCGGTG GCGGTGGCGGCGGCGGC GGCGGCGGCGGCGGCGG CGGCGGCGGCGCAGGCA GGGGCCACGGGCGCAGA GGCCGGAGCCGCTGCAG TCGCAAGTCACTGCACGT GGACTTTAAGGAGCTGG GC-3' (SEQ ID NO: 78) | TALDGTRGAQGSGGGGG GGGGGGGGGGGGGGGA GRGHGRRGRSRCSRKSL HVDFKELG (SEQ ID NO: 355) | 61.74 | ±16.41 |

NB: Binding is below detection limit (KD > 1 mM)

Example 6: Production of Recombinant Polypeptides

To determine whether affinity constants could be enhanced, the individual domains in Table 2 were fused with one another to produce recombinant polypeptides using the PCR-Fusion procedure described by Atanassov et al. (2009, *Plant Methods*, 5:14), with some modifications. PCR-fusion was carried out using Phusion DNA polymerase (Finnzymes; Finland) and a standard thermal cycler. Gateway recombination reactions were performed with BP Clonase II and LR Clonase II enzyme mixes (Invitrogen). Competent *E. coli* DH5a cells, were prepared according to Nojima et al. (1990, *Gene*, 96 (1): 23-28). Plasmid DNA and PCR fragments were purified using QIAprep® Spin Miniprep Kit and QIAquick® Gel Extraction and PCR purification kits (Qiagen, Germany).

DNA template(s), PCR primers, and the DNA/polypeptide sequences of the resultant recombinant polypeptides are provided in Table 3. PCR-fusion involves two or three parallel PCR amplifications from plasmid template(s). PCR fusion of the amplified fragments through a single overlap extension was carried out on gel purified PCR fragments from these parallel reactions. Cycling parameters were identical for all PCR amplifications in this manuscript using reaction mix and conditions according to Phusion DNA polymerase guidelines (NewEnglandBiolabs. Phusion™ High-Fidelity DNA Polymerase. Manual). Annealing temperatures from plasmid templates were 55° C.

For fusion of two PCR fragments, 30 μl overlap extension reactions were used, which contained: 16 μl mixture of the two PCR fragments (normally 8 μl for each one; approx. 200-800 ng, DNA), 6 μl of 5× Phusion HF Buffer, 3 μl of 2 mM dNTP mix, 0.3 μl of Phusion™ DNA Polymerase (2 U/μl). No primers were added to the overlap extension mixture. When three DNA fragments were fused, an 18 μl mixture of the PCR fragments (normally 6 μl for each one) was used. Generally, equal volumes of purified PCR fragments were used without checking exact DNA concentrations. If the molar ratios of the amplified PCR fragments appeared to differ substantially (e.g., by more than 5-7 fold, following estimation of DNA band intensities after agarose electrophoresis), volumes from purified PCR fragments were adjusted accordingly. The reaction mix was incubated at 98° C. for 30 sec., 60° C. for 1 min and 72° C. for 7 min. DNA obtained after the overlap extension reaction was purified using a PCR purification kit. PCR products were digested and coned in the pQE-80L-Kana vector for protein/polypeptide expression as previously described. The affinity of purified protein/polypeptide to ActRIIBecd was monitored by previously discussed BIAcore™ T100/T200 (GE Healthcare) and the data were analyzed by using BIAevaluation software ver. 4.1 (GE Healthcare) in Example 5.

TABLE 3

| Clone No. for Template | DNA sequence/Recombinant Polypeptide sequence | Primers | Affinity constant Mean$_{[nM]}$ | SD$_{[nM]}$ |
|---|---|---|---|---|
| 9 + 11 | 5'-GCCCAAGCCAAACATAAAGGGTATAAACGCCTTAAGTCCAGCTGTAAGAGACACCCTTTGTACGCTCAAGCCAAACACAAAGGTCGGAAACGCCTTAAGTCCAGCTGTAAGAGACACCCTTTGTAC-3' (SEQ ID NO: 79)/AQAKHKGYKRLKSSCKRHPLYAQAKHKGRKRLKSSCKRHPLY (SEQ ID NO: 80) | First pair: 5'-TTAACCATGGCCCAAGCCAAACAT-3' (SEQ ID NO: 81) 5'-GTTTGGCTTGAGCGTACAAAGGGTG-3' (SEQ ID NO: 82) Second pair: 5'-CACCCTTTGTACGCTCAAGCCAAAC-3' (SEQ ID NO: 83) 5'-GGATCCTTAGTACAAAGGGTGTCTC-3' (SEQ ID NO: 84) | 59.11 | ±19.71 |
| 11 + 9 | 5'-GCTCAAGCCAAACACAAAGGTCGGAAACGCCTTAAGTCCAGCTGTAAGAGACACCCTTTGTACGCCCAAGCCAAACATAAAGGGTATAAACGCCTTAAGTCCAGCTGTAAGAGACACCCTTTGTAC-3' (SEQ ID NO: 85)/AQAKHKGRKRLKSSCKRHPLYAQAKHKGYKRLKSSCKRHPLY (SEQ ID NO: 86) | First pair: 5'-TTAACCATGGCTCAAGCCAAACACA-3' (SEQ ID NO: 87) 5'-GTTTGGCTTGGGCGTACAAAGGGTG-3' (SEQ ID NO: 88) Second pair: 5'-CACCCTTTGTACGCCCAAGCCAAAC-3' (SEQ ID NO: 89) 5'-GGATCCTTAGTACAAAGGGTGTCTC-3' (SEQ ID NO: 90) | 58.22 | ±18.15 |
| 17 + 18 | 5'-GTGGATTTCAGCGACGTTGGGTGGAATGACTGGATCGTGGCACCGCCGGGGTATCACGCCTTCTATTGCCACGGAGAATGCCCGTTCCCACTGGCTGATCATCTGAACTCAGATAACCATGCCATTGTTCAGACCCTCGTTAATTCTGTTGTGGATTTCTCTGACGTTGGGTGGAATGACCATGCTGTGGCACCGCCGGGGTATCACGCCTTCTATTGCCACGGAGAATGCCCGTTCCCACTGGCTGATCATCTGAACTC | First pair: 5'-TTAACCATGGTGGATTTCAGCGACG-3' (SEQ ID NO: 93) 5'-CAGAGAAATCCACAACAGAATTAAC-3' (SEQ ID NO: 94) Second pair: 5'-GTTAATTCTGTTGTGGATTTCTCTG-3' (SEQ ID NO: 95) 5'-GGATCCTTAAACAG | 65.77 | ±19.56 |

TABLE 3-continued

| Clone No. for Template | DNA sequence/Recombinant Polypeptide sequence | Primers | Affinity constant Mean$_{[nM]}$ | SD$_{[nM]}$ |
|---|---|---|---|---|
| | AACGAACCATGCCATTG TTCAGACCCTTGTTAATT CTGTT-3' (SEQ ID NO: 91)/ VDFSDVGWNDWIVAPPG YHAFYCHGECPFPLADHL NSDNHAIVQTLVNSVVDF SDVGWNDHAVAPPGYHA FYCHGECPFPLADHLNST NHAIVQTLVNSV (SEQ ID NO: 92) | AATTAACAAGG-3' (SEQ ID NO: 96) | | |
| 18 + 17 | 5'- GTGGATTTCTCTGACGTT GGGTGGAATGACCATGC TGTGGCACCGCCGGGGT ATCACGCCTTCTATTGCC ACGGAGAATGCCCGTTC CCACTGGCTGATCATCTG AACTCAACGAACCATGC CATTGTTCAGACCCTTGT TAATTCTGTTGTGGATTT CAGCGACGTTGGGTGGA ATGACTGGATCGTGGCA CCGCCGGGGTATCACGC CTTCTATTGCCACGGAG AATGCCCGTTCCCACTG GCTGATCATCTGAACTC AGATAACCATGCCATTG TTCAGACCCTCGTTAATT CTGTT-3' (SEQ ID NO: 97)/ VDFSDVGWNDHAVAPPG YHAFYCHGECPFPLADHL NSTNHAIVQTLVNSVVDF SDVGWNDWIVAPPGYHA FYCHGECPFPLADHLNSD NHAIVQTLVNSV (SEQ ID NO: 98) | First pair: 5'- TTAACCATGGTGGA TTTCTCTGACG-3' (SEQ ID NO: 99) 5'- CGCTGAAATCCACA ACAGAATTAAC-3' (SEQ ID NO: 100) Second pair: 5'- GTTAATTCTGTTGTG GATTTCAGCG-3' (SEQ ID NO: 101) 5'- GGATCCTTAAACAG AATTAACGAGG-3' (SEQ ID NO: 102) | 66.38 | ±16.41 |
| 23 + 24 | 5'- AATAGCAAAATACCCAA GGCATGCTGTGTCCCGA CAGAACTCAGTGCCATT AGCATGCTGTACCTTGA CGAGAATGAGAAGCCTG TACTCAAGAACTATCAG GACATGGTAGTCGAAGG GTGTGGGTGTCGCAATA GCAAAGATCCCAAGGCA TGCTGTGTCCCGACAGA ACTCAGTGCCATAAGCA TGCTGTACCTTGACGAG AATGAGAAGGTGGTACT CAAGAACTATCAGGACA TGGTAGTCCATGGGTGT GGGTGTCGC-3' (SEQ ID NO: 103)/ NSKIPKACCVPTELSAISM LYLDENEKPVLKNYQDM VVEGCGCRNSKDPKACC VPTELSAISMLYLDENEK VVLKNYQDMVVHGCGC R (SEQ ID NO: 104) | First pair: 5'- TTAACCATGAATAG CAAAATACCCA-3' (SEQ ID NO: 105) 5'- GATCTTTGCTATTGC GACACCCACAC-3' (SEQ ID NO: 106) Second pair: 5'- GTGTGGGTGTCGCA ATAGCAAAGATC-3' (SEQ ID NO: 107) 5'- GGATCCTTACGACA CCCACACCCAT-3' (SEQ ID NO: 108) | 61.77 | ±15.74 |
| 24 + 23 | 5'- AATAGCAAAGATCCCAA GGCATGCTGTGTCCCGA CAGAACTCAGTGCCATA AGCATGCTGTACCTTGA CGAGAATGAGAAGGTGG TACTCAAGAACTATCAG GACATGGTAGTCCATGG GTGTGGGTGTCGCAATA GCAAAATACCCAAGGCA TGCTGTGTCCCGACAGA ACTCAGTGCCATTAGCA | First pair: 5'- TTAACCATGAATAG CAAAGATCCCA-3' (SEQ ID NO: 111) 5'- GTATTTTGCTATTGC GACACCCACAC-3' (SEQ ID NO: 112) Second pair: 5'- GTGTGGGTGTCGCA | 62.74 | ±17.84 |

TABLE 3-continued

| Clone No. for Template | DNA sequence/ Polypeptide sequence | Primers | Affinity constant Mean$_{[nM]}$ | SD$_{[nM]}$ |
|---|---|---|---|---|
| | TGCTGTACCTTGACGAG AATGAGAAGCCTGTACT CAAGAACTATCAGGACA TGGTAGTCGAAGGGTGT GGGTGTCGC-3' (SEQ ID NO: 109)/ NSKDPKACCVPTELSAIS MLYLDENEKVVLKNYQD MVVHGCGCRNSKIPKAC CVPTELSAISMLYLDENE KPVLKNYQDMVVEGCGC R (SEQ ID NO: 110) | ATAGCAAAATAC-3' (SEQ ID NO: 113) 5'- GGATCCTTAGCGAC ACCCACACCCT-3' (SEQ ID NO: 114) | | |
| 12 + 25 | 5'- GCTCAAGCCAAACACAA ACAGTACAAACGCCTTA AGTCCAGCTGTAAGAGA CACCCTTTGTACACGTAT CCAGCCTCTCCGAAGCC GATGAGGCATAAAATGC GGAGCTGCGCGTGCTGC GCCGGAGGTCTCCGGAA CCGAACAGGGACAGTG-3' (SEQ ID NO: 115)/ AQAKHKQYKRLKSSCKR HPLYTYPASPKPMRHKM RSCACCAGGLRNRTGTV (SEQ ID NO: 116) | First pair: 5'- TTAACCATGGCTCA AGCCAAACACAA-3' (SEQ ID NO: 117) 5'- GAGGCTGGATACGT GTACAAAGGGTG-3' (SEQ ID NO: 118) Second pair: 5'- CACCCTTTGTACACG TATCCAGCCTC-3' (SEQ ID NO: 119) 5'- GGATCCTTACACTG TCCCTGTTCGG-3' (SEQ ID NO: 120) | 51.21 | ±12.34 |
| 25 + 12 | 5'- ACGTATCCAGCCTCTCCG AAGCCGATGAGGCATAA AATGCGGAGCTGCGCGT GCTGCGCCGGAGGTCTC CGGAACCGAACAGGGAC AGTGGCTCAAGCCAAAC ACAAACAGTACAAACGC CTTAAGTCCAGCTGTAA GAGACACCCTTTGTAC-3' (SEQ ID NO: 121)/ TYPASPKPMRHKMRSCA CCAGGLRNRTGTVAQAK HKQYKRLKSSCKRHPLY (SEQ ID NO: 122) | First pair: 5'- TTAACCATGACGTAT CCAGCCTCTCC-3' (SEQ ID NO: 123) 5'- GTTTGGCTTGAGCCA CTGTCCCTGTTC-3' (SEQ ID NO: 124) Second pair: 5'- GAACAGGGACAGTG GCTCAAGCCAAAC-3' (SEQ ID NO: 125) 5'- GGATCCTTAGTACA AAGGGTGTCTC-3' (SEQ ID NO: 126) | NB | |
| 16 + 26 | 5'- GTGGATTTCAGCGACGT TGGGTGGAATGACTGGG CTGTGGCACCGCCGGGG TATCACGCCTTCTATTGC CACGGAGAATGCCCGTT CCCACTGGCTGATCATCT GAACTCAGATAACCATG CCATTGTTCAGACCCTCG TTAATTCTGTTACGTATC CCGCCTCTCCGAAGCCG ATGAGGCATTCAATGCG GAGCTGCGCGTGCTGCG CCGGAGGTCTCCGGAAC CAGACAGGGACAGTG-3' (SEQ ID NO: 127)/ VDFSDVGWNDWAVAPP GYHAFYCHGECPFPLADH LNSDNHAIVQTLVNSVTY PASPKPMRHSMRSCACCA GGLRNQTGTV (SEQ ID NO: 128) | First pair: 5'- TTAACCATGGTGGA TTTCAGCGACG-3' (SEQ ID NO: 129) 5'- GGCGGGATACGTAA CAGAATTAACG-3' (SEQ ID NO: 130) Second pair: 5'- CGTTAATTCTGTTAC GTATCCCGCC-3' (SEQ ID NO: 131) 5'- GGATCCTTACACTG TCCCTGTCTGG-3' (SEQ ID NO: 132) | 57.78 | ±19.11 |

TABLE 3-continued

| Clone No. for Template | DNA sequence/Recombinant Polypeptide sequence | Primers | Affinity constant Mean[nM] | SD[nM] |
|---|---|---|---|---|
| 26 + 16 | 5'-ACGTATCCCGCCTCTCCG AAGCCGATGAGGCATTC AATGCGGAGCTGCGCGT GCTGCGCCGGAGGTCTC CGGAACCAGACAGGGAC AGTGGTGGATTTCAGCG ACGTTGGGTGGAATGAC TGGGCTGTGGCACCGCC GGGGTATCACGCCTTCT ATTGCCACGGAGAATGC CCGTTCCCACTGGCTGAT CATCTGAACTCAGATAA CCATGCCATTGTTCAGAC CCTCGTTAATTCTGTT-3' (SEQ ID NO: 133)/ TYPASPKPMRHSMRSCAC CAGGLRNQTGTVVDFSD VGWNDWAVAPPGYHAF YCHGECPFPLADHLNSDN HAIVQTLVNSV (SEQ ID NO: 134) | First pair: 5'-TTAACCATGACGTAT CCCGCCTCTCC-3' (SEQ ID NO: 135) 5'-CGCTGAAATCCACC ACTGTCCCTGTC-3' (SEQ ID NO: 136) Second pair: 5'-GACAGGGACAGTGG TGGATTTCAGCG-3' (SEQ ID NO: 137) 5'-GGATCCTTAAACAG AATTAACGAGGG-3' (SEQ ID NO: 138) | 61.74 | ±13.69 |
| 12 + 28 | 5'-GCTCAAGCCAAACACAA ACAGTACAAACGCCTTA AGTCCAGCTGTAAGAGA CACCCTTTGTACGAGCCC CTGGGCGGCGCGCGCTG GGAAGCGTTCGACGTGA CGGACGCGGTGCAGAGC CACCGCCGCTCGCCACG AGCCTCCCGCAAGTGCT GCCTGGGGCTGCGCGCG GTGACGGCCTCG-3' (SEQ ID NO: 139)/ AQAKHKQYKRLKSSCKR HPLYEPLGGARWEAFDVT DAVQSHRRSPRASRKCCL GLRAVTAS (SEQ ID NO: 140) | First pair: 5'-TTAACCATGGCTCA AGCCAAACACAAAC-3' (SEQ ID NO: 141) 5'-CCGCCCAGGGGCTC GTACAAAGGGTGTC-3' (SEQ ID NO: 142) Second pair: 5'-GACACCCTTTGTACG AGCCCCTGGGCGG-3' (SEQ ID NO: 143) 5'-GGATCCTTACGAGG CCGTCACCGCGCGC-3' (SEQ ID NO: 144) | 59.14 | ±16.11 |
| 28 + 12 | 5'-GAGCCCCTGGGCGGCGC GCGCTGGGAAGCGTTCG ACGTGACGGACGCGGTG CAGAGCCACCGCCGCTC GCCACGAGCCTCCCGCA AGTGCTGCCTGGGGCTG CGCGCGGTGACGGCCTC GGCTCAAGCCAAACACA AACAGTACAAACGCCTT AAGTCCAGCTGTAAGAG ACACCCTTTGTAC-3' (SEQ ID NO: 145)/ EPLGGARWEAFDVTDAV QSHRRSPRASRKCCLGLR AVTASAQAKHKQYKRLK SSCKRHPLY (SEQ ID NO: 146) | First pair: 5'-TTAACCATGGAGCC CCTGGGCGGCG-3' (SEQ ID NO: 147) 5'-GTTTGGCTTGAGCCG AGGCCGTCAC-3' (SEQ ID NO: 148) Second pair: 5'-GTGACGGCCTCGGCT CAAGCCAAAC-3' (SEQ ID NO: 149) 5'-GGATCCTTAGTACA AAGGGTGTCTC-3' (SEQ ID NO: 150) | 57.89 | ±18.67 |
| 16 + 29 | 5'-GTGGATTTCAGCGACGT TGGGTGGAATGACTGGG CTGTGGCACCGCCGGGG TATCACGCCTTCTATTGC CACGGAGAATGCCCGTT CCCACTGGCTGATCATCT GAACTCAGATAACCATG CCATTGTTCAGACCCTCG TTAATTCTGTTGAGCCCC TGGGCGGCGCGCGCTGG GAAGCGTTCGACGTGAC GGACGCGGTGCAGAGCC | First pair: 5'-TTAACCATGGTGGA TTTCAGCGACG-3' (SEQ ID NO: 153) 5'-GCCCAGGGGCTCAA CAGAATTAACG-3' (SEQ ID NO: 154) Second pair: 5'-CGTTAATTCTGTTGA GCCCCTGGGC-3' | 58.71 | ±18.14 |

TABLE 3-continued

| Clone No. for Template | DNA sequence/Recombinant Polypeptide sequence | Primers | Affinity constant Mean[nM] | SD[nM] |
|---|---|---|---|---|
| | ACCGCCGCTCGCAGCGA GCCTCCCGCAAGTGCTG CCTGGTTCTGCGCGCGGT GACGGCCTCG-3' (SEQ ID NO: 151)/ VDFSDVGWNDWAVAPPG YHAFYCHGECPFPLADHL NSDNHAIVQTLVNSVEPL GGARWEAFDVTDAVQSH RRSQRASRKCCLVLRAVT AS (SEQ ID NO: 152) | (SEQ ID NO: 155) 5'- GGATCCTTACGAGG CCGTCACCGCG-3' (SEQ ID NO: 156) | | |
| 29 + 16 | 5'- GAGCCCCTGGGCGGCGC GCGCTGGGAAGCGTTCG ACGTGACGGACGCGGTG CAGAGCCACCGCCGCTC GCAGCGAGCCTCCCGCA AGTGCTGCCTGGTTCTGC GCGCGGTGACGGCCTCG GTGGATTTCAGCGACGT TGGGTGGAATGACTGGG CTGTGGCACCGCCGGGG TATCACGCCTTCTATTGC CACGGAGAATGCCCGTT CCCACTGGCTGATCATCT GAACTCAGATAACCATG CCATTGTTCAGACCCTCG TTAATTCTGTT-3' (SEQ ID NO: 157)/ EPLGGARWEAFDVTDAV QSHRRSQRASRKCCLVLR AVTASVDFSDVGWNDWA VAPPGYHAFYCHGECPFP LADHLNSDNHAIVQTLVN SV (SEQ ID NO: 158) | First pair: 5'- TTAACCATGGAGCC CCTGGGCGGCG-3' (SEQ ID NO: 159) 5'- GCTGAAATCCACCG AGGCCGTCACC-3' (SEQ ID NO: 160) Second pair: 5'- GGTGACGGCCTCGG TGGATTTCAGC-3' (SEQ ID NO: 161) 5'- GGATCCTTAAACAG AATTAACGAGG-3' (SEQ ID NO: 162) | 54.31 | ±12.89 |
| 30 + 12 | 5'- ACCGCCCTAGATGGGAC TCGGGGAGCGCAGGGAA GCGGTGGTGGCGGCGGT GGCGGTGGCGGCGGCGG CGGCGGCGGCGGCGGCG GCGGCGGCGGCGCAGGC AGGGGCCACGGGCGCAG AGGCCGGAGCGCTGCA GTCGCAAGTCACTGCAC GTGGACTTTAAGGAGCT GGGCGCTCAAGCCAAAC ACAAACAGTACAAACGC CTTAAGTCCAGCTGTAA GAGACACCCTTTGTAC-3' (SEQ ID NO: 163)/ TALDGTRGAQGSGGGGG GGGGGGGGGGGGGGA GRGHGRRGRSRCSRKSLH VDFKELGAQAKHKQYKR LKSSCKRHPLY (SEQ ID NO: 164) | First pair: 5'- TTAACCATGACCGC CCTAGATGGGAC-3' (SEQ ID NO: 165) 5'- GTTTGGCTTGAGCGC CCAGCTCCTTA-3' (SEQ ID NO: 166) Second pair: 5'- TAAGGAGCTGGGCG CTCAAGCCAAAC-3' (SEQ ID NO: 167) 5'- GGATCCTTAGTACA AAGGGTGTCTCT-3' (SEQ ID NO: 168) | 61.12 | ±13.71 |
| 12 + 30 | 5'- GCTCAAGCCAAACACAA ACAGTACAAACGCCTTA AGTCCAGCTGTAAGAGA CACCCTTTGTACACCGCC CTAGATGGGACTCGGGG AGCGCAGGGAAGCGGTG GTGGCGGCGGTGGCGGT GGCGGCGGCGGCGGCGG CGGCGGCGGCGGCGGCG GCGGCGCAGGCAGGGGC CACGGGCGCAGAGGCCG GAGCCGCTGCAGTCGCA AGTCACTGCACGTGGAC TTTAAGGAGCTGGGC-3' | First pair: 5'- TTAACCATGGCTCA AGCCAAACACA-3' (SEQ ID NO: 171) 5'- CATCTAGGGCGGTGT ACAAAGGGTG-3' (SEQ ID NO: 172) Second pair: 5'- CACCCTTTGTACACC GCCCTAGATG-3' (SEQ ID NO: 173) 5'- | 59.11 | ±12.47 |

TABLE 3-continued

| Clone No. for Template | DNA sequence/Recombinant Polypeptide sequence | Primers | Affinity constant Mean[nM] | SD[nM] |
|---|---|---|---|---|
| | (SEQ ID NO: 169)/ AQAKHKQYKRLKSSCKR HPLYTALDGTRGAQGSG GGGGGGGGGGGGGGG GGGAGRGHGRRGRSRCS RKSLHVDFKELG (SEQ ID NO: 170) | GGATCCTTAGCCCA GCTCCTTAAAG-3' (SEQ ID NO: 174) | | |
| 16 + 30 | 5'-GTGGATTTCAGCGACGT TGGGTGGAATGACTGGG CTGTGGCACCGCCGGGG TATCACGCCTTCTATTGC CACGGAGAATGCCCGTT CCCACTGGCTGATCATCT GAACTCAGATAACCATG CCATTGTTCAGACCCTCG TTAATTCTGTTACCGCCC TAGATGGGACTCGGGGA GCGCAGGGAAGCGGTGG TGGCGGCGGTGGCGGTG GCGGCGGCGGCGGCGGC GGCGGCGGCGGCGGCGG CGGCGCAGGCAGGGGCC ACGGGCGCAGAGGCCGG AGCCGCTGCAGTCGCAA GTCACTGCACGTGGACT TTAAGGAGCTGGGC-3' (SEQ ID NO: 175)/ VDFSDVGWNDWAVAPPG YHAFYCHGECPFPLADHL NSDNHAIVQTLVNSVTAL DGTRGAQGSGGGGGGGG GGGGGGGGGGGAGRG HGRRGRSRCSRKSLHVDF KELG (SEQ ID NO: 176) | First pair: 5'-TTAACCATGGTGGA TTTCAGCGACG-3' (SEQ ID NO: 177) 5'-CATCTAGGGCGGTA ACAGAATTAAC-3' (SEQ ID NO: 178) Second pair: 5'-GTTAATTCTGTTACC GCCCTAGATG-3' (SEQ ID NO: 179) 5'-GGATCCTTAGCCCA GCTCCTTAAAG-3' (SEQ ID NO: 180) | NB | |
| 12 + 16 | 5'-GCTCAAGCCAAACACAA ACAGTACAAACGCCTTA AGTCCAGCTGTAAGAGA CACCCTTTGTACGTGGAT TTCAGCGACGTTGGGTG GAATGACTGGGCTGTGG CACCGCCGGGGTATCAC GCCTTCTATTGCCACGGA GAATGCCCGTTCCCACT GGCTGATCATCTGAACT CAGATAACCATGCCATT GTTCAGACCCTCGTTAAT TCTGTT-3' (SEQ ID NO: 181)/ AQAKHKQYKRLKSSCKR HPLYVDFSDVGWNDWAV APPGYHAFYCHGECPFPL ADHLNSDNHAIVQTLVNS V (SEQ ID NO: 182) | First pair: 5'-TTAACCATGGCTCA AGCCAAACACA-3' (SEQ ID NO: 183) 5'-CGCTGAAATCCACGT ACAAAGGGTG-3' (SEQ ID NO: 184) Second pair: 5'-CACCCTTTGTACGTG GATTTCAGCG-3' (SEQ ID NO: 185) 5'-GGATCCTTAAACAG AATTAACGAGG-3' (SEQ ID NO: 186) | 67.42 | ±19.51 |
| 10 + 15 | 5'-GCTCAAGCCAAACACAA ACAGCGGAAACGCCTTA AGTCCAGCTGTAAGAGA CACCCTTTGTACGTGGAC TTCAGTGACGTGGGGTG GAATGACTGGATTGTGG CTCCCCCGGGGTATCAC GCCTTTTACTGCCACGGA GAATGCCCTTTTCCTCTG GCTGATCATCTGAACTCC ACTAATCATGCCATTGTT CAGACGTTGGTCAACTC TGTT (SEQ ID NO: 187)/ AQAKHKQRKRLKSSCKR HPLYVDFSDVGWNDWIV APPGYHAFYCHGECPFPL | First pair: 5'-TTAACCATGGCTCA AGCCAAACACA-3' (SEQ ID NO: 189) 5'-CACTGAAGTCCACGT ACAAAGGGTG-3' (SEQ ID NO: 190) Second pair: 5'-CACCCTTTGTACGTG GACTTCAGTG-3' (SEQ ID NO: 191) 5'-GGATCCTTAAACAG AGTTGACCAAC-3' | 31.27 | ±12.74 |

TABLE 3-continued

| Clone No. for Template | DNA sequence/Recombinant Polypeptide sequence | Primers | Affinity constant Mean$_{[nM]}$ | SD$_{[nM]}$ |
|---|---|---|---|---|
| | ADHLNSTNHAIVQTLVNSV (SEQ ID NO: 188) | (SEQ ID NO: 192) | | |
| 15 + 10 | 5'-GTGGACTTCAGTGACGTGGGGTGGAATGACTGGATTGTGGCTCCCCCGGGGTATCACGCCTTTTACTGCCACGGAGAATGCCCTTTTCCTCTGGCTGATCATCTGAACTCCACTAATCATGCCATTGTTCAGACGTTGGTCAACTCTGTTGCTCAAGCCAAACACAAACAGCGGAAACGCCTTAAGTCCAGCTGTAAGAGACACCCTTTGTAC-3' (SEQ ID NO: 193)/VDFSDVGWNDWIVAPPGYHAFYCHGECPFPLADHLNSTNHAIVQTLVNSVAQAKHKQRKRLKSSCKRHPLY (SEQ ID NO: 194) | First pair: 5'-TTAACCATGGTGGACTTCAGTGACG-3' (SEQ ID NO: 195) 5'-GTTTGGCTTGAGCAACAGAGTTGAC-3' (SEQ ID NO: 196) Second pair: 5'-GTCAACTCTGTTGCTCAAGCCAAAC-3' (SEQ ID NO: 197) 5'-GGATCCTTAGTACAAAGGGTGTCTC-3' (SEQ ID NO: 198) | 29.74 | ±13.51 |
| 15 + 21 | 5'-GTGGACTTCAGTGACGTGGGGTGGAATGACTGGATTGTGGCTCCCCCGGGGTATCACGCCTTTTACTGCCACGGAGAATGCCCTTTTCCTCTGGCTGATCATCTGAACTCCACTAATCATGCCATTGTTCAGACGTTGGTCAACTCTGTTAACTCTAAGATTCCTAAGGCATGCTGTGTCCCGACAGAACTCAGTGCTATCTCGATGCTGTACCTTGACGAGAATGAAAAGGTTGTATTAAAGAACTATCAGGACATGGTTGTGGAGGGTTGTGGGTGTCGC (SEQ ID NO: 199)/VDFSDVGWNDWIVAPPGYHAFYCHGECPFPLADHLNSTNHAIVQTLVNSVNSKIPKACCVPTELSAISMLYLDENEKVVLKNYQDMVVEGCGCR (SEQ ID NO: 200) | First pair: 5'-TTAACCATGGTGGACTTCAGTGACG-3' (SEQ ID NO: 201) 5'-GAATCTTAGAGTTAACAGAGTTGAC-3' (SEQ ID NO: 202) Second pair: 5'-GTCAACTCTGTTAACTCTAAGATTC-3' (SEQ ID NO: 203) 5'-GGATCCTTAGCGACACCCACAACCC-3' (SEQ ID NO: 204) | 32.64 | ±12.78 |
| 21 + 15 | 5'-AACTCTAAGATTCCTAAGGCATGCTGTGTCCCGACAGAACTCAGTGCTATCTCGATGCTGTACCTTGACGAGAATGAAAAGGTTGTATTAAAGAACTATCAGGACATGGTTGTGGAGGGTTGTGGGTGTCGCGTGGACTTCAGTGACGTGGGGTGGAATGACTGGATTGTGGCTCCCCCGGGGTATCACGCCTTTTACTGCCACGGAGAATGCCCTTTTCCTCTGGCTGATCATCTGAACTCCACTAATCATGCCATTGTTCAGACGTTGGTCAACTCTGTT-3' (SEQ ID NO: 205)/NSKIPKACCVPTELSAISMLYLDENEKVVLKNYQDMVVEGCGCRVDFSDVGWNDWIVAPPGYHAFYCHGECPFPLADHLNSTNHAIVQTLVNSV (SEQ ID NO: 206) | First pair: 5'-TTAACCATGAACTCTAAGATTCCTA-3' (SEQ ID NO: 207) 5'-ACTGAAGTCCACGCGACACCCACAA-3' (SEQ ID NO: 208) Second pair: 5'-TTGTGGGTGTCGCGTGGACTTCAGT-3' (SEQ ID NO: 209) 5'-GGATCCTTAAACAGAGTTGACCAAC-3' (SEQ ID NO: 210) | 31.04 | ±16.58 |

TABLE 3-continued

| Clone No. for Template | DNA sequence/Recombinant Polypeptide sequence | Primers | Affinity constant Mean[nM] | SD[nM] |
|---|---|---|---|---|
| 21 + 10 | 5'-AACTCTAAGATTCCTAA GGCATGCTGTGTCCCGA CAGAACTCAGTGCTATC TCGATGCTGTACCTTGAC GAGAATGAAAAGGTTGT ATTAAAGAACTATCAGG ACATGGTTGTGGAGGGT TGTGGGTGTCGCGCTCA AGC CAAACACAAACAGC GGAAACGCCTTAAGTCC AGCTGTAAGAGACACCC TTTGTAC-3' (SEQ ID NO: 211)/ NSKIPKACCVPTELSAISM LYLDENEKVVLKNYQDM VVEGCGCRAQAKHKQRK RLKSSCKRHPLY (SEQ ID NO: 212) | First pair: 5'-TTAACCATGAACTCT AAGATTCCTA-3' (SEQ ID NO: 213) 5'-TTGGCTTGAGCGCGA CACCCACAAC-3' (SEQ ID NO: 214) Second pair: 5'-GTTGTGGGTGTCGCG CTCAAGCCAA-3' (SEQ ID NO: 215) 5'-GGATCCTTAGTACA AAGGGTGTCTC-3' (SEQ ID NO: 216) | 30.21 | ±12.76 |
| 10 + 21 | 5'-GCTCAAGCCAAACACAA ACAGCGGAAACGCCTTA AGTCCAGCTGTAAGAGA CACCCTTTGTACAACTCT AAGATTCCTAAGGCATG CTGTGTCCCGACAGAAC TCAGTGCTATCTCGATGC TGTACCTTGACGAGAAT GAAAAGGTTGTATTAAA GAACTATCAGGACATGG TTGTGGAGGGTTGTGGG TGTCGC (SEQ ID NO: 217)/ AQAKHKQRKRLKSSCKR HPLYNSKIPKACCVPTELS AISMLYLDENEKVVLKNY QDMVVEGCGCR (SEQ ID NO: 218) | First pair: 5'-TTAACCATGGCTCA AGCCAAACACA-3' (SEQ ID NO: 219) 5'-GAATCTTAGAGTTGT ACAAAGGGTG-3' (SEQ ID NO: 220) Second pair: 5'-CACCCTTTGTACAAC TCTAAGATTC-3' (SEQ ID NO: 221) 5'-GGATCCTTAGCGAC ACCCACAACCC-3' (SEQ ID NO: 222) | 27.31 | ±11.79 |
| 8 + 14 | 5'-GGCCAAGCCAAACGCAA AGGGTATAAACGCCTTA AGTCCAGCTGTAAGAGA CACCCTTTGTACGTGGAT TTCAAGGACGTTGGGTG GAATGACCATGCTGTGG CACCGCCGGGGTATCAC GCCTTCTATTGCCACGGA GAATGCCCGTTCCCACT GGCTGATCATCTGAACT CAGATAACCATGCCATT GTTCAGACCAAGGTTAA TTCTGTT-3' (SEQ ID NO: 223)/ GQAKRKGYKRLKSSCKR HPLYVDFKDVGWNDHAV APPGYHAFYCHGECPFPL ADHLNSDNHAIVQTKVNS V (SEQ ID NO: 224) | First pair: 5'-TTAACCATGGGCCA AGCCAAACGCA-3' (SEQ ID NO: 225) 5'-CCTTGAAATCCACGT ACAAAGGGTG-3' (SEQ ID NO: 226) Second pair: 5'-CACCCTTTGTACGTG GATTTCAAGG-3' (SEQ ID NO: 227) 5'-GGATCCTTAAACAG AATTAACCTTG-3' (SEQ ID NO: 228) | 35.14 | ±13.64 |
| 14 + 8 | 5'-GTGGATTTCAAGGACGT TGGGTGGAATGACCATG CTGTGGCACCGCCGGGG TATCACGCCTTCTATTGC CACGGAGAATGCCCGTT CCCACTGGCTGATCATCT GAACTCAGATAACCATG CCATTGTTCAGACCAAG GTTAATTCTGTTGGCCAA GCCAAACGCAAAGGGTA TAAACGCCTTAAGTCCA GCTGTAAGAGACACCCT TTGTAC-3' (SEQ ID | First pair: 5'-TTAACCATGGTGGA TTTCAAGGACG-3' (SEQ ID NO: 231) 5'-GTTTGGCTTGGCCAA CAGAATTAAC-3' (SEQ ID NO: 232) Second pair: 5'-GTTAATTCTGTTGGC CAAGCCAAAC-3' (SEQ ID NO: 233) | 33.79 | ±16.51 |

TABLE 3-continued

| Clone No. for Template | DNA sequence/Recombinant Polypeptide sequence | Primers | Affinity constant Mean[nM] | SD[nM] |
|---|---|---|---|---|
| | 229)/ VDFKDVGWNDHAVAPPG YHAFYCHGECPFPLADHL NSDNHAIVQTKVNSVGQ AKRKGYKRLKSSCKRHPL Y (SEQ ID NO: 230) | 5'-GGATCCTTAGTACA AAGGGTGTCTC-3' (SEQ ID NO: 234) | | |
| 19 + 8 | 5'-AATAGCAAAGATCCCAA GGCATGCTGTGTCCCGA CAGAACTCAGTGCCCCC AGCCCGCTGTACCTTGA CGAGAATGAGAAGCCTG TACTCAAGAACTATCAG GACATGGTAGTCCATGG GTGTGGGTGTCGCGGCC AAGCCAAACGCAAAGGG TATAAACGCCTTAAGTC CAGCTGTAAGAGACACC CTTTGTAC-3' (SEQ ID NO: 235)/ NSKDPKACCVPTELSAPSP LYLDENEKPVLKNYQDM VVHGCGCRGQAKRKGYK RLKSSCKRHPLY (SEQ ID NO: 236) | First pair: 5'-TTAACCATGAATAG CAAAGATCCCA-3' (SEQ ID NO: 237) 5'-TTGGCTTGGCCGCGA CACCCACACC-3' (SEQ ID NO: 238) Second pair: 5'-GGTGTGGGTGTCGC GGCCAAGCCAA-3' (SEQ ID NO: 239) 5'-GGATCCTTAGTACA AAGGGTGTCTC-3' (SEQ ID NO: 240) | 33.51 | ±15.71 |
| 8 + 19 | 5'-GGCCAAGCCAAACGCAA AGGGTATAAACGCCTTA AGTCCAGCTGTAAGAGA CACCCTTTGTACAATAGC AAAGATCCCAAGGCATG CTGTGTCCCGACAGAAC TCAGTGCCCCCAGCCCG CTGTACCTTGACGAGAA TGAGAAGCCTGTACTCA AGAACTATCAGGACATG GTAGTCCATGGGTGTGG GTGTCGC-3' (SEQ ID NO: 241)/ GQAKRKGYKRLKSSCKR HPLYNSKDPKACCVPTEL SAPSPLYLDENEKPVLKN YQDMVVHGCGCR (SEQ ID NO: 242) | First pair: 5'-TTAACCATGGGCCA AGCCAAACGCA-3' (SEQ ID NO: 243) 5'-GATCTTTGCTATTGT ACAAAGGGTG-3' (SEQ ID NO: 244) Second pair: 5'-CACCCTTTGTACAAT AGCAAAGATC-3' (SEQ ID NO: 245) 5'-GGATCCTTAGCGAC ACCCACACCCA-3' (SEQ ID NO: 246) | 31.12 | ±13.42 |
| 19 + 14 | 5'-AATAGCAAAGATCCCAA GGCATGCTGTGTCCCGA CAGAACTCAGTGCCCCC AGCCCGCTGTACCTTGA CGAGAATGAGAAGCCTG TACTCAAGAACTATCAG GACATGGTAGTCCATGG GTGTGGGTGTCGCGTGG ATTTCAAGGACGTTGGG TGGAATGACCATGCTGT GGCACCGCCGGGGTATC ACGCCTTCTATTGCCACG GAGAATGCCCGTTCCCA CTGGCTGATCATCTGAA CTCAGATAACCATGCCA TTGTTCAGACCAAGGTT AATTCTGTT-3' (SEQ ID NO: 247)/ NSKDPKACCVPTELSAPSP LYLDENEKPVLKNYQDM VVHGCGCRVDFKDVGW NDHAVAPPGYHAFYCHG ECPFPLADHLNSDNHAIV QTKVNSV (SEQ ID NO: 248) | First pair: 5'-TTAACCATGAATAG CAAAGATCCCA-3' (SEQ ID NO: 249) 5'-CTTGAAATCCACGCG ACACCCACAC-3' (SEQ ID NO: 250) Second pair: 5'-GTGTGGGTGTCGCGT GGATTTCAAG-3' (SEQ ID NO: 251) 5'-GGATCCTTAAACAG AATTAACCTTG-3' (SEQ ID NO: 252) | 32.09 | ±13.03 |

TABLE 3-continued

| Clone No. for Template | DNA sequence/Recombinant Polypeptide sequence | Primers | Affinity constant Mean$_{[nM]}$ | SD$_{[nM]}$ |
|---|---|---|---|---|
| 14 + 19 | 5'-GTGGATTTCAAGGACGTTGGGTGGAATGACCATGCTGTGGCACCGCCGGGGTATCACGCCTTCTATTGCCACGGAGAATGCCCGTTCCCACTGGCTGATCATCTGAACTCAGATAACCATGCCATTGTTCAGACCAAGGTTAATTCTGTTAATAGCAAAGATCCCAAGGCATGCTGTGTCCCGACAGAACTCAGTGCCCCCAGCCCGCTGTACCTTGACGAGAATGAGAAGCCTGTACTCAAGAACTATCAGGACATGGTAGTCCATGGGTGTGGGTGTCGC-3' (SEQ ID NO: 253)/VDFKDVGWNDHAVAPPGYHAFYCHGECPFPLADHLNSDNHAIVQTKVNSVNSKDPKACCVPTELSAPSPLYLDENEKPVLKNYQDMVVHGCGCR (SEQ ID NO: 254) | First pair: 5'-TTAACCATGGTGGATTTCAAGGACG-3' (SEQ ID NO: 255) 5'-GATCTTTGCTATTAACAGAATTAAC-3' (SEQ ID NO: 256) Second pair: 5'-GTTAATTCTGTTAATAGCAAAGATC-3' (SEQ ID NO: 257) 5'-GGATCCTTAGCGACACCCACACCCA-3' (SEQ ID NO: 258) | 30.98 | ±12.07 |
| 10 + 15 + 21 | 5'-GCTCAAGCCAAACACAAACAGCGGAAACGCCTTAAGTCCAGCTGTAAGAGACACCCTTTGTACGTGGACTTCAGTGACGTGGGGTGAATGACTGGATTGTGGCTCCCCCGGGGTATCACGCCTTTTACTGCCACGGAGAATGCCCTTTTCCTCTGGCTGATCATCTGAACTCCACTAATCATGCCATTGTTCAGACGTTGGTCAACTCTGTTAACTCTAAGATTCCTAAGGCATGCTGTGTCCCGACAGAACTCAGTGCTATCTCGATGCTGTACCTTGACGAGAATGAAAAGGTTGTATTAAAGAACTATCAGGACATGGTTGTGGAGGGTTGTGGGTGTCGC-3' (SEQ ID NO: 259)/AQAKHKQRKRLKSSCKRHPLYVDFSDVGWNDWIVAPPGYHAFYCHGECPFPLADHLNSTNHAIVQTLVNSVNSKIPKACCVPTELSAISMLYLDENEKVVLKNYQDMVVEGCGCR (SEQ ID NO: 260) | First pair: 5'-TTAACCATGGCTCAAGCCAAACACA-3' (SEQ ID NO: 261) 5'-CACTGAAGTCCACGTACAAAGGGTG-3' (SEQ ID NO: 262) Second pair: 5'-CACCCTTTGTACGTGGACTTCAGTG-3' (SEQ ID NO: 263) 5'-GAATCTTAGAGTTAACAGAGTTGAC-3' (SEQ ID NO: 264) Third pair: 5'-GTCAACTCTGTTAACTCTAAGATTC-3' (SEQ ID NO: 265) 5'-GGATCCTTAGCGACACCCACAACCC-3' (SEQ ID NO: 266) | 17.25 | ±11.20 |
| 15 + 10 + 21 | 5'-GTGGACTTCAGTGACGTGGGGTGGAATGACTGGATTGTGTGGCTCCCCCGGGGTATCACGCCTTTTACTGCCACGGAGAATGCCCTTTTCCTCTGGCTGATCATCTGAACTCCACTAATCATGCCATTGTTCAGACGTTGGTCAACTCTGTTGCTCAAGCCAAACACAAACAGCGGAAACGCCTTAAGTCCAGCTGTAAGAGACACCCTTTGTACAACTCTAAGATTCCTAAGGCATGCTGTGTCCCGACAGAACTCAGTGCTATCTCGATGCTGTACCT | First pair: 5'-TTAACCATGGTGGACTTCAGTGACG-3' (SEQ ID NO: 269) 5'-GTTTGGCTTGAGCAACAGAGTTGAC-3' (SEQ ID NO: 270) Second pair: 5'-GTCAACTCTGTTGCTCAAGCCAAAC-3' (SEQ ID NO: 271) 5'-GAATCTTAGAGTTGTACAAAGGGTG-3' | 15.14 | ±13.21 |

TABLE 3-continued

| Clone No. for Template | DNA sequence/Recombinant Polypeptide sequence | Primers | Affinity constant Mean[nM] | SD[nM] |
|---|---|---|---|---|
| | TGACGAGAATGAAAAGG TTGTATTAAAGAACTATC AGGACATGGTTGTGGAG GGTTGTGGGTGTCGC-3' (SEQ ID NO: 267)/ VDFSDVGWNDWIVAPPG YHAFYCHGECPFPLADHL NSTNHAIVQTLVNSVAQA KHKQRKRLKSSCKRHPLY NSKIPKACCVPTELSAISM LYLDENEKVVLKNYQDM VVEGCGCR (SEQ ID NO: 268) | (SEQ ID NO: 272) Third pair: 5'- CACCCTTTGTACAAC TCTAAGATTC-3' (SEQ ID NO: 273) 5'- GGATCCTTAGCGAC ACCCACAACCC-3' (SEQ ID NO: 274) | | |
| 21 + 15 + 10 | 5'-AACTCTAAGATTCCTAA GGCATGCTGTGTCCCGA CAGAACTCAGTGCTATC TCGATGCTGTACCTTGAC GAGAATGAAAAGGTTGT ATTAAAGAACTATCAGG ACATGGTTGTGGAGGGT TGTGGGTGTCGCGTGGA CTTCAGTGACGTGGGGT GGAATGACTGGATTGTG GCTCCCCCGGGGTATCA CGCCTTTTACTGCCACGG AGAATGCCCTTTTCCTCT GGCTGATCATCTGAACT CCACTAATCATGCCATTG TTCAGACGTTGGTCAACT CTGTTGCTCAAGCCAAA CACAAACAGCGGAAACG CCTTAAGTCCAGCTGTA AGAGACACCCTTTGTAC-3' (SEQ ID NO: 275)/ NSKIPKACCVPTELSAISM LYLDENEKVVLKNYQDM VVEGCGCRVDFSDVGWN DWIVAPPGYHAFYCHGEC PFPLADHLNSTNHAIVQTL VNSVAQAKHKQRKRLKS SCKRHPLY (SEQ ID NO: 276) | First pair: 5'- TTAACCATGAACTCT AAGATTCCTA-3' (SEQ ID NO: 277) 5'- CACTGAAGTCCACG CGACACCCACA-3' (SEQ ID NO: 278) Second pair: 5'- TGTGGGTGTCGCGTG GACTTCAGTG-3' (SEQ ID NO: 279) 5'- GTTTGGCTTGAGCAA CAGAGTTGAC-3' (SEQ ID NO: 280) Third pair: 5'- GTCAACTCTGTTGCT CAAGCCAAAC-3' (SEQ ID NO: 281) 5'- GGATCCTTAGTACA AAGGGTGTCTC-3' (SEQ ID NO: 282) | 14.21 | ±13.51 |
| 21 + 10 + 15 | 5'-AACTCTAAGATTCCTAA GGCATGCTGTGTCCCGA CAGAACTCAGTGCTATC TCGATGCTGTACCTTGAC GAGAATGAAAAGGTTGT ATTAAAGAACTATCAGG ACATGGTTGTGGAGGGT TGTGGGTGTCGCGCTCA AGCCAAACACAAACAGC GGAAACGCCTTAAGTCC AGCTGTAAGAGACACCC TTTGTACGTGGACTTCAG TGACGTGGGGTGGAATG ACTGGATTGTGGCTCCCC CGGGGTATCACGCCTTTT ACTGCCACGGAGAATGC CTTTTCCTCTGGCTGAT CATCTGAACTCCACTAAT CATGCCATTGTTCAGAC GTTGGTCAACTCTGTT-3' (SEQ ID NO: 283)/ NSKIPKACCVPTELSAISM LYLDENEKVVLKNYQDM VVEGCGCRAQAKHKQRK RLKSSCKRHPLYVDFSDV GWNDWIVAPPGYHAFYC HGECPFPLADHLNSTNHA IVQTLVNSV (SEQ ID NO: 284) | First pair: 5'- TTAACCATGAACTCT AAGATTCCTA-3' (SEQ ID NO: 285) 5'- GTTTGGCTTGAGCGC GACACCCACA-3' (SEQ ID NO: 286) Second pair: 5'- TGTGGGTGTCGCGCT CAAGCCAAAC-3' (SEQ ID NO: 287) 5'- CACTGAAGTCCACGT ACAAAGGGTG-3' (SEQ ID NO: 288) Third pair: 5'- CACCCTTTGTACGTG GACTTCAGTG-3' (SEQ ID NO: 289) 5'- GGATCCTTAAACAG AGTTGACCAAC-3' (SEQ ID NO: 290) | 16.71 | ±14.25 |

TABLE 3-continued

| Clone No. for Template | DNA sequence/Recombinant Polypeptide sequence | Primers | Affinity constant Mean$_{[nM]}$ | SD$_{[nM]}$ |
|---|---|---|---|---|
| 8 + 14 + 19 | 5'-GGCCAAGCCAAACGCAAAGGGTATAAACGCCTTAAGTCCAGCTGTAAGAGACACCCTTTGTACGTGGATTTCAAGGACGTTGGGTGGAATGACCATGCTGTGGCACCGCCGGGGTATCACGCCTTCTATTGCCACGGAGAATGCCCGTTCCCACTGGCTGATCATCTGAACTCAGATAACCATGCCATTGTTCAGACCAAGGTTAATTCTGTTAATAGCAAAGATCCCAAGGCATGCTGTGTCCCGACAGAACTCAGTGCCCCCAGCCCGCTGTACCTTGACGAGAATGAGAAGCCTGTACTCAAGAACTATCAGGACATGGTAGTCCATGGGTGTGGGTGTCGC-3' (SEQ ID NO: 291)/GQAKRKGYKRLKSSCKRHPLYVDFKDVGWNDHAVAPPGYHAFYCHGECPFPLADHLNSDNHAIVQTKVNSVNSKDPKACCVPTELSAPSPLYLDENEKPVLKNYQDMVVHGCGCR (SEQ ID NO: 292) | First pair:<br>5'-TTAACCATGGGCCAAGCCAAACGCA-3' (SEQ ID NO: 293)<br>5'-CCTTGAAATCCACGTACAAAGGGTG-3' (SEQ ID NO: 294)<br>Second pair:<br>5'-CACCCTTTGTACGTGGATTTCAAGG-3' (SEQ ID NO: 295)<br>5'-GATCTTTGCTATTAACAGAATTAAC-3' (SEQ ID NO: 296)<br>Third pair:<br>5'-GTTAATTCTGTTAATAGCAAAGATC-3' (SEQ ID NO: 297)<br>5'-GGATCCTTAGCGACACCCACACCCA-3' (SEQ ID NO: 298) | 15.64 | ±13.24 |
| 14 + 8 + 19 | 5'-GTGGATTTCAAGGACGTTGGGTGGAATGACCATGCTGTGGCACCGCCGGGGTATCACGCCTTCTATTGCCACGGAGAATGCCCGTTCCCACTGGCTGATCATCTGAACTCAGATAACCATGCCATTGTTCAGACCAAGGTTAATTCTGTTGGCCAAGCCAAACGCAAAGGGTATAAACGCCTTAAGTCCAGCTGTAAGAGACACCCTTTGTACAATAGCAAAGATCCCAAGGCATGCTGTGTCCCGACAGAACTCAGTGCCCCCAGCCCGCTGTACCTTGACGAGAATGAGAAGCCTGTACTCAAGAACTATCAGGACATGGTAGTCCATGGGTGTGGGTGTCGC-3' (SEQ ID NO: 299)/VDFKDVGWNDHAVAPPGYHAFYCHGECPFPLADHLNSDNHAIVQTKVNSVGQAKRKGYKRLKSSCKRHPLYNSKDPKACCVPTELSAPSPLYLDENEKPVLKNYQDMVVHGCGCR (SEQ ID NO: 300) | First pair:<br>5'-TTAACCATGGTGGATTTCAAGGACG-3' (SEQ ID NO: 301)<br>5'-GTTTGGCTTGGCCAACAGAATTAAC-3' (SEQ ID NO: 302)<br>Second pair:<br>5'-GTTAATTCTGTTGGCCAAGCCAAAC-3' (SEQ ID NO: 303)<br>5'-GATCTTTGCTATTGTACAAAGGGTG-3' (SEQ ID NO: 304)<br>Third pair:<br>5'-CACCCTTTGTACAATAGCAAAGATC-3' (SEQ ID NO: 305)<br>5'-GGATCCTTAGCGACACCCACACCCA-3' (SEQ ID NO: 306) | 17.65 | ±14.78 |
| 19 + 8 + 14 | 5'-AATAGCAAAGATCCCAAGGCATGCTGTGTCCCGACAGAACTCAGTGCCCCCAGCCCGCTGTACCTTGACGAGAATGAGAAGCCTGTACTCAAGAACTATCAGGACATGGTAGTCCATGGGTGTGGGTGTCGCGGCCAAGCCAAACGCAAAGGGTATAAACGCCTTAAGTCAGCTGTAAGAGACACC | First pair:<br>5'-TTAACCATGAATAGCAAAGATCCCA-3' (SEQ ID NO: 309)<br>5'-GTTTGGCTTGGCCGCGACACCCACA-3' (SEQ ID NO: 310)<br>Second pair:<br>5'-TGGGTGTCGCGGC | 15.97 | ±12.01 |

TABLE 3-continued

| Clone No. for Template | DNA sequence/Recombinant Polypeptide sequence | Primers | Affinity constant Mean[nM] | SD[nM] |
|---|---|---|---|---|
| | CTTTGTACGTGGATTTCA AGGACGTTGGGTGGAAT GACCATGCTGTGGCACC GCCGGGGTATCACGCCT TCTATTGCCACGGAGAA TGCCCGTTCCCACTGGCT GATCATCTGAACTCAGA TAACCATGCCATTGTTCA GACCAAGGTTAATTCTG TT-3' (SEQ ID NO: 307)/ NSKDPKACCVPTELSAPSP LYLDENEKPVLKNYQDM VVHGCGCRGQAKRKGYK RLKSSCKRHPLYVDFKDV GWNDHAVAPPGYHAFYC HGECPFPLADHLNSDNHA IVQTKVNSV (SEQ ID NO: 308) | CAAGCCAAAC-3' (SEQ ID NO: 311) 5'- CCTTGAAATCCACGT ACAAAGGGTG-3' (SEQ ID NO: 312) Third pair: 5'- CACCCTTTGTACGTG GATTTCAAGG-3' (SEQ ID NO: 313) 5'- GGATCCTTAAACAG AATTAACCTTG-3' (SEQ ID NO: 314) | | |
| 19 + 14 + 8 | 5'- AATAGCAAAGATCCCAA GGCATGCTGTGTCCCGA CAGAACTCAGTGCCCCC AGCCCGCTGTACCTTGA CGAGAATGAGAAGCCTG TACTCAAGAACTATCAG GACATGGTAGTCCATGG GTGTGGGTGTCGCGTGG ATTTCAAGGACGTTGGG TGGAATGACCATGCTGT GGCACCGCCGGGGTATC ACGCCTTCTATTGCCACG GAGAATGCCCGTTCCCA CTGGCTGATCATCTGAA CTCAGATAACCATGCCA TTGTTCAGACCAAGGTT AATTCTGTTGGCCAAGC CAAACGCAAAGGGTATA AACGCCTTAAGTCCAGC TGTAAGAGACACCCTTT GTAC-3' (SEQ ID NO: 315)/ NSKDPKACCVPTELSAPSP LYLDENEKPVLKNYQDM VVHGCGCRVDFKDVGW NDHAVAPPGYHAFYCHG ECPFPLADHLNSDNHAIV QTKVNSVGQAKRKGYKR LKSSCKRHPLY (SEQ ID NO: 316) | First pair: 5'- TTAACCATGAATAG CAAAGATCCCA-3' (SEQ ID NO: 317) 5'- CTTGAAATCCACGCG ACACCCACAC-3' (SEQ ID NO: 318) Second pair: 5'- GTGTGGGTGTCGCGT GGATTTCAAG-3' (SEQ ID NO: 319) 5'- GTTTGGCTTGGCCAA CAGAATTAAC-3' (SEQ ID NO: 320) Third pair: 5'- GTTAATTCTGTTGGC CAAGCCAAAC-3' (SEQ ID NO: 321) 5'- GGATCCTTAGTACA AAGGGTGTCTC-3' (SEQ ID NO: 322) | 14.12 | ±10.27 |
| 10 + 14 + 21 | 5'- GCTCAAGCCAAACACAA ACAGCGGAAACGCCTTA AGTCCAGCTGTAAGAGA CACCCTTTGTACGTGGAT TTCAAGGACGTTGGGTG GAATGACCATGCTGTGG CACCGCCGGGGTATCAC GCCTTCTATTGCCACGGA GAATGCCCGTTCCCACT GGCTGATCATCTGAACT CAGATAACCATGCCATT GTTCAGACCAAGGTTAA TTCTGTTAACTCTAAGAT TCCTAAGGCATGCTGTGT CCCGACAGAACTCAGTG CTATCTCGATGCTGTACC TTGACGAGAATGAAAAG GTTGTATTAAAGAACTA TCAGGACATGGTTGTGG AGGGTTGTGGGTGTCGC- 3' (SEQ ID NO: 323)/ AQAKHKQRKRLKSSCKR HPLYVDFKDVGWNDHAV APPGYHAFYCHGECPFPL | First pair: 5'- TTAACCATGGCTCA AGCCAAACAC-3' (SEQ ID NO: 325) 5'- CTTGAAATCCACGTA CAAAGGGTG-3' (SEQ ID NO: 326) Second pair: 5'- CACCCTTTGTACGTG GATTTCAAG-3' (SEQ ID NO: 327) 5'- GAATCTTAGAGTTAA CAGAATTAAG-3' (SEQ ID NO: 328) Third pair: 5'- GTTAATTCTGTTAAC TCTAAGATTC-3' (SEQ ID NO: 329) 5'- GGATCCTTAGCGAC | 17.98 | ±11.61 |

TABLE 3-continued

| Clone No. for Template | DNA sequence/Recombinant Polypeptide sequence | Primers | Affinity constant Mean$_{[nM]}$ | SD$_{[nM]}$ |
|---|---|---|---|---|
| | ADHLNSDNHAIVQTKVNS VNSKIPKACCVPTELSAIS MLYLDENEKVVLKNYQD MVVEGCGCR (SEQ ID NO: 324) | ACCCACAACCC-3' (SEQ ID NO: 330) | | |
| 8 + 15 + 19 | 5'-GGCCAAGCCAAACGCAA AGGGTATAAACGCCTTA AGTCCAGCTGTAAGAGA CACCCTTTGTACGTGGAC TTCAGTGACGTGGGGTG GAATGACTGGATTGTGG CTCCCCCGGGGTATCAC GCCTTTTACTGCCACGGA GAATGCCCTTTTCCTCTG GCTGATCATCTGAACTCC ACTAATCATGCCATTGTT CAGACGTTGGTCAACTC TGTTAATAGCAAAGATC CCAAGGCATGCTGTGTC CCGACAGAACTCAGTGC CCCCAGCCCGCTGTACCT TGACGAGAATGAGAAGC CTGTACTCAAGAACTAT CAGGACATGGTAGTCCA TGGGTGTGGGTGTCGC-3' (SEQ ID NO: 331)/ GQAKRKGYKRLKSSCKR HPLYVDFSDVGWNDWIV APPGYHAFYCHGECPFPL ADHLNSTNHAIVQTLVNS VNSKDPKACCVPTELSAP SPLYLDENEKPVLKNYQD MVVHGCGCR (SEQ ID NO: 332) | First pair: 5'-TTAACCATGGGCCA AGCCAAACGC-3' (SEQ ID NO: 333) 5'-ACTGAAGTCCACGT ACAAAGGGTC-3' (SEQ ID NO: 334) Second pair: 5'-CACCCTTTGTACGTG GACTTCAGT-3' (SEQ ID NO: 335) 5'-GATCTTTGCTATTAA CAGAGTTGAC-3' (SEQ ID NO: 336) Third pair: 5'-GTCAACTCTGTTAAT AGCAAAGATC-3' (SEQ ID NO: 337) 5'-GGATCCTTAGCGAC ACCCACACCCA-3' (SEQ ID NO: 338) | 16.49 | ±12.04 |
| 10 + 19 + 14 | 5'-GCTCAAGCCAAACACAA ACAGCGGAAACGCCTTA AGTCCAGCTGTAAGAGA CACCCTTTGTACAATAGC AAAGATCCCAAGGCATG CTGTGTCCCGACAGAAC TCAGTGCCCCCAGCCCG CTGTACCTTGACGAGAA TGAGAAGCCTGTACTCA AGAACTATCAGGACATG GTAGTCCATGGGTGTGG GTGTCGCGTGGATTTCA AGGACGTTGGGTGGAAT GACCATGCTGTGGCACC GCCGGGGTATCACGCCT TCTATTGCCACGGAGAA TGCCCGTTCCCACTGGCT GATCATCTGAACTCAGA TAACCATGCCATTGTTCA GACCAAGGTTAATTCTG TT-3' (SEQ ID NO: 339)/ AQAKHKQRKRLKSSCKR HPLYNSKDPKACCVPTEL SAPSPLYLDENEKPVLKN YQDMVVHGCGCRVDFKD VGWNDHAVAPPGYHAFY CHGECPFPLADHLNSDNH AIVQTKVNSV (SEQ ID NO: 340) | First pair: 5'-TTAACCATGGCTCA AGCCAAACACA-3' (SEQ ID NO: 341) 5'-GATCTTTGCTATTGT ACAAAGGGTG-3' (SEQ ID NO: 342) Second pair: 5'-CACCCTTTGTACAAT AGCAAAGATC-3' (SEQ ID NO: 343) 5'-CTTGAAATCCACGCG ACACCCACAC-3' (SEQ ID NO: 344) Third pair: 5'-GTGTGGGTGTCGCGT GGATTTCAAG-3' (SEQ ID NO: 345) 5'-GGATCCTTAAACAG AATTAACCTTG-3' (SEQ ID NO: 346) | 16.98 | ±13.97 |
| 8 + 21 + 15 | 5'-GGCCAAGCCAAACGCAA AGGGTATAAACGCCTTA AGTCCAGCTGTAAGAGA CACCCTTTGTACAACTCT AAGATTCCTAAGGCATG CTGTGTCCCGACAGAAC | First pair: 5'-TTAACCATGGGCCA AGCCAAACGC-3' (SEQ ID NO: 349) 5'-GAATCTTAGAGTTGT | 17.11 | ±12.10 |

TABLE 3-continued

| Clone No. for Template | DNA sequence/Recombinant Polypeptide sequence | Primers | Affinity constant Mean$_{[nM]}$ SD$_{[nM]}$ |
|---|---|---|---|
| | TCAGTGCTATCTCGATGC<br>TGTACCTTGACGAGAAT<br>GAAAAGGTTGTATTAAA<br>GAACTATCAGGACATGG<br>TTGTGGAGGGTTGTGGG<br>TGTCGCGTGGACTTCAGT<br>GACGTGGGGTGGAATGA<br>CTGGATTGTGGCTCCCCC<br>GGGGTATCACGCCTTTTA<br>CTGCCACGGAGAATGCC<br>CTTTTCCTCTGGCTGATC<br>ATCTGAACTCCACTAATC<br>ATGCCATTGTTCAGACGT<br>TGGTCAACTCTGTT-3'<br>(SEQ ID NO: 347)/<br>GQAKRKGYKRLKSSCKR<br>HPLYNSKIPKACCVPTELS<br>AISMLYLDENEKVVLKNY<br>QDMVVEGCGCRVDFSDV<br>GWNDWIVAPPGYHAFYC<br>HGECPFPLADHLNSTNHA<br>IVQTLVNSV (SEQ ID NO: 348) | ACAAAGGGTG-3'<br>(SEQ ID NO: 350)<br>Second pair:<br>5'-<br>CACCCTTTGTACAAC<br>TCTAAGATTC-3' (SEQ<br>ID NO: 351)<br>5'-<br>TCACTGAAGTCCACG<br>CGACACCCAC-3'<br>(SEQ ID NO: 352)<br>Third pair:<br>5'-<br>GTGGGTGTCGCGTG<br>GACTTCAGTGA-3'<br>(SEQ ID NO: 353)<br>5'-<br>GGATCCTTAAACAG<br>AGTTGACCAAC-3'<br>(SEQ ID NO: 354) | |

NB: Binding is below detection limit (KD > 1 mM)

The data shows that the affinity constant ($K_D$) was lower for recombinant polypeptides formed from the following combinations of two clones as compared to the individual polypeptides from each single clone: clone no. 10 operably linked with clone no. 15 (SEQ ID NO: 188), clone no. 15 operably linked with clone no. 10 (SEQ ID NO: 194), clone no. 15 operably linked with clone no. 21 (SEQ ID NO: 200), clone no. 21 operably linked with clone no. 15 (SEQ ID NO: 206), clone no. 21 operably linked with clone no. 10 (SEQ ID NO: 212), clone no. 10 operably linked with clone no. 21 (SEQ ID NO: 218), clone no. 8 operably linked with clone no. 14 (SEQ ID NO: 224), clone no. 14 operably linked with clone no. 8 (SEQ ID NO: 230), clone no. 19 operably linked with clone no. 8 (SEQ ID NO: 236), clone no. 8 operably linked with clone no. 19 (SEQ ID NO: 242), clone no. 19 operably linked with clone no. 14 (SEQ ID NO: 248), and clone no. 14 operably linked with clone no. 19 (SEQ ID NO: 254). In other words, the recombinant polypeptides resulting from the noted combinations had a higher affinity against ActRIIBecd than the individual polypeptides from each of clone no. 8 (SEQ ID NO: 35), clone no. 10 (SEQ ID NO: 39), clone no. 14 (SEQ ID NO: 47), clone no. 15 (SEQ ID NO: 49), clone no. 19 (SEQ ID NO: 57), and clone no. 21 (SEQ ID NO: 61).

In addition, recombinant polypeptides were produced from combinations of three clones using clone no. 8 (SEQ ID NO: 35), clone no. 10 (SEQ ID NO: 39), clone no. 14 (SEQ ID NO: 47), clone no. 15 (SEQ ID NO: 49), clone no. 19 (SEQ ID NO: 57), and clone no. 21 (SEQ ID NO: 61). Surprisingly, the $K_D$ of recombinant polypeptides formed from the following combinations of three clones was lower than for polypeptides from the individual clones or from combinations of two clones: clone no. 10 operably linked with clone nos. 15 and 21 (SEQ ID NO: 260), clone no. 15 operably linked with clone nos. 10 and 21 (SEQ ID NO: 268), clone no. 21 operably linked with clone nos. 15 and 10 (SEQ ID NO: 276), clone no. 21 operably linked with clone nos. 10 and 15 (SEQ ID NO: 284), clone no. 8 operably linked with clone nos. 14 and 19 (SEQ ID NO: 292), clone no. 14 operably linked with clone nos. 8 and 19 (SEQ ID NO: 300), clone no. 19 operably linked with clone nos. 8 and 14 (SEQ ID NO: 308), clone no. 19 operably linked with clone nos. 14 and 8 (SEQ ID NO: 316), clone no. 10 operably linked with clone nos. 14 and 21 (SEQ ID NO: 324), clone no. 8 operably linked with clone nos. 15 and 19 (SEQ ID NO: 332), clone no. 10 operably linked with clone nos. 19 and 14 (SEQ ID NO: 340), and clone no. 8 operably linked with clone nos. 21 and 15 (SEQ ID NO: 348).

Example 7: Post-Translation Modification

The effect of post-translation modification (PTM) on $K_D$ values of the recombinant polypeptides was investigated. One example of PTM is disulfide bond connection. Data showing the relation between disulfide bond location and binding affinity is provided in TABLE 4, which shows that PTM affects the binding affinity of the recombinant polypeptides against ActRIIBecd. The PTM assay was performed according to the following experiments.

A. Enzymatic Digestion and Dimethyl Labeling

Polypeptides were prepared as in Examples 4 and 6. Standard proteins were purchased from Sigma (St. Louise, Mo.). Optionally, 5 mM NEM (N-ethylmaleimide) (Sigma) in 100 mM sodium acetate (J. T. Baker, Phillipsburg, N.J.), pH 6, was used to block free cysteines at room temperature for 30 min. Enzymatic digestion was performed directly in sodium acetate at 37° C. overnight with 1:50 trypsin (Promega, Madison, Wis.). Protein digest was diluted three times with 100 mM sodium acetate (pH 5) before dimethyl labeling.

In certain embodiments, recombinant polypeptides prepared as in Examples 4 and 6 were diluted with 50 mM TEABC (Triethylammonium bicarbonate, T7408, Sigma-Aldrich) buffer (pH7) and split into two tubes for different enzymatic digestion. First, NEM (N-ethylmaleimide, E3876, Sigma-Aldrich) was added at a final concentration of 5 mM to block free cysteines. The alkylation reaction was performed for 30 min at room temperature. After NEM alkylation, one tube was added with trypsin (V5111, Promega) (1:65) at 37° C. for 18 hrs followed by Glu-C (P8100S, New England BioLabs) (1:50) digestion at 37° C. overnight. Another one was added with Glu-C (1:50) at 37° C. for 18 hrs followed by chymotrypsin (1:50) digestion at 37° C. overnight.

To perform dimethyl labeling, 2.5 µL of 4% (w/v) formaldehyde-$H_2$ (J. T. Baker) or 2.5 µL of 4% (w/v) formaldehyde-$D_2$ (Aldrich) was added to 50 µL of protein digest followed by the addition of 2.5 µL of 600 mM sodium cyanoborohydride (Sigma), and the reaction was performed at pH 5-6 for 30 min.

B. Mass Spectrometry

ESI Q-TOF equipped with a CapLC system (Waters, Milford, Mass.,) utilizing a capillary column (75 µm i.d., 10 cm in length, Csun, Taiwan) was used to perform the survey scan (MS, m/z 400-1600; MS/MS, m/z 50-2000). The alkylated and dimethyl-labeled protein digest was subject to LC-MS/MS analysis with a linear gradient from 5% to 50% acetonitrile containing 0.1% formic acid over 45 min.

In certain embodiments, the digested and dimethyl labeled protein digest were analyzed with Q-Exactive Plus mass spectrometer coupled with Ultimate 3000 RSLC system. The LC separation was performed using the C18 column (Acclaim PepMap RSLC, 75 µm×150 mm, 2 µm, 100 Å) with the gradient shown below:

| Time (min) | A % | B % | Flow (µL/min) |
|---|---|---|---|
| 0 | 99 | 1 | 0.25 |
| 6 | 99 | 1 | 0.25 |
| 45 | 70 | 30 | 0.25 |
| 48 | 40 | 60 | 0.25 |
| 50 | 20 | 80 | 0.25 |
| 60 | 20 | 80 | 0.25 |
| 65 | 99 | 1 | 0.25 |
| 70 | 99 | 1 | 0.25 |

Mobile phase A: 0.1% formic acid
Mobile phase B: 95% acetonitrile/0.1% formic acid Full MS scan was performed with the range of m/z 300-2000, and the ten most intense ions from MS scan were subjected to fragmentation for MS/MS spectra.

C. Data Analysis.

MassLynx 4.0 was used to produce peak lists from raw data (subtract 30%, smooth 3/2 Savitzky Golay and center three channels 80% centroid). A relatively high subtraction can be applied to eliminate background noise. True $a_1$ ions usually appear as major peaks so that they can be kept in the peak list.

D. Reversed-Phase Chromatography.

An Agilent 1100 HPLC system with a binary pump was equipped with a UV detector and an autosampler. The proteins were injected onto a Zorbax 300SB C8 column (150_2.1 mm, 5_m, 300 A) operated at 75° C. The flow rate was 0.5 ml/min. Mobile-phase A was water containing 0.1% trifluoroacetic acid. Mobile-phase B was 70% isopropyl alcohol, 20% acetonitrile, and aqueous 0.1% trifluoroacetic acid. Samples were injected at a loading condition of 10% B and increased to 19% B over 2 min. A linear elution gradient of 1.1% B/min started at 2 min and ended at 24 min. The column was then flushed for 5 min with 95% B. The column was reequilibrated with the loading condition for 5 min. This method was able to partially resolve disulfide isoforms.

TABLE 4

| SEQ ID NO | Recombinant Polypeptide Sequence | Identified Cysteine Pairs | Affinity Constant Mean$_{[nM]}$ | SD$_{[nM]}$ |
|---|---|---|---|---|
| 188 | AQAKHKQRKRLKSSCKRH PLYVDFSDVGWNDWIVAP PGYHAFYCHGECPFPLADH LNSTNHAIVQTLVNSV | C15—C44$^a$ | 42.32 | ±2.12 |
| 188 | AQAKHKQRKRLKSSCKRH PLYVDFSDVGWNDWIVAP PGYHAFYCHGECPFPLADH LNSTNHAIVQTLVNSV | C44—C48$^a$ | 21.47 | ±1.72 |
| 194 | VDFSDVGWNDWIVAPPGY HAFYCHGECPFPLADHLNS TNHAIVQTLVNSVAQAKH KQRKRLKSSCKRHPLY | C23—C65$^a$ | 45.98 | ±2.01 |
| 194 | VDFSDVGWNDWIVAPPGY HAFYCHGECPFPLADHLNS TNHAIVQTLVNSVAQAKH KQRKRLKSSCKRHPLY | C23—C27$^a$ | 18.14 | ±1.67 |
| 200 | VDFSDVGWNDWIVAPPGY HAFYCHGECPFPLADHLNS TNHAIVQTLVNSVNSKIPK ACCVPTELSAISMLYLDEN EKVVLKNYQDMVVEGCG CR | C23—C27$^a$, C58—C91$^a$, C59—C93$^a$ | 18.62 | ±1.41 |
| 200 | VDFSDVGWNDWIVAPPGY HAFYCHGECPFPLADHLNS TNHAIVQTLVNSVNSKIPK | C23—C27$^a$, C58—C93$^a$, C59—C91$^a$ | 20.13 | ±2.06 |

TABLE 4-continued

| SEQ ID NO | Recombinant Polypeptide Sequence | Identified Cysteine Pairs | Affinity Constant Mean[nM] | SD[nM] |
|---|---|---|---|---|
| | ACCVPTELSAISMLYLDEN EKVVLKNYQDMVVEGCG CR | | | |
| 200 | VDFSDVGWNDWIVAPPGY HAFYCHGECPFPLADHLNS TNHAIVQTLVNSVNSKIPK ACCVPTELSAISMLYLDEN EKVVLKNYQDMVVEGCG CR | C23–C27$^a$, C58–C91$^b$, C59–C93$^b$ | 19.75 | ±1.98 |
| 200 | VDFSDVGWNDWIVAPPGY HAFYCHGECPFPLADHLNS TNHAIVQTLVNSVNSKIPK ACCVPTELSAISMLYLDEN EKVVLKNYQDMVVEGCG CR | C23–C58$^a$ | 47.62 | ±2.89 |
| 206 | NSKIPKACCVPTELSAISML YLDENEKVVLKNYQDMV VEGCGCRVDFSDVGWND WIVAPPGYHAFYCHGECPF PLADHLNSTNHAIVQTLVN SV | C67–C71$^a$, C8–C41$^a$, C9–C43$^a$ | 15.49 | ±3.12 |
| 206 | NSKIPKACCVPTELSAISML YLDENEKVVLKNYQDMV VEGCGCRVDFSDVGWND WIVAPPGYHAFYCHGECPF PLADHLNSTNHAIVQTLVN SV | C8–C71$^a$ | 49.66 | ±1.09 |
| 206 | NSKIPKACCVPTELSAISML YLDENEKVVLKNYQDMV VEGCGCRVDFSDVGWND WIVAPPGYHAFYCHGECPF PLADHLNSTNHAIVQTLVN SV | C67–C71$^a$, C8–C43$^a$, C9–C41$^a$ | 17.73 | ±1.70 |
| 206 | NSKIPKACCVPTELSAISML YLDENEKVVLKNYQDMV VEGCGCRVDFSDVGWND WIVAPPGYHAFYCHGECPF PLADHLNSTNHAIVQTLVN SV | C67–C71$^a$, C8–C43$^b$, C9–C41$^b$ | 16.97 | ±2.15 |
| 212 | NSKIPKACCVPTELSAISML YLDENEKVVLKNYQDMV VEGCGCRAQAKHKQRKRL KSSCKRHPLY | C59–C59$^b$, C8–C41$^a$, C9–C43$^a$ | 18.13 | ±2.21 |
| 212 | NSKIPKACCVPTELSAISML YLDENEKVVLKNYQDMV VEGCGCRAQAKHKQRKRL KSSCKRHPLY | C59–C59$^b$, C8–C43$^a$, C9–C41$^a$ | 19.34 | ±1.56 |
| 212 | NSKIPKACCVPTELSAISML YLDENEKVVLKNYQDMV VEGCGCRAQAKHKQRKRL KSSCKRHPLY | C41–C59$^a$ | 44.33 | ±3.09 |
| 218 | AQAKHKQRKRLKSSCKRH PLYNSKIPKACCVPTELSAI SMLYLDENEKVVLKNYQD MVVEGCGCR | C15–C15$^b$, C29–C62$^a$, C30–C64$^a$ | 16.22 | ±1.62 |
| 218 | AQAKHKQRKRLKSSCKRH PLYNSKIPKACCVPTELSAI SMLYLDENEKVVLKNYQD MVVEGCGCR | C15–C15$^b$, C29–C64$^a$, C30–C62$^a$ | 18.42 | ±1.79 |
| 218 | AQAKHKQRKRLKSSCKRH PLYNSKIPKACCVPTELSAI SMLYLDENEKVVLKNYQD MVVEGCGCR | C15–C30$^a$ | 40.89 | ±2.62 |

TABLE 4-continued

| SEQ ID NO | Recombinant Polypeptide Sequence | Identified Cysteine Pairs | Affinity Constant Mean [nM] | SD [nM] |
|---|---|---|---|---|
| 224 | GQAKRKGYKRLKSSCKRH PLYVDFKDVGWNDHAVAP PGYHAFYCHGECPFPLADH LNSDNHAIVQTKVNSV | C44—C48[a] | 22.31 | ±1.99 |
| 224 | GQAKRKGYKRLKSSCKRH PLYVDFKDVGWNDHAVAP PGYHAFYCHGECPFPLADH LNSDNHAIVQTKVNSV | C15—C44[a] | 48.93 | ±2.88 |
| 230 | VDFKDVGWNDHAVAPPG YHAFYCHGECPFPLADHLN SDNHAIVQTKVNSVGQAK RKGYKRLKSSCKRHPLY | C23—C27[a] | 17.94 | ±2.31 |
| 230 | VDFKDVGWNDHAVAPPG YHAFYCHGECPFPLADHLN SDNHAIVQTKVNSVGQAK RKGYKRLKSSCKRHPLY | C27—C65[a] | 52.23 | ±1.63 |
| 236 | NSKDPKACCVPTELSAPSP LYLDENEKPVLKNYQDMV VHGCGCRGQAKRKGYKRL KSSCKRHPLY | C59—C59[b], C8—C41[a], C9—C43[a] | 16.21 | ±2.10 |
| 236 | NSKDPKACCVPTELSAPSP LYLDENEKPVLKNYQDMV VHGCGCRGQAKRKGYKRL KSSCKRHPLY | C41—C59[a] | 49.51 | ±3.30 |
| 236 | NSKDPKACCVPTELSAPSP LYLDENEKPVLKNYQDMV VHGCGCRGQAKRKGYKRL KSSCKRHPLY | C59—C59[b], C8—C43[a], C9—C41[a] | 17.05 | ±1.27 |
| 242 | GQAKRKGYKRLKSSCKRH PLYNSKDPKACCVPTELSA PSPLYLDENEKPVLKNYQD MVVHGCGCR | C15—C15[b], C29—C62[a], C30—C64[a] | 17.78 | ±2.09 |
| 242 | GQAKRKGYKRLKSSCKRH PLYNSKDPKACCVPTELSA PSPLYLDENEKPVLKNYQD MVVHGCGCR | C29—C30[a] | 48.66 | ±3.15 |
| 242 | GQAKRKGYKRLKSSCKRH PLYNSKDPKACCVPTELSA PSPLYLDENEKPVLKNYQD MVVHGCGCR | C15—C15[b], C29—C64[a], C30—C62[a] | 18.11 | ±1.63 |
| 248 | NSKDPKACCVPTELSAPSP LYLDENEKPVLKNYQDMV VHGCGCRVDFKDVGWND HAVAPPGYHAFYCHGECPF PLADHLNSDNHAIVQTKVN SV | C67—C71[a], C8—C41[a], C9—C43[a] | 18.52 | ±1.74 |
| 248 | NSKDPKACCVPTELSAPSP LYLDENEKPVLKNYQDMV VHGCGCRVDFKDVGWND HAVAPPGYHAFYCHGECPF PLADHLNSDNHAIVQTKVN SV | C41—C43[a] | 47.81 | ±3.22 |
| 248 | NSKDPKACCVPTELSAPSP LYLDENEKPVLKNYQDMV VHGCGCRVDFKDVGWND HAVAPPGYHAFYCHGECPF PLADHLNSDNHAIVQTKVN SV | C67—C71[a], C8—C43[a], C9—C41[a] | 19.98 | ±2.14 |
| 248 | NSKDPKACCVPTELSAPSP LYLDENEKPVLKNYQDMV VHGCGCRVDFKDVGWND | C67—C71[a], C8—C43[b], C9—C41[b] | 19.25 | ±3.01 |

TABLE 4-continued

| SEQ ID NO | Recombinant Polypeptide Sequence | Identified Cysteine Pairs | Affinity Constant Mean $_{[nM]}$ | SD $_{[nM]}$ |
|---|---|---|---|---|
| | HAVAPPGYHAFYCHGECPF PLADHLNSDNHAIVQTKVN SV | | | |
| 254 | VDFKDVGWNDHAVAPPG YHAFYCHGECPFPLADHLN SDNHAIVQTKVNSVNSKDP KACCVPTELSAPSPLYLDE NEKPVLKNYQDMVVHGC GCR | C23—C27$^a$, C58—C91$^a$, C59—C93$^a$ | 17.55 | ±1.74 |
| 254 | VDFKDVGWNDHAVAPPG YHAFYCHGECPFPLADHLN SDNHAIVQTKVNSVNSKDP KACCVPTELSAPSPLYLDE NEKPVLKNYQDMVVHGC GCR | C23—C27$^a$, C58—C93$^a$, C59—C91$^a$ | 19.06 | ±2.39 |
| 254 | VDFKDVGWNDHAVAPPG YHAFYCHGECPFPLADHLN SDNHAIVQTKVNSVNSKDP KACCVPTELSAPSPLYLDE NEKPVLKNYQDMVVHGC GCR | C23—C58$^a$ | 44.43 | ±2.05 |
| 254 | VDFKDVGWNDHAVAPPG YHAFYCHGECPFPLADHLN SDNHAIVQTKVNSVNSKDP KACCVPTELSAPSPLYLDE NEKPVLKNYQDMVVHGC GCR | C23—C27$^a$, C58—C91$^b$, C59—C93$^b$ | 18.73 | ±1.65 |
| 260 | AQAKHKQRKRLKSSCKRH PLYVDFSDVGWNDWIVAP PGYHAFYCHGECPFPLADH LNSTNHAIVQTLVNSVNSK IPKACCVPTELSAISMLYLD ENEKVVLKNYQDMVVEGC GCR | C15—C80$^a$, C44—C112$^a$, C48—C114$^a$, C79—C79$^b$ | 6.56 | ±1.12 |
| 260 | AQAKHKQRKRLKSSCKRH PLYVDFSDVGWNDWIVAP PGYHAFYCHGECPFPLADH LNSTNHAIVQTLVNSVNSK IPKACCVPTELSAISMLYLD ENEKVVLKNYQDMVVEGC GCR | C79—C80$^a$ | 29.14 | ±1.35 |
| 260 | AQAKHKQRKRLKSSCKRH PLYVDFSDVGWNDWIVAP PGYHAFYCHGECPFPLADH LNSTNHAIVQTLVNSVNSK IPKACCVPTELSAISMLYLD ENEKVVLKNYQDMVVEGC GCR | C15—C15$^b$, C79—C114$^a$, C80—C112$^a$, C44—C48$^a$ | 7.64 | ±1.03 |
| 260 | AQAKHKQRKRLKSSCKRH PLYVDFSDVGWNDWIVAP PGYHAFYCHGECPFPLADH LNSTNHAIVQTLVNSVNSK IPKACCVPTELSAISMLYLD ENEKVVLKNYQDMVVEGC GCR | C80—C114$^a$, C79—C112$^a$, C44—C48$^a$ | 8.31 | ±1.07 |
| 260 | AQAKHKQRKRLKSSCKRH PLYVDFSDVGWNDWIVAP PGYHAFYCHGECPFPLADH LNSTNHAIVQTLVNSVNSK IPKACCVPTELSAISMLYLD ENEKVVLKNYQDMVVEGC GCR | C15—C15$^b$, C80—C114$^a$, C79—C112$^a$, C44—C48$^a$ | 7.45 | ±1.67 |
| 260 | AQAKHKQRKRLKSSCKRH PLYVDFSDVGWNDWIVAP PGYHAFYCHGECPFPLADH | C80—C114$^b$, C79—C112$^b$, C44—C48$^a$ | 6.89 | ±0.96 |

TABLE 4-continued

| SEQ ID NO | Recombinant Polypeptide Sequence | Identified Cysteine Pairs | Affinity Constant Mean$_{[nM]}$ | SD$_{[nM]}$ |
|---|---|---|---|---|
| | LNSTNHAIVQTLVNSVNSK IPKACCVPTELSAISMLYLD ENEKVVLKNYQDMVVEGC GCR | | | |
| 268 | VDFSDVGWNDWIVAPPGY HAFYCHGECPFPLADHLNS TNHAIVQTLVNSVAQAKH KQRKRLKSSCKRHPLYNSK IPKACCVPTELSAISMLYLD ENEKVVLKNYQDMVVEGC GCR | C23—C27$^a$, C65—C65$^b$, C79—C112$^a$, C80—C114$^a$ | 7.21 | ±1.32 |
| 268 | VDFSDVGWNDWIVAPPGY HAFYCHGECPFPLADHLNS TNHAIVQTLVNSVAQAKH KQRKRLKSSCKRHPLYNSK IPKACCVPTELSAISMLYLD ENEKVVLKNYQDMVVEGC GCR | C23—C79$^a$ | 29.57 | ±2.71 |
| 268 | VDFSDVGWNDWIVAPPGY HAFYCHGECPFPLADHLNS TNHAIVQTLVNSVAQAKH KQRKRLKSSCKRHPLYNSK IPKACCVPTELSAISMLYLD ENEKVVLKNYQDMVVEGC GCR | C23—C27$^a$, C65—C65$^b$, C79—C114$^a$, C80—C112$^a$ | 8.74 | ±2.08 |
| 268 | VDFSDVGWNDWIVAPPGY HAFYCHGECPFPLADHLNS TNHAIVQTLVNSVAQAKH KQRKRLKSSCKRHPLYNSK IPKACCVPTELSAISMLYLD ENEKVVLKNYQDMVVEGC GCR | C23—C27$^a$, C65—C65$^b$, C79—C112$^b$, C80—C114$^b$ | 7.96 | ±0.75 |
| 268 | VDFSDVGWNDWIVAPPGY HAFYCHGECPFPLADHLNS TNHAIVQTLVNSVAQAKH KQRKRLKSSCKRHPLYNSK IPKACCVPTELSAISMLYLD ENEKVVLKNYQDMVVEGC GCR | C23—C27$^a$, C65—C65$^b$, C79—C114$^b$, C80—C112$^b$ | 8.03 | ±2.45 |
| 276 | NSKIPKACCVPTELSAISML YLDENEKVVLKNYQDMV VEGCGCRVDFSDVGWND WIVAPPGYHAFYCHGECPF PLADHLNSTNHAIVQTLVN SVAQAKHKQRKRLKSSCK RHPLY | C67—C71$^a$, C8—C41$^a$, C9—C43$^a$, C109—C109$^b$ | 5.71 | ±1.60 |
| 276 | NSKIPKACCVPTELSAISML YLDENEKVVLKNYQDMV VEGCGCRVDFSDVGWND WIVAPPGYHAFYCHGECPF PLADHLNSTNHAIVQTLVN SVAQAKHKQRKRLKSSCK RHPLY | C8—C9$^a$ | 27.93 | ±2.35 |
| 276 | NSKIPKACCVPTELSAISML YLDENEKVVLKNYQDMV VEGCGCRVDFSDVGWND WIVAPPGYHAFYCHGECPF PLADHLNSTNHAIVQTLVN SVAQAKHKQRKRLKSSCK RHPLY | C67—C71$^a$, C8—C43$^a$, C9—C41$^a$, C109—C109$^b$ | 7.66 | ±1.05 |
| 276 | NSKIPKACCVPTELSAISML YLDENEKVVLKNYQDMV VEGCGCRVDFSDVGWND WIVAPPGYHAFYCHGECPF | C67—C71$^a$, C8—C43$^b$, C9—C41$^b$, C109—C109$^b$ | 6.31 | ±1.38 |

TABLE 4-continued

| SEQ ID NO | Recombinant Polypeptide Sequence | Identified Cysteine Pairs | Affinity Constant Mean$_{[nM]}$ | SD$_{[nM]}$ |
|---|---|---|---|---|
|  | PLADHLNSTNHAIVQTLVN SVAQAKHKQRKRLKSSCK RHPLY |  |  |  |
| 276 | NSKIPKACCVPTELSAISML YLDENEKVVLKNYQDMV VEGCGCRVDFSDVGWND WIVAPPGYHAFYCHGECPF PLADHLNSTNHAIVQTLVN SVAQAKHKQRKRLKSSCK RHPLY | C67–C71$^a$, C8–C41$^b$, C9–C43$^b$, C109–C109$^b$ | 8.13 | ±1.77 |
| 284 | NSKIPKACCVPTELSAISML YLDENEKVVLKNYQDMV VEGCGCRAQAKHKQRKRL KSSCKRHPLYVDFSDVGW NDWIVAPPGYHAFYCHGE CPFPLADHLNSTNHAIVQT LVNSV | C59–C59$^b$, C8–C41$^a$, C9–C43$^a$, C88–C92$^a$ | 4.89 | ±1.13 |
| 284 | NSKIPKACCVPTELSAISML YLDENEKVVLKNYQDMV VEGCGCRAQAKHKQRKRL KSSCKRHPLYVDFSDVGW NDWIVAPPGYHAFYCHGE CPFPLADHLNSTNHAIVQT LVNSV | C8–C9$^a$ | 31.79 | ±3.15 |
| 284 | NSKIPKACCVPTELSAISML YLDENEKVVLKNYQDMV VEGCGCRAQAKHKQRKRL KSSCKRHPLYVDFSDVGW NDWIVAPPGYHAFYCHGE CPFPLADHLNSTNHAIVQT LVNSV | C59–C59$^b$, C8–C43$^a$, C9–C41$^a$, C88–C92$^a$ | 6.88 | ±1.35 |
| 284 | NSKIPKACCVPTELSAISML YLDENEKVVLKNYQDMV VEGCGCRAQAKHKQRKRL KSSCKRHPLYVDFSDVGW NDWIVAPPGYHAFYCHGE CPFPLADHLNSTNHAIVQT LVNSV | C59–C59$^b$, C8–C41$^b$, C9–C43$^b$, C88–C92$^a$ | 5.79 | ±1.76 |
| 284 | NSKIPKACCVPTELSAISML YLDENEKVVLKNYQDMV VEGCGCRAQAKHKQRKRL KSSCKRHPLYVDFSDVGW NDWIVAPPGYHAFYCHGE CPFPLADHLNSTNHAIVQT LVNSV | C59–C59$^b$, C8–C43$^b$, C9–C41$^b$, C88–C92$^a$ | 6.91 | ±1.55 |
| 292 | GQAKRKGYKRLKSSCKRH PLYVDFKDVGWNDHAVAP PGYHAFYCHGECPFPLADH LNSDNHAIVQTKVNSVNSK DPKACCVPTELSAPSPLYL DENEKPVLKNYQDMVVHG CGCR | C15–C80$^a$, C44–C112$^a$, C48–C114$^a$, C79–C79$^b$ | 4.77 | ±0.67 |
| 292 | GQAKRKGYKRLKSSCKRH PLYVDFKDVGWNDHAVAP PGYHAFYCHGECPFPLADH LNSDNHAIVQTKVNSVNSK DPKACCVPTELSAPSPLYL DENEKPVLKNYQDMVVHG CGCR | C79–C80$^a$ | 28.99 | ±2.66 |
| 292 | GQAKRKGYKRLKSSCKRH PLYVDFKDVGWNDHAVAP PGYHAFYCHGECPFPLADH LNSDNHAIVQTKVNSVNSK DPKACCVPTELSAPSPLYL DENEKPVLKNYQDMVVHG CGCR | C15–C15$^b$, C79–C114$^a$, C80–C112$^a$, C44–C48$^a$ | 5.81 | ±3.57 |

TABLE 4-continued

| SEQ ID NO | Recombinant Polypeptide Sequence | Identified Cysteine Pairs | Affinity Constant Mean $_{[nM]}$ | SD $_{[nM]}$ |
|---|---|---|---|---|
| 292 | GQAKRKGYKRLKSSCKRHPLYVDFKDVGWNDHAVAPPGYHAFYCHGECPFPLADHLNSDNHAIVQTKVNSVNSKDPKACCVPTELSAPSPLYLDENEKPVLKNYQDMVVHGCGCR | C80—C114$^a$, C79—C112$^a$, C44—C48$^a$ | 6.19 | ±1.37 |
| 292 | GQAKRKGYKRLKSSCKRHPLYVDFKDVGWNDHAVAPPGYHAFYCHGECPFPLADHLNSDNHAIVQTKVNSVNSKDPKACCVPTELSAPSPLYLDENEKPVLKNYQDMVVHGCGCR | C80—C114$^b$, C79—C112$^b$, C44—C48$^a$ | 5.54 | ±1.30 |
| 300 | VDFKDVGWNDHAVAPPGYHAFYCHGECPFPLADHLNSDNHAIVQTKVNSVGQAKRKGYKRLKSSCKRHPLYNSKDPKACCVPTELSAPSPLYLDENEKPVLKNYQDMVVHGCGCR | C23—C27$^a$, C65—C65$^b$, C79—C112$^a$, C80—C114$^a$ | 5.14 | ±1.39 |
| 300 | VDFKDVGWNDHAVAPPGYHAFYCHGECPFPLADHLNSDNHAIVQTKVNSVGQAKRKGYKRLKSSCKRHPLYNSKDPKACCVPTELSAPSPLYLDENEKPVLKNYQDMVVHGCGCR | C23—C79$^a$ | 32.69 | ±2.45 |
| 300 | VDFKDVGWNDHAVAPPGYHAFYCHGECPFPLADHLNSDNHAIVQTKVNSVGQAKRKGYKRLKSSCKRHPLYNSKDPKACCVPTELSAPSPLYLDENEKPVLKNYQDMVVHGCGCR | C23—C27$^a$, C65—C65$^b$, C79—C114$^a$, C80—C112$^a$ | 7.37 | ±1.71 |
| 300 | VDFKDVGWNDHAVAPPGYHAFYCHGECPFPLADHLNSDNHAIVQTKVNSVGQAKRKGYKRLKSSCKRHPLYNSKDPKACCVPTELSAPSPLYLDENEKPVLKNYQDMVVHGCGCR | C23—C27$^a$, C65—C65$^b$, C79—C112$^b$, C80—C114$^b$ | 6.44 | ±1.72 |
| 308 | NSKDPKACCVPTELSAPSPLYLDENEKPVLKNYQDMVVHGCGCRGQAKRKGYKRLKSSCKRHPLYVDFKDVGWNDHAVAPPGYHAFYCHGECPFPLADHLNSDNHAIVQTKVNSV | C59—C59$^b$, C8—C41$^a$, C9—C43$^a$, C88—C92$^a$ | 5.98 | ±1.43 |
| 308 | NSKDPKACCVPTELSAPSPLYLDENEKPVLKNYQDMVVHGCGCRGQAKRKGYKRLKSSCKRHPLYVDFKDVGWNDHAVAPPGYHAFYCHGECPFPLADHLNSDNHAIVQTKVNSV | C8—C9$^a$ | 31.22 | ±2.07 |
| 308 | NSKDPKACCVPTELSAPSPLYLDENEKPVLKNYQDMVVHGCGCRGQAKRKGYKRLKSSCKRHPLYVDFKDVGWNDHAVAPPGYHAFYCHGECPFPLADHLNSDNHAIVQTKVNSV | C59—C59$^b$, C8—C43$^a$, C9—C41$^a$, C88—C92$^a$ | 6.11 | ±1.33 |
| 308 | NSKDPKACCVPTELSAPSPLYLDENEKPVLKNYQDMV | C59—C59$^b$, C8—C41$^b$, C9—C43$^b$, C88—C92$^a$ | 6.73 | ±1.55 |

TABLE 4-continued

| SEQ ID NO | Recombinant Polypeptide Sequence | Identified Cysteine Pairs | Affinity Constant Mean [nM] | SD [nM] |
|---|---|---|---|---|
| | VHGCGCRGQAKRKGYKRL KSSCKRHPLYVDFKDVGW NDHAVAPPGYHAFYCHGE CPFPLADHLNSDNHAIVQT KVNSV | | | |
| 316 | NSKDPKACCVPTELSAPSP LYLDENEKPVLKNYQDMV VHGCGCRVDFKDVGWND HAVAPPGYHAFYCHGECPF PLADHLNSDNHAIVQTKVN SVGQAKRKGYKRLKSSCK RHPLY | C67—C71$^a$, C8—C41$^a$, C9—C43$^a$, C109—C109$^b$ | 5.34 | ±1.37 |
| 316 | NSKDPKACCVPTELSAPSP LYLDENEKPVLKNYQDMV VHGCGCRVDFKDVGWND HAVAPPGYHAFYCHGECPF PLADHLNSDNHAIVQTKVN SVGQAKRKGYKRLKSSCK RHPLY | C8—C67$^a$ | 28.91 | ±2.65 |
| 316 | NSKDPKACCVPTELSAPSP LYLDENEKPVLKNYQDMV VHGCGCRVDFKDVGWND HAVAPPGYHAFYCHGECPF PLADHLNSDNHAIVQTKVN SVGQAKRKGYKRLKSSCK RHPLY | C67—C71$^a$, C8—C43$^a$, C9—C41$^a$, C109—C109$^b$ | 6.17 | ±1.04 |
| 316 | NSKDPKACCVPTELSAPSP LYLDENEKPVLKNYQDMV VHGCGCRVDFKDVGWND HAVAPPGYHAFYCHGECPF PLADHLNSDNHAIVQTKVN SVGQAKRKGYKRLKSSCK RHPLY | C67—C71$^a$, C8—C43$^b$, C9—C41$^b$, C109—C109$^b$ | 5.78 | ±1.18 |
| 324 | AQAKHKQRKRLKSSCKRH PLYVDFKDVGWNDHAVAP PGYHAFYCHGECPFPLADH LNSDNHAIVQTKVNSVNSK IPKACCVPTELSAISMLYLD ENEKVVLKNYQDMVVEGC GCR | C15—C15$^b$, C79—C114$^a$, C80—C112$^a$, C44—C48$^a$ | 8.42 | ±1.59 |
| 324 | AQAKHKQRKRLKSSCKRH PLYVDFKDVGWNDHAVAP PGYHAFYCHGECPFPLADH LNSDNHAIVQTKVNSVNSK IPKACCVPTELSAISMLYLD ENEKVVLKNYQDMVVEGC GCR | C79—C80$^a$ | 29.33 | ±2.10 |
| 324 | AQAKHKQRKRLKSSCKRH PLYVDFKDVGWNDHAVAP PGYHAFYCHGECPFPLADH LNSDNHAIVQTKVNSVNSK IPKACCVPTELSAISMLYLD ENEKVVLKNYQDMVVEGC GCR | C80—C114$^a$, C79—C112$^a$, C44—C48$^a$ | 7.22 | ±2.15 |
| 324 | AQAKHKQRKRLKSSCKRH PLYVDFKDVGWNDHAVAP PGYHAFYCHGECPFPLADH LNSDNHAIVQTKVNSVNSK IPKACCVPTELSAISMLYLD ENEKVVLKNYQDMVVEGC GCR | C15—C15$^b$, C80—C114$^b$, C79—C112$^b$, C44—C48$^a$ | 9.11 | ±1.77 |
| 340 | AQAKHKQRKRLKSSCKRH PLYNSKDPKACCVPTELSA PSPLYLDENEKPVLKNYQD MVVHGCGCRVDFKDVGW NDHAVAPPGYHAFYCHGE | C15—C15$^b$, C29—C62$^a$, C30—C64$^a$, C88—C92$^a$ | 5.77 | ±1.17 |

TABLE 4-continued

| SEQ ID NO | Recombinant Polypeptide Sequence | Identified Cysteine Pairs | Affinity Constant Mean[nM] | SD[nM] |
|---|---|---|---|---|
| | CPFPLADHLNSDNHAIVQT KVNSV | | | |
| 340 | AQAKHKQRKRLKSSCKRH PLYNSKDPKACCVPTELSA PSPLYLDENEKPVLKNYQD MVVHGCGCRVDFKDVGW NDHAVAPPGYHAFYCHGE CPFPLADHLNSDNHAIVQT KVNSV | C15—C29[a] | 30.05 | ±2.63 |
| 340 | AQAKHKQRKRLKSSCKRH PLYNSKDPKACCVPTELSA PSPLYLDENEKPVLKNYQD MVVHGCGCRVDFKDVGW NDHAVAPPGYHAFYCHGE CPFPLADHLNSDNHAIVQT KVNSV | C15—C15[b], C29—C64[a], C30—C62[a], C88—C92[a] | 7.19 | ±1.95 |
| 340 | AQAKHKQRKRLKSSCKRH PLYNSKDPKACCVPTELSA PSPLYLDENEKPVLKNYQD MVVHGCGCRVDFKDVGW NDHAVAPPGYHAFYCHGE CPFPLADHLNSDNHAIVQT KVNSV | C15—C15[b], C29—C64[b], C30—C62[b], C88—C92[a] | 6.37 | ±1.55 |
| 332 | GQAKRKGYKRLKSSCKRH PLYVDFSDVGWNDWIVAP PGYHAFYCHGECPFPLADH LNSTNHAIVQTLVNSVNSK DPKACCVPTELSAPSPLYL DENEKPVLKNYQDMVVHG CGCR | C15—C15[b], C80—C114[a], C79—C112[a], C44—C48[a] | 5.98 | ±1.11 |
| 332 | GQAKRKGYKRLKSSCKRH PLYVDFSDVGWNDWIVAP PGYHAFYCHGECPFPLADH LNSTNHAIVQTLVNSVNSK DPKACCVPTELSAPSPLYL DENEKPVLKNYQDMVVHG CGCR | C79—C80[a] | 28.54 | ±2.36 |
| 332 | GQAKRKGYKRLKSSCKRH PLYVDFSDVGWNDWIVAP PGYHAFYCHGECPFPLADH LNSTNHAIVQTLVNSVNSK DPKACCVPTELSAPSPLYL DENEKPVLKNYQDMVVHG CGCR | C15—C15[b], C80—C112[a], C79—C114[a], C44—C48[a] | 7.18 | ±1.84 |
| 332 | GQAKRKGYKRLKSSCKRH PLYVDFSDVGWNDWIVAP PGYHAFYCHGECPFPLADH LNSTNHAIVQTLVNSVNSK DPKACCVPTELSAPSPLYL DENEKPVLKNYQDMVVHG CGCR | C15—C15[b], C80—C114[b], C79—C112[b], C44—C48[a] | 7.42 | ±1.94 |
| 348 | GQAKRKGYKRLKSSCKRH PLYNSKIPKACCVPTELSAI SMLYLDENEKVVLKNYQD MVVEGCGCRVDFSDVGW NDWIVAPPGYHAFYCHGE CPFPLADHLNSTNHAIVQT LVNSV | C15—C15[b], C29—C62[a], C30—C64[a], C88—C92[a] | 5.10 | ±1.07 |
| 348 | GQAKRKGYKRLKSSCKRH PLYNSKIPKACCVPTELSAI SMLYLDENEKVVLKNYQD MVVEGCGCRVDFSDVGW NDWIVAPPGYHAFYCHGE CPFPLADHLNSTNHAIVQT LVNSV | C29—C30[a] | 29.09 | ±3.33 |

TABLE 4-continued

| SEQ ID NO | Recombinant Polypeptide Sequence | Identified Cysteine Pairs | Affinity Constant Mean$_{[nM]}$ | SD$_{[nM]}$ |
|---|---|---|---|---|
| 348 | GQAKRKGYKRLKSSCKRH PLYNSKIPKACCVPTELSAI SMLYLDENEKVVLKNYQD MVVEGCGCRVDFSDVGW NDWIVAPPGYHAFYCHGE CPFPLADHLNSTNHAIVQT LVNSV | C15–C15$^b$, C29–C64$^a$, C30–C62$^a$, C88–C92$^a$ | 6.77 | ±1.92 |
| 348 | GQAKRKGYKRLKSSCKRH PLYNSKIPKACCVPTELSAI SMLYLDENEKVVLKNYQD MVVEGCGCRVDFSDVGW NDWIVAPPGYHAFYCHGE CPFPLADHLNSTNHAIVQT LVNSV | C15–C15$^b$, C29–C62$^b$, C30–C64$^b$, C88–C92$^a$ | 6.31 | ±1.45 |

$^{a)}$ Intramolecular disulfide bond connection.
$^{b)}$ Intermolecular disulfide bond connection for dimerization.

As shown in TABLE 4, the disulfide bond between different cysteine locations affects affinity constant ($K_D$) values. In addition, the data show that a disulfide bond between two recombinant polypeptides in a dimer significantly reduces the $K_D$ values. In other words, dimerization might assist in vitro molecular bonding between the dimers of recombinant polypeptides and the ActRIIBecd.

Some recombinant polypeptides were observed to spontaneously form dimeric proteins as shown in Table 4. All of the dimeric proteins could be fractionated out of the recombinant polypeptide monomers by gel filtration as described in Example 4B. In this embodiment, the dimeric proteins were homodimeric proteins because their monomers were the same. In the other embodiments, the dimeric proteins could be heterodimeric proteins if the stably transformed *E. coli* cells as described in Example 4 co-express two different recombinant polypeptides selected from the group of SEQ ID NOs: 260, 268, 276, 284, 292, 300, 308, 316, 324, 332, 340, and 348.

Example 8: Alkaline Phosphatase Bioactivity Assay

The ability of the recombinant polypeptides to bind to cellular receptors and induce signal transduction pathways was investigated using an assay for alkaline phosphatase induction in C2C12 cells, which has been described. See, e.g., Peel et al. J Craniofacial Surg. 2003; 14:284-291 and Hu et al. Growth Factors 2004; 22:29033.

C2C12 cells (ATCC accession number CRL-1772, Manassas, Va.) were passaged before confluent and resuspended at 1×10$^5$ cells/mL in DMEM supplemented with 10% heat-inactivated fetal bovine serum. 100 μL of cell suspension was seeded per well of a 96 well tissue culture plate (Corning, Cat #3595). Aliquots of serial diluted standard and test sample were added and the cultures maintained at 37° C. and 5% CO$_2$. Test samples included conditioned media, purified recombinant polypeptide, and as a positive control a commercially available purified recombinant human BMP-2 "rhBMP-2" (R&D Systems, Minneapolis, USA). rhBMP-2 has been shown to play an important role in the development of bone and cartilage by, for example, Mundy G R., et al. (2004, *Growth Factors*. 22 (4): 233-41). Negative control cultures (cultured in media without added sample or rhBMP-2) were cultured for 2 to 7 days. Medium was changed every two days.

At harvest cultures were rinsed with normal saline (0.90% NaCl, pH 7.4) and discard the rinsed saline. 50 μL extraction solution (Takara Bio, catalogue #MK301) was added to those cultures and then sonicated at room temperature for 10 minutes. The lysate was assayed for alkaline phosphatase (ALP) by monitoring the hydrolysis of nitrophenol phosphate in alkaline buffer (Sigma-Aldrich, St. Louis Mo., catalog P5899) as described in Peel et al. J Craniofacial Surg. 2003; 14:284-291 or by using the TRACP & ALP assay kit (Takara Bio, catalogue #MK301) according to manufacturer's instructions. ALP activity was determined by recording absorbance at 405 nm. An activity score was calculated by mean ALP activity of duplicate samples. Serial diluted samples and its relevant activity score were diagramed by 4-parameter curve fit so as to calculate the concentration $EC_{50}$ of each recombinant polypeptide. Data is shown in TABLE 5. In some embodiments, the ALP activity the cellular protein content in each well is normalized by using the Coomasie (Bradford) Protein Assay (Pierce Biotechnology Inc., catalogue #23200). The normalized ALP activity for each sample is calculated by dividing the ALP activity per well by the protein content per well.

In another embodiment, alkaline phosphatase assay described by Katagiri, T., et al. (1990, Biochem. Biophys. Res. Commun. 172, 295-299) is performed. Mouse fibroblast cells from the line C3H10T1/2 in BME-Earle medium plus 10% fetal calf serum are incubated at 1×10$^5$ cells/mL in 1-mL aliquots in a 24-well plate for 24 h at 37° C. and 10% CO$_2$. After removal of the supernatant, 1 mL fresh medium is added with various concentrations of sample. After a further cultivation for 4 days, cells are lysed in 0.2 mL buffer (0.1 M glycerol, pH 9.6, 1% NP-40, 1 mM MgCl$_2$, 1 mM ZnCl$_2$) and alkaline phosphatase activity is determined in 50 μL aliquots of the cleared lysate using 150 μL 0.3 mM p-nitrophenyl phosphate in the pH 9.6 buffer as substrate. Absorbance at 405 nm is recorded after 20 min incubation at 37° C. The activity is related to the protein content (BCA protein assay, Pierce Chemical Co.) in each sample.

TABLE 5

| SEQ ID NO | Identified Cysteine Pairs | $EC_{50}$ [nM] | Mean $K_D$ [nm] |
|---|---|---|---|
| 188 | C15-C44$^a$ | NA | 42.32 |
| 188 | C44-C48$^a$ | 28.4 | 21.47 |

TABLE 5-continued

| SEQ ID NO | Identified Cysteine Pairs | EC$_{50}$ [nM] | Mean K$_D$ [nm] |
|---|---|---|---|
| 194 | C23-C65$^a$ | NA | 45.98 |
| 194 | C23-C27$^a$ | NA | 18.14 |
| 200 | C23-C27$^a$, C58-C91$^a$, C59-C93$^a$ | 31.2 | 18.62 |
| 200 | C23-C27$^a$, C58-C93$^a$, C59-C91$^a$ | NA | 20.13 |
| 200 | C23-C27$^a$, C58-C91$^b$, C59-C93$^b$ | 35.1 | 19.75 |
| 200 | C23-C58$^a$ | NA | 47.62 |
| 206 | C67-C71$^a$, C8-C41$^a$, C9-C43$^a$ | 37.6 | 15.49 |
| 206 | C8-C71$^a$ | NA | 49.66 |
| 206 | C67-C71$^a$, C8-C43$^a$, C9-C41$^a$ | NA | 17.73 |
| 206 | C67-C71$^a$, C8-C43$^b$, C9-C41$^b$ | 40.1 | 16.97 |
| 212 | C59-C59$^b$, C8-C41$^a$, C9-C43$^a$ | 35.1 | 18.13 |
| 212 | C59-C59$^b$, C8-C43$^a$, C9-C41$^a$ | 36.7 | 19.34 |
| 212 | C41-C59$^a$ | NA | 44.33 |
| 218 | C15-C15$^b$, C29-C62$^a$, C30-C64$^a$ | 33.9 | 16.22 |
| 218 | C15-C15$^b$, C29-C64$^a$, C30-C62$^a$ | 37.6 | 18.42 |
| 218 | C15-C30$^a$ | NA | 40.89 |
| 224 | C44-C48$^a$ | NA | 21.47 |
| 224 | C15-C44$^a$ | NA | 48.93 |
| 230 | C23-C27$^a$ | NA | 17.94 |
| 230 | C27-C65$^a$ | NA | 52.23 |
| 236 | C59-C59$^b$, C8-C41$^a$, C9-C43$^a$ | 28.5 | 16.21 |
| 236 | C41-C59$^a$ | NA | 49.51 |
| 236 | C59-C59$^b$, C8-C43$^a$, C9-C41$^a$ | 29.7 | 17.05 |
| 242 | C15-C15$^b$, C29-C62$^a$, C30-C64$^a$ | 30.1 | 17.78 |
| 242 | C29-C30$^a$ | NA | 48.66 |
| 242 | C15-C15$^b$, C29-C64$^a$, C30-C62$^a$ | 33.9 | 18.11 |
| 248 | C67-C71$^a$, C8-C41$^a$, C9-C43$^a$ | 29.4 | 18.52 |
| 248 | C41-C43$^a$ | NA | 47.81 |
| 248 | C67-C71$^a$, C8-C43$^a$, C9-C41$^a$ | NA | 19.98 |
| 248 | C67-C71$^a$, C8-C43$^b$, C9-C41$^b$ | 30.5 | 19.25 |
| 254 | C23-C27$^a$, C58-C91$^a$, C59-C93$^a$ | 31.4 | 17.55 |
| 254 | C23-C27$^a$, C58-C93$^a$, C59-C91$^a$ | NA | 19.06 |
| 254 | C23-C58$^a$ | NA | 44.43 |
| 254 | C23-C27$^a$, C58-C91$^b$, C59-C93$^b$ | 34.4 | 18.73 |
| 260 | C15-C80$^a$, C44-C112$^a$, C48-C114$^a$, C79-C79$^b$ | 14.1 | 6.56 |
| 260 | C79-C80$^a$ | 67.8 | 29.14 |
| 260 | C15-C15$^b$, C79-C114$^a$, C80-C112$^a$, C44-C48$^a$ | 1.1 | 7.64 |
| 260 | C80-C114$^a$, C79-C112$^a$, C44-C48$^a$ | 19.4 | 8.31 |
| 260 | C15-C15$^b$, C80-C114$^a$, C79-C112$^b$, C44-C48$^a$ | 1.3 | 7.45 |
| 260 | C79-C114$^a$, C80-C112$^a$, C44-C48$^a$ | 15.6 | 6.17 |
| 260 | C44-C48$^a$ | 9.8 | 8.04 |
| 260 | C15-C15$^b$, C80-C114$^b$, C79-C112$^b$, C44-C48$^a$ | 1.0 | 4.04 |
| 260 | C15-C15$^b$, C79-C114$^b$, C80-C112$^b$, C44-C48$^a$ | 1.9 | 4.03 |
| 260 | C80-C114$^b$, C79-C112$^b$, C44-C48$^a$ | 13.4 | 6.89 |
| 260 | C79-C114$^b$, C80-C112$^b$, C44-C48$^a$ | 10.5 | 6.05 |
| 268 | C23-C27$^a$, C65-C65$^b$, C79-C112$^a$, C80-C114$^a$ | 18.4 | 7.21 |
| 268 | C23-C79$^a$ | 71.1 | 29.57 |
| 268 | C23-C27$^a$, C65-C65$^b$, C79-C114$^a$, C80-C112$^a$ | 20.4 | 8.74 |
| 268 | C23-C27$^a$, C65-C65$^b$, C79-C112$^b$, C80-C114$^b$ | 18.6 | 7.96 |
| 268 | C23-C27$^a$, C65-C65$^b$, C79-C114$^b$, C80-C112$^b$ | 24.5 | 8.03 |
| 268 | C23-C27$^a$ | 23.4 | 8.41 |
| 276 | C67-C71$^a$, C8-C41$^a$, C9-C43$^a$, C109-C109$^b$ | 21.9 | 5.71 |
| 276 | C8-C9$^a$ | 130.1 | 27.93 |
| 276 | C67-C71$^a$, C8-C43$^a$, C9-C41$^a$, C109-C109$^b$ | 25.7 | 7.66 |
| 276 | C67-C71$^a$, C8-C43$^b$, C9-C41$^b$, C109-C109$^b$ | 31.7 | 6.31 |
| 276 | C67-C71$^a$, C8-C41$^b$, C9-C43$^b$, C109-C109$^b$ | 26.3 | 8.13 |
| 276 | C67-C71$^a$ | 22.5 | 7.41 |
| 284 | C59-C59$^b$, C8-C41$^a$, C9-C43$^a$, C88-C92$^a$ | 27.1 | 4.89 |
| 284 | C8-C9$^a$ | 83.9 | 31.79 |
| 284 | C59-C59$^b$, C8-C43$^a$, C9-C41$^a$, C88-C92$^a$ | 36.7 | 6.88 |
| 284 | C59-C59$^b$, C8-C41$^b$, C9-C43$^b$, C88-C92$^a$ | 33.9 | 5.79 |
| 284 | C59-C59$^b$, C8-C43$^b$, C9-C41$^b$, C88-C92$^a$ | 19.5 | 6.91 |
| 284 | C88-C92$^a$ | 25.9 | 8.14 |
| 292 | C15-C80$^a$, C44-C112$^a$, C48-C114$^a$, C79-C79$^b$ | 10.7 | 4.77 |
| 292 | C79-C80$^a$ | 89.4 | 28.99 |
| 292 | C15-C15$^b$, C79-C114$^a$, C80-C112$^a$, C44-C48$^a$ | 22.5 | 5.81 |
| 292 | C80-C114$^a$, C79-C112$^a$, C44-C48$^a$ | 19.8 | 6.19 |
| 292 | C80-C114$^b$, C79-C112$^b$, C44-C48$^a$ | 22.3 | 5.54 |
| 292 | C44-C48$^a$ | 27.5 | 7.81 |
| 300 | C23-C27$^a$, C65-C65$^b$, C79-C112$^a$, C80-C114$^a$ | 17.6 | 5.14 |
| 300 | C23-C79$^a$ | 86.1 | 32.69 |
| 300 | C23-C27$^a$, C65-C65$^b$, C79-C114$^a$, C80-C112$^a$ | 12.1 | 7.37 |
| 300 | C23-C27$^a$, C65-C65$^b$, C79-C112$^b$, C80-C114$^b$ | 27.7 | 6.44 |
| 300 | C23-C27$^a$ | 16.5 | 8.92 |
| 308 | C59-C59$^b$, C8-C41$^a$, C9-C43$^a$, C88-C92$^a$ | 33.9 | 5.98 |
| 308 | C8-C9$^a$ | 77.4 | 31.22 |
| 308 | C59-C59$^b$, C8-C43$^a$, C9-C41$^a$, C88-C92$^a$ | 20.4 | 6.11 |
| 308 | C59-C59$^b$, C8-C41$^b$, C9-C43$^b$, C88-C92$^a$ | 36.7 | 6.73 |
| 308 | C88-C92$^a$ | 38.2 | 7.8 |
| 308 | C8-C43$^a$, C9-C41$^a$, C88-C92$^a$ | 21.7 | 10.9 |
| 316 | C67-C71$^a$, C8-C41$^a$, C9-C43$^a$, C109-C109$^b$ | 21.0 | 5.34 |
| 316 | C8-C67$^a$ | 109.1 | 28.91 |
| 316 | C67-C71$^a$, C8-C43$^a$, C9-C41$^a$, C109-C109$^b$ | 41.5 | 6.17 |
| 316 | C67-C71$^a$, C8-C43$^b$, C9-C41$^b$, C109-C109$^b$ | 18.5 | 5.78 |
| 316 | C67-C71$^a$ | 33.9 | 4.67 |
| 324 | C15-C15$^b$, C79-C114$^a$, C80-C112$^a$, C44-C48$^a$ | 17.7 | 8.42 |
| 324 | C79-C80$^a$ | 88.7 | 29.33 |
| 324 | C80-C114$^a$, C79-C112$^a$, C44-C48$^a$ | 27.1 | 7.22 |
| 324 | C15-C15$^b$, C80-C114$^b$, C79-C112$^b$, C44-C48$^a$ | 37.6 | 9.11 |
| 324 | C44-C48$^a$ | 29.5 | 8.75 |
| 340 | C15-C15$^b$, C29-C62$^a$, C30-C64$^a$, C88-C92$^a$ | 18.9 | 5.77 |
| 340 | C15-C29$^a$ | 78.4 | 30.05 |
| 340 | C15-C15$^b$, C29-C64$^a$, C30-C62$^a$, C88-C92$^a$ | 21.2 | 7.19 |
| 340 | C15-C15$^b$, C29-C64$^b$, C30-C62$^b$, C88-C92$^a$ | 26.7 | 6.37 |
| 340 | C88-C92$^a$ | 36.7 | 5.64 |
| 332 | C15-C15$^b$, C80-C114$^a$, C79-C112$^a$, C44-C48$^a$ | 22.4 | 5.98 |
| 332 | C79-C80$^a$ | 102.3 | 28.54 |
| 332 | C15-C15$^b$, C80-C112$^a$, C79-C114$^a$, C44-C48$^a$ | 14.9 | 7.18 |
| 332 | C15-C15$^b$, C80-C114$^b$, C79-C112$^b$, C44-C48$^a$ | 33.6 | 7.42 |
| 348 | C15-C15$^b$, C29-C62$^a$, C30-C64$^a$, C88-C92$^a$ | 20.5 | 5.10 |
| 348 | C29-C30$^a$ | 90.3 | 29.09 |
| 348 | C15-C15$^b$, C29-C64$^a$, C30-C62$^a$, C88-C92$^a$ | 18.9 | 6.77 |
| 348 | C15-C15$^b$, C29-C62$^b$, C30-C64$^b$, C88-C92$^a$ | 35.6 | 6.31 |
| 348 | C88-C92$^a$ | 27.6 | 4.51 |
| rhBMP-2 | NA | 45.2 | NA |

NA: not yet analyzed
$^a$Intramolecular disulfide bond connection.
$^b$Intermolecular disulfide bond connection for dimerization.

As shown by TABLE 5, most of the recombinant polypeptides with certain disulfide connections have a value of EC$_{50}$ lower than that of rhBMP-2. In other words, most of the recombinant polypeptides with certain disulfide connections were able to induce a signal transduction pathway related to bone or cartilage formation or osteogenesis.

Example 9: In Vivo Osteoinductive Activity

Osteoinductive activity of a homodimeric protein including two recombinant polypeptides produced according to Example 6 (i.e., SEQ ID NO: 260, including intramolecular disulfide bond C44-C48) and porous beta-tricalcium phosphate (β-TCP) as a carrier material was evaluated in ulnar shaft defects in rabbits. The calcium phosphate carrier has a calcium to phosphate ratio of about 0.4 to about 1.65.

20 mm-sized circumferential defects were created in the shaft of surgically exposed right and left ulnae in each of 40 female rabbits (strain NZW, Japan SLC, Inc.). Briefly, combined anesthesia was carried out with ketamine hydrochloride (Ketalar, Daiichi Sankyo Co., Ltd.) and xylazine (Selactar 2% injection solution, Bayer Medical Co., Ltd.) at a combined rate of 3:1. The same solution was used for additional anesthesia in long operations. Before operating, Flumarin (flomoxef sodium, Shionogi & Co., Ltd.) was administered subcutaneously as an antibiotic agent. Fur in the general region of the forearm was shaved with an electric shaver and disinfected with Hibitane alcohol (0.5% chlorhexidine gluconate-ethanol solution, Sumitomo Dainippon Pharma, Co., Ltd.). A longitudinal incision was made on each caudomedial part of limb over the ulna. Muscle tissue was lifted to expose the ulna. A mark was made with a scalpel 25 mm from the hand joint of the exposed ulna. Proper holes were drilled longitudinally and vertically at the mark using a 15 mm diameter drill, paying close attention not to break the bone. The bone was split with a luer bone rongeurs. A mark was also made at 20 mm away in the proximal direction, and split similarly. When split, the ulna was covered with periosteum, which was then removed, and the bone fragments were thoroughly cleaned with saline.

Each ulna then received an implant or no implant according to one of Groups A-G, shown in Table 6, below. Groups A-D ulnae received a single implant of β-TCP carrying a specified amount of homodimeric protein. Group E ulnae received a single implant of β-TCP alone, without any homodimeric protein. Group F ulnae received a single implant of a bone autograft. Group G ulnae received no implant. Afterwards, muscle and dermal tissues were promptly sutured.

TABLE 6

| Group | β-TCP (mg) | Homodimeric protein (μg) | Homodimeric protein dose per β-TCP (mg/g) |
|---|---|---|---|
| A | 200 | 2 | 0.01 |
| B | 200 | 6 | 0.03 |
| C | 200 | 20 | 0.1 |
| D | 200 | 60 | 0.3 |
| E | 200 | 0 | 0 |
| F | Autograft (iliac bone fragments): 0.55 g on average (no β-TCP or homodimeric protein) | | |
| G | Defect only (no β-TCP or homodimeric protein) | | |

β-TCP as used in Groups A-E was in the form of 1-3 mm granules with a porosity of 75% and a pore diameter of 50-350 μm (Superpore™, pentax, "HOYA" Bone Graft Substitute, Japan).

In certain embodiments, β-TCP as used in Groups A-E is in the form of 1-3 mm granules with a porosity of 70% or more and a pore diameter of 300-600 μm ("Wiltrom" Osteocera Bone Graft Substitute, Wiltrom Co., Ltd., Taiwan, R.O.C.).

Homodimeric protein including recombinant polypeptides (i.e., SEQ ID NO: 260) in Groups A-D was prepared from frozen lots immediately before implantation for each animal using 0.5 mM hydrochloric acid (standard solution diluted with injection solvent (Otsuka Pharmaceutical Co., Ltd.)). Fluid volume was set at 180 μl for unilateral implantation and was dropped evenly across 200 mg of β-TCP granules in a sterilized Petri dish. When the fluid was completely dropped, the β-TCP granules were gently stirred with a spatula, allowed to sit for more than 15 minutes at room temperature, and then implanted.

For Group F, autograft bone was obtained from either the right or left wing of the ilium using luer bone rongeurs. Bones were processed into chips, and the same amount of bone was implanted as the amounts in Groups A-E.

X-Ray Evaluation

Figure 1B:
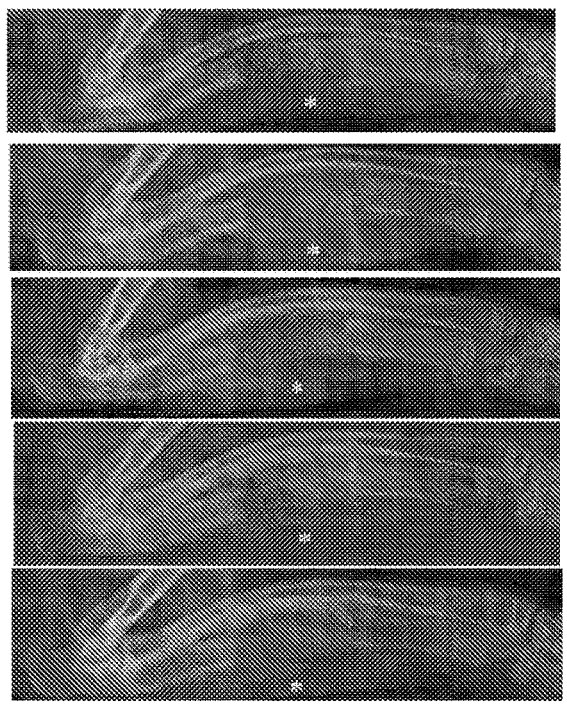
Figure 1B:
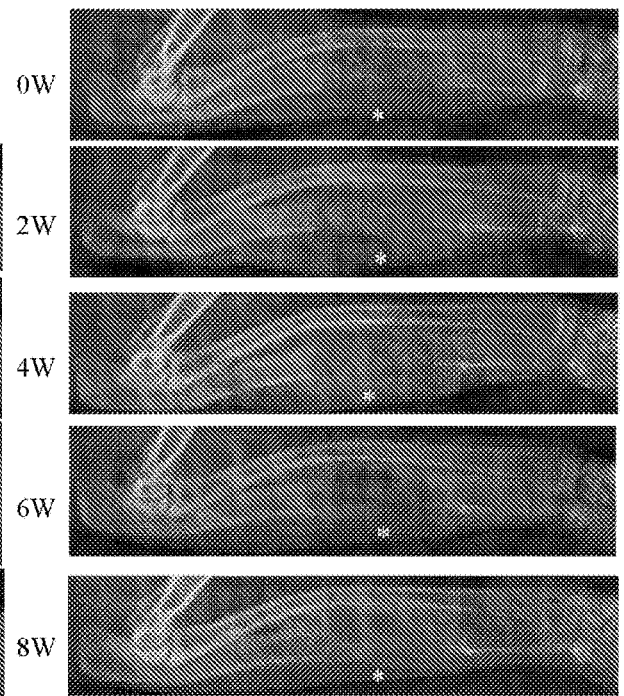
Figure 1B:
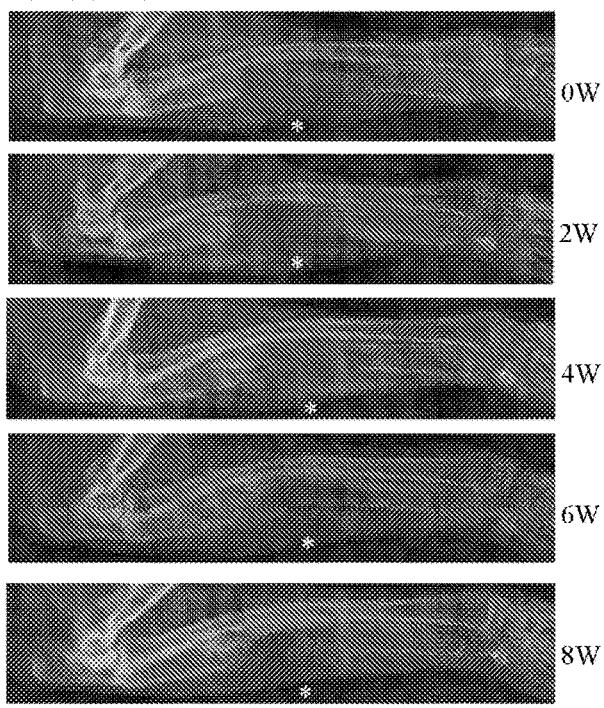

Lateral and frontal X-ray images (i.e., radiographs) were taken immediately after implantation and once every two weeks thereafter until 8 weeks after implantation. The condition of the implanted sites and the degree of bone formation were evaluated using the radiographs. Representative examples of X-ray images for each group are shown in FIG. 1A (Groups A-D) and FIG. 1B (Groups E-G).

At 2 weeks, contrast of granules of grafting material and the boundary with the recipient bed were clearly seen in all groups. At 4 weeks, TCP granules became unclear in the homodimeric protein groups (i.e., Groups A-D), showing absorption of the granules and progress of bone formation. The boundaries between the implanted site and the recipient bed were unclear in some samples in Group C and in Group D with high dose of the homodimeric protein. At 6 weeks, the boundary between the implanted site and the recipient bed became unclear in Group B. Improved continuity in the recipient bed and formation of the bone cortex were observed in some samples in Group C and in Group D. At 8 weeks, the boundary at the recipient bed became even more unclear in Groups A and B. Continuity in the recipient bed and formation of bone cortex improved in Group C. Reconstruction of the region of the ulnar defect was observed in Group D, as shown in the image at 6 weeks.

In Group E with TCP alone, bone formation in the recipient bed was observed over time. However, remaining TCP granules were clearly seen even at 8 weeks, showing insufficient bone formation at the implantation site and poor continuity in the recipient bed. Thus, repair of defects in Group E was still incomplete at 8 weeks.

In Group F with autograft, progress of bone formation was observed over time, and fusion with the recipient bed was achieved at 8 weeks. However, formation was not uniform.

In Group G with only the defect and no implant, slight bone formation in the radius was observed at 8 weeks without any other repair of the defect.

Computerized Tomography (CT) Scanning

Figure 2A:
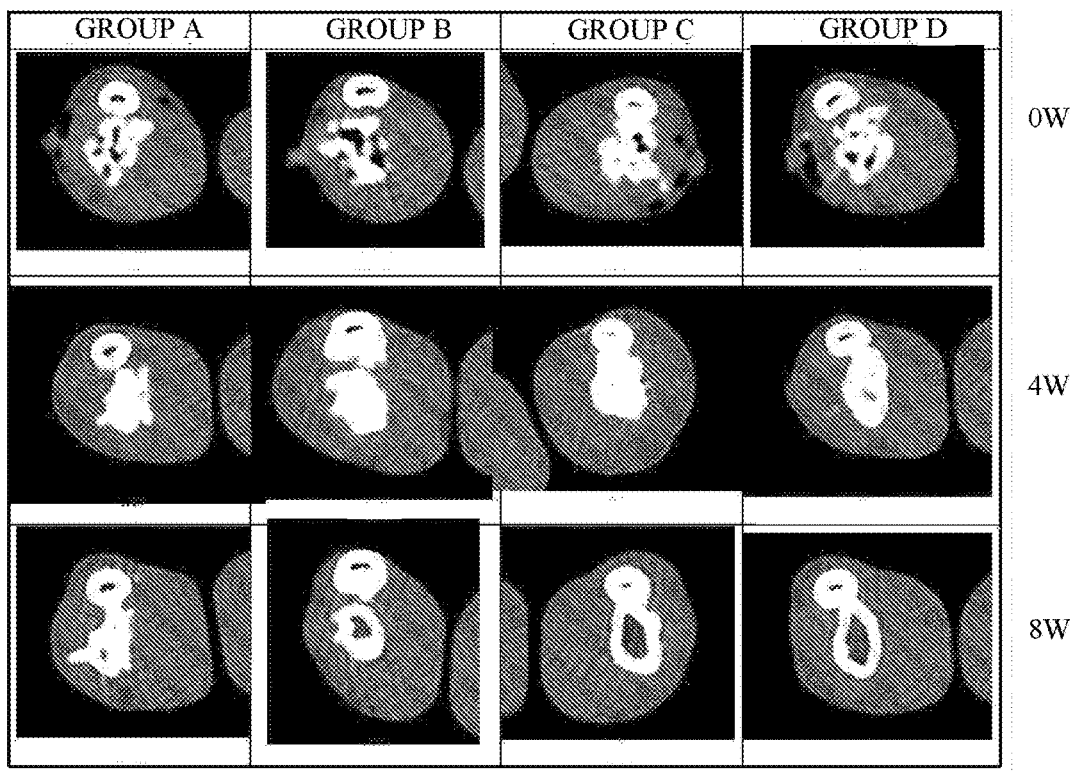
FIGS. 2A to 2B show representative computerized tomography (CT) scanning images for experimental Groups A-G. Change in cross-sectional images over time at the center of the implantation site (Groups A-F) or defect site (Group G) is shown 0 weeks (i.e., immediately after surgery, "W") and at 4 and 8 weeks after surgery (i.e., "4 W" and "8 W," respectively). Groups A-G are as described for FIG. 1.
Figure 2B:
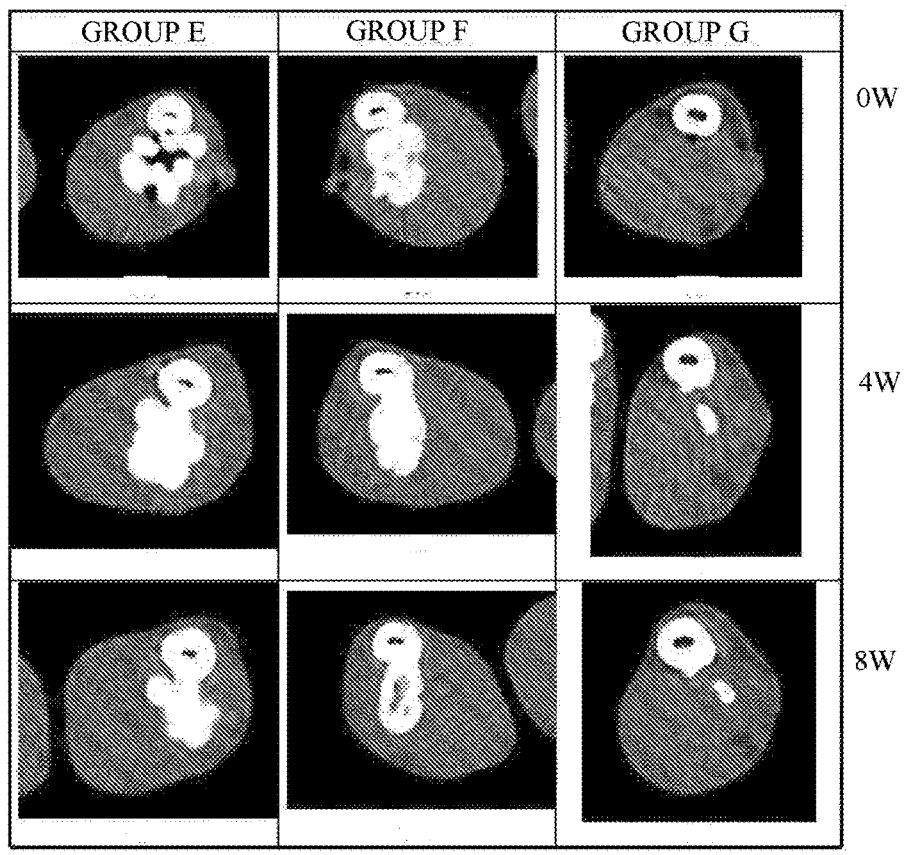

Axial orientation was performed at 1 mm intervals using CT scanning (GE Yokogawa Medical Systems Ltd.) immediately, at 4 weeks, and at 8 weeks after implantation. Images were mainly taken at the implant sites. Change in cross-sectional images over time at the center of the implanted sites are shown for representative examples in FIG. 2A (Groups A-D) and FIG. 2B (Groups E-G).

In Groups A to D with homodimeric protein, the granules observed immediately after implantation were partially degraded in the cross-sectional image at 4 weeks, suggesting bone formation. In Group D having a dose of 60 g, further progress in bone formation was observed, and the formation of bone-marrow cavities in some samples was observed. At 8 weeks, progress in the formation of bone-marrow cavities and bone cortex was observed in the images for groups with doses over 6 g. In Group E with only TCP, an agglomerated mass of granules remained even at 8 weeks. In Group F with autograft, formation of bone-marrow cavities was observed at 8 weeks, as in the remodeling process. In Group G with only defect, only slight bone formation was observed.

Torsional Strength Test

The grafting materials were removed from rabbits that were euthanized 8 weeks after implantation, and a torsional strength test was conducted for each group on the ulnae samples from which the radii were separated. 858 Mini Bionix II (MTS Systems Corporation) was used for the test. The test was conducted on a 50 mm-long area, namely, the 20 mm-long reconstructed area in the ulnar shaft at the center, and the 15 mm-long areas on both the proximal and distal sides of the reconstructed area. The edges of each side were fixed with dental resin. The resin parts were chucked in a measurement equipment. The left ulna was turned counterclockwise and the right ulna clockwise at a rotation rate of 30°/min, in order to determine maximum torque at failure. The separately obtained ulnae of healthy rabbits were also examined and compared. These healthy ulnae were obtained from Japanese white rabbits, a different type than those used in Groups A-E. The Japanese white rabbits were, however, the same age and gender as for Groups A-E at the time of euthanization, namely 26 weeks old and female.

Figure 3:
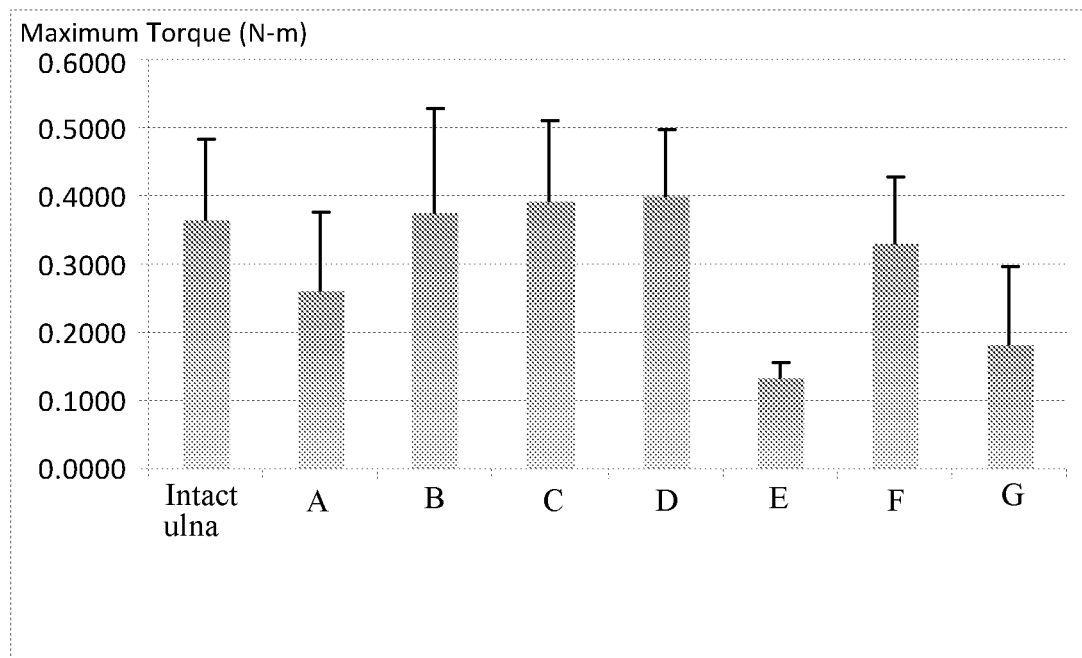
FIG. 3 shows a graphical representation of the results of torsional strength tests for an intact ulna that was not surgically altered and for experimental Groups A-G (i.e., "A"-"G," respectively). The maximum torque in Newton-meters ("N-m") is shown. Groups A-G are as described for FIG. 1.
Figure 4:
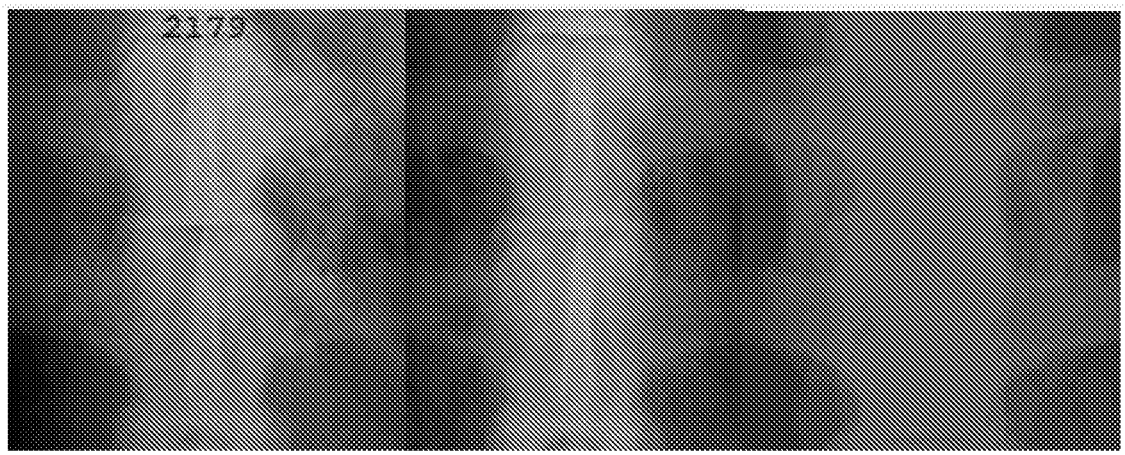
FIGS. 4-9 show representative X-ray images of sheep spines for experimental Groups 1-6. Groups 1-3 received a single implant of 3.5 g of β-TCP carrying 10.5, 3.5, or 1.05 mg, respectively, of a homodimeric protein including two recombinant polypeptides (i.e., SEQ ID NO:260, including intramolecular disulfide bonds C44-C48, C80-C112, and C79-C114). Group 4 received a single implant of 3.5 g of β-TCP without any homodimeric protein. Group 5 received a single implant of bone autograft. Group 6 received a single implant of absorbable collagen sponge with 3.15 mg of rhBMP-2.
Figure 5:
Figure 6:
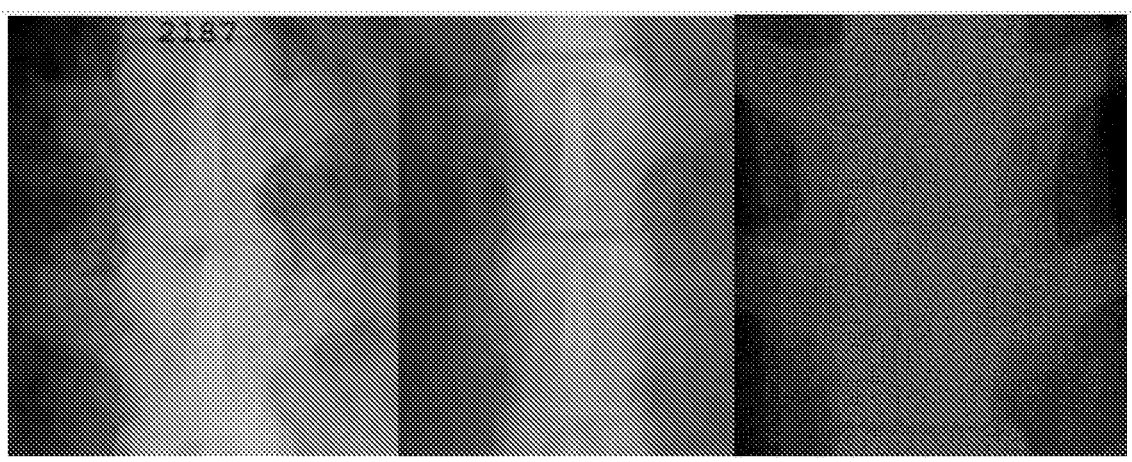
Figure 7:
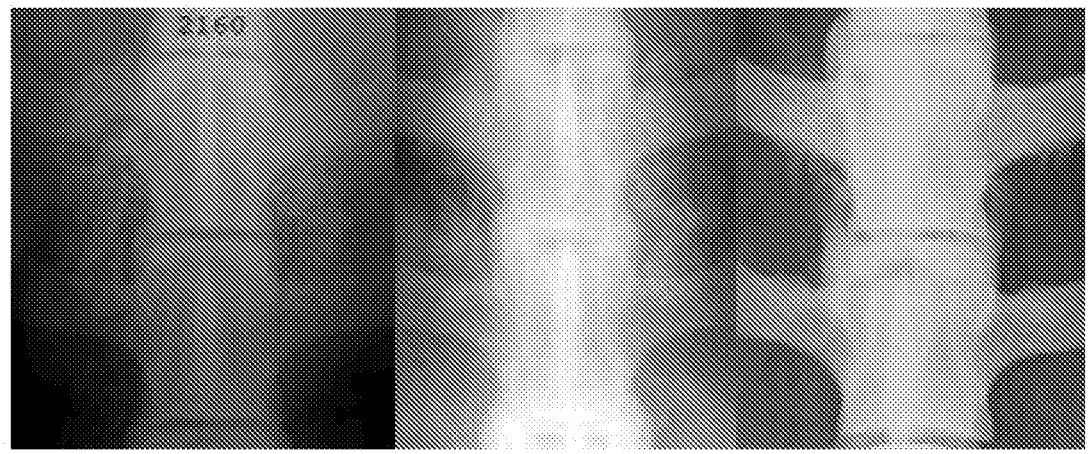
Figure 8:
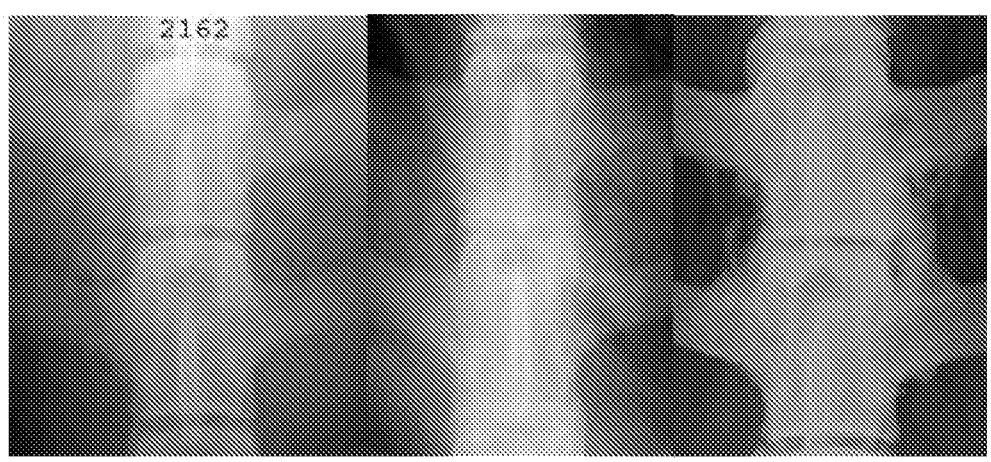
Figure 9:
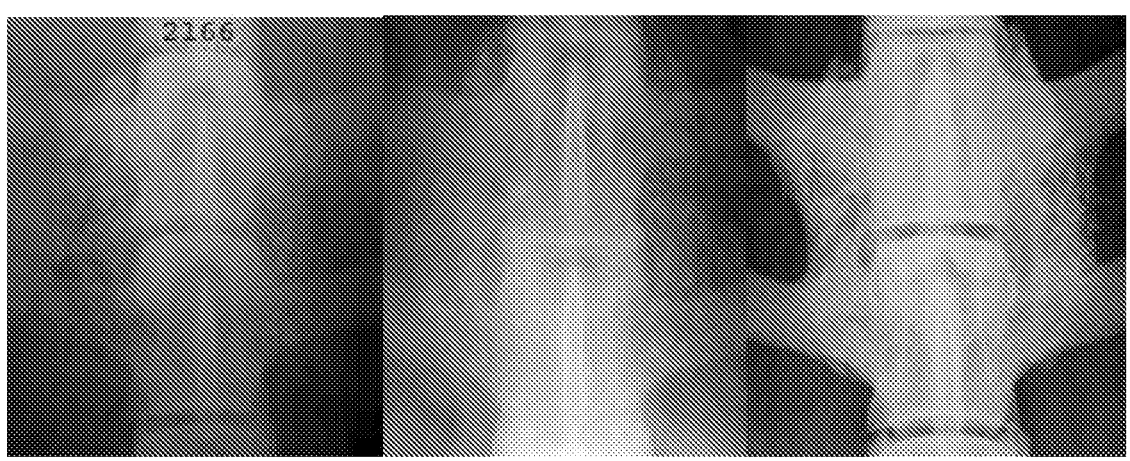

The maximum torque of each group obtained by the torsional strength test is shown in FIG. 3. In Groups A-D with homodimeric protein, maximum torque was dose-dependently high.

Significantly high values were seen in Groups A-D with a dose of 2 µg and over of homodimeric protein as compared to Group E with TCP alone.

Significantly high values were also seen in Groups B-D with a dose of 6 µg and over of homodimeric protein as compared to Group G with defect only.

No significant difference was observed among groups with an intact ulna, autograft, or homodimeric protein.

Due to insufficient bone formation in Groups E and G, it was difficult to ensure the support in some samples when the radii were separated. Therefore, only 2 samples from Group E and 4 sample from Group G were used in the test, while 6 samples were used from each of Groups A-D and F.

Table 7 below shows a comparison of test conditions and results between this study and the evaluation of CHO-derived BMP-2 in Kokubo et al., *Biomaterials* 24:1643-1651 (2003), using the same animal model. Compared to the report by Kokubo et al., this study was conducted under more difficult conditions, such as a larger bone defect, a smaller dose of active agent, and a shorter duration of implantation prior to torsional strength testing. However, ulnae were shown to be successfully repaired in this study, and maximum torque in this study was remarkably similar.

TABLE 7

| Source of data | Carrier | Size of defect (mm) | Weeks after implantation | Length of torsion of test specimen (mm) | Chemical agent dose | Maximum torque |
| --- | --- | --- | --- | --- | --- | --- |
| Kokubo et al. | PGS* | 15 | 16 | 45 | 100 µg BMP-2 | 0.307 |
| | | | | | 400 µg BMP-2 | 0.365 |
| | | | | | 1000 µg BMP-2 | 0.413 |
| This Study | TCP granule | 20 | 8 | 50 | 2 µg h.p.^ | 0.262 |
| | | | | | 6 µg h.p. | 0.375 |
| | | | | | 20 µg h.p. | 0.392 |
| | | | | | 60 µg h.p. | 0.400 |

*PGS: PLGA-coated Gelatin Sponge
^h.p.: homodimeric protein

Histological Evaluation

Specimens were prepared for all animals in 8 week and 4 week groups. Tissue obtained at the time of necropsy were preserved in 4% paraformaldehyde solution and decalcified with 10% EDTA. The tissue was then paraffin-embedded. Thinly-sliced samples were prepared on the plane running parallel to the long axis of the radius, hematoxylin and eosin (HE) stained, and histologically evaluated. Conditions of bone formation and fusion to the recipient bed were determined.

In Groups A to D with homodimeric protein, bone formation progressed to a trabecular pattern at 4 weeks. Active bone formation was observed in samples with a high dose of homodimeric protein. A significantly large amount of new bone and angiogenesis were observed in Group D with a dose of 60 µg. Remaining material was observed in some samples in Groups A and B with a low dose, while almost none was observed in Groups C and D. In Groups A and B, cartilage formation was observed in some samples near the boundary with the recipient bed. In all samples, the recipient bed was directly connected to the newly formed bone in a trabecular pattern. At 8 weeks, a trabecular pattern and remaining materials were still observed in Group A with a dose of 2 µg. Cartilage was also observed near the boundary with the recipient bed. Even though remodeling was insufficient, progress in bone formation was observed. The formation of bone cortex in the radii was observed in some samples. In Groups B to D with doses over 6 µg, bone cortex and bone marrow were being formed by remodeling. The progress was more significant in higher dose groups. Continuity in the recipient site also increased.

In Group E with TCP alone, bone formation on the grafting materials was observed in the radii, but remaining materials were still clearly seen even at 8 weeks, showing insufficient bone formation on the shaft and poor continuity.

In Group F with autograft, good bone formation on the grafted bone fragments was seen at 4 weeks, and new bone was in contact with the recipient bed. Cartilage formation was seen near the boundary with the recipient bed. At 8 weeks, progress in remodeling of new bone and formation of bone cortex were observed, but remaining grafted bone fragments were still observed.

In Group G with only defect, bone formation was observed only in the radii, and repair of the defect was not achieved.

Example 10: In Vivo Ovine Posterolateral Fusion Study

Osteoinductive activity of a homodimeric protein including a recombinant polypeptide ("Rcp") produced according to Example 6 (i.e., SEQ ID NO: 260, including intramolecular disulfide bonds C44-C48, C80-C112 and C79-C114) and porous beta-tricalcium phosphate (β-TCP) as a carrier material was evaluated in ovine posterolateral fusion model. The calcium phosphate carrier had a calcium to phosphate ratio of about 1.2 to about 1.8.

The ovine posterolateral fusion model used sheep sedated with Zoletil® (8-12 mg/kg, IM), and gassed down with isofluorane (2%) and oxygen (2 litres per minute). An endotracheal tube was inserted and the animal ventilated; anesthesia was maintained using isofluorane (2 to 3%) and oxygen (2-4 litres per minute). Antibiotics (Keflin®: 1 gm IV; Benacillin 5 ml IM) were given. Carprofen (an NSAID, 4 ml IM) and Temgesic® (Burprenorphine 0.324 mg SC) were injected prior to surgery. Crystalloid fluids (Hartmann's solution) were given intravenously at 4 to 10 ml/kg/h prior to and during the surgery as required.

A 15-cm midline incision was made parallel to the lumbar transverse process at the L3-L4 level. Blunt retroperitoneal dissection exposed the anterolateral aspect of the lumbar spine. This left the diaphragm undisturbed. The soft tissues were retracted. A pneumatic burr (Midas Rex) was used to decorticate the transverse processes (15 mm lateral) and adjacent vertebral body between the levels in all animals.

The graft materials were placed between the decorticated surfaces of the transverse processes and the vertebral bodies (paraspinal bed) according to one of Groups 1-6, shown in Table 8, below. Groups 1-3 received a single implant of β-TCP carrying a specified amount of homodimeric protein. Group 4 received a single implant of β-TCP alone, without any homodimeric protein. Group 6 received a single implant of absorbable collagen sponge (ACS) with a specified amount of rhBMP-2, a well-established osteoinductive factor as positive control. Group 5 received a single implant of bone autograft. Autografts were harvested from the iliac crests in the autograft group animals. The bones were morcelized using a rongeur and 5.0 g of autograft bone used for each side of the fusion. The incisions were closed with 2-0 absorbable suture and the skin approximated using 3-0 suture.

β-TCP as used in Groups 1-4 was in the form of 2-4 mm granules with a porosity of 70% and a pore diameter of 50-350 μm (Superpore™, pentax, "HOYA" Bone Graft Substitute, Japan).

In certain embodiments, β-TCP as used in Groups 1-4 is in the form of 2-8 mm granules with a porosity of 65% or more and a pore diameter of 250-730 μm ("Wiltrom" Osteocera Bone Graft Substitute, Wiltrom Co., Ltd., Taiwan, R.O.C.).

In Group 1, homodimeric protein including Rep (i.e., SEQ ID NO: 260) stock solution H was prepared by adding 2 ml injection water to each of vials with 10 mg homodimeric protein. The stock solution H was mixed with injection water by 3:1 on volume ratio to form Homodimeric Protein High Dose Solution (containing 10.5 mg homodimeric protein in 2.8 ml solution). 2.8 ml Homodimeric Protein High Dose Solution was delivered by dropping evenly into 3.5 g β-TCP granule.

In Group 2, homodimeric protein stock solution ML (2.5 mg/ml) was prepared by adding 4 ml injection water to each of vial with 10 mg homodimeric protein. The stock solution ML was mixed with injection water by 1:1 on volume ratio to form homodimeric protein Middle Dose Solution (containing 3.5 mg homodimeric protein in 2.8 ml solution). 2.8 ml Homodimeric Protein Middle Dose Solution was delivered by dropping evenly into 3.5 g β-TCP granule.

In Group 3, homodimeric protein stock solution ML (2.5 mg/ml) was prepared by adding 4 ml injection water to each of vial with 10 mg homodimeric protein. The stock solution ML was mixed with injection water by 17:3 on volume ratio to form homodimeric protein Low Dose Solution (containing 1.05 mg homodimeric protein in 2.8 ml solution). 2.8 ml homodimeric protein Low Dose Solution was delivered by dropping evenly into 3.5 g β-TCP granule.

Group 6 was conducted to compare commercial product Infuse® and Mastergraft® as graft materials, both are distributed by Medtronic. Infuse® consisted of rh-BMP-2 prepared by CHO expression system and absorbable collagen sponge ("ACS"). Mastergraft® is granular calcium phosphate bone substitute consisting of 85% β-TCP and 15% Hydroxyapatite. Application of Infuse® combined with Mastergraft® on posterolateral lumber fusion showed efficacy and was reported by E. Dawson et. al., on the clinical study with evidence level 2 (J Bone Joint Surg Am. 2009; 91: 1604-13). Graft material for Group 6 consisted of 3.15 mg rh-BMP-2, 4 cc ACS and 5 cc Mastergraft® per site, and procedure of graft material preparation were followed as E. Dawson's report. Lot number of Infuse® and Mastergraft® were recorded on operation record.

The animals were monitored daily for the first 7 days following surgery and observations recorded on post-operative monitoring sheets for each animal.

TABLE 8

| Group/No. | Homodimeric protein (mg/site) | | Carrier | Fixation | Time point | Sample Size |
|---|---|---|---|---|---|---|
| 1 | h.p.^ High | 10.5 | 3.5 g β-TCP | None | 12 wks | 6 |
| 2 | h.p.^ Middle | 3.5 | 3.5 g β-TCP | None | 12 wks | 6 |
| 3 | h.p.^ Low | 1.05 | 3.5 g β-TCP | None | 12 wks | 6 |
| 4 | None | N/A | 3.5 g β-TCP | None | 12 wks | 6 |
| 5 | None | N/A | Autograft | None | 12 wks | 6 |
| 6 | Infuse ® + Mastergraft ® | 3.15 rh-BMP-2 mg/site | ACS 4 cc Mastergraft ® 5 cc | None | 12 wks | 6 |

^ h.p.: homodimeric protein

Posteroanterior radiographs of all animals were taken at 4 weeks. The animals were sedated with Zoletil® (8-12 mg/kg, IM), and gassed down with Isofluorane (2%) and oxygen (2 litres per minute). The radiographs were used to compare to the post-operative X-rays for the presence of new bone and absorption of the TCP material. At 12 weeks post surgery all animals were sacrificed via lethal cardiac injection of Lethobarb.

To monitor the time of bone formation, three different fluorochromes were intravenously injected at three time points as indicated in the Table 9 below.

TABLE 9

The date and dosage of fluorochrome used*

|  | Alizarin complexone | Calcien | Engemycin ® |
|---|---|---|---|
| Supplier | Sigma | Sigma | Schering Plough |
| Solvent | 1.4% NaHCO$_3$ | 1.4% NaHCO$_3$ | Physiological saline |
| pH | 6-8 | 6-8 | 6-8 |
| Dosage (mg/kg body weight) | 28 mg/kg (=2 ml/kg) | 10 mg/kg (=2 ml/kg) | 20 mg/kg (=2 ml/kg) |
| Time to inject after | 6 weeks | 8 weeks | 10 weeks |

*All filtered through 0.22 μm filters before use

X-Ray Evaluation

The lumbar spines (L1-L6) were harvested and photographed using a digital camera. The harvested spines were faxitroned using a Faxitron® Machine (settings 24 kV for 45 seconds). Digital radiographs were taken in the posterior-anterior (PA) were graded for evidence of new bone formation and fusion by three blinded observers on the right and left sides. A qualitative grading system was used to assess the radiographs (Table 10). Fusion was assessed based on a continuous pattern of bone from one transverse process to the next level (0=non-continuous, 1-continuous). The amount of bone between the transverse processes on each side of the fusion masses was graded based on percentage as outlined in Table 10. The amount of TCP resorption was noted based on a comparison to time 0 radiographs with the same amount of material.

TABLE 10

Radiographic grading parameters

| Fusion | Yes = 1 | No = 0 |
|---|---|---|
| Amount of bone | 5 | 80-100% |
|  | 4 | 60-80% |
|  | 3 | 40-60% |
|  | 2 | 20-40% |
|  | 1 | 0-20% |

Posteroanterior radiographs of all animals were taken post-operatively, at 4 weeks, and at 12 weeks following harvest. Representative Xrays of each group are shown in FIGS. 4-9. Granules were evident in post-operative Xrays for Groups 1, 2, 3, 4, 5 and 6. At the four-week time point, few granules were visible for Group 1 and 2, though their presence could be noted. More granules were apparent in group 3 and 4, while Group 6 clearly showed remaining particles or granules. At 12 weeks, particles or granules could not be distinguished from bone for Groups 1, 2 and 3. Group 4 showed little bone formation and no clearly visible particles. Particles were still evident at 12 weeks for Group 6.

Radiographic assessment was performed by 3 blinded observers. The grading consisted of a binomial assessment of fusion and a 5-level assessment of the amount of bone present within the fusion mass. Results are shown in Table 11. The mean value of individual grades for each animal were first calculated, then the mean and standard deviation for each group was calculated.

TABLE 11

Pooled results of grading showing mean and (standard deviation)

| Group | Left Fusion | Right Fusion | Left Bone | Right Bone |
|---|---|---|---|---|
| 1 | 0.777 (0.17) | 1 (0) | 4.83 (0.27) | 4.11 (0.68) |
| 2 | 0.777 (0.40) | 0.833 (0.40) | 3.50 (1.09) | 4.22 (0.75) |
| 3 | 0.666 (0.51) | 0.833 (0.40) | 3.44 (1.40) | 3.06 (1.25) |
| 4 | 0.222 (0.40) | 0.166 (0.40) | 1.11 (0.17) | 1 (0) |
| 5 | 0.277 (0.44) | 0.611 (0.38) | 3.06 (1.28) | 3.06 (1.25) |
| 6 | 1 (0) | 1 (0) | 4.78 (0.17) | 4.83 (0.18) |

Example 11: In Vivo Osteoinductive Activity in Sheep Interbody Fusion Model

Osteoinductive activity of a homodimeric protein including recombinant polypeptides produced according to Example 6 (i.e., SEQ ID NO: 260, including intramolecular C44-C48 and intermolecular C79-C112 and C80-C114 disulfide bonds), porous beta-tricalcium phosphate (β-TCP) as a carrier material and a peek cage as an accommodator was evaluated in an interbody fusion model in sheep. The calcium phosphate carrier has a calcium to phosphate ratio of about 0.7 to about 1.7.

Pre-Surgery Preparation

Animals (Species: *Ovis Aries*; Breed: Border Leicester Merino Cross; Source: UNSW approved supplier—Hay Field Station, Hay, NSW and animals were purchased following UNSW Animal Care and Ethics Committee approval; Age: 4 years old age; and Gender: Female (Ewe)) were prepared for surgery according to standard operating procedures. Twenty-four hours prior to surgery, pre-emptive analgesia was administered, by applying a transdermal fentanyl patch (100 mg-2 mcg/kg/hr) to the right foreleg of each animal (left foreleg was used for iv line). Prior to application, the wool was clipped and the skin cleaned with alcohol swabs to ensure adequate absorption. Animals were fasted and water withheld a minimum of 12 hours prior to surgery.

Surgery

Sheep allocated to the study were randomly selected on the day of surgery. Once a sheep was selected, it was assigned a number and ear-tagged according to standard operating procedures. This identification number was recorded in the study notebook.

On the day of surgery and prior to commencement, the Study Veterinarian examined each animal to ensure that it was free of disease or any condition that might interfere with the purpose or conduct of the study. Notes were made in the Study Notebook against the animal number as to the condition of each animal and its suitability for inclusion in the study.

Animals were induced, anaesthetised, maintained, and monitored during the procedure according to standard operating procedures. The left foreleg was used for cephalic intra-venous access. Blood was taken for pre-operative analysis according to standard operating procedures, prior to i.v. administration of Hartman's solution. Blood samples were labelled "PRE-OP" along with study ID, animal number and date and sent to IDEXX Australia for routine biochemistry (4 ml) and haematology (4 ml).

Surgery was performed according to a modified version of standard operating procedures.

Surgical Procedure—L45 XLIF+ Pedicle Screws

Prior to surgery, all animals were under food restriction (NPO) for forty-eight hours and housed in the isolation pen care facility. Following administration of anesthetic medications and induction of general anesthesia, the posterior lumbar region, iliac crest and proximal tibia were aseptically prepared.

Graft Mixing Procedure

The homodimeric protein (10 mg/vial) was dissolved in 0.3 mL distilled water to make a 33.3 mg/mL HP stock solution A. A block of β-TCP (approx. 150 mg) was placed into an interbody cage. For each group, "Hp solution" that was diluted or divided from HP stock solution A was dropped evenly across the block of β-TCP (approx. 150 mg) placed on a sterilized Petri dish. After the fluids were completely dropped, the block of β-TCP was allowed to stand for more than 15 minutes at room temperature before implantation.

Group A-F used the above-described homodimeric protein (Hp) combined with 3-TCP carrier as graft material, with the homodimeric protein dose per site shown in Table 12. Preparations of mixing procedures were as follows.

TABLE 12

| Group | Animal | Carrier βTCP | Hp mg/site | Level | Cage | Pedicle screws | Time point |
|---|---|---|---|---|---|---|---|
| A | 1 | 150 mg | 4.0 mg | L45 | Yes | Yes | 12 wks |
| B | 2 | 150 mg | 2.0 mg | L45 | Yes | Yes | 12 wks |
| C | 3 | 150 mg | 1.0 mg | L45 | Yes | Yes | 12 wks |
| D | 4 | 150 mg | 0.5 mg | L45 | Yes | Yes | 12 wks |
| E | 5 | 150 mg | 0.1 mg | L45 | Yes | Yes | 12 wks |
| F | 6 | 150 mg | 0 mg | L45 | Yes | Yes | 12 wks |
| G | 7 | 150 mg | Autograft (iliac crest) | L45 | Yes | Yes | 12 wks |
| A | 8 | 150 mg | 4.0 mg | L45 | Yes | Yes | 12 wks |
| B | 9 | 150 mg | 2.0 mg | L45 | Yes | Yes | 12 wks |
| C | 10 | 150 mg | 1.0 mg | L45 | Yes | Yes | 12 wks |
| D | 11 | 150 mg | 0.5 mg | L45 | Yes | Yes | 12 wks |
| E | 12 | 150 mg | 0.1 mg | L45 | Yes | Yes | 12 wks |
| F | 13 | 150 mg | 0 mg | L45 | Yes | Yes | 12 wks |
| G | 14 | 150 mg | Autograft (iliac crest) | L45 | Yes | Yes | 12 wks |
| X | 15 | 150 mg | 0 mg | L45 | Yes | Yes | 0 wks |

For group A, Hp 4 mg/site: Prepared Hp stock solution A (33.3 mg/mL) by adding 0.3 mL injection water to each of the glass vials with 10 mg homodimeric protein in it as Hp stock solution A. Put a β-TCP block (approx. 150 mg) into the peek cage. Delivered 120 μL Hp stock solution A by drops evenly into 150 mg β-TCP block.

For group B, homodimeric protein 2 mg/site: Mixed water and Hp stock solution A in a 1:1 volume:volume ratio, then obtained Hp solution B (16.7 mg/mL). Put a β-TCP block (approx. 150 mg) into the cage. Delivered 120 μL Hp solution B by drops evenly into 150 mg β-TCP block.

For group C, homodimeric protein 1 mg/site: Mixed water and Hp solution B in a 1:1 volume:volume ratio, then obtained Hp solution C (8.3 mg/mL). Put a β-TCP block (approx. 150 mg) into the cage. Delivered 120 μL Hp solution C by drops evenly into 150 mg β-TCP block.

For group D, homodimeric protein 0.5 mg/site: Mixed water and Hp solution C in a 1:1 volume:volume ratio, then obtained Hp solution D (4.2 mg/mL). Put a β-TCP block (approx. 150 mg) into cage. Delivered 120 μL Hp solution D by drops evenly into 150 mg β-TCP block.

For group E, homodimeric protein 0.1 mg/site: Mixed water and Hp solution D in a 1:4 volume:volume ratio, then obtained Hp solution E (0.8 mg/mL). Put a β-TCP block (approx. 150 mg) into cage. Delivered 120 μL Hp solution E by drops evenly into 150 mg β-TCP block.

For group F, homodimeric protein 0 mg/site: Put a β-TCP block (approx. 150 mg) into cage. Delivered 120 μL water by drops evenly into 150 mg β-TCP block.

Interbody Peek Cage

The transverse processes were palpated to identify the appropriate spinal levels. The level was verified by fluoroscopy. Caspar pins were placed into the L4 and L5 vertebral bodies and a Caspar retractor used to distract the disc space. The disc was removed with sharp dissection and curettes and the endplates prepared. The interbody device filled with the graft material was carefully placed into the disc space and the retractors released. The soft tissues were re-apposed and the skin closed in layers.

Figure 10:
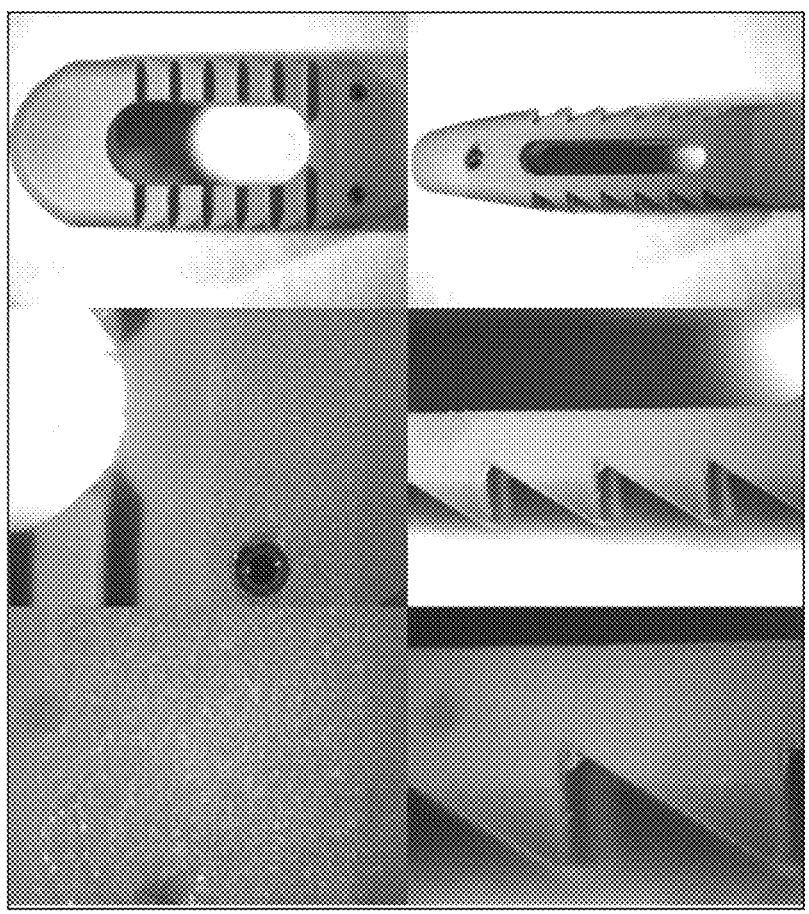
FIG. 10 shows a graphical representation of an interbody cage. The left images in each row show a top view of the interbody cage, while the right images show a side view. Magnification: top row=×0.67, middle row=×2, bottom row=×4. Cage dimensions: about 8 mm×24 mm×10 mm.

FIG. 10 shows the appearance of an interbody cage.

Pedicle Screws

Following completion of the XLIF, the animal was repositioned in the prone position and draped using sterile technique; an initial skin incision was made in the dorsal mid-line of the low back centered over the L3-S1 levels. Blunt dissection using a Cobb elevator and electrocautery, when necessary, was performed in the sagittal plane along the neural arch—permitting exposure of the L45 facets and transverse processes and insertion of pedicle screws and rods at this level.

Radiographs were taken immediately following surgery in the postero-anterior plane using a mobile x-ray machine (POSKOM) and digital cassettes (AGFA). The data were stored in DICOM format and exported to JPG images using ezDICOM medical viewer software. This is performed according to standard operating procedures.

Post-Operative Monitoring

Animals were monitored daily for the first 7 days and recorded. Animals were examined at least once daily for the duration of the study by veterinary technicians and recorded weekly. Any health concerns identified by the technicians were reported to the veterinary staff for further evaluation and management by the PI.

Sheep were monitored as per the study site standard operating procedure. The surgical incision, appetite, changes in skin and hair, eyes and mucous membranes, respiratory system, circulatory system, posture/gait, behaviour patterns (occurrence of tremors, convulsions, excess salivation, and lethargy) were monitored daily for the first post-operative week and weekly thereafter. Signs monitored thereafter were alertness/attentiveness, appetite, and surgical site, appearance of eyes, ambulation, and ability to keep the head raised. Criteria for intervention were signs of infection.

Post-operatively, animals received oral antibiotics (Kelfex) and analgesics (buprenorphine, 0.005-0.01 mg/kg IM) for the first 3 days. Daily neurological assessments were made for the first 7 days post-operatively. Post-operative pain relief was provided thereafter based on clinical monitoring.

Explant

At the designated time point, each animal had its identification number confirmed before being induced and anaesthetized, as per standard operating procedures.

After anaesthetic induction, blood was taken from either the jugular or cephalic vein, according to standard operating procedures. Samples were labelled "with study ID, animal number and date. The samples were transported to SORL in a sealed biohazard bag and maintained below 30 degrees C. and sent to IDEXX Australia for Routine biochemistry (4 mLs) and haematology (4 mLs). Transportation times were noted in the notebook.

While still under an aesthesia, animals were euthanized by lethal injection of Lethobarb according to standard operating procedures. The carcass was transported immediately to SORL and kept at a temperature of less than 30 degrees C.

Each animal was examined and dissected according to standard operating procedures. The Lumbar Spine was harvested and photographed using a digital camera. The surgical sites were examined for signs of adverse reaction or infection and the results noted and photographed.

Immediately after harvest, the stability of the fusion mass was assessed by manual palpation in all animals 12 weeks. Two trained and experienced blinded observers worked together to assess the fusion mass in lateral bending and flexion—extension with the pedicle rods intact as well as removed.

The fusions were graded as either fused (rigid, no movement) or not fused (not rigid, movement detected) when manual palpation evaluated in lateral bending on the right and left sides and flexion—extension at the treated level. The mobility of the untreated level was used as a relative comparison at the time of manual palpation when evaluated in lateral bending on the right and left sides as well as flexion—extension.

Range of Motion (ROM) Testing

The L45 segments were carefully harvested from the spine. A 4 mm×15 mm screw was inserted into the vertebral bodies and used to assist in potting the samples.

Figure 11:
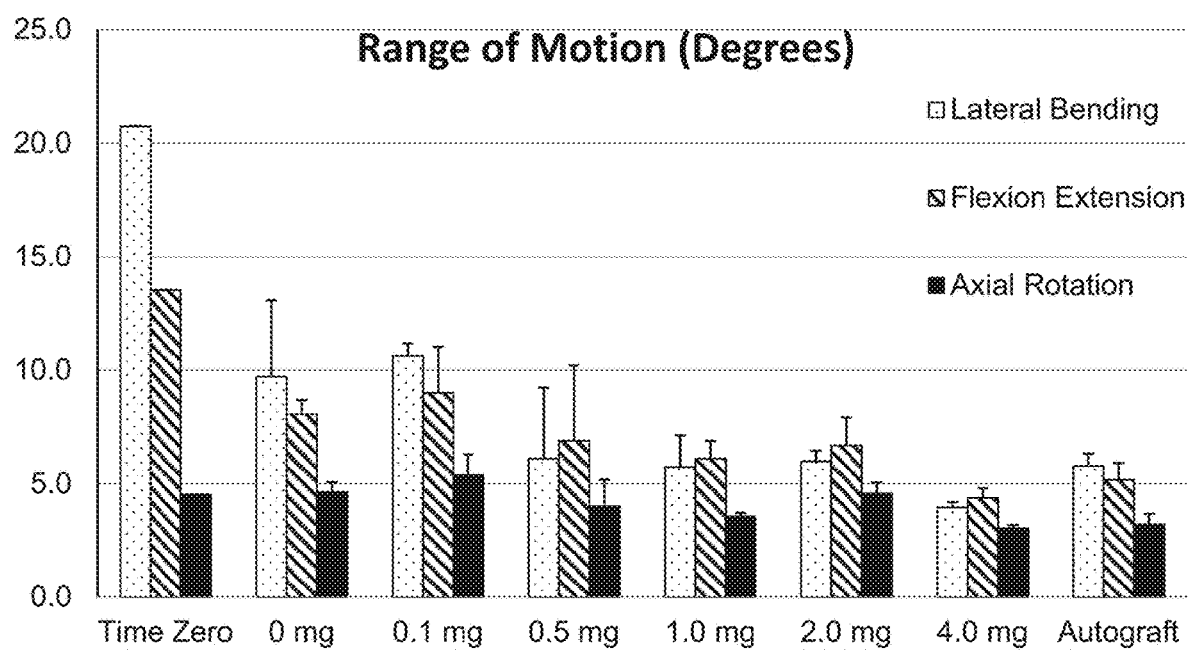
FIG. 11 shows a graphical representation of the range of motion in degrees for: a sheep spine receiving an implant of 150 mg of β-TCP measured at 0 weeks (i.e., "Time Zero"); sheep spines receiving implants of 150 mg of β-TCP carrying 0, 0.1, 0.5, 1.0, 2.0, or 4.0 mg, respectively, of a homodimeric protein including two recombinant polypeptides (i.e., SEQ ID NO:260, including intramolecular disulfide bond C44-C48, and intermolecular disulfide bonds C79-C112 and C80-C114) measured at 12 weeks; and a sheep spine receiving an implant of bone autograft measured at 12 weeks. Sheep were female, strain Ewe. The figure shows the mean and standard deviations for the range of motion for each testing condition and direction.

The segments were carefully potted in a resin for ROM evaluation. Range of motion in flexion—extension (FE), lateral bending (LB) and axial rotation (AR) were determined using a Denso Robot. The rods were removed prior to testing. A 7.5 Nm pure moment will applied to the spines in FE, LB and AR and resulting angular deformation recorded with the testing equipment. Each loading profile were repeated 3 times and a mean value for FE, LB and AR obtained for each treated level as shown in FIG. 11. Samples were fixed in phosphate buffered formalin after mechanical testing for paraffin histology on one side and PMMA histology for the other side of the fusion as outlined below. ROM data were analysed using ANOVA using SPSS.

As shown in Table 13, manual palpation indicated non-rigid motion segments for doses below 0.5 mg, and rigid motion segments for doses of 0.5 mg and above, as well as for autograft.

TABLE 13

| Group | Animal | ID | Hp mg/site | Time (weeks) | Manual Palpation FE* | Manual Palpation LB^ |
|---|---|---|---|---|---|---|
| X | 15 | W2780 | 0 mg | 0 | not rigid | not rigid |
| F | 6 | W2781 | 0 mg | 12 | not rigid | not rigid |
| F | 13 | W2792 | 0 mg | 12 | not rigid | not rigid |
| E | 5 | w2790 | 0.1 mg | 12 | not rigid | not rigid |
| E | 12 | W2791 | 0.1 mg | 12 | not rigid | not rigid |
| D | 4 | W2788 | 0.5 mg | 12 | rigid | rigid |
| D | 11 | W2789 | 0.5 mg | 12 | rigid | rigid |
| C | 3 | W2786 | 1.0 mg | 12 | rigid | rigid |
| C | 10 | W2787 | 1.0 mg | 12 | rigid | rigid |
| B | 2 | W2784 | 2.0 mg | 12 | rigid | rigid |
| B | 9 | W2785 | 2.0 mg | 12 | rigid | rigid |
| A | 1 | W2782 | 4.0 mg | 12 | rigid | rigid |
| A | 8 | W2783 | 4.0 mg | 12 | rigid | rigid |
| G | 7 | W2793 | Autograft (Iliac Crest) | 12 | rigid | rigid |
| G | 14 | W2794 | Autograft (Iliac Crest) | 12 | rigid | rigid |

*FE: Flexion extension
^ LB: Lateral bending

As shown in FIG. 11, range of motion showed little change for any treatment in axial rotation. However, flexion extension decreased from intact for all treatment groups and showed a trend towards increased stability with increasing homodimeric protein dose. Autograft and 1.0 mg homodimeric protein were the most comparable. Lateral bending was reduced for all treatments as well, to <50% of the intact value for all treatments. Lateral bending also showed a reduction in ROM as with increasing homodimeric protein dose. The dose influence was most prevalent at the 0.1 mg to 0.5 mg stage.

Micro Computed Tomography—Spine

Micro Computed tomography (CT) was performed on the spines using an Inveon Scanner (Siemens, USA). Slice thickness were set to approximately 50 microns for all scans. CT scans were stored in DICOM format. Three dimensional models were reconstructed based and examined in the axial, sagittal, and coronal planes. The DICOM stacks were sent to the Study Sponsor for additional analysis.

Axial, sagittal and coronal images as well as anterior and posterior 3D models were provided for each animal. The micro-CT reconstructions were evaluated by reviewing the coronal and sagittal planes to examine fusions between the treated levels. The micro-CT were graded using the same Radiographic grading score (Table 14) considering the entire micro-CT stack by two trained and experienced observers blinded to treatment groups. Each fusion will also be graded with a scale of 1 to 4 representing the amount of bone qualitatively at the level: 0-25%, 2: 26-50%, 3: 51-75%, 4: 76-100%.

TABLE 14

Grading scale for micro CT

| Number | Grade | Description |
|---|---|---|
| 0 | No new bone | No new bone formation visible |
| 1 | Visible new bone | New bone formation visible but no continuous bone |

TABLE 14-continued

Grading scale for micro CT

| Number | Grade | Description |
|---|---|---|
| 2 | Visible new bone | Continuous bridging new bone with visible lucency |
| 3 | Probable fusion | Continuous bridging new bone formation |

Figure 12A:
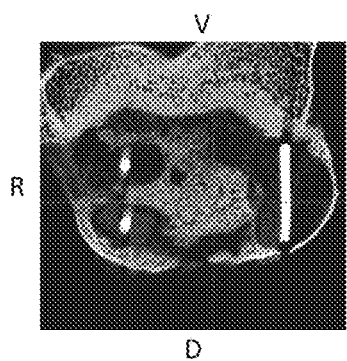
FIGS. 12A-C show representative micro computed tomography (CT) axial, coronal, and sagittal images, respectively, of a sheep spine that received an implant with homodimeric protein in an amount of 0.1 mg/site as described for FIG. 11. "V," "D," "R," "L," "S," and "I" refer to ventral, dorsal, right, left, superior, and inferior directions, respectively. The site generated bone that largely filled the space within the cage; however, lucency was present at both endplate interfaces.
Figure 12B:
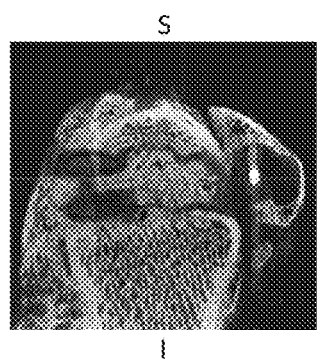
Figure 12C:
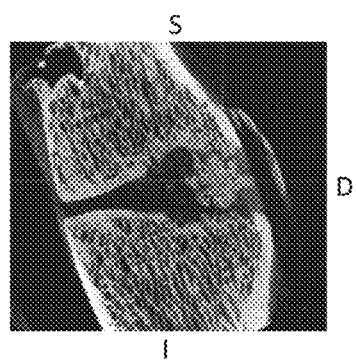
Figure 13A:
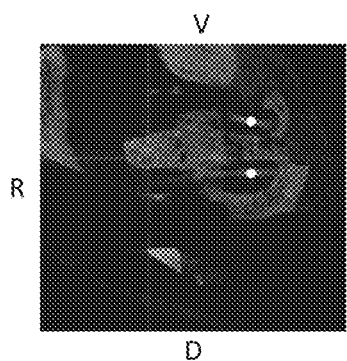
FIGS. 13A-C show representative CT axial, coronal, and sagittal images, respectively, of a sheep spine for that received an implant with homodimeric protein in an amount of 0.5 mg/site as described for FIG. 11. "V," "D," "R," "L," "S," and "I" are as described for FIGS. 12A-C. The site demonstrated good bone quality but with the presence of some lucent lines within the graft.
Figure 13B:
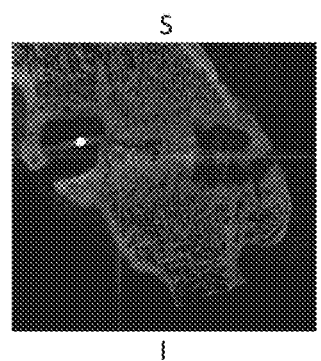
Figure 13C:
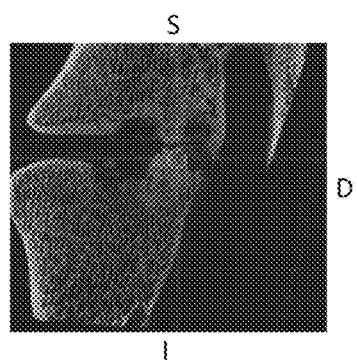
Figure 14A:
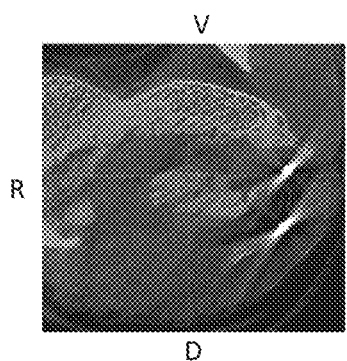
FIGS. 14A-C show representative CT axial, coronal, and sagittal images, respectively, of a sheep spine that received an autograft as described for FIG. 11. "V," "D," "R," "L," "S," and "I" are as described for FIGS. 12A-C. The site did not fully fill the cage with bone at the time point. Additionally, there was some lucency within the endplate.
Figure 14B:
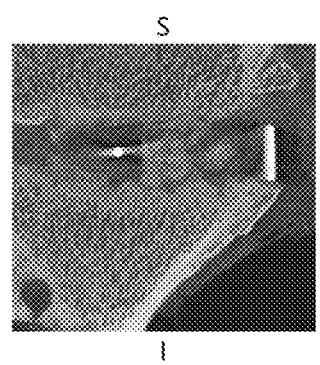
Figure 14C:
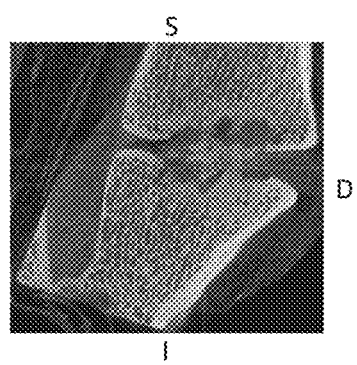

Representative images of the micro-CT for each animal were prepared in three orthogonal planes as well as three dimensional models in the anterior and posterior views. Micro computed tomography (CT) scanning were performed on all animals following radiography using a Siemens Inveon in-vivo microcomputer tomography scanner to obtain high resolution radiographic images of the spinal fusions in three planes. This was performed according to standard operating procedures; however, in addition thicker reconstructions were also be taken and examined for each animal using a 500 micron summation image technique. Note, the 3D reconstructions were reviewed to evaluate the overall fusion status and representative images were provided in the report and appendices for all animals. This was performed according to standard operating procedures with some modification. The sagittal and coronal CT images were reviewed and an overall grade for the fusion given based on Table 14. See FIGS. 12-14.

Fusion Grading

0 Hp mg/sites demonstrated residual TCP and some bone formation primarily at the endplate. With 0.1 Hp mg/site new bone was generated and minimal residual TCP was present but solid bone bridging was not present. With 0.5 Hp mg/site good bone quality was generated but with the presence of some lucent lines within the graft. With doses of 1.0 Hp mg/site and 2.0 Hp mg/site the inter-cage space was filled with good quality bone with minimal lucent areas. 4.0 Hp mg/site generated a high grade of bone based on volume; however, there was lucency within the bone including some large and small pockets. Autograft (iliac crest) demonstrated variable results with fair to good bone formation and areas of non-union. The following table summarizes the grading of each site.

Fusion grading based on Micro CT analysis were as shown in Table 15. Overall bone grade and fusion grade peaked with 1.0 and 2.0 mg Hp doses. Bone grade was graded with a scale of 1 to 4 representing the amount of bone qualitatively at the level: 0-25%, 2: 26-50%, 3: 51-75%, 4: 76-100%. Fusion grading was done from 0-3 based on 0—No new bone, 1—visible new bone, but not continuous, 2—possible fusion with lucency, 3—probable fusion with bridging bone.

TABLE 15

| Group | ID | Hp mg/site | Time | Bone | Fusion |
|---|---|---|---|---|---|
| F | W2781 | 0 mg | 12 | 2 | 1 |
| F | W2792 | 0 mg | 12 | 2 | 1 |
| E | w2790 | 0.1 mg | 12 | 3 | 1 |
| E | W2791 | 0.1 mg | 12 | 3 | 1 |
| D | W2788 | 0.5 mg | 12 | 4 | 2 |
| D | W2789 | 0.5 mg | 12 | 4 | 2 |
| C | W2786 | 1.0 mg | 12 | 4 | 2 |
| C | W2787 | 1.0 mg | 12 | 4 | 3 |
| B | W2784 | 2.0 mg | 12 | 4 | 2 |
| B | W2785 | 2.0 mg | 12 | 4 | 3 |
| A | W2782 | 4.0 mg | 12 | 4 | 2 |
| A | W2783 | 4.0 mg | 12 | 3 | 2 |
| G | W2793 | Autograft(Iliac Crest) | 12 | 4 | 2 |
| G | W2794 | Autograft(Iliac Crest) | 12 | 2 | 2 |

Example 12: Controlled Release System Preparation (Double Emulsion Method/Basic Substance/Hydrophilic Drug)

In one embodiment, 0.25 g of PLGA (Lactic acid/Glycolic acid ratio 65/35, MW 40000-75000, Sigma-Aldrich) dissolved in 2.5 mL of dichloromethane (Merck) was shaken with a shaker (1000 rpm) for 5 minutes to form a 10% PLGA solution (10% oil phase solution). 2.5 mL double-distilled water (DDW) was slowly mixed the 10% PLGA solution and stirred at 1,000 rpm for 15 minutes to form a first emulsion (w/o). The first emulsion was added to 10 mL of a 0.1% (w/v) polyvinyl alcohol (PVA) (MW~130000, Fluka) second aqueous solution and stirred at 500 rpm and evacuated the gas for 5 minutes to form a second emulsion (w/o/w). The second emulsion was continuously stirred for 4 hours and then left standing for one minute. Particles in the pellet were collected by centrifugation at 4,000 rpm for 5 minutes. The particles were washed with 5 mL of DDW for minutes. After centrifugation and washing three times, centrifuged particles were collected and lyophilized 3 days to form PLGA microparticles. 2 mg and/or 4 mg β-TCP powder (Sigma-Aldrich) was mixed with 50 µL DDW and 10 µg of the homodimeric protein (Hp) including recombinant polypeptide produced according to Example 6 (i.e., SEQ ID NO: 260) to form a slurry. The slurry was then mixed or coated on the surface of 50 mg PLGA microparticles and lyophilized 3 days to form PLGA microparticles, one of the controlled release system. In certain embodiments, the lyophilized controlled release system could be pressed to form a flat piece.

In alternative embodiment, 2.5 mL dichloromethane was mixed with 0.25 g of poly lactic-co-glycolic acid, PLGA 65:35 (Supplier, Sigma) and stirred (1000 rpm) for 5 minutes which became a 10% oil phase solution (P1). 0.25 mL of double-distilled water (DDW) was added into P1 and stirred (1000 rpm) for 15 minutes which became first emulsion phase (w/o, P2). The P2 was placed into 10 mL of 0.1% (w/v) polyvinyl alcohol (PVA) (MW~130000, Fluka) and stirred (500 rpm) for 4 hours (P3). Centrifugation of P3 at 4,000 rpm for 5 minutes, the supernatant was discarded, and the residual solution was collected. 5 mL of PBS was added into P3 and repeat for three times, the residual solution was collected and lyophilized. The lyophilized powder of PLGA microsphere was weighted, and the production rate (%) was calculated. The 0.06 mL of DDW was mixed with 2 mg of β-TCP powder (Sigma-Aldrich), then 20 µg of the homodimeric protein was added into β-TCP for stirring 5 minutes. After that, 50 mg of PLGA microsphere was added into the mixture and stirred evenly. The microsphere containing was lyophilized and pressed a tablet with a size Φ10 mm. (The appropriate pressure was 5~10 Kg).

In some embodiments, the 2 mg and/or 4 mg β-TCP powder could be replaced with either 4 mg tricalcium phosphate (TCP) or 1 mg alpha-tricalcium phosphate (α-TCP). In certain embodiments, the PLGA65/35 could be replaced with PLGA50/50, polylactic acid (PLA) or polyglycolic acid (PGA).

Evaluation of Homodimeric Protein (Hp) Release from PLGA/Hp-β-TCP 100 mg of PLGA/Hp-β-TCP was soaked in 1 mL human serum, and shaken with 60 rpm at 37° C. Human serum solution containing released homodimeric protein was collected at 15 min, 1 hour, day 1, 2, 3, 7, 10 and 14, and at each time point was replaced with 800 μL of fresh human serum. The collected human serum was stored at −80° C. and all samples were analyzed simultaneously with a direct ELISA assay.

Figure 15A:
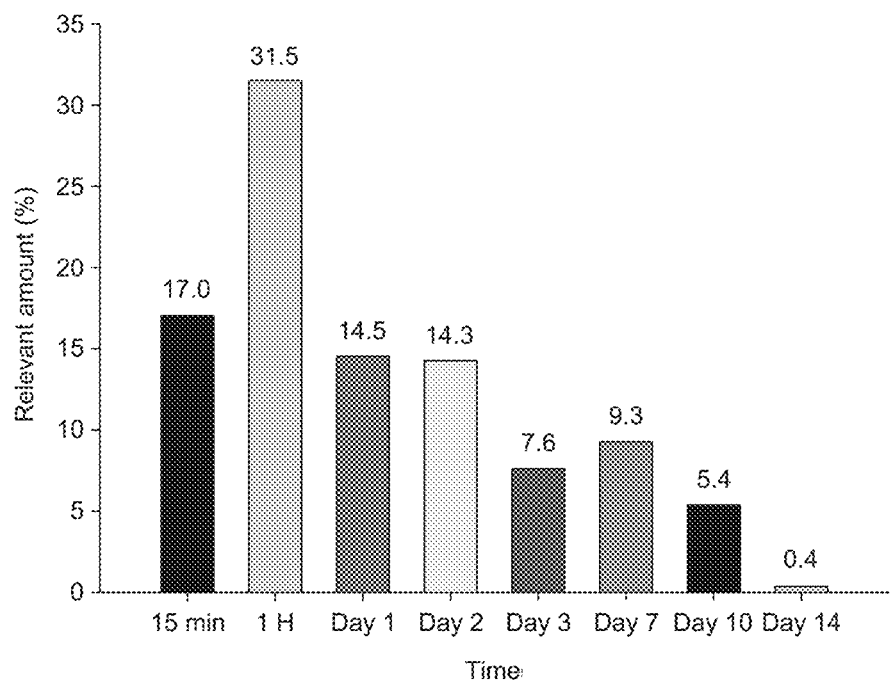
FIGS. 15a and 15b show the relative amount of the homodimeric protein released (FIG. 15a) and the cumulative percentage of the homodimeric protein released (FIG. 15b) from microparticles over a 14-day release period.
Figure 15B:
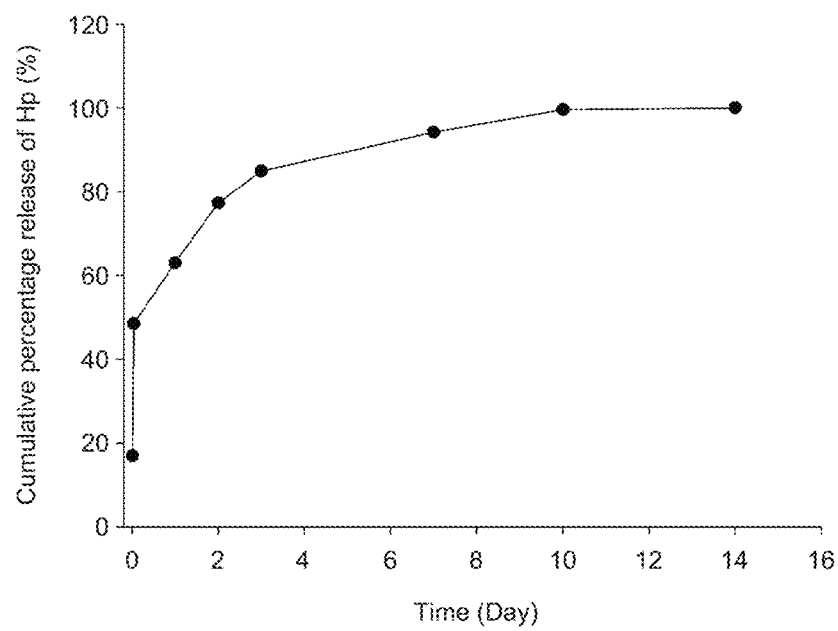

The release profile of the PLGA microparticles coated with β-TCP and the homodimeric protein is shown in FIGS. 15a and 15b. Homodimeric protein physically adsorbed on the surface of the PLGA microparticles was shown to continuously release therefrom to an in-vitro solution via diffusion and PLGA hydrolysis. Results from an ELISA kit showed that 17% and 31.5% of relative amount of homodimeric protein was released at 15 min and 1 hr, respectively. The relative releasing percentages of homodimeric protein were 14.5% (at 60 min to day 1), 14.3% (day 1 to day 2), 7.6% (day 2 to day 3), 9.3% (day 3 to day 7), 5.4% (day 7 to day 10) and 0.4% (day 10 to day 14) and that has shown a slow-release pattern. This formulation of PLGA/Hp-β-TCP alleviated the common issue of burst release [Giteau et al., *Int J Pharm* 350:14 (2008)]; most delivery systems deliver a burst release during the first few hours, often releasing over 60% of the encapsulated/surface bound product [Woodruff et al., *J Mol Histol* 38:425 (2007) and Sawyer et al., *Biomaterials* 30:2479 (2009)].

Figure 16:
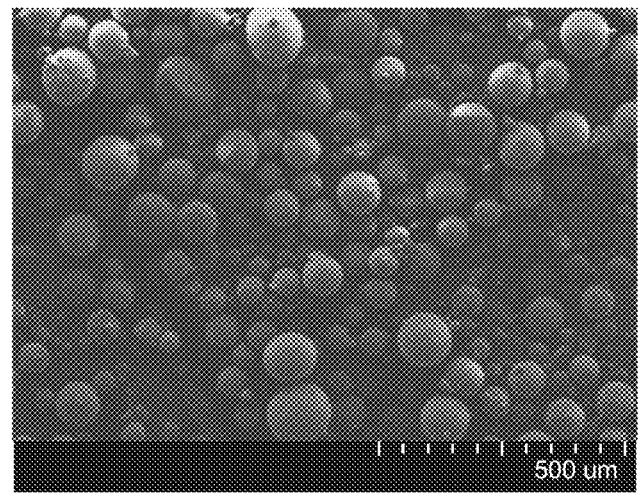
FIG. 16 shows a representative scanning electron microscopy image of poly lactic-co-glycolic acid/homodimeric protein-tricalcium phosphate ("PLGA/Hp-β-TCP") stored at −20° C., 4° C. and 25° C. for six months.

FIG. 16 shows morphology and a diameter distribution of the PLGA microparticles under an electron microscope. The PLGA microparticles were globular and had a diameter distribution ranging from 100 μm to 150 μm.

In another embodiment, 2 g of PLGA was dissolved in 20 mL of dichloromethane (DCM) to form a 10% PLGA/DCM solution. Biphasic calcium phosphate (BCP) powder was dispersed in water to form an aqueous solution. The aqueous solution was then mixed with the PLGA/DCM solution and stirred with a magnetic stirrer for 30 minutes to form an emulsion. Next, the emulsion was fed into a granular machine to perform a spray granulation process to form PLGA microparticles.

Evaluation the New Bone Formation of PLGA/Hp-β-TCP on Balb/C Mice Osteonecrosis Model Surgery Procedure In the animal osteonecrosis model, in order to simulate the real osteonecrosis situation, the whole tibia periosteum was stripped. A 2 mm length of the mid-shaft of the tibia on the right side of a mouse was cut out with a saw. The cut surface of the bone was frozen using liquid nitrogen for 5 min to mimic necrotic bone. Next, the fragment was reversed and put back to its original site in the tibia and fixed to both ends with the other parts of the tibia by using a syringe needle (No. 26) as an intramedullary fixation. After a test article was placed around the bone fracture, the wound was closed with silk sutures. The mice were divided into six groups, including necrotic bone control (C), PLGA/β-TCP (PT), PLGA/0.2 μg Hp-β-TCP (POT-0.2), PLGA/0.8 μg Hp-β-TCP (POT-0.8), PLGA/1.6 μg Hp-β-TCP (POT-1.6) and PLGA/3.2 μg Hp-β-TCP (POT-3.2) groups. Three to six mice in each experimental group were observed at 4 weeks after surgery.

Soft X-Ray Observation

At 4 weeks after the operation, the tibia bone fractures were radiographically examined by soft X-rays (SOFTEX, Model M-100, Japan) at 43 KVP and 2 mA for 1.5 s. The appropriate magnification was applied throughout the observation period, and the resultant micrographs were compared among all carriers together with controls.

Figure 17:
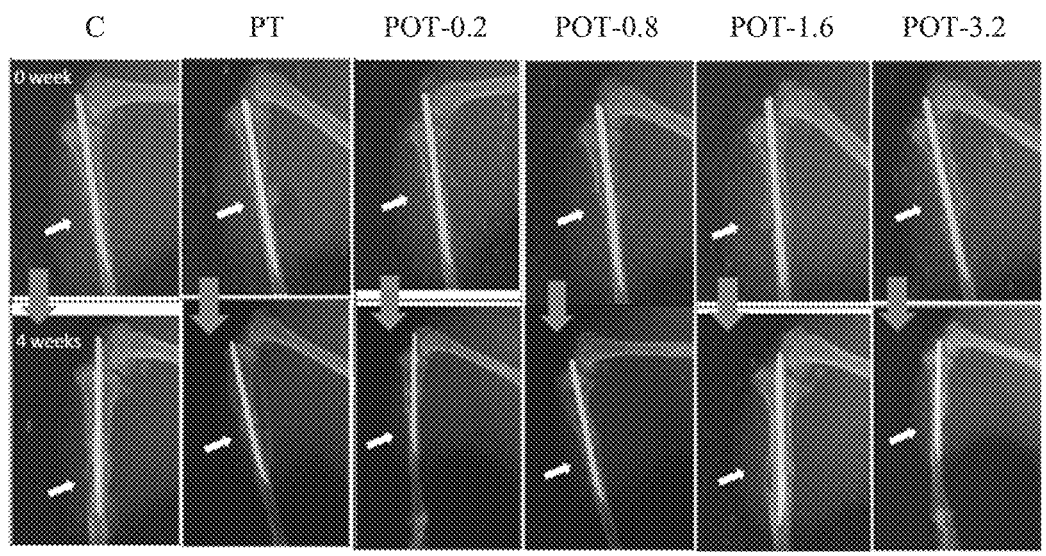
FIG. 17 shows representative X-ray images of Balb/C mice tibias at 0 weeks and after 4 weeks of implantation of PLGA/Hp-β-TCP as described for FIG. 16 and with different dosages of homodimeric protein. White arrows in each image identify the bone defects. (Groups=C: necrotic bone control (i.e., bone fragment without implantation of any scaffold), PT: PLGA/β-TCP (i.e., no homodimeric protein), POT-0.2: PLGA/0.2 µg Hp-β-TCP, POT-0.8: PLGA/0.8 µg Hp-β-TCP, POT-1.6: PLGA/1.6 µg Hp-β-TCP and POT-3.2: PLGA/3.2 µg Hp-β-TCP).

FIG. 17 shows the X-ray photographs of mice tibia osteonecrosis fragment callus formation at 4 weeks after implantation of PLGA/Hp-β-TCP containing different homodimeric protein doses compared to control (C) or PLGA/β-TCP (PT) groups. An incomplete fusion was noted in control group, and a small gap was existed in osteonecrosis region in PT group. Clear fusion masses were observed in POT-0.2, POT-0.8, POT-1.6 and POT-3.2 groups. The results indicated that the efficacy of bone repair on PLGA/Hp-β-TCP groups were greater than control and PT groups.

Histological Analysis of Bone Tissue

Histochemical analyses were concurrently employed to assess the microscopic changes in the bone tissue. Prior to hematoxylin-eosin (H&E) staining, all samples of bone tissue were decalcified using 0.5% EDTA. The resultant samples were embedded into paraffin wax, and 5 μm sections were prepared. Sections were routinely stained with H&E and observed with a microscope. At 400× magnification, the callus area was compared with that of the control group.

Figure 18:
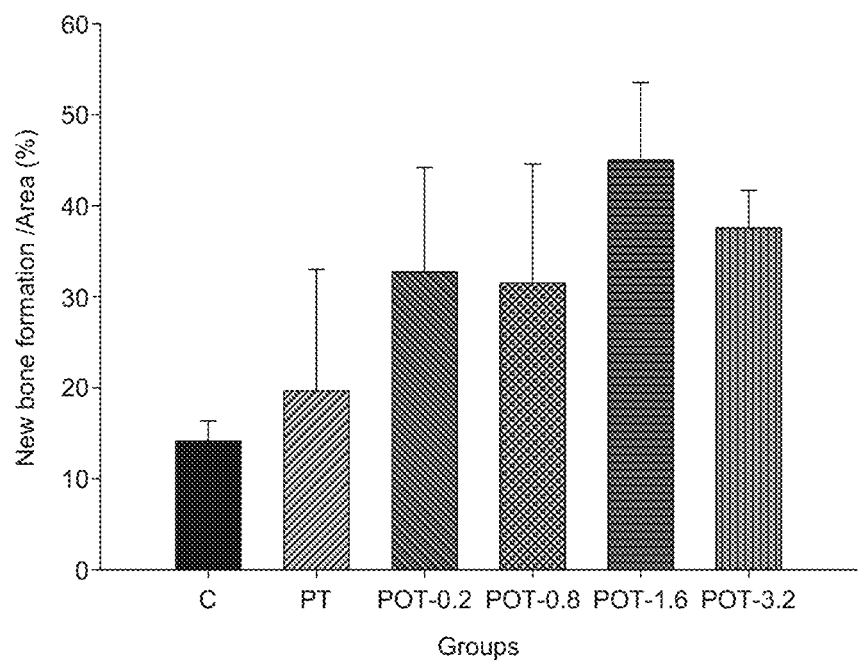
FIG. 18 shows a graphical representation of the percentages of new bone formation/area in osteonecrosis bone after 4 weeks of implantation, with the groups as described for FIG. 17.
Figure 19:
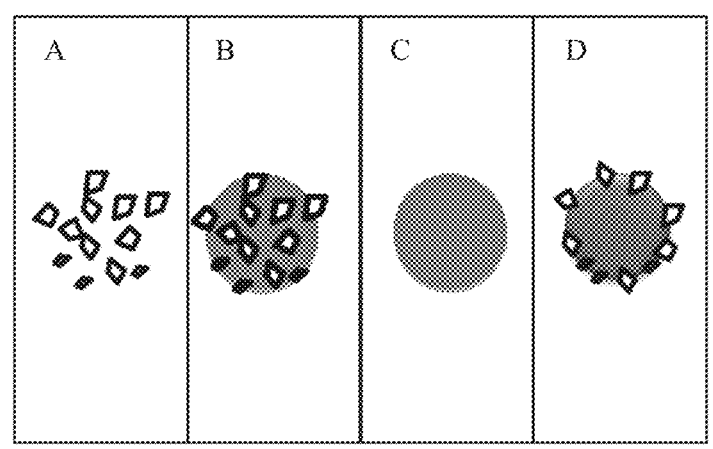
FIGS. 19A-D show cross-section representations of example formulations of the present disclosure: granules of a carrier (e.g., β-TCP) carrying polypeptides/proteins of the disclosure (FIG. 19A), a putty mixed with the granules carrying polypeptides/proteins of the disclosure (FIG. 19B), a putty comprising polypeptides/proteins of the disclosure (FIG. 19C), and a putty comprising polypeptides/proteins of the disclosure with granules carrying polypeptides/proteins of the disclosure distributed evenly in the outer layer of the putty (FIG. 19D).

As shown in FIG. 18, the new bone formation was evaluated after 4 weeks of implantation of PLGA/Hp-β-TCP (POT). The bone formation rate of the PLGA/β-TCP (PT) group shows a similar result as compared to the control group. Bone formation rate was enhanced in the POT groups as compared to the PT and control groups, which was increased in a dose-dependent manner except for the POT-3.2 group. These results demonstrated potential advantages of homodimeric protein controlled-release carriers that can induce bone regeneration on Balb/C mice osteonecrosis model.

Example 13: Sustained Release System

Putty Preparation

Powders were prepared and mixed according to the formulas in Table 16. The powders were stored at 4° C. overnight. On the day that the putty was prepared, all materials (i.e., the powder, β-TCP, glycerol and deionized water) were illuminated with UV light for 20 minutes. According to the animal experimental bone defect range of 2×0.5×0.5 cm, putty weights of about 0.9 g were prepared in accordance with the formulas as shown in Table 16.

TABLE 16

Putty formulation

| | | Formula A | Formula B | Formula C | Formula D | Formula E | Formula F | Formula G |
|---|---|---|---|---|---|---|---|---|
| Powder | CaSO$_4$•1/2H$_2$O*[1] | — | 96% 0.864 g | 96% 0.864 g | 96% 0.864 g | 96% 0.864 g | — | — |
| | CaSO$_4$•2H$_2$O*[2] | — | — | — | — | — | 48% 0.432 g | 48% 0.432 g |

TABLE 16-continued

| | | Putty formulation | | | | | | |
|---|---|---|---|---|---|---|---|---|
| | | Formula A | Formula B | Formula C | Formula D | Formula E | Formula F | Formula G |
| | HPMC*3 | — | 4% 0.036 g | 4% 0.036 g | 4% 0.036 g | 4% 0.036 g | 4% 0.036 g | 4% 0.036 g |
| | $Ca_3(PO_4)_2$*5 | — | — | — | — | — | 48% 0.432 g | 48% 0.432 g |
| Liquid | Glycerol*7 | — | 126 μl | 126 μl | 126 μl | 126 μl | 252 μl | 252 μl |
| | Hp*4 | — | — | 40 μl of 0.5 mg/ml | 40 μl of 0.25 mg/ml | — | 40 μl of 0.25 mg/ml | 40 μl of 0.5 mg/ml |
| | Deionized water | — | 54 μl | 14 μl | 14 μl | 54 μl | 68 μl | 108 μl |
| L/P (Lictuid/powder) | | — | 0.2 | 0.2 | 0.2 | 0.2 | 0.4 | 0.4 |
| β-TCP*6 (2-3 mm) | | 50 mg | 50 mg | — | 50 mg | 50 mg | 50 mg | — |
| | Hp*4 | 160 μl of 0.125 mg/ml | 40 μl of 0.5 mg/ml | — | 40 μl of 0.25 mg/ml | 40 μl of 0.5 mg/ml | 40 μl of 0.25 mg/ml | — |
| | Cross-section | See FIG. 20A | See FIG. 20B | See FIG. 20C | See FIG. 20D | See FIG. 20D | See FIG. 20D | See FIG. 20C |

*1Calcium Sulfate Hemihydrate (MT3, Taiwan),
*2Calcium Sulfate Dihydrate (J. T. baker, USA),
*3Hydroxypropyl Methylcellulose (Sigma-Aldrich, USA),
*4Homodimeric protein (Hp) including recombinant polypeptide produced according to Example 6 (i.e., SEQ ID NO: 260) final volume 20 μg,
*5Calcium Phosphate (Sigma-Aldrich, USA),
*6Tricalcium Phosphate Beta Form (Wiltrom, Taiwan),
*7Glycerol (Showa, Japan)

Formula A: 160 microliters of 0.125 mg/mL Hp solution was dripped in approx. 50 mg β-TCP, in sterile conditions, and allowed to adsorb for 15 minutes.

Formula B: 40 microliters of 0.5 mg/mL Hp solution was dripped in approx. 50 mg β-TCP, in sterile conditions, and allowed to adsorb for 15 minutes. Powder and liquid (as shown in Table 16 for Formula B) and previously prepared β-TCP granules were mixed together and molded.

Formula C: Powder and liquid (as shown in Table 16 for Formula C) were mixed evenly.

Formula D: 40 microliters of 0.25 mg/mL Hp solution was dripped in approx. 50 mg β-TCP, in sterile conditions, and allowed to adsorb for 15 minutes to form Hp/β-TCP granules. Powder and liquid (as shown in Table 16 for Formula D) were mixed together to form a matrix and the matrix was molded in a specific shape. Hp/β-TCP granules were evenly distributed in the outer layer of the matrix.

Formula E: 40 microliters of 0.5 mg/mL Hp solution was dripped in approx. 50 mg β-TCP, in sterile conditions, and allowed to adsorb for 15 minutes to form Hp/β-TCP granules. Powder and liquid (as shown in Table 16 for Formula E) were mixed together to form a matrix and the matrix was molded in a specific shape. Hp/β-TCP granules were evenly distributed in the outer layer of the matrix.

Formula F: 40 microliters of 0.25 mg/mL Hp solution was dripped in approx. 50 mg β-TCP, in sterile conditions, and allowed to adsorb for 15 minutes to form Hp/β-TCP granules. Powder and liquid (as shown in Table 16 for Formula F) were mixed together to form a matrix and the matrix was molded in a specific shape. Hp/β-TCP granules were evenly distributed in the outer layer of the matrix.

Formula G: Powder and liquid (as shown in Table 16 for Formula G) were mixed evenly.

Sample Preparation

Formula putty shown in Table 16 were placed in 15 ml tube. Putty with or without β-TCP soaked with Hp was placed in 3 mL human serum, and allowed to stand at 37° C., under 5% $CO_2$. Human serum solution containing released Hp was collected at initial, 1 hour, Day 1, 2, 3, 7, 10, 14 and 21, and at each time point was replaced with 2500 μL of fresh human serum. The collected human serum was stored at −80° C. and all samples were analyzed simultaneously with a direct ELISA assay within the day.

OIF Quantification

To quantify the total concentration of homodimeric protein, an in vitro release test was used. Homodimeric protein concentrations in the human serum were quantified using ELISA-methods (the assay was obtained from inVentive Health clinical systems, USA). The analyses were performed according to the instructions of the manufacturer. Briefly, samples, QC samples and standards were added to 107 capture antibody (generated from Pharma Foods International Co., Ltd.) coated 96 well plates. After incubation and removal of the unbound substances, HRP-I07 detection antibody was added. This step was followed by a further washing step and incubation with a substrate. The color reaction was stopped and the optical density measured at the appropriate wavelength. The concentration of homodimeric protein was back calculated off of the non-linear regression of the standard deviations.

Figure 20:
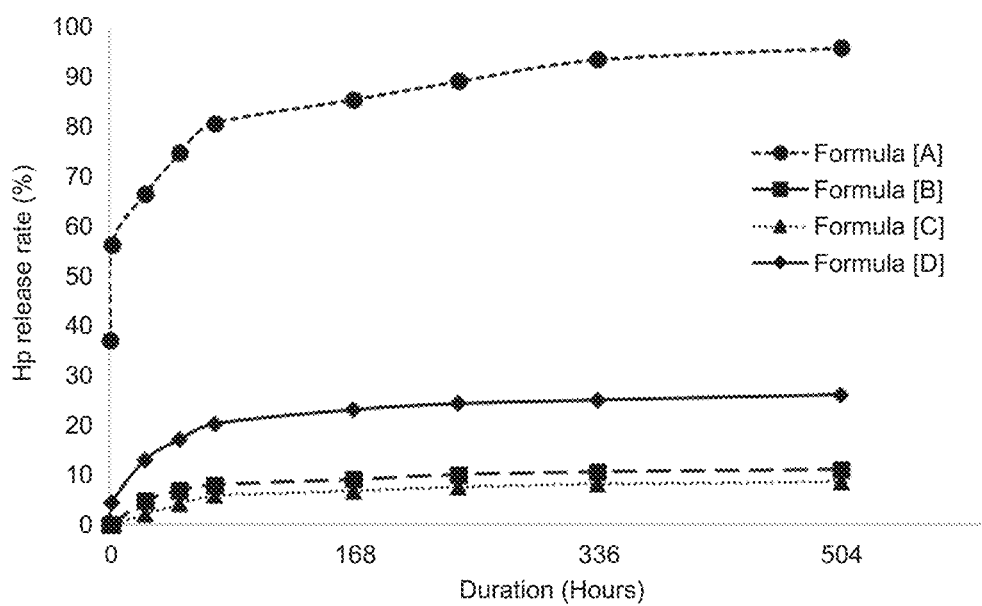
FIG. 20 shows a graphical representation of the cumulative percentage of homodimeric protein released over a duration of specified hours.

The purpose was to evaluate the release of homodimeric protein from a bioresorbable osteoconductive composite such as beta-TCP or putty, and to assess its suitability for bone regeneration. Homodimeric protein released from formula A was observed to have a burst release profile at the beginning, but after the burst period (around 0 to 1 hour) a slow-release pattern as shown in FIG. 20 was observed. Compared with formula A, the homodimeric protein in formula B and C was wrapped up by putty or the matrix, so that it cannot be released at the beginning hours. In contrast, when homodimeric protein contained in β-TCP granules was distributed on the surface of the putty or the matrix, such as formula D, a sustained release effect was achieved. It was known that putty was a bone graft substitute with a proven ability to accelerate bone regeneration. The composition of the putty determines plasticizing capacity, hardening or curing. Thereafter, different proportions of the formulation, for example, the choice of calcium sulfate dihydrate or calcium sulfate to prepare putty could achieve sustained release of the dosage form.

The development of bone substitute materials trends toward materials that are bio-absorbable, osteoconduction, osteoinduction, as well as biocompatible. In other words, the direction of development for composite bone defect filling material is a material that is multi-functional. In the designed putty, pores can be generated in the bone substitute for ingrowth of bone cells, while homodimeric protein can be released over a long term for induction of osteoclasts and activation of osteocytes in the slow process of material decomposition. Therefore, the healing of bone defects will be effectively accelerated.

Example 14: Clinical Study Design

Study Design 1

A Randomized, evaluator-blind, controlled study investigating the efficacy and safety of three dosage levels of the homodimeric protein (Hp) including recombinant polypeptide produced according to Example 6 (i.e., SEQ ID NO: 260)/β-TCP in treatment of open tibial fractures with need of bone grafting will be performed. A total of approx. 35 patients having initial open tibial fractures (Gustilo type IIIA or IIIB) will participate in the study and will be divided (randomized) into four groups and one control group (approx. 5 patients), each of the other groups consisting of approx. 10 patients (vide infra). A vial contains 5.5 mg lyophilized power of homodimeric protein. After reconstitution (the exact volume of water used to get the intended concentration will be as stated in Table 17), the reconstituted homodimeric protein will be mixed with the β-TCP to make the final concentration of 1.5 mg/g (Group 2), 2 m g/g (Group 3) or 3 mg/g (Group 4) the Hp/β-TCP, then certain amount of these mixture will be applied to the fracture site within 3 months after the fracture occurred. Patients in the control group (Group 1) will receive autogenous bone graft but lacking the homodimeric protein and/or β-TCP. Subjects will be followed for efficacy and safety for the main study period of 30 weeks and an extension safety follow-up to 52 weeks after definitive treatment. In some embodiments, the total amount of β-TCP used is based on the physician's judgment and adjustment.

post-menopausal for at least 1 year) and male subject's partners of childbearing potential must agree to use medically acceptable contraception methods throughout the study period. Medically acceptable contraception methods include hormonal patch, implant or injection intrauterine device, or double barrier method (condom with foam or vaginal spermicidal suppository, diaphragm with spermicidal). Complete abstinence can be considered an acceptable contraception method. Oral contraceptive is an acceptable contraception method prior to the study, but an alternative method will be required during the study;

Subjects will be excluded if ANY of the following Exclusion Criteria apply:

Head injury with initial loss conscious;

Purulent drainage from the fracture, or evidence of active osteomyelitis;

Compartment syndrome;

Pathological fractures; history of Paget's disease or other osteodystrophy; or history of heterotopic ossification;

Endocrine or metabolic disorder that affects osteogenesis (e.g., hypo- or hyper-thyroidism or parathyroidism, renal osteodystrophy, Ehlers-Danlos syndrome, or osteogenesis imperfecta)

Has abnormal renal and/or hepatic functions, with Creatinine or ALT value >5 times the upper normal limit;

History of malignancy, radiotherapy, or chemotherapy for any malignancy within the last 5 years;

An autoimmune disease (e.g. Systemic Lupus Erythematosus or dermatomyositis);

Previous exposure to rhBMP-2;

Hypersensitivity to protein pharmaceuticals, e.g, monoclonal antibodies, gamma globulins, and tricalcium phosphate;

Treatment with any investigational therapy within 28 days of implantation surgery;

TABLE 17

| Hp (mg/vial) | WFI (mL) | Hp Concentration (mg/mL) | Hp Volume required (mL) | β-TCP required (g) | Final Concentration Applied (Hp (mg)/β-TCP (g)) |
|---|---|---|---|---|---|
| 5.5 | 3.0 | 1.8 | 2 | 2.4 | 1.5 (Group 2) |
| 5.5 | 2.3 | 2.4 | 2 | 2.4 | 2.0 (Group 3) |
| *5.5 × 2 (Two vials of Hp) | 1.5 × 2 (1.5 ml for each Hp vial) | 3.6 | 1 × 2 (1 ml from each vial, total 2 ml) | 2.4 | 3.0 (Group 4) |

*For final concentration 3.0 mg/g (Hp/β-TCP), 2 vials of lyophilized powder will be mixed with 1 vial β-TCP; each vial of lyophilized powder will be reconstituted by 1.5 ml WFI; and 1 ml from each reconstituted Hp (total 2 ml) will be mixed with 1 vial (2.4 g) β-TCP.

Patient Inclusion/Exclusion Criteria

Subjects will be included if ALL of the following Inclusion Criteria apply:

The subject is ≥20 years old;

Females of non-childbearing potential or who have a negative result on pregnancy test within 72 hours prior to surgery, or males;

Initial open tibial fractures (Gustilo type IIIA or IIIB) and bone graft within 3 months of fracture;

In bilateral open tibial fractures, the random treatment assignment is for the right tibia;

Definite therapy is performed within 3 months after the initial injury; and

Female subjects of childbearing potential (i.e., women who have not been surgically sterilized or have not been Treatment for 7 days or more with prednisone (cumulative dose>150 mg within 6 months or other steroids with equivalent dose, refer to Appendix 1), calcitonin (within 6 months). Treatment of Bisphosphonates (for 30 days or more within 12 months), therapeutic doses of fluoride (for 30 days within 12 months);

The female subject who is lactating; and

Any condition that is not suitable to participate in the study based on the physician's judgement.

Assessments of Efficacy

Primary Endpoint:

The primary study efficacy endpoint is the proportion of subjects who received secondary intervention within 30 weeks after definitive wound closure.

Secondary Endpoints:

The proportion of subjects who received secondary intervention within postoperative Week 6, Week 12, Week 18, Week 24, Week 42 and Week 52 after definitive wound closure;

Time from definitive wound closure to secondary intervention;

Rate of clinical fracture healing within postoperative Week 6, Week 12, Week 18, Week 24, Week 30, Week 42 and Week 52 after definitive wound closure;

Time from definitive wound closure to clinical fracture healing;

Rate of radiographic healing within postoperative Week 6, Week 12, Week 18, Week 24, Week 30, Week 42 and Week 52 after definitive wound closure;

Time from definitive wound closure to radiographic healing;

The term "secondary intervention" is in relation to any procedure that is performed or any occurrence of an event that has the potential to stimulate fracture healing, including but not limited to bone graft, exchange nailing, plate fixation, nail dynamization, ultrasound, electrical stimulation, or magnetic field stimulation or others that might promote healing.

The term "clinical fracture-healing" refers to the absence of tenderness on manual palpation from fracture site. In some embodiments, the term "clinical fracture-healing" refers to no or mild pain (pain score 0-3) at the fracture site with full weight-bearing and pain will be documented using the visual analogue scale.

The term "radiographic fracture healing" refers to a condition that in view of the anteroposterior and lateral radiographs, investigators and/or an independent radiologist identified Cortical bridging and/or disappearance of the fracture lines on 3 cortices of the 4 cortices at fracture site.

Assessment of Methods

Safety Assessment Methods

Adverse effect (AE): type, severity, management and outcome.

Systematic AE: any systematic sign, symptom, disease, laboratory test result, radiographic finding, or physiologic observation that occurred or worsened after treatment, regardless of causality.

Local AE: including inflammation, infection (any suspected or confirmed superficial or deep infection involving soft tissue or bone, with or without bacteriologic confirmation), hardware failure, pain (new or increased), peripheral edema, heterotopic ossification/soft-tissue calcification, and complications related to wound-healing.

Efficacy Assessment Methods

The primary and secondary efficacy outcomes will be analyzed based on Full Analysis Set (FAS) and Per Protocol (PP) population. The primary analysis will be conducted on the FAS population.

The primary efficacy endpoint is the proportion of subjects who received secondary intervention within 30 weeks after definitive wound closure. The primary analysis will be conducted on the FAS population using Cochran-Armitage trend test to indicate the linear trend in response rates with increasing homodimeric protein dosages. A supportive analysis using the PP population will be performed for the primary efficacy endpoint.

In addition, the secondary efficacy endpoints will be analyzed or summarized as below:

The proportion of subjects with clinical fracture healing and the proportion of subjects with radiographic healing within 30 weeks after definitive wound closure will be compared separately using Cochran-Armitage trend test to indicate the linear trend in response rates with increasing homodimeric protein dosages.

The assessment of time from definitive wound closure to secondary intervention, time from definitive wound closure to clinical fracture healing and time from definitive wound closure to radiographic healing will be summarized separately by group using descriptive statistics (Mean, SD).

The proportion of subjects who received secondary intervention, the proportion of subjects with clinical fracture healing and the proportion of subjects with radiographic healing within postoperative Week 6, Week 12, Week 18, Week 24, Week 42 and Week 52 after definitive wound closure will be summarized separately by group using descriptive statistics (n, %). If applicable, 95% CI of each group will be calculated based on Clopper-Pearson exact CI method for a single binomial proportion.

Study Design 2

A Randomized, evaluator-blind, controlled study to evaluate the safety and efficacy of three dosage levels of homodimeric protein (Hp) including the recombinant polypeptide produced according to Example 6 (i.e., SEQ ID NO: 260)/β-TCP in combination with the cage and posterior supplemental fixation in patients with single level (between L1 to S1) degenerative disk disease (DDD) using posterior open approach for lumbar interbody fusion. Subjects of 24 will be randomly assigned (1:1:1:1) to 4 groups (1 control group and 3 different dose groups), and the clinical study investigational device for treatment of each group are below:

Control group (6 subjects): standard of care (posterior open approach for lumbar interbody fusion with cage) plus either autogenous bone graft implantation (with or without β-TCP);

1 mg Hp/site (6 subjects): standard of care plus 1 mg homodimeric protein per site;

2 mg Hp/site (6 subjects): standard of care plus 2 mg homodimeric protein per site; and 3 mg Hp/site (6 subjects): standard of care plus 3 mg homodimeric protein per site.

Homodimeric protein will be supplied as 5.5 mg Hp/vial lyophilized powder with water for injections. After reconstitution, the homodimeric protein will be mixed with the 0-TCP, with the final concentration of 1 mg, 2 mg or 3 mg Hp/site. Then certain amount of the mixture will be applied into the cage, which was determined by the size of cage used.

Homodimeric protein will be reconstituted (the exact volume of water used to get the intended concentration will be stated in Table 18) in three different concentration stock solutions and every 0.24 ml from each stock solution is required to mixed with block β-TCP (0.3 g) in the polyetheretherketone (PEEK) cage (Wiltrom Co., Ltd./xxx series).

The final concentration of homodimeric protein applied at DDD site is: 1.0; 2.0; 3.0 mg Hp/site.

Stock solution of homodimeric protein: 5.5 (mg)/1.32 (ml)=4.2 (mg/ml);

Final concentration of homodimeric protein (mg)/site: 4.2 (mg/ml)×0.24 (ml)=1.0 mg

TABLE 18

| Hp (mg/vial) | WFI (mL) | Concentration (mg/mL) | Volume required (mL) | β-TCP required (g) | Final Concentration Applied (Hp (mg)/ β-TCP (g)) | Hp/site (mg) |
|---|---|---|---|---|---|---|
| 5.5 | 1.32 | 4.2 | 0.24 | 0.3 | 3.3 | 1.0 |
| 5.5 | 0.65 | 8.4 | 0.24 | 0.3 | 6.7 | 2.0 |
| 5.5 | 0.44 | 12.5 | 0.24 | 0.3 | 10.0 | 3.0 |

The source of autograft can be posterior superior iliac spine (PSIS) or bone chips obtained from posterior laminectomy. Autograft can be mixed with β-TCP if the amount of autograft is insufficient. Unilateral or bilateral posterolateral fusion (can be one or two sides) with local graft and posterior supplemental fixation measures can be used in all groups based on investigator's judgment. Intravenous vancomycin (500 mg every 6 hours) will be given prior to operation and for 3 consecutive days.

Subjects will be followed for efficacy and safety for the main study period of 24 weeks and an extension safety follow-up to 24 months after index surgery. In some embodiments, clinical investigators and an independent evaluator will assess the efficacy by evaluating the radiographic results during the trial.

Inclusion Criteria:

Subjects will be included if ALL of the following inclusion criteria apply:

The subject is ≥20 years old;

With single level DDD from L1 to S1 as noted by back pain of discogenic origin, with or without radiculopathy secondary to nerve root compression, manifested by, history of radiating leg or buttock pain, paresthesias, numbness or weakness, or history of neurogenic claudication;

Has radiographic evidence of advanced degenerative lumbosacral disease, such as decreased disk height; herniated nucleus pulposus; hypertrophy or thickening of the ligamentum flavum, annulus fibrosis, or facet joint capsule; hypertrophied facet joints, facet joint space narrowing, or facet periarticular osteophyte formation; trefoil canal shape; or lateral (subarticular) stenosis; or vertebral endplate osteophyte formation; and at least one of the following:

Sagittal plane translation (slippage) of the superior (cranial) vertebral body anterior or posterior to the inferior (caudal) vertebral body is greater than 4 mm or angulation is greater than 10°, or Coronal plane translation (slippage) of the superior (cranial) vertebral body lateral to the inferior (caudal) vertebral body is greater than 4 mm, or narrowing (stenosis) of the lumbar spinal canal and/or intervertebral foramen;

Non responsive to non-operative treatment for at least 6 months;

Females of non-childbearing potential or who have a negative result on pregnancy test within 72 hours prior to surgery, or males;

Female subjects of childbearing potential (i.e., women who have not been surgically sterilized or have not been post-menopausal for at least 1 year) and male subject's partners of childbearing potential must agree to use medically acceptable contraception methods throughout the study period. Medically acceptable contraception methods include hormonal patch, implant or injection intrauterine device, or double barrier method (condom with foam or vaginal spermicidal suppository, diaphragm with spermicidal). Complete abstinence can be considered an acceptable contraception method. Oral contraceptive is an acceptable contraception method prior to the study, but an alternative method will be required during the study;

If female, subject is not breast-feeding;

Willing to provide signed informed consent form (ICF) prior to participation in any study-related procedures and adhere to the study requirements for the length of the trial.

Exclusion Criteria:

Subjects will be excluded if ANY of the following exclusion criteria apply:

Greater than Grade 1 spondylolisthesis (Meyerding's classification, refer to Appendix 1);

Spinal instrumentation implantation or interbody fusion procedure history at the involved level or vertebral body fracture at the planned pedicle screw insertion level;

Established osteomalacia;

Active malignancy or prior malignancy history in past 5 years (except cured cutaneous basal cell carcinoma and cervical carcinoma in situ);

Active local or systemic infection;

Gross obesity, defined as BMI≥30;

Fever>38° C.;

Mentally incompetent. If questionable, obtain psychiatric consult;

Waddell Signs of Inorganic Behavior ≥3 (refer to Appendix 2);

Alcohol or drug abuse, as defined by currently undergoing treatment for alcohol and/or drug abuse. Alcohol abuse is a pattern of drinking that results in harm to one's health, interpersonal relationships, or ability to work;

Autoimmune disease (e.g. Systemic Lupus Erythematosus or dermatomyositis);

Hypersensitivity to protein pharmaceuticals (monoclonal antibodies or gamma globulins);

Previous exposure to rhBMP-2;

Endocrine or metabolic disorders affecting osteogenesis (e.g., hypo- or hyper-thyroidism or parathyroidism, renal osteodystrophy, Ehlers-Danlos syndrome, or osteogenesis imperfecta);

Treatment for 7 days or more with prednisone [cumulative dose >150 mg within 6 months or other steroids with equivalent dose (refer to Appendix 3)], calcitonin (within 6 months). Treatment of Bisphosphonates (for 30 days or more within 12 months), therapeutic doses of fluoride (for 30 days within 12 months), and anti-neoplastic, immunostimulating or immunosuppressive agents within 30 days prior to implantation of the assigned treatment;

Treatment with any investigational therapy within 28 days of implantation surgery;

Has scoliosis greater than 30 degrees;

Subjects have the history or clinical manifestations of significant CNS, cardiovascular, pulmonary, hepatic, renal, metabolic, gastrointestinal, urological, endocrine or hematological disease;

Has a medical disease or condition that would preclude accurate clinical evaluation of the safety and effectiveness of the treatments in this study, such as motor weakness, sensory loss, or painful conditions that inhibit normal ambulation or other activities of daily living;

Has abnormal renal and/or hepatic functions, with Creatinine or ALT or AST value >5 times the upper normal limit;

Has a documented allergy or intolerance to PEEK;

History of hypersensitivity or allergy to Vancomycin;

Any condition that it is not suitable for subjects to participate in the study based on the physician's judgement.
Planned Study Duration:

Screening period: 14 days. Ensure the subject has signed the ICF and assess whether the subject is eligible for the study. The assessments include physical examination, vital signs, electrocardiogram, blood or urine pregnancy test, laboratory examination, pre-operative clinical and radiology evaluation. The data of demography, medical history, concomitant medication and adverse events should be collected.

Treatment period: 1 day. Check whether the subject is eligible for the study, obtain the baseline sample/data and administrate the investigational products. The assessments include physical examination, vital signs and radiology examination. The data of operation information, concomitant medication and adverse events should be collected.

Follow-up period: Subjects will be followed for the main study period of 24 weeks and an extension safety follow-up to 24 months after the implantation. Perform the assessments at Week 6, Week 12, Week 18, Week 24, Month 12, Month 18, Month 24 after treatment. The assessments include concomitant treatments, physical examination, laboratory evaluations, vital signs and radiographic examination (anterior/posterior and lateral views, flexion/extension films). High resolution thin-slice CT scans (1 mm slices with 1 mm index on axial sagittal and coronal reconstructions) will be performed at Week 24 and Month 24.
Assessments of Efficacy Primary Endpoint:

The primary study efficacy endpoint is the proportion of subjects having fusion success at postoperative Week 24.

Secondary Endpoints:

The proportion of subjects having fusion success at postoperative Month 12, Month 18, and Month 24.

Time from baseline to radiographic fusion.

The proportion of subjects who have additional surgical procedures/interventions within postoperative Week 24, Month 12, Month 18 and Month 24; the operation time (from skin incision to wound closure), blood loss (during the operation) and hospital stay will be recorded.

Success rate of Oswestry Disability Index (ODI, refer to Appendix 4) at postoperative Week 24, Month 12, Month 18 and Month 24; ODI Questionnaire was used to assess patient back function. The ODI score ranges from 0-100. The best score is 0 (no disability) and the worst is 100 (maximum disability). Success rate of ODI is reported as percent of subjects whose ODI score met: pre-operative score−postoperative score≥15.

Success rate of improvement in Visual Analogous Scale (VAS, refer to Appendix 5) at postoperative Week 24, Month 12, Month 18 and Month 24. Success rate of back pain is reported as percent of subjects whose improvement in back pain met: pre-operative score−post-operative score>0. Success rate of leg pain is reported as percent of subjects whose improvement in leg pain met: pre-operative score−postoperative score>0.
Efficacy Analyses The primary and secondary efficacy outcomes will be analyzed based on Full Analysis Set (FAS) and Per Protocol (PP) population. The primary analysis will be conducted on the FAS population.

The primary study efficacy endpoint is the proportion of subjects having fusion success at postoperative Week 24. The primary analysis will be conducted on the FAS population by using Cochran-Armitage trend test to indicate the linear trend in response rates with increasing homodimeric protein dosages. A supportive analysis for the PP population will be performed for the primary efficacy endpoint.

In addition, the secondary efficacy endpoints will be analyzed or summarized as below:

The proportion of subjects having fusion success at postoperative Month 12, Month 18, Month 24 and the proportion of subjects who have additional surgical procedures/interventions within postoperative Week 24, Month 12, Month 18 and Month 24 will be compared separately by using Cochran-Armitage trend test to indicate the linear trend in response rates with increasing homodimeric protein dosages.

The assessment of time from baseline to radiographic fusion will be summarized by group using descriptive statistics (Mean, SD).

The assessment of operation time (from skin incision to wound closure), blood loss (during the operation) and hospital stay will be summarized separately by arm using descriptive statistics (Mean, SD).

Success rate of ODI at postoperative Week 24, Month 12, Month 18 and Month 24 and success rate of VAS at postoperative Week 24, Month 12, Month 18 and Month 24 will be summarized separately by arm using descriptive statistics (n, %). If applicable, 95% CI of each arm will be calculated based on Clopper-Pearson exact CI method for a single binomial proportion.

The disclosure is not to be limited in scope by the specific embodiments described herein. Indeed, various modifications of the disclosure in addition to those described will become apparent to those skilled in the art from the foregoing description and accompanying figures. Such modifications are intended to fall within the scope of the appended claims.

Other embodiments are within the following claims.

What is claimed is:

1. A recombinant polypeptide comprising:
   a first domain selected from the group consisting of SEQ ID NO: 35 and SEQ ID NO: 39;
   a second domain selected from the group consisting of SEQ ID NO: 47 and SEQ ID NO: 49; and
   a third domain selected from the group consisting of SEQ ID NO: 57 and SEQ ID NO: 61; wherein the second domain comprises an intramolecular disulfide bond.

2. The recombinant polypeptide of claim 1, wherein the second domain comprises an intramolecular disulfide bond between the twenty-third amino acid of the second domain and the twenty-seventh amino acid of the second domain.

3. The recombinant polypeptide of claim 1, wherein the recombinant polypeptide is capable of inducing alkaline phosphatase activity.

4. The recombinant polypeptide of claim 1, wherein the third domain comprises two intramolecular disulfide bonds between the amino acid sequences PKACCVPTE (SEQ ID NO: 356) and GCGCR (SEQ ID NO: 357).

5. The recombinant polypeptide of claim 4, wherein the recombinant polypeptide comprises:

(a) a first intramolecular disulfide bond between the fourth amino acid of the amino acid sequence PKACCVPTE (SEQ ID NO: 356) and the second amino acid of the amino acid sequence GCGCR (SEQ ID NO: 357), and a second intramolecular disulfide bond between the fifth amino acid of the amino acid sequence PKACCVPTE (SEQ ID NO: 356) and the fourth amino acid of the amino acid sequence GCGCR (SEQ ID NO: 357), or (b) a first intramolecular disulfide bond between the fifth amino acid of the amino acid sequence PKACCVPTE (SEQ ID NO: 356) and the second amino acid of the amino acid sequence GCGCR (SEQ ID NO: 357), and a second intramolecular disulfide bond between the fourth amino acid of the amino acid sequence PKACCVPTE (SEQ ID NO: 356) and the fourth amino acid of the amino acid sequence GCGCR (SEQ ID NO: 357).

6. The recombinant polypeptide of claim 1, wherein the recombinant polypeptide comprises an amino acid sequence selected from the group consisting of: SEQ ID NO: 260, SEQ ID NO: 268, SEQ ID NO: 276, SEQ ID NO: 284, SEQ ID NO: 292, SEQ ID NO: 300, SEQ ID NO: 308, SEQ ID NO: 316, SEQ ID NO: 324, SEQ ID NO: 332, SEQ ID NO: 340, and SEQ ID NO: 348.

7. A homodimeric protein comprising two identical recombinant polypeptides of claim 1, wherein the homodimeric protein comprises an intermolecular disulfide bond between the first domains of the two recombinant polypeptides.

8. The homodimeric protein of claim 7, wherein the homodimeric protein comprises an intermolecular disulfide bond between the fifteenth amino acid in the first domain of one recombinant polypeptide and the fifteenth amino acid in the first domain of the other recombinant polypeptide.

9. The homodimeric protein of claim 7, wherein the homodimeric protein comprises two intermolecular disulfide bonds between the amino acid sequence PKACCVPTE (SEQ ID NO: 356) in the third domain of one recombinant polypeptide and the amino acid sequence GCGCR (SEQ ID NO: 357) in the third domain of the other recombinant polypeptide.

10. The homodimeric protein of claim 9, wherein the homodimeric protein comprises:
    (a) a first intermolecular disulfide bond between the fourth amino acid of the amino acid sequence PKACCVPTE (SEQ ID NO: 356) in the third domain of the one recombinant polypeptide and the second amino acid of the amino acid sequence GCGCR (SEQ ID NO: 357) in the third domain of the other recombinant polypeptide, and a second intermolecular disulfide bond between the fifth amino acid of the amino acid sequence PKACCVPTE (SEQ ID NO: 356) in the third domain of the one recombinant polypeptide and the fourth amino acid of the amino acid sequence GCGCR (SEQ ID NO: 357) in the third domain of the other recombinant polypeptide, or
    (b) a first intermolecular disulfide bond between the fifth amino acid of the amino acid sequence PKACCVPTE (SEQ ID NO: 356) in the third domain of the one recombinant polypeptide and the second amino acid of the amino acid sequence GCGCR (SEQ ID NO: 357) in the third domain of the other recombinant polypeptide, and a second intermolecular disulfide bond between the fourth amino acid of the amino acid sequence PKACCVPTE (SEQ ID NO: 356) in the third domain of the one recombinant polypeptide and the fourth amino acid of the amino acid sequence GCGCR (SEQ ID NO: 357) in the third domain of the other recombinant polypeptide.

11. A heterodimeric protein comprising two different recombinant polypeptides of claim 1, wherein the heterodimeric protein comprises an intermolecular disulfide bond between the first domains of the two different recombinant polypeptides.

12. The heterodimeric protein of claim 11, wherein the heterodimeric protein comprises an intermolecular disulfide bond between the fifteenth amino acid in the first domain of one recombinant polypeptide and the fifteenth amino acid in the first domain of the other recombinant polypeptide.

13. An isolated nucleic acid molecule comprising a polynucleotide sequence encoding the recombinant polypeptide of claim 1.

14. A recombinant nucleic acid molecule comprising an expression control region operably linked to the isolated nucleic acid molecule of claim 13.

15. An isolated *Escherichia coli* host cell comprising the isolated nucleic acid molecule of claim 13.

16. A method of making a recombinant vector comprising inserting the isolated nucleic acid molecule of claim 13 into a vector.

17. A method of making a recombinant host cell comprising introducing the isolated nucleic acid molecule of claim 13 into an *Escherichia coli* host cell.

18. A method of producing a recombinant polypeptide, comprising: culturing the isolated *Escherichia coli* host cell of claim 15, and isolating the recombinant polypeptide.

19. A composition comprising the recombinant polypeptide of claim 1.

* * * * *